(12) United States Patent
Herath et al.

(10) Patent No.: US 12,304,897 B2
(45) Date of Patent: May 20, 2025

(54) 15-PGDH INHIBITORS

(71) Applicant: KYORIN PHARMACEUTICAL CO., LTD., Chiyoda-ku (JP)

(72) Inventors: Shyama Herath, La Jolla, CA (US); Mariangela Urbano, La Jolla, CA (US); Eun-Kyong Kim, La Jolla, CA (US); Chixu Chen, La Jolla, CA (US); Qiang Li, La Jolla, CA (US); Julia Ayers, La Jolla, CA (US); Kaikoo Nakamura, La Jolla, CA (US); Xiuwen Zhu, La Jolla, CA (US); Hugh Rosen, La Jolla, CA (US); Jonathan S. Rosenblum, La Jolla, CA (US); Melissa C. Zhang, La Jolla, CA (US); Yongsheng Liu, La Jolla, CA (US); Masahiro Ueno, Shimotsuga-gun (JP)

(73) Assignee: KYORIN PHARMACEUTICAL CO., LTD., Chiyoda-ku (JP)

( * ) Notice: Subject to any disclaimer, the term of this patent is extended or adjusted under 35 U.S.C. 154(b) by 745 days.

(21) Appl. No.: 17/310,268

(22) PCT Filed: Jan. 29, 2020

(86) PCT No.: PCT/US2020/015683
§ 371 (c)(1),
(2) Date: Jul. 27, 2021

(87) PCT Pub. No.: WO2020/160151
PCT Pub. Date: Aug. 6, 2020

(65) Prior Publication Data
US 2022/0073494 A1 Mar. 10, 2022

Related U.S. Application Data

(60) Provisional application No. 62/799,361, filed on Jan. 31, 2019.

(51) Int. Cl.
*C07D 401/10* (2006.01)
*C07D 211/38* (2006.01)
(Continued)

(52) U.S. Cl.
CPC .......... *C07D 401/10* (2013.01); *C07D 211/38* (2013.01); *C07D 217/24* (2013.01); *C07D 401/14* (2013.01); *C07D 403/10* (2013.01); *C07D 405/14* (2013.01); *C07D 409/14* (2013.01); *C07D 471/04* (2013.01);
(Continued)

(58) Field of Classification Search
CPC .. C07D 401/10; C07D 211/38; C07D 217/24; C07D 401/14; C07D 403/10; C07D 405/14; C07D 409/14; C07D 471/04; C07D 471/10; C07D 487/04; C07D 498/04; C07D 211/86; C07D 237/32; C07D 401/12; C07D 405/10; C07D 413/14
See application file for complete search history.

(56) References Cited

U.S. PATENT DOCUMENTS

| 6,245,760 | B1 | 6/2001 | He et al. |
| 6,303,627 | B1 | 10/2001 | Koch et al. |

(Continued)

FOREIGN PATENT DOCUMENTS

| EP | 965 587 A1 | 12/1999 |
| EP | 2 210 891 A1 | 7/2010 |

(Continued)

OTHER PUBLICATIONS

Office Action issued May 15, 2023, in corresponding European Patent Application No. 20 708 859.2, 4 pages.

(Continued)

*Primary Examiner* — Valerie Rodriguez-Garcia
*Assistant Examiner* — Kyle Nottingham
(74) *Attorney, Agent, or Firm* — Oblon, McClelland, Maier & Neustadt, L.L.P.

(57) ABSTRACT

A compound having one of formula (1), formula (2), formula (3) and formula (4) or a pharmacologically acceptable salt thereof.

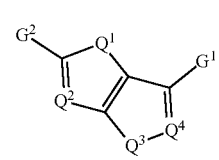

(1)

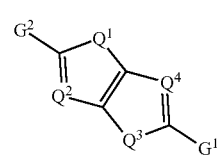

(2)

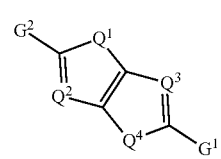

(3)

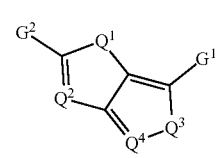

(4)

24 Claims, No Drawings

(51) Int. Cl.
- C07D 217/24 (2006.01)
- C07D 401/14 (2006.01)
- C07D 403/10 (2006.01)
- C07D 405/14 (2006.01)
- C07D 409/14 (2006.01)
- C07D 471/04 (2006.01)
- C07D 471/10 (2006.01)
- C07D 487/04 (2006.01)
- C07D 498/04 (2006.01)

(52) U.S. Cl.
CPC ......... *C07D 471/10* (2013.01); *C07D 487/04* (2013.01); *C07D 498/04* (2013.01)

(56) References Cited

U.S. PATENT DOCUMENTS

| | | |
|---|---|---|
| 6,576,766 B1 | 6/2003 | Weigele et al. |
| 2003/0158179 A1 | 8/2003 | Klug et al. |
| 2004/0052760 A1 | 3/2004 | Michelet et al. |
| 2004/0053931 A1 | 3/2004 | Cox et al. |
| 2004/0106604 A1 | 6/2004 | Beight et al. |
| 2004/0259858 A1 | 12/2004 | Klug et al. |
| 2005/0267304 A1 | 12/2005 | Cox et al. |
| 2006/0034786 A1 | 2/2006 | Michelet et al. |
| 2006/0063758 A1 | 3/2006 | Klug et al. |
| 2006/0148794 A1 | 7/2006 | Klug et al. |
| 2007/0010670 A1 | 1/2007 | Hirata et al. |
| 2007/0077215 A1 | 4/2007 | Boulle et al. |
| 2007/0092467 A1 | 4/2007 | Rozot et al. |
| 2007/0135633 A1 | 6/2007 | Ishikawa et al. |
| 2007/0191603 A1 | 8/2007 | Ackermann et al. |
| 2008/0004259 A1 | 1/2008 | Arrington et al. |
| 2008/0064871 A1 | 3/2008 | Hirata et al. |
| 2008/0275040 A1 | 11/2008 | Johnson et al. |
| 2008/0305169 A1 | 12/2008 | Miki et al. |
| 2010/0292259 A1 | 11/2010 | Kaneko et al. |
| 2010/0331341 A1* | 12/2010 | Andersson ............... A61P 25/24 544/364 |
| 2011/0034440 A1 | 2/2011 | Nakao et al. |
| 2011/0172217 A1 | 7/2011 | Fujioka et al. |
| 2011/0288074 A1 | 11/2011 | Schann et al. |
| 2013/0324501 A1 | 12/2013 | Armani et al. |
| 2015/0105373 A1 | 4/2015 | Mikami et al. |
| 2016/0289196 A1 | 10/2016 | Choi et al. |
| 2017/0121346 A1 | 5/2017 | Sprengeler et al. |
| 2017/0152268 A1 | 6/2017 | Kim et al. |
| 2019/0119236 A1 | 4/2019 | Pandey et al. |
| 2019/0152988 A1 | 5/2019 | Sprengeler et al. |
| 2019/0233438 A1 | 8/2019 | Okuyama et al. |
| 2020/0095206 A1 | 3/2020 | Markowitz et al. |
| 2023/0061429 A1 | 3/2023 | Konradi et al. |

FOREIGN PATENT DOCUMENTS

| | | |
|---|---|---|
| EP | 3 176 163 A1 | 6/2017 |
| EP | 3 372 601 A1 | 9/2018 |
| JP | 2007-161608 A | 6/2007 |
| JP | 2008037850 A * | 2/2008 |
| JP | 2008-531542 A | 8/2008 |
| JP | 2014-505053 A | 2/2014 |
| JP | 2018-533581 A | 11/2018 |
| JP | 2022-507020 A | 1/2022 |
| WO | WO 97/33866 A1 | 9/1997 |
| WO | WO 99/24442 A1 | 5/1999 |
| WO | WO 01/02369 A2 | 1/2001 |
| WO | WO 01/66114 A1 | 9/2001 |
| WO | WO 02/094833 A1 | 11/2002 |
| WO | WO 03/000688 A1 | 1/2003 |
| WO | WO 03/028726 A1 | 4/2003 |
| WO | WO 03/035064 A1 | 5/2003 |
| WO | WO 2004/034963 A2 | 4/2004 |
| WO | WO 2004/089416 A2 | 10/2004 |
| WO | WO 2005/021530 A1 | 3/2005 |
| WO | WO 2006/086255 A2 | 8/2006 |
| WO | WO 2007/005668 A2 | 1/2007 |
| WO | WO 2008/001076 A1 | 1/2008 |
| WO | WO 2008/115719 A1 | 9/2008 |
| WO | WO 2009/017838 A2 | 2/2009 |
| WO | WO 2009/035997 A2 | 3/2009 |
| WO | WO 2009/051119 A1 | 4/2009 |
| WO | WO 2009/098458 A2 | 8/2009 |
| WO | WO 2010/124121 A1 | 10/2010 |
| WO | WO-2010124114 A1 * | 10/2010 ........... C07D 205/04 |
| WO | WO 2011/057757 A1 | 5/2011 |
| WO | WO 2012/094462 A2 | 7/2012 |
| WO | WO 2012/106343 A2 | 8/2012 |
| WO | WO 2013/003383 A1 | 1/2013 |
| WO | WO 2013/158649 A1 | 10/2013 |
| WO | WO 2013/190123 A1 | 12/2013 |
| WO | WO 2015/065716 A1 | 5/2015 |
| WO | WO 2015/115673 A1 | 8/2015 |
| WO | WO 2016/100184 A1 | 6/2016 |
| WO | WO 2016/137010 A1 | 9/2016 |
| WO | WO 2016/144958 A1 | 9/2016 |
| WO | WO 2016/168472 A1 | 10/2016 |
| WO | WO 2017/075394 A1 | 5/2017 |
| WO | WO 2017/147328 A1 | 8/2017 |
| WO | WO 2018/017582 A1 | 1/2018 |
| WO | WO 2018/145080 A1 | 8/2018 |
| WO | WO 2019/183364 A1 | 9/2019 |
| WO | WO 2020/097389 A1 | 5/2020 |
| WO | WO 2021/151014 A1 | 7/2021 |

OTHER PUBLICATIONS

Japanese Office Action issued Dec. 5, 2023 in Japanese Application 2021-544505, 5 pages.
English translation of United Arab Emirates Office Action and Search Report issued Dec. 26, 2023 in United Arab Emirates Application P6001144/2021, 9 pages.
Fehér, C. et al., "Palladium-catalysed reactions of 6-halogeno-1,1'-binaphthyl derivatives. A detailed investigation of structure/reactivity and structure/selectivity relationships", Tetrahedron, vol. 67, No. 34, 2011, pp. 6327-6333.
Urwyler, S. et al., Drug Design, in Vitro Pharmacology, and Structure—Activity Relationships of 3-Acylamino-2-aminopropionic Acid Derivatives, a Novel Class of Partial Agonists at the Glycine Site on the N-Methyl-$_D$-aspartate (NMDA) Receptor Complex, Journal of Medicinal Chemistry, vol. 52, No. 16, 2009, pp. 5093-5107.
Japanese Office Action issued Apr. 2, 2024 in Japanese Patent Application No. 2021-544505, 4 pages.
European Office Action issued Apr. 11, 2024 in European Patent Application No. 20708859.2, 3 pages.
International Search Report and Written Opinion issued Jul. 6, 2020 in PCT/US2020/015683, 23 pages.
Katherine L. Lee et al., "Discovery of Clinical Candidate 1-{[(2S ,3S ,4S)-3-Ethyl-4-fluoro-5-oxopyrrolidin-2-yl]methoxy}-7-methoxyisoquinoline-6-carboxamide (PF-06650833), a Potent, Selective Inhibitor of Interleukin-1 Receptor Associated Kinase 4 (IRAK4), by Fragment-Based Drug Design", Journal of Medicinal Chemistry, vol. 60, No. 13, Jun. 14, 2017, pp. 5521-5542, XP055554811.
David C. Pryde et al., "Discovery of a Series of Indazole TRPA1 Antagonists", ACS Medicinal Chemistry Letters, vol. 8, No. 6, May 22, 2017, pp. 666-671, XP055688807.
Patcharaporn Khajondetchairit et al., "Design, synthesis, and evaluation of the anticancer activity of 2-amino-aryl-7-aryl-benzoxazole Compounds", Chemical Biology & Drug Design, vol. 90, No. 5, Nov. 1, 2017, pp. 987-994, XP055688815.
Susana Alvarez et al., "Modulation of Retinoic Acid Receptor Subtypes by 5- and 8-Substituted (Naphthalen-2-yl)-based Arotinoids", Chemmedch Em, vol. 10, No. 8, Aug. 1, 2015, pp. 1378-1391, XP055688874.
Landge Sudhir et al., "Discovery of benzothiazoles as antimycobacterial agents: Synthesis, structure-activity relationships and binding studies with *Mycobacterium tuberculosis* decaprenylphosphoryl-[beta]-d-ribose 2'-oxidase", Bioorganic & Medicinal Chemistry, vol. 23, No. 24, Nov. 18, 2015, pp. 7694-7710, XP029342479.

(56) References Cited

OTHER PUBLICATIONS

Tai H-H. et al., "Prostaglandin catabolizing enzymes", Prostaglandins Other Lipid Mediat., 2002, vol. 68-69, pp. 483-493.

Takeshi Shimizu, et al., "Recent Understanding of Prostanoids and Leukotrienes in the Pathogenesis of Airway Inflammation", The Oto-rhino- and laryngological clinic, 2007, vol. 100, No. 3, pp. 157-166.

Takahisa Murata et al., "Anti-inflammatory role of $PGD_2$ in acute lung inflammation and therapeutic application of its signal enhancement", PNAS, 2013, vol. 110, No. 13, pp. 5205-5210.

Trista E. North et al., "Prostaglandin E2 regulates vertebrate haematopoietic stem cell Homeostasis", Nature, 2007, vol. 447, No. 7147, 1007-1011.

Paul D. Bozyk et al., "Prostaglandin E2 and the Pathogenesis of Pulmonary Fibrosis", Am J Respir Cell Mol Biol 2011, vol. 45, 445-452.

M. Kinoshita et al., "Roles of Prostaglandins, Nitric Oxide and the Capsaicin-Sensitive Sensory Nerves in Gastroprotection Produced by Ecabet Sodium", J. Pharmacol. Exp. Ther., 1995, vol. 275, No. 1, pp. 494-501.

Makoto Arita et al., The Journal of Japan Rhinologic Society, 2012, vol. 51, No. 1, pp. 60-62.

Zenglin Liao et al., "Resolvin D1 attenuates inflammation in lipopolysaccharide-induced acute lung injury through a process involving the PPARγ/NF-KB pathway", Respiratory Research 2012, vol. 13, pp. 110-121.

Allisson Freire Bento et al., "Omega-3 Fatty Acid-Derived Mediators 17(R)-Hydroxy Docosahexaenoic Acid, Aspirin-Triggered Resolvin D1 and Resolvin D2 Prevent Experimental Colitis in Mice", J. Immunol. 2011, vol. 187, 1957-1969.

Xiahong Chen et al., "Resolvin D1 attenuates $CCl_4$-induced acute liver injury involving up-regulation of HO-1 in mice", Immunopharmacol. Immunotoxicol. 2016, vol. 38, No. 2, 9 pages.

Adel Hamza et al., "Understanding human 15-hydroxyprostaglandin dehydrogenase binding with $NAD^+$ and $PGE_2$ by homology modeling, docking and molecular dynamics simulation", Bioorganic & Medicinal Chemistry 2005, 13, 4544-4551.

Hoon Cho et al., "Role of glutamine 148 of human 15-hydroxyprostaglandin dehydrogenase in catalytic oxidation of prostaglandin $E_2$", Bioorganic & Medicinal Chemistry 2006, 14, 6486-6491.

Ying Wu et al., "Synthesis and SAR of thiazolidinedione derivatives as 15-PGDH inhibitors", Bioorganic & Medicinal Chemistry 2010, 18, 1428-1433.

Dubok Choi et al., "Control of the intracellular levels of prostaglandin $E_2$ through inhibition of the 15-hydroxyprostaglandin dehydrogenase for wound healing", Bioorganic & Medicinal Chemistry 2013, 21, 4477-4484.

Yu Lan Piao et al., "Cell-based biological evaluations of 5-(3-bromo-4-phenethoxybenzylidene)thiazolidine-2,4-dione as promising wound healing agent", Bioorganic & Medicinal Chemistry 2015, 23, 2098-2103.

Dongdong Lu et al., "15-Hydroxyprostaglandin Dehydrogenase (15-PGDH)-Derived 15-KETO-$PGE_2$ Inhibits Cholangiocarcinoma Cell Growth Through Interaction With PPARγ, SMAD2/3 and TAP63", J. Biol. Chem.-2013-Lu-jbc.M113.453886.

Lu Yao et al., "15-hydroxyprostaglandin dehydrogenase (15-PGDH) prevents lipopolysaccharide (LPS)-induced acute liver injury", PLoS ONE 12(4): e0176106. https://doi.org/10.1371/journal.pone. 0176106.

Annavarapu Hari Kishore et al., "Prostaglandin dehydrogenase is a target for successful induction of cervical ripening", PNAS 2017 E6427-E6436 www.pnas.org/cgi/doi/10.1073/pnas.1704945114.

Dongdong Lu et al., "15-PGDH inhibits hepatocellular carcinoma growth through 15-keto-$PGE_2$/PPARγ-mediated activation of $p21^{WAF1/Cip1}$", Oncogene. Feb. 27, 2014; 33(9): 1101-1112. doi:10.1038/onc. 2013.69.

A. R. Palla et al., Inhibition of prostaglandin-degrading enzyme 15-PGDH rejuvenates aged muscle mass and strength Science 371, 483 (2021).

Yongyou Zhang et al., "Inhibition of the prostaglandin-degrading enzyme 15-PGDH potentiates tissue regeneration", Science 2015 • vol. 348 Issue 6240 http://dx.doi.org/10.1126/science.aaa2340.

Amar Desai et al., "A second-generation 15-PGDH inhibitor promotes bone marrow transplant recovery independent of age, transplant dose, and G-CSF support", Haematologica 2018 doi:10.3324/haematol.2017.178376.

Stephanie G. Dakin et al., "Increased 15-PGDH expression leads to dysregulated resolution responses in stromal cells from patients with chronic tendinopathy", Scientific Reports | 7: 11009 | DOI:10.1038/s41598-017-11188-y.

Ying Wu et al., "Synthesis and Biological Evaluation of Novel Thiazolidinedione Analogues as 15-Hydroxyprostaglandin Dehydrogenase Inhibitors", J. Med. Chem. 2011, 54, 5260-5264.

Yusuke Watanabe et al., "KAG-308, a newly-identified $EP_4$-selective agonist shows efficacy for treating ulcerative colitis and can bring about lower risk of colorectal carcinogenesis by oral administration", European Journal of Pharmacology 754(2015)179-189.

Kousuke Tani et al., "Development of a Highly Selective EP2-Receptor Agonist. Part 1: Identification of 16-hydroxy-17,17-trimethylene $PGE_2$ Derivatives", Bioorganic & Medicinal Chemistry 10 (2002) 1093-1106.

Kousuke Tani et al., "Development of a Highly Selective EP2-receptor Agonist. Part 2:Identification of 16-Hydroxy-17,17-trimethylene 9β-chloro PGF Derivatives", Bioorganic & Medicinal Chemistry 10 (2002) 1107-1114.

Tohru Kambe et al., "Discovery of novel prostaglandin analogs as potent and selective EP2/EP4 dual agonists", Bioorganic & Medicinal Chemistry 20 (2012) 2235-2251.

Zhong Zhao et al., "Synthesis and evaluation of novel pyrazolidinone analogs of $PGE_2$ as $EP_2$ and $EP_4$ receptors agonists", Bioorganic & Medicinal Chemistry Letters 17 (2007) 6572-6575.

Toru Maruyama et al., "Design and Synthesis of a Selective EP4-Receptor Agonist. Part 2: 3,7-DithiaPGE1 Derivatives with High Selectivity", Bioorganic & Medicinal Chemistry 10 (2002) 989-1008.

Seiji Ogawa et al., "Discovery of G Protein-Biased EP2 Receptor Agonists", ACS Med. Chem. Lett. 2016, 7, 306-311.

Tijana Markovic et al., "Structural features of subtype-selective EP receptor modulators", Drug Discov Today (2016), http://dx.doi.org/10.1016/j.drudis.2016.08.003.

Viktoria Konya et al., "E-type prostanoid receptor 4 (EP4) in disease and therapy", Pharmacology & Therapeutics 138 (2013) 485-502.

Andrew Fensome et al., "Structure-activity relationships of norepinephrine reuptake inhibitors with benzothiadiazine dioxide or dihydrosulfostyril cores", Bioorganic & Medicinal Chemistry Letters 20 (2010) 1555-1558.

Tomoyuki Tanaka et al., "Discovery of benzothiazine derivatives as novel, orally-active anti-epileptic drug candidates with broad anticonvulsant effect", Bioorganic & Medicinal Chemistry Letters 25 (2015) 4518-4521.

Álvaro Gutiérrez-Bonet et al., "Fe-Catalyzed Regiodivergent [1,2]-Shift of α-Aryl Aldehydes", J. Am. Chem. Soc. 2013, 135, 12576-12579.

Yasunari Monguchi et al., "Pd/C-Et3N-mediated catalytic hydrodechlorination of aromatic chlorides under mild conditions", Tetrahedron, 2006 62, 7926-7933.

Nicholas A. Meanwell et al., "Fluorine and Fluorinated Motifs in the Design and Application of Bioisosteres for Drug Design", J. Med. Chem., 2018, 61, 5822-5880.

Corwin Hansch et al., "A Survey of Hammett Substituent Constants and Resonance and Field Parameters", Chem. Rev., 1991, 91, 165-195.

Gang Zhou et al., "Development of Novel Benzomorpholine Class of Diacylglycerol Acyltransferase | Inhibitors", ACS Med. Chem. Lett., 2014, 5, 544-549.

Duveau, D.Y. et al., "Structure-activity relationship studies and biological characterization of human $NAD^+$-dependent 15-hydroxyprostaglandin dehydrogenase inhibitors", Bioorganic & Medicinal Chemistry Letters, 2014, 24(2), pp. 630-635.

(56) References Cited

OTHER PUBLICATIONS

Antczak, M.I. et al., "Inhibitors of 15-Prostaglandin Dehydrogenase to Potentiate Tissue Repair", Journal of Medicinal Chemistry, 2017, 60(9), pp. 3979-4001.
Niesen, F.H. et al., "High-Affinity Inhibitors of Human $NAD^+$-Dependent 15-Hydroxyprostaglandin Dehydrogenase: Mechanisms of Inhibition and Structure-Activity Relationships", PLos One, 2010, 5(11).
Roshanak Monzavi, "Symptoms, Treatment and Prevention of Type 1 Diabetes", (Children's Hospital Los Angeles, Published Jul. 13, 2015). (Year: 2015).
Office Action mailed Mar. 31, 2025, in co-pending U.S. Appl. No. 17/417,201, 11 pages.

\* cited by examiner

15-PGDH INHIBITORS

CROSS-REFERENCE TO RELATED APPLICATIONS

The present application is a national stage application of International Application No. PCT/US2020/015683, filed Jan. 29, 2020, which is based upon and claims the benefit of priority to U.S. Provisional Application No. 62/799,361, filed Jan. 31, 2019. The entire contents of these applications are incorporated herein by reference.

BACKGROUND OF THE INVENTION

Field of the Invention

The present invention relates to derivatives or pharmacologically acceptable salts thereof having a 15-PGDH inhibitory activity which are useful as pharmaceutical products, pharmaceutical compositions containing them, and their medical use.

Description of the Related Art

As a compound having a 15-PGDH inhibitory function, International Publication No. WO 2018/145080 describes a compound represented by the formula (I) having an amide group.

Chemical formula 1

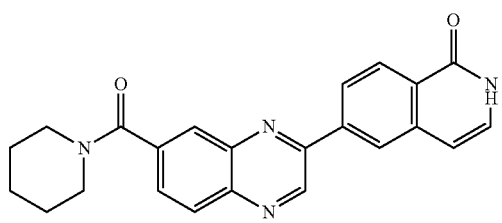

(I)

SUMMARY OF THE INVENTION

As a result of studies, the present inventors found that the compounds represented by the following formula (1) (hereinafter, also referred to as the compound (1)) have a strong 15-PGDH inhibitory function as medicaments.

Aspects of the present invention are:

[1] A compound selected from formula (1) to (4) or a pharmacologically acceptable salt thereof:

Chemical formula 2

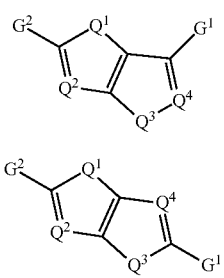

(1)

(2)

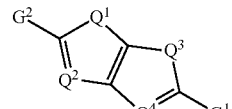

(3)

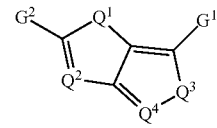

(4)

wherein $G^1$ is a phenyl group optionally having substituent(s) selected from the group A, a 5-membered aromatic heterocyclic group optionally having substituent(s) selected from the group A, a 6-membered aromatic heterocyclic group optionally having substituent(s) selected from the group A, a bicyclic aromatic heterocyclic group having 8 to 10 atoms and optionally having substituent(s) selected from the group A, a fused heterocyclic group having 9 or 10 atoms and optionally having substituent(s) selected from the group A, $C_3$-$C_8$ cycloalkyl group optionally having substituent(s) selected from the group A or 3 to 8-membered heterocycloalkyl group optionally having substituent(s) selected from the group A;

$G^2$ is a —C(=O)—X, —C(=O)—CHR$^1$R$^2$, —CH(OH)—CHR$^1$R$^2$, —CH(NY$_2$)—CHR$^1$R$^2$, —S—CHR$^1$R$^2$, —S(=O)$_2$—X, —S(=O)—CHR$^1$R$^2$ or —SO$_2$—CHR$^1$R$^2$ where X is —NR$^1$R$^2$;

$Q^1$ is —C(R$^3$)=C(R$^4$)—, —C(R$^5$)=N—, —N=C(R$^5$)—, —O— or —S—:

$Q^2$ is —C(R$^8$)= or —N=;

$Q^3$ is —C(R$^7$)=C(R$^8$)—, —C(R$^9$)=N—, —N=C(R$^9$)—, —NY—, —O— or —S—;

$Q^4$ is —C(R$^{10}$)= or —N=;

$R^1$ and $R^2$ are each independently selected from hydrogen, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

or $R^1$ and $R^2$ are taken together with the nitrogen atom to which they attached to form a 3 to 10-membered nitrogen atom containing heterocycloalkyl group optionally having substituent(s) selected from the group B or the carbon atom to which they attached to form a 3 to 10-membered cycloalkyl group optionally having substituent(s) selected from the group B;

the 3 to 10-membered nitrogen atom containing heterocycloalkyl group optionally having unsaturated bond is a monocyclic ring or fused, bridged or spiro bicyclic ring; and the 3 to 10-membered nitrogen atom containing heterocycloalkyl group optionally contains silicon atom, oxygen atom or sulfur atom in substitution for a carbon atom;

$R^3$ and $R^4$ are each independently selected from hydrogen, halogen, —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^5$ is hydrogen, —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^6$ is hydrogen, halogen, —CN, —COOY, —NHC(O)Y, $C_1$-$C_6$alkyl optionally having substituent (s) selected from the group C, $C_1$-$C_6$alkoxy optionally having substituent(s) selected from the group C or $C_3$-$C_8$ cycloalkyl optionally having substituent(s) selected from the group C;

$R^7$ and $R^8$ are each independently selected from hydrogen, halogen, —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^9$ is hydrogen or —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^{10}$ is hydrogen, halogen, —CN, —COOY, —NHC(O)Y, $C_1$-$C_6$ alkyl optionally having substituent (s) selected from the group C, $C_1$-$C_6$alkoxy optionally having substituent(s) selected from the group C or $C_3$-$C_8$ cycloalkyl optionally having substituent(s) selected from the group C;

Y is independently selected from hydrogen, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

A group is halogen, hydroxyl, carbonyl, nitrile, carboxyl, formyl, $C_1$-$C_6$alkyl optionally having substituent(s) selected from the group A1, $C_1$-$C_6$alkylcarbonyl optionally having substituent(s) selected from the group A1, $C_1$-$C_6$alkoxy optionally having substituent(s) selected from the group A1, $C_1$-$C_6$alkoxycarbonyl optionally having substituent(s) selected from the group A1, $C_1$-$C_6$alkylsulfonyl optionally having substituent(s) selected from the group A1, $C_1$-$C_6$ alkylsulfonylamino optionally having substituent(s) selected from the group A1, $C_3$-$C_8$ cycloalkyl optionally having substituent(s) selected from the group A1, $C_3$-$C_8$ cycloalkylcarbonyl optionally having substituent(s) selected from the group A1, $C_3$-$C_8$ cycloalkoxy optionally having substituent(s) selected from the group A1, $C_3$-$C_8$ cycloalkylsulfonyl optionally having substituent(s) selected from the group A1, $C_3$-$C_8$ cycloalkylsulfonylamino optionally having substituent(s) selected from the group A1, $C_5$-$C_7$ heterocycloalkyl optionally having substituent(s) selected from the group A1, $C_5$-$C_7$ heterocycloalkylcarbonyl optionally having substituent(s) selected from the group A1, $C_5$-$C_7$ heterocycloalkylamino optionally having substituent(s) selected from the group A1, $C_5$-$C_7$ heterocycloalkylaminocarbonyl optionally having substituent(s) selected from the group A1, aminocarbonyl optionally substituted with one or two $C_1$-$C_6$alkyl optionally having substituent(s) selected from the group A1, aminosulfonyl optionally substituted with one or two $C_1$-$C_6$alkyl optionally having substituent(s) selected from the group A1, amino optionally substituted with one or two $C_1$-$C_6$alkyl optionally having substituent(s) selected from the group A1, phenyl optionally having substituent(s) selected from the group B, 5-membered aromatic heterocyclic group optionally having substituent(s) selected from the group B, 6-membered aromatic heterocyclic group optionally having substituent(s) selected from the group B or heterocyclic group optionally having substituent(s) selected from the group B;

A1 group is halogen, hydroxyl, amino, carbonyl, nitrile, carboxyl, formyl, $C_1$-$C_6$alkyl optionally having substituent(s) selected from the group A2, $C_1$-$C_6$alkylcarbonyl optionally having substituent(s) selected from the group A2, $C_1$-$C_6$alkoxy optionally having substituent(s) selected from the group A2, $C_1$-$C_6$alkoxycarbonyl optionally having substituent(s) selected from the group A2, $C_1$-$C_6$alkylsulfonyl optionally having substituent(s) selected from the group A2, $C_1$-$C_6$ alkylsulfonylamino optionally having substituent(s) selected from the group A2, $C_3$-$C_8$ cycloalkyl optionally having substituent(s) selected from the group A2, $C_5$-$C_7$ heterocycloalkyl optionally having substituent(s) selected from the group A2, $C_5$-$C_7$ heterocycloalkylcarbonyl optionally having substituent(s) selected from the group A2, $C_5$-$C_7$ heterocycloalkylamino optionally having substituent(s) selected from the group A2, $C_5$-$C_7$ heterocycloalkylaminocarbonyl optionally having substituent(s) selected from the group A2, aminocarbonyl optionally substituted with one or two $C_1$-$C_6$alkyl optionally having substituent(s) selected from the group A2, amino optionally substituted with one or two $C_1$-$C_6$alkyl optionally having substituent(s) selected from the group A2, 5-membered aromatic heterocyclic group optionally having substituent(s) selected from the group B, 6-membered aromatic heterocyclic group optionally having substituent(s) selected from the group B or heterocyclic group optionally having substituent(s) selected from the group B;

A2 group is halogen, hydroxyl, nitrile, carboxyl, formyl, $C_1$-$C_6$alkyl, $C_1$-$C_6$ alkylcarbonyl, $C_1$-$C_6$ alkoxy, $C_1$-$C_6$alkoxycarbonyl, $C_1$-$C_6$alkylsulfonylamino, 5-membered aromatic heterocyclic group, 6-membered aromatic heterocyclic group, heterocyclic group or 5 to 7-membered heterocycloalkyl group;

B group is halogen, hydroxyl, carbonyl, carboxyl, $C_1$-$C_6$alkyl, halo-$C_1$-$C_6$alkyl, hydroxy-$C_1$-$C_6$alkyl, $C_1$-$C_6$ alkylcarbonyl, $C_1$-$C_6$ alkoxy, halo-$C_1$-$C_6$ alkoxy, $C_1$-$C_6$ alkoxycarbonyl, $C_1$-$C_6$ alkyl substituted with $C_1$-$C_6$ alkoxy, $C_1$-$C_6$alkyl substituted with $C_1$-$C_6$alkoxycarbonyl, $C_3$-$C_8$ cycloalkyl, $C_3$-$C_8$ cycloalkylcarbonyl, $C_3$-$C_8$ cycloalkoxy, aminocarbonyl optionally substituted with one or two $C_1$-$C_6$alkyl, $C_1$-$C_6$ alkylsulfonyl, aminosulfonyl optionally substituted with one or two $C_1$-$C_6$alkyl, $C_1$-$C_6$alkylsulfonylamino, amino optionally substituted with one or two $C_1$-$C_6$alkyl or 5 to 7-membered heterocycloalkyl group;

C group is halogen, hydroxyl, carboxyl, $C_1$-$C_6$ alkylcarbonyl, $C_1$-$C_6$ alkoxy, $C_1$-$C_6$ alkoxycarbonyl, aminocarbonyl optionally substituted with one or two $C_1$-$C_6$alkyl, amino optionally substituted with one or two $C_1$-$C_6$alkyl or 5 to 7-membered heterocycloalkyl group;

provided that wherein $Q^3$ is —N=C($R^9$)—, $R^9$ is methyl and $G^1$ is

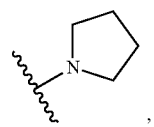 [SMILES: *N1CCCC1]

, then G² is not

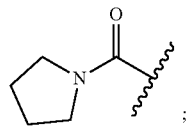 [SMILES: *C(=O)N1CCCC1]
;

and

Q³ is —N=C(R⁹)—, R⁹ is hydrogen and G¹ is

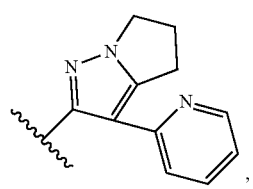 [SMILES: *c1nn2c(c1-c1ccccn1)CCC2]
, then G² is not

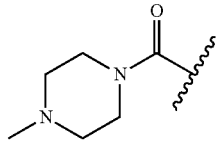
.

[2] The compound or a pharmacologically acceptable salt thereof according to [1], wherein a formula selected from formula (1) to (4) is the formula (1):

Chemical formula 3

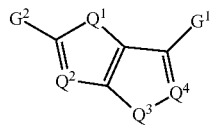

(1)

wherein G¹, G², Q¹, Q², Q³ and Q⁴ are as defined in [1];
R¹ and R² are taken together with the nitrogen atom to which they attached to form a 3 to 10-membered nitrogen atom containing heterocycloalkyl group optionally having substituent(s) selected from the group B; the 3 to 10-membered nitrogen atom containing heterocycloalkyl group optionally having unsaturated bond is a monocyclic ring or fused, bridged or spiro bicyclic ring; and the 3 to 10-membered nitrogen atom containing heterocycloalkyl group optionally contains silicon atom, oxygen atom or sulfur atom in substitution for a carbon atom.

[3] The compound or a pharmacologically acceptable salt thereof according to [2], wherein the formula (1) is:

Chemical formula 4

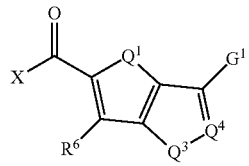

wherein Q¹ is —C(R³)=C(R⁴)—, —C(R⁵)=N— or —N=C(R⁵)—; Q³, Q⁴, G¹, X, R³, R⁴ and R⁶ are as defined in [1].

[4] The compound or a pharmacologically acceptable salt thereof according to [3], wherein the formula (1) is:

Chemical formula 5

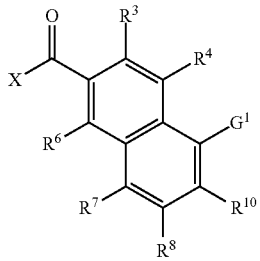

wherein G¹, X, R³, R⁴, R⁶, R⁷, R⁸ and R¹⁰ are as defined in [1].

[5] The compound or a pharmacologically acceptable salt thereof according to [2]1, wherein the formula (1) is:

Chemical formula 6

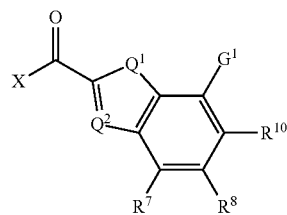

wherein Q¹, Q², G¹, X, R⁷, R⁸, and R¹⁰ are as defined in [1].

[6] The compound or a pharmacologically acceptable salt thereof according to [4], wherein the formula (1) is:

Chemical formula 7

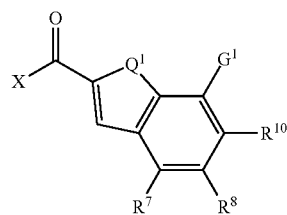

wherein Q¹, G¹, X, R⁷, R⁸, and R¹⁰ are as defined in [1].

[7] The compound or a pharmacologically acceptable salt thereof according to [5], wherein the formula (1) is:

Chemical formula 8

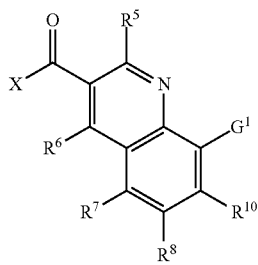

wherein $G^1$, X, $R^5$, $R^6$, $R^7$, $R^8$, and $R^{10}$ are as defined in [1].

[8] The compound or a pharmacologically acceptable salt thereof according to any one of [3] to [7], wherein X is selected from the group consisting of the following A1), A2), A3), A4), A5), A6), A7), A8), A9), and A10):

Chemical formula 9

A1)
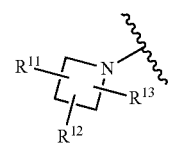

A2)
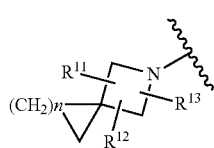

A3)
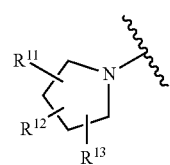

A4)
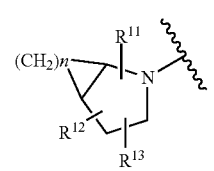

A5)
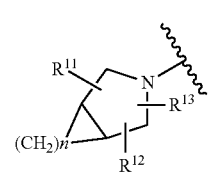

A6)
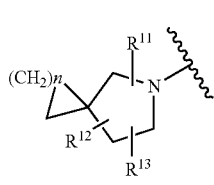

A7)
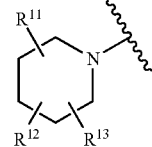

A8)
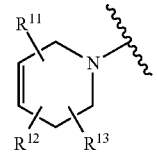

A9)
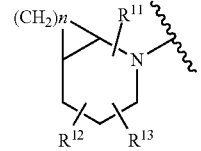

A10)
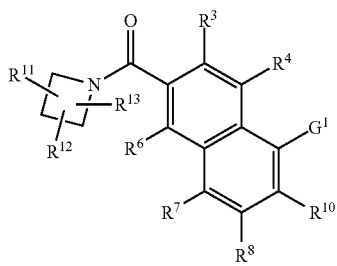

wherein G, $R^7$, $R^8$, $R^{10}$, G, $R^3$, $R^4$, $R^5$, and $R^6$ are as defined in [1]; $R^{11}$, $R^{12}$, and $R^{13}$ are the same or different and are hydrogen, halogen, $C_1$-$C_6$ alkyl, halo($C_1$-$C_6$) alkyl, $C_1$-$C_6$ alkoxy or halo($C_1$-$C_6$) alkoxy; and n is an integer of 1 to 3.

[9] The compound or a pharmacologically acceptable salt thereof according to [4], wherein the formula (1) is selected from the group consisting of the following B1), B2), B3), B4), B5), B6), B7), B8), B9), and B10):

Chemical formula 10

B1)

B2)

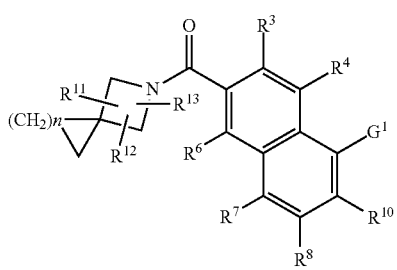

B3) 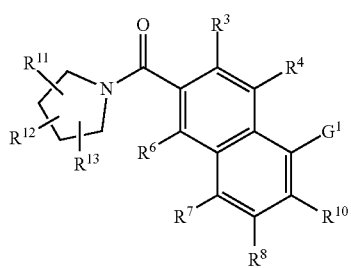
B4) 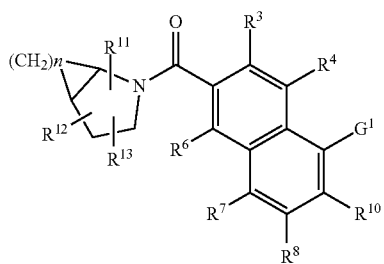
B5) 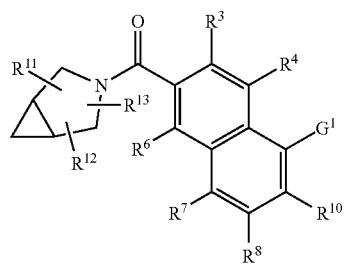
B6) 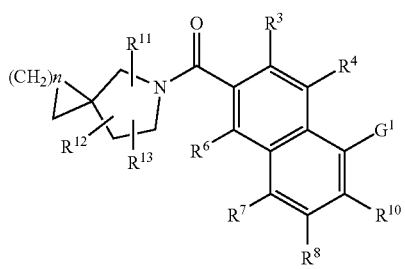
B7) 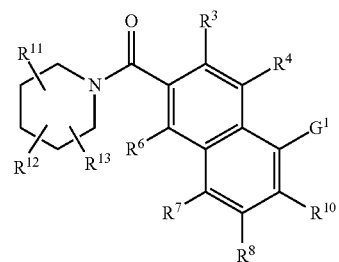
B8) 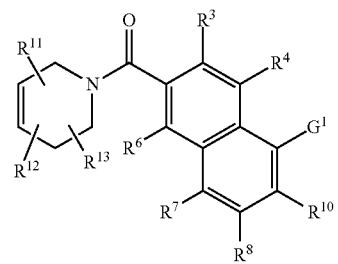
B9) 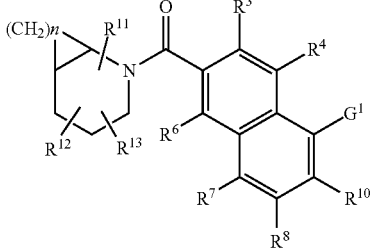
B10) 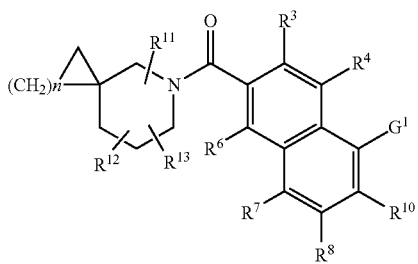
wherein $G^1$, $R^3$, $R^4$, $R^6$, $R^7$, $R^8$, and $R^{10}$ are as defined in [1]; and $R^{11}$, $R^{12}$, $R^{13}$, and n are as defined in [8].
[10] The compound or a pharmacologically acceptable salt thereof according to any one of [2] to [9], wherein in the formula (1), $G^1$ is selected from the group consisting of the following C1) to C44):
Chemical formula 11
C1) 
C2) 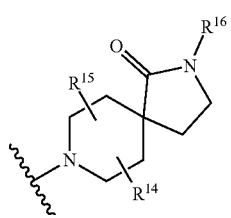
C3) 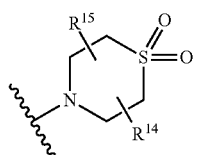
C4) 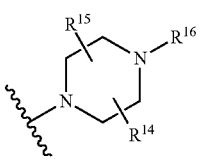

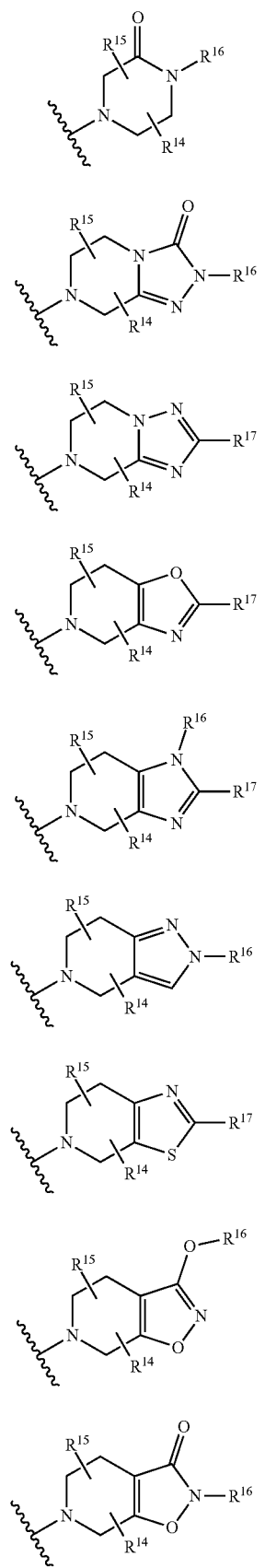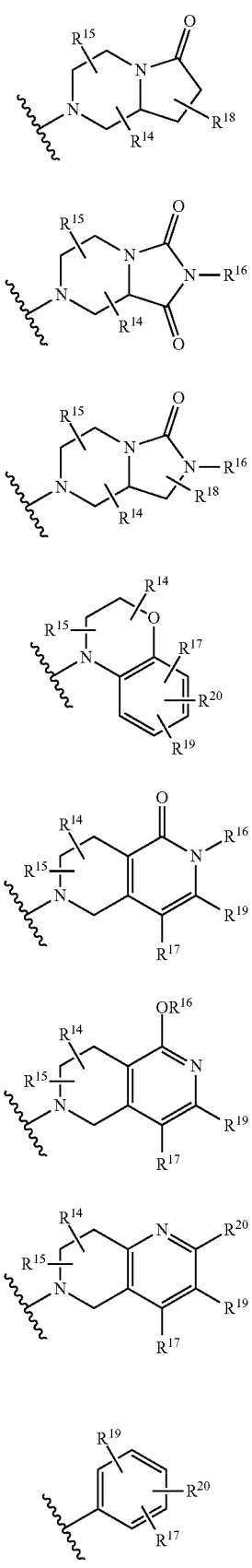

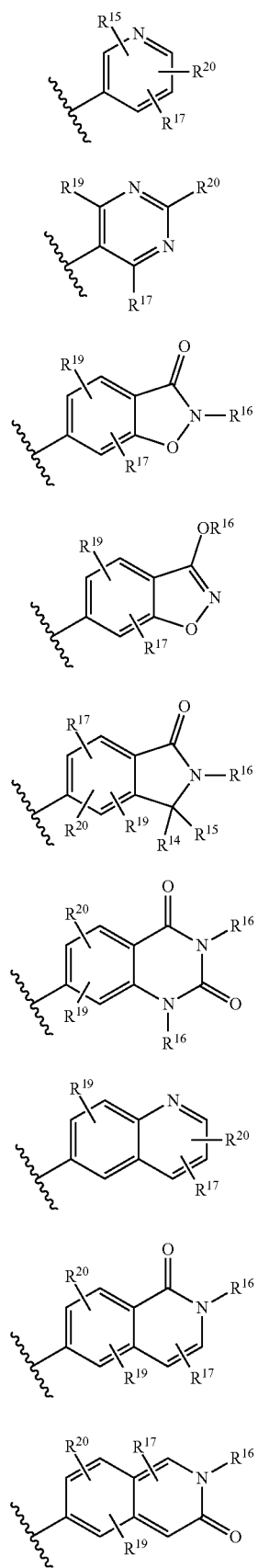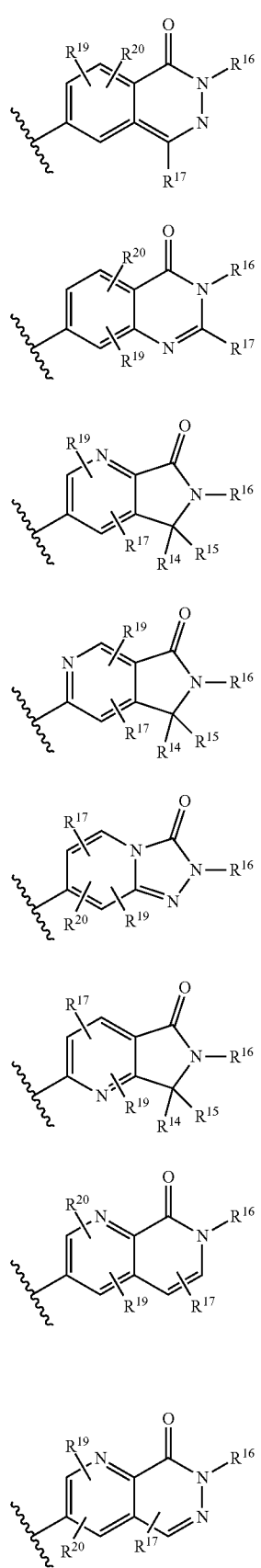

-continued

C39)
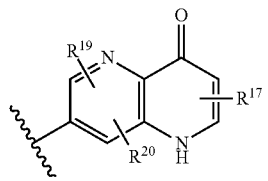

C40)
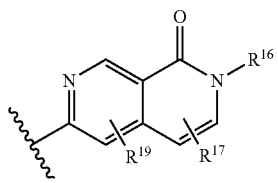

C41)
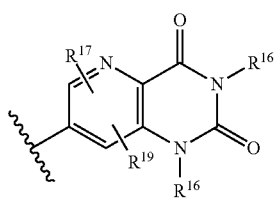

C42)
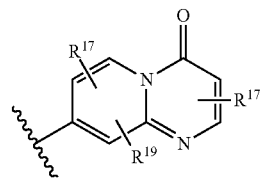

C43)
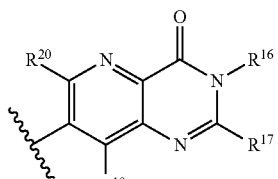

C44)
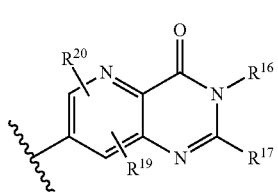

wherein the nitrogen atom(s) in the aromatic ring is/are optionally N-oxide $R^{14}$, $R^{15}$, $R^{17}$, $R^{18}$, $R^{19}$ and $R^{20}$ are the same or different and are hydrogen, halogen, hydroxy, nitrile, carboxyl, formyl, aminocarbonyl having an amino group which optionally contains one or more substituents selected from the group A1, and optionally containing 1 or 2 $C_1$-$C_6$ alkyl groups, or one selected from $C_1$-$C_6$ alkyl, amino, $C_1$-$C_6$ alkylcarbonyl, $C_1$-$C_6$ alkoxy, $C_1$-$C_6$ alkoxycarbonyl, $C_1$-$C_6$ alkylsulfonylamino, $C_1$-$C_6$ alkylsulfonyl, and $C_3$-$C_8$ cycloalkyl, which are optionally substituted with one or more substituents selected from the group A1; and $R^{16}$ is hydrogen, $C_1$-$C_6$ alkylaminosulfonyl, one selected from $C_1$-$C_6$ alkyl, $C_1$-$C_6$ alkylcarbonyl, $C_1$-$C_6$ alkoxycarbonyl, $C_1$-$C_6$ alkylsulfonyl, $C_3$-$C_8$ cycloalkyl, 5- to 7-membered heterocycloalkylcarbonyl, and 5- to 7-membered heterocycloalkylaminocarbonyl, which are optionally substituted with one or more substituents selected from the group A1, aminocarbonyl optionally containing 1 or 2 $C_1$-$C_6$ alkyl groups optionally substituted with one or more substituents selected from the group A1, or a 5- or 6-membered heteroaromatic ring optionally substituted with one or more substituents selected from the group B.

[11] The compound or a pharmacologically acceptable salt thereof according to [1], wherein a formula selected from the formula (1) to (4) is the formula (2):

Chemical formula 12

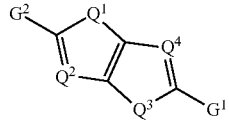

(2)

wherein $G^1$, $G^2$, $Q^1$, $Q^2$, $Q^3$ and $Q^4$ are as defined in [1];

$R^1$ and $R^2$ are taken together with the nitrogen atom to which they attached to form a 3 to 10-membered nitrogen atom containing heterocycloalkyl group optionally having substituent(s) selected from the group B; the 3 to 10-membered nitrogen atom containing heterocycloalkyl group optionally having unsaturated bond is a monocyclic ring or fused, bridged or spiro bicyclic ring; and the 3 to 10-membered nitrogen atom containing heterocycloalkyl group optionally contains silicon atom, oxygen atom or sulfur atom in substitution for a carbon atom.

[12] The compound or a pharmacologically acceptable salt thereof according to [11], wherein the formula (2) is:

Chemical formula 13

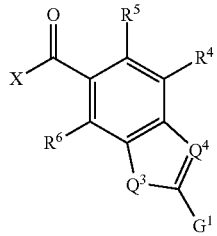

wherein $Q^3$, $Q^4$, $G^1$, X, $R^3$, $R^4$ and $R^6$ are as defined in [1].

[13] The compound or a pharmacologically acceptable salt thereof according to [12], wherein the formula (2) is:

Chemical formula 14

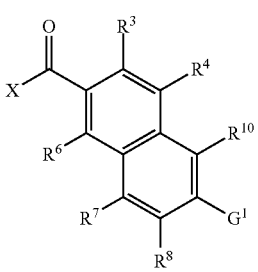

wherein $G^1$, X, $R^3$, $R^4$, $R^6$, $R^7$, $R^8$, and $R^{10}$ are as defined in [1].

[14] The compound or a pharmacologically acceptable salt thereof according to [11], wherein the formula (2) is:

Chemical formula 15

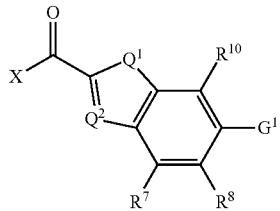

wherein $Q^1$, $Q^2$, $G^1$, X, $R^7$, $R^8$, and $R^{10}$ are as defined in [1].

[15] The compound or a pharmacologically acceptable salt thereof according to [14], wherein the formula (2) is:

Chemical formula 16

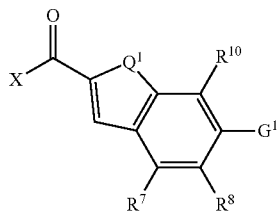

wherein $Q^1$, $G^1$, X, $R^7$, $R^8$ and $R^{10}$ are as defined in [1].

[16] The compound or a pharmacologically acceptable salt thereof according to [15], wherein the formula (2) is:

Chemical formula 17

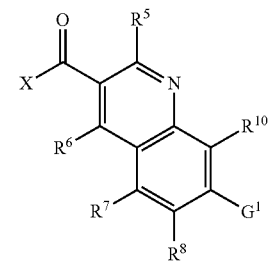

wherein $G^1$, X, $R^5$, $R^6$, $R^7$, $R^8$, and $R^{10}$ are as defined in [1].

[17] The compound or a pharmacologically acceptable salt thereof according to [1], wherein a formula selected from formula (1) to (4) is the formula (3):

(3)

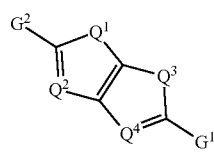

wherein $G^1$, $G^2$, $Q^1$, $Q^2$, $Q^3$ and $Q^4$ are as defined in [1];
$R^1$ and $R^2$ are taken together with the nitrogen atom to which they attached to form a 3 to 10-membered nitrogen atom containing heterocycloalkyl group optionally having substituent(s) selected from the group B; the 3 to 10-membered nitrogen atom containing heterocycloalkyl group optionally having unsaturated bond is a monocyclic ring or fused, bridged or spiro bicyclic ring; and the 3 to 10-membered nitrogen atom containing heterocycloalkyl group optionally contains silicon atom, oxygen atom or sulfur atom in substitution for a carbon atom.

[18] The compound or a pharmacologically acceptable salt thereof according to [17], wherein the formula (3) is:

Chemical formula 18

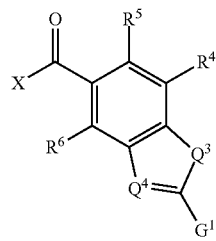

wherein $Q^3$, $Q^4$, $G^1$, X, $R^3$, $R^4$, and $R^6$ are as defined in [1].

[19] The compound or a pharmacologically acceptable salt thereof according to [18], wherein the formula (3) is:

Chemical formula 19

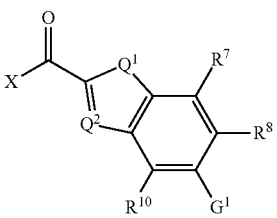

wherein $G^1$, X, $R^3$, $R^4$, $R^6$, $R^7$, $R^8$ and $R^{10}$ are as defined in [1].

[20] The compound or a pharmacologically acceptable salt thereof according to [18], wherein the formula (3) is:

Chemical formula 20

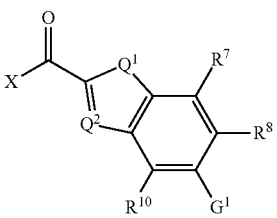

wherein $Q^1$, $Q^2$, $G^1$, X, $R^7$, $R^8$ and $R^{10}$ are as defined in [1].

[21] The compound or a pharmacologically acceptable salt thereof according to [20], wherein the formula (3) is:

Chemical formula 21

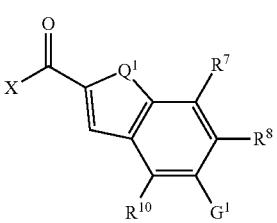

wherein $Q^1$, $G^1$, X, $R^7$, $R^8$ and $R^{10}$ are as defined in [1].

[22] The compound or a pharmacologically acceptable salt thereof according to [21], wherein the formula (3) is:

Chemical formula 22

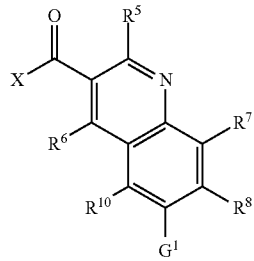

wherein $G^1$, X, $R^5$, $R^6$, $R^7$, $R^8$, and $R^{10}$ are as defined in [1].

[23] The compound or a pharmacologically acceptable salt thereof according to any one of [11] to [23], wherein X is selected from the group consisting of the following A1), A2), A3), A4), A5), A6), A7), A8), A9), and A10):

Chemical formula 23

A1)

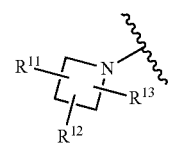

A2)

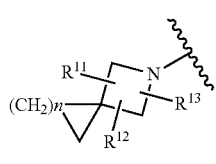

A3)

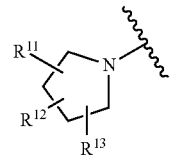

A4)

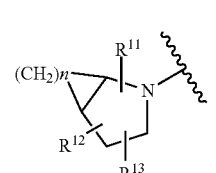

A5)

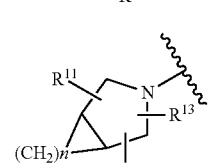

A6)

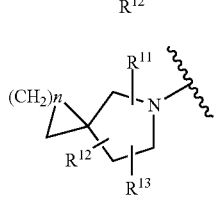

A7)

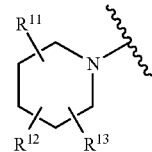

A8)

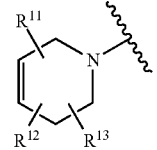

A9)

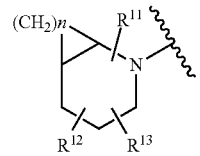

A10)

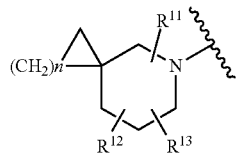

wherein G, $R^7$, $R^8$, $R^{10}$, G, $R^3$, $R^4$, $R^5$ and $R^6$ are as defined in [1]; $R^{11}$, $R^{12}$, and $R^{13}$ are the same or different and are hydrogen, halogen, $C_1$-$C_6$ alkyl, halo($C_1$-$C_6$) alkyl, $C_1$-$C_6$ alkoxy or halo($C_1$-$C_6$) alkoxy; and n is an integer of 1 to 3.

[24] The compound or a pharmacologically acceptable salt thereof according to any one of [11] to [23], wherein in the formula (2) or (3), $G^1$ is selected from the group consisting of the following C1) to C44):

Chemical formula 24

C1)

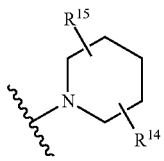

C2)

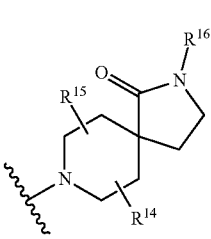

C3)

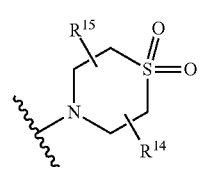

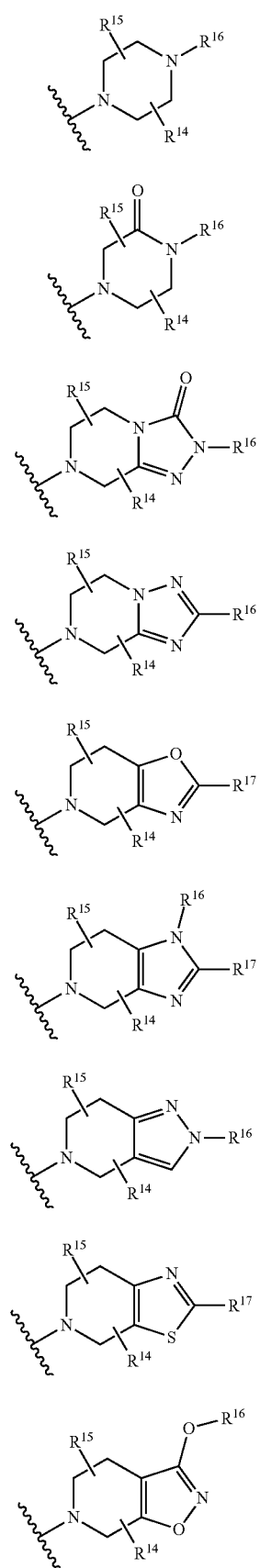
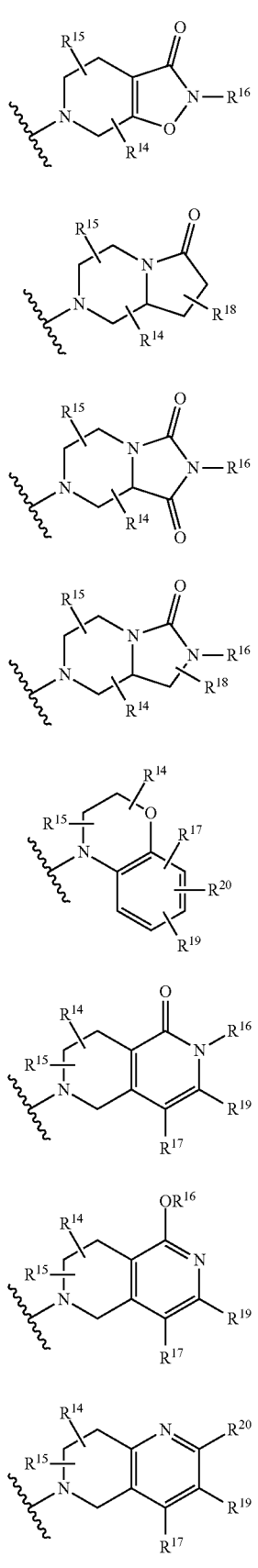

-continued
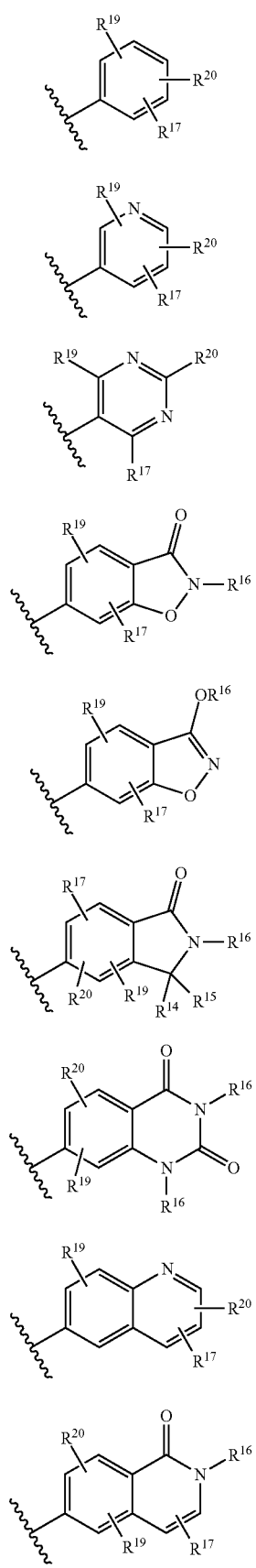
C21)
C22)
C23)
C24)
C25)
C26)
C27)
C28)
C29)
-continued
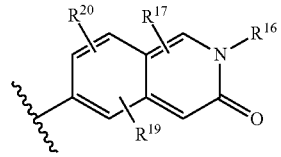
C30)
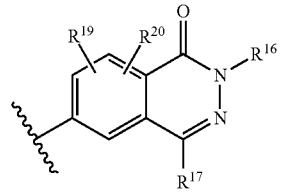
C31)
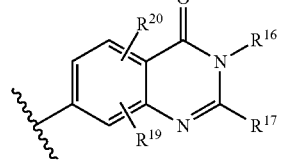
C32)
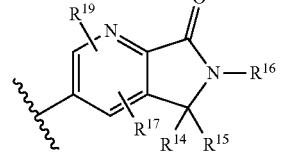
C33)
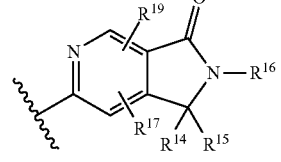
C34)
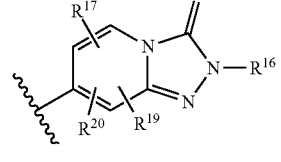
C35)
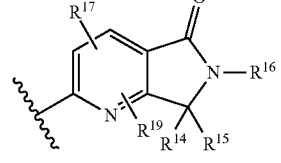
C36)
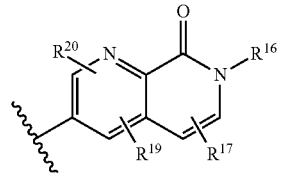
C37)

-continued

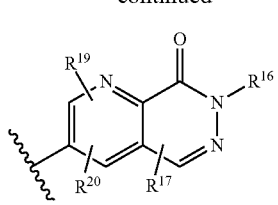
C38)

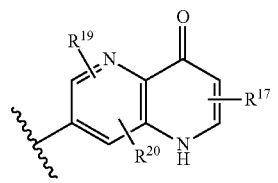
C39)

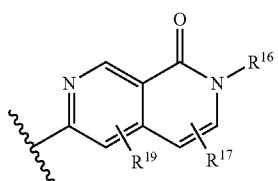
C40)

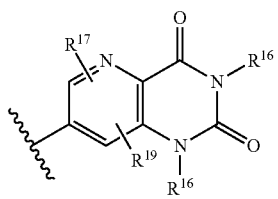
C41)

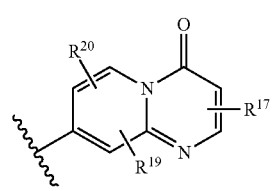
C42)

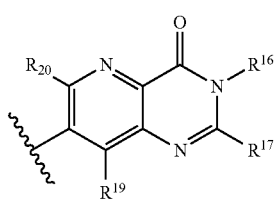
C43)

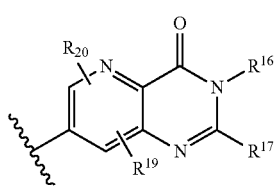
C44)

wherein the nitrogen atom(s) in the aromatic ring is/are optionally N-oxide; $R^{14}$, $R^{15}$, $R^{17}$, $R^{18}$, $R^{19}$, and $R^{20}$ are the same or different and are hydrogen, halogen, hydroxy, nitrile, carboxyl, formyl, aminocarbonyl having an amino group which optionally contains one or more substituents selected from the group A1, and optionally containing 1 or 2 $C_1$-$C_6$ alkyl groups, or one selected from $C_1$-$C_6$ alkyl, amino, $C_1$-$C_6$ alkylcarbonyl, $C_1$-$C_6$ alkoxy, $C_1$-$C_6$ alkoxycarbonyl, $C_1$-$C_6$ alkylsulfonylamino, $C_1$-$C_6$ alkylsulfonyl, and $C_3$-$C_8$ cycloalkyl, which are optionally substituted with one or more substituents selected from the group A1; and $R^{16}$ is hydrogen, $C_1$-$C_6$ alkylaminosulfonyl, one selected from $C_1$-$C_6$ alkyl, $C_1$-$C_6$ alkylcarbonyl, $C_1$-$C_6$ alkoxycarbonyl, $C_1$-$C_6$ alkylsulfonyl, $C_3$-$C_8$ cycloalkyl, 5- to 7-membered heterocycloalkylcarbonyl, and 5- to 7-membered heterocycloalkylaminocarbonyl, which are optionally substituted with one or more substituents selected from the group A1, aminocarbonyl optionally containing 1 or 2 $C_1$-$C_6$ alkyl groups optionally substituted with one or more substituents selected from the group A1, or a 5- or 6-membered heteroaromatic ring optionally substituted with one or more substituents selected from the group B.

[25] The compound or a pharmacologically acceptable salt thereof according to [1], wherein the compounds represented by any one of the formulae (1) to (4) are selected from the following structures:

Chemical formula 25

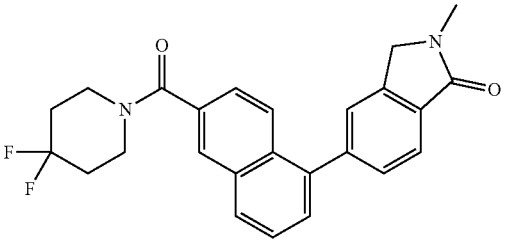
1

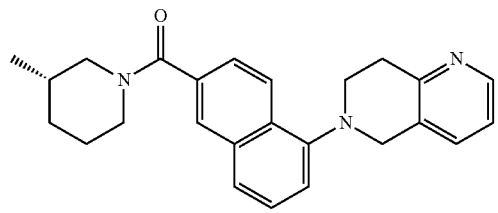
2

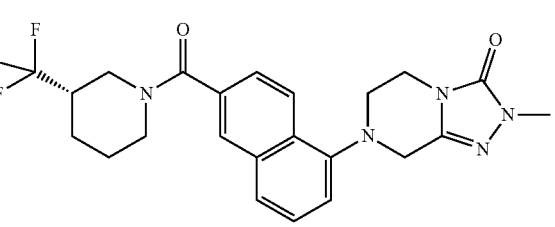
3

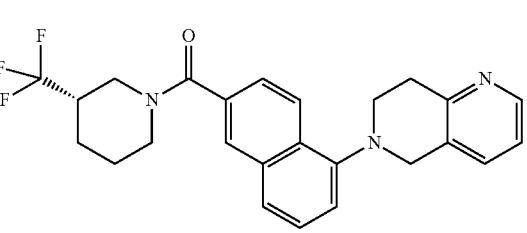
4

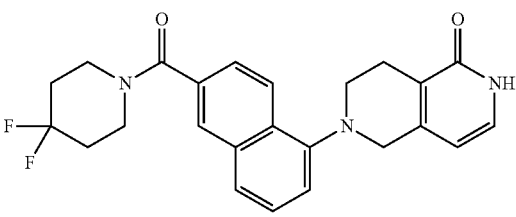
5

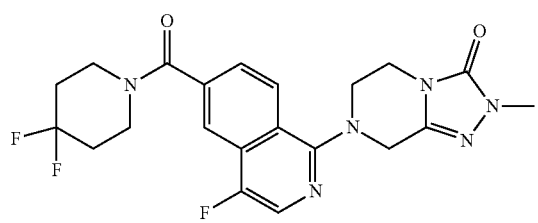
20
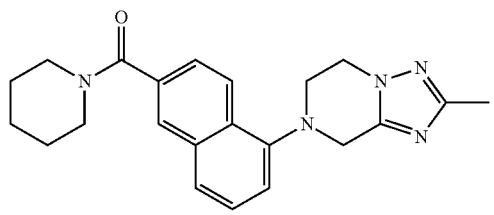
21
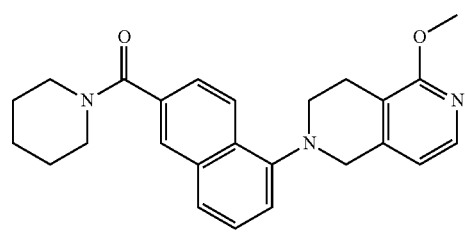
22
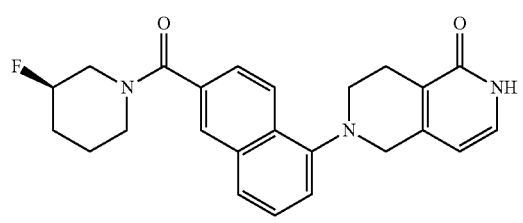
23
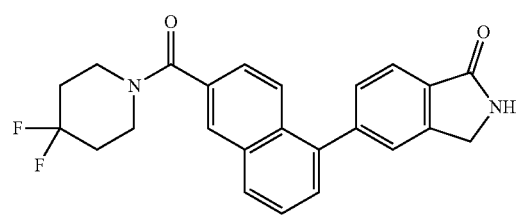
24
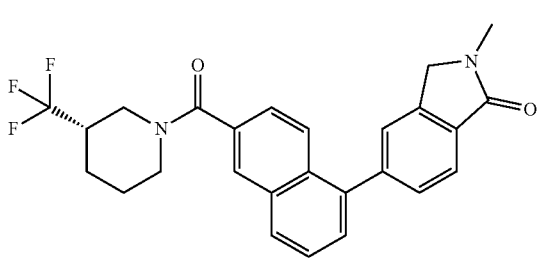
25
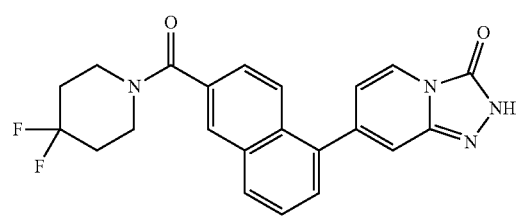
26
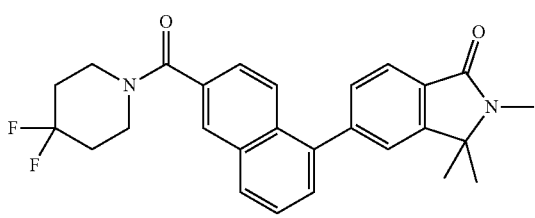
27
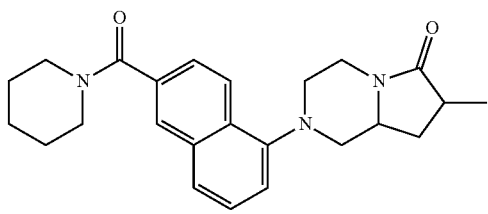
28
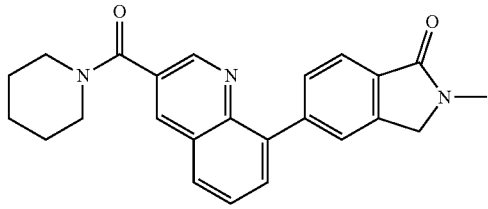
29
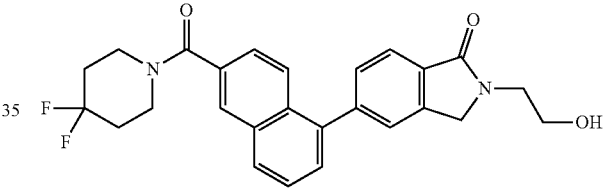
30
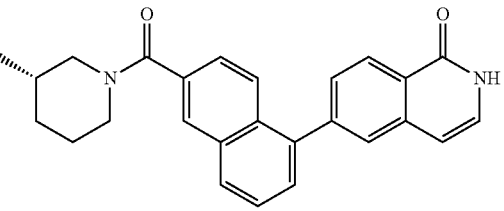
31
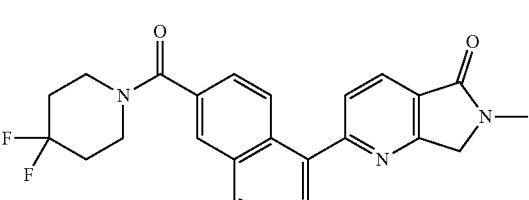
32

34
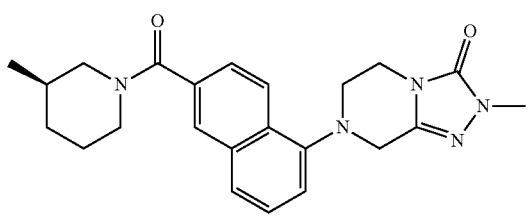
35
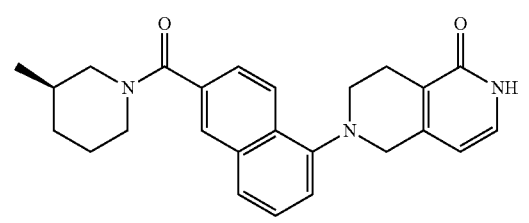
36
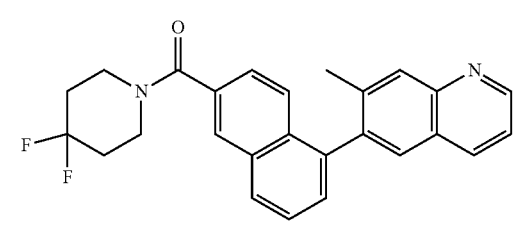
37
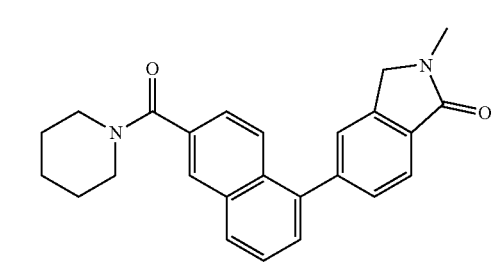
38
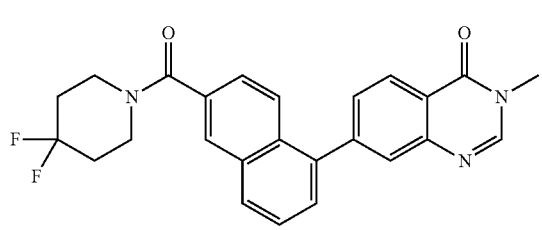
39
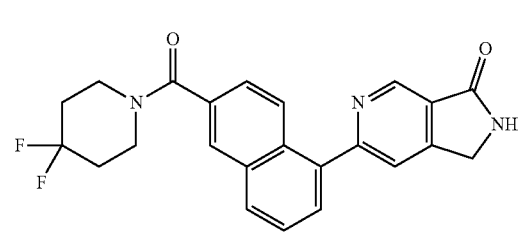
40
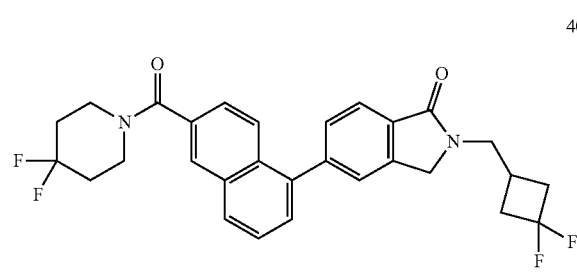
41
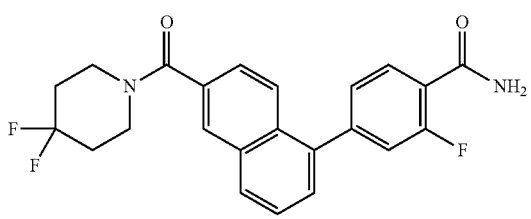
42
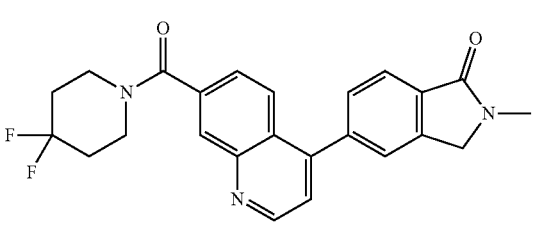
43
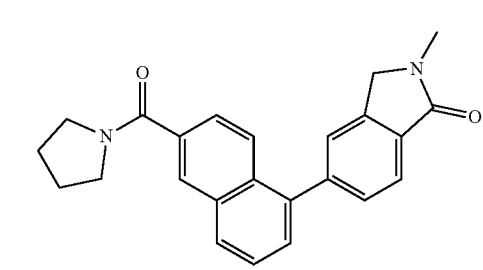
44
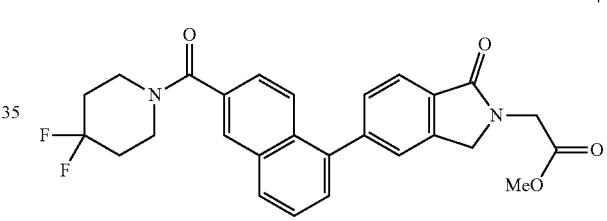
45
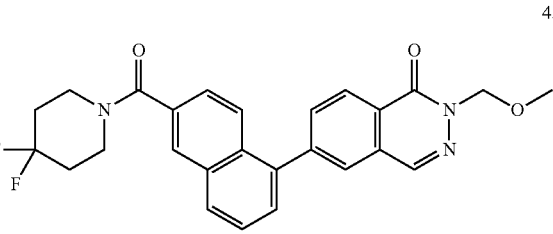
46
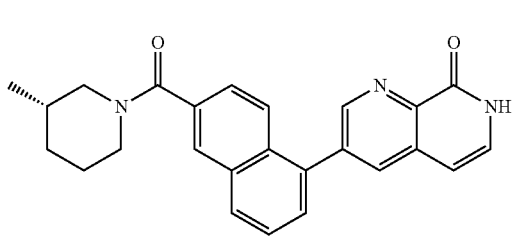
47
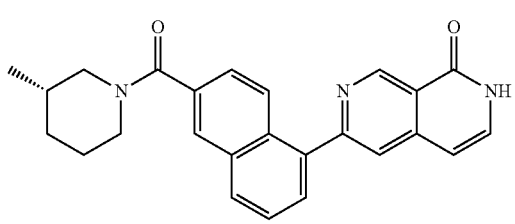

33
-continued
48
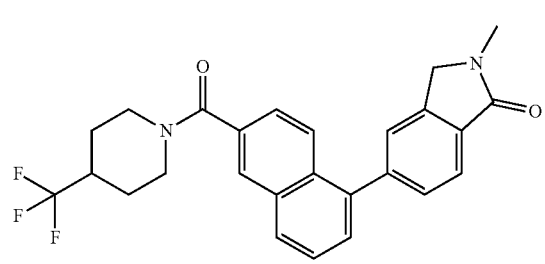
49
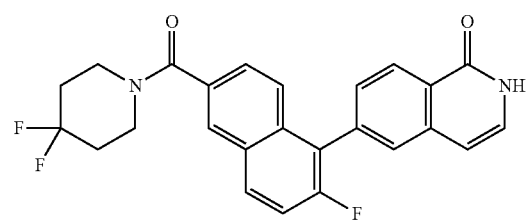
50
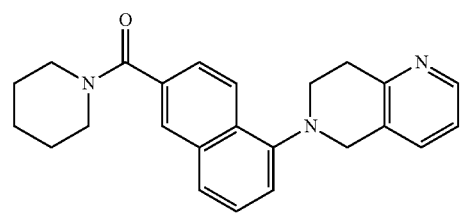
51
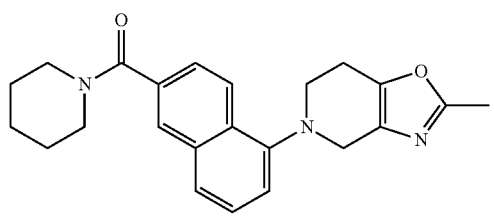
52
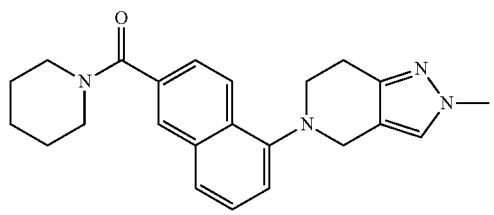
53
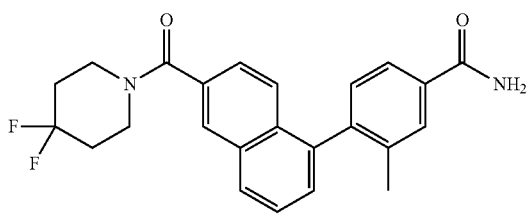
54
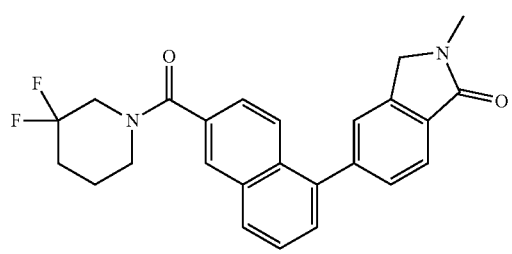
34
-continued
55
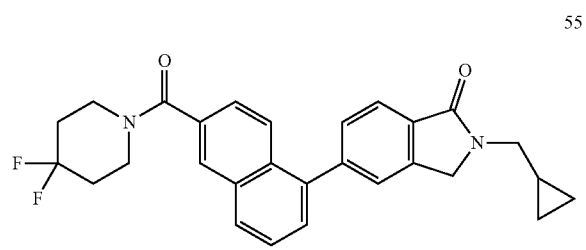
56
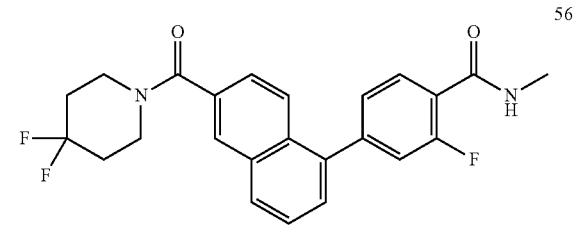
57
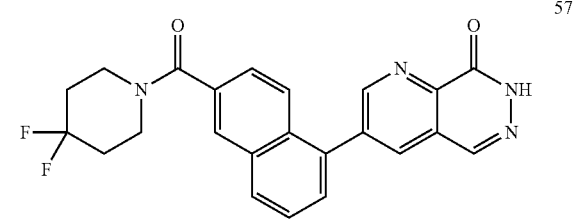
58
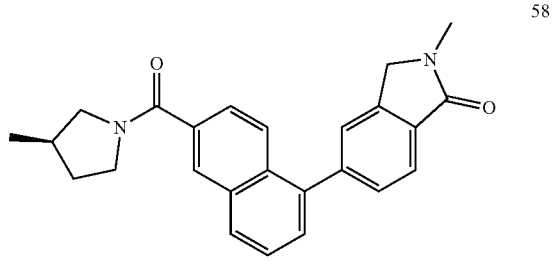
59
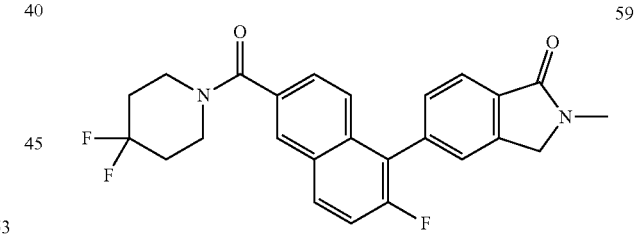
60
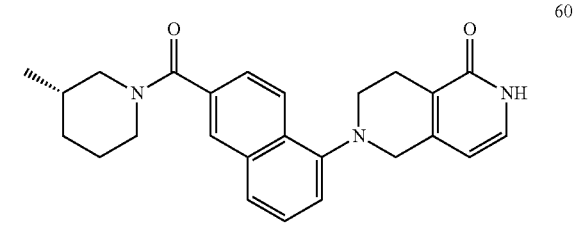
61
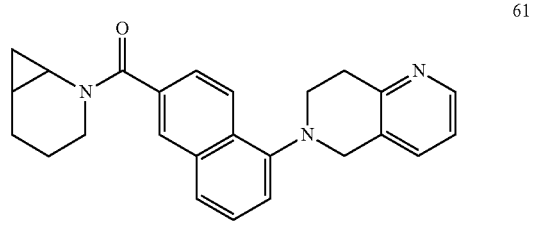

-continued
62
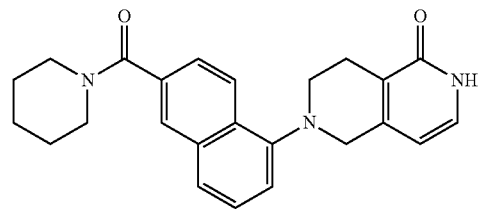
63
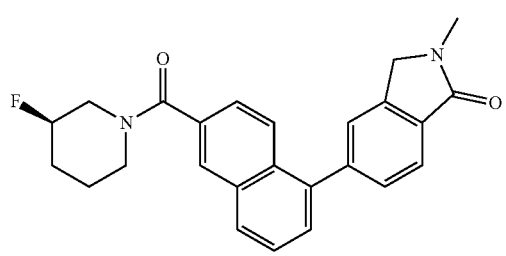
64
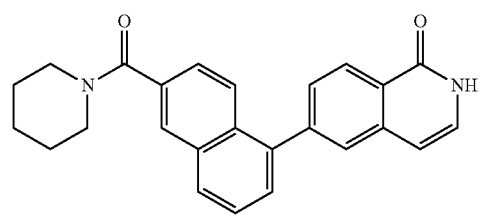
65
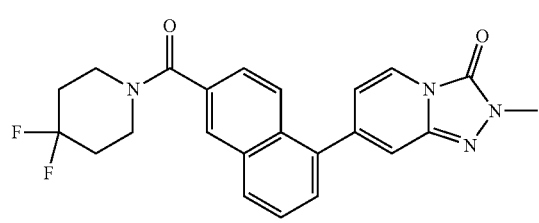
66
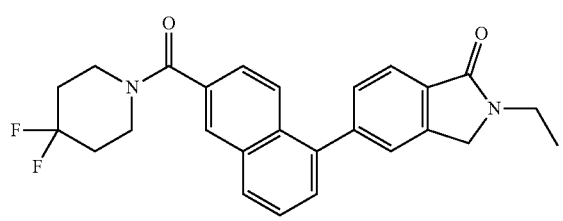
67
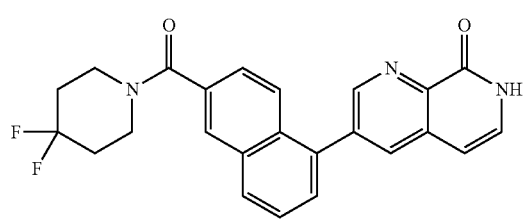
68
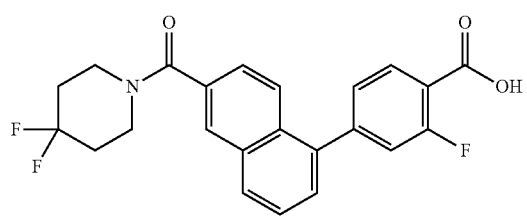
-continued
69
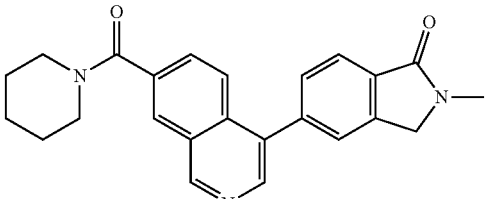
70
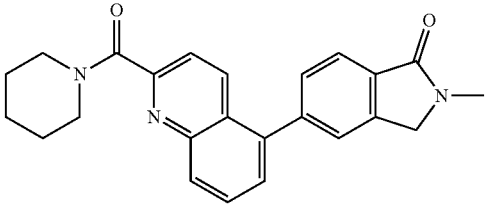
71
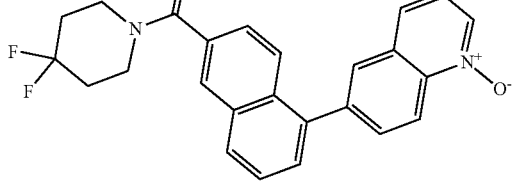
72
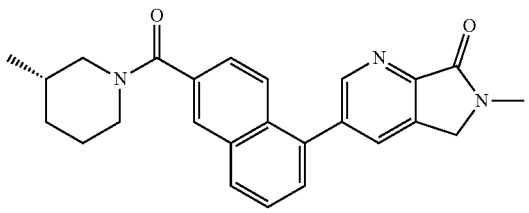
73
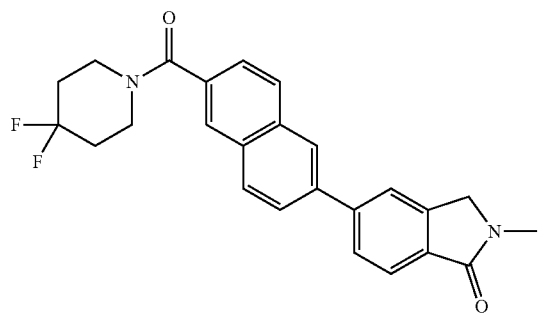
74
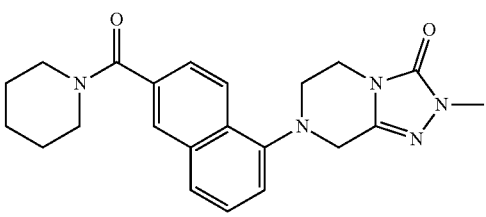
75
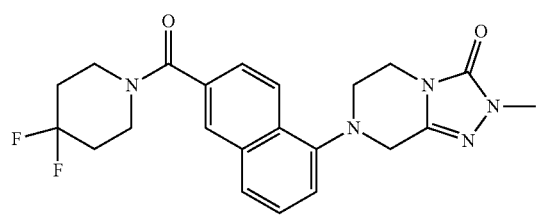

-continued
76
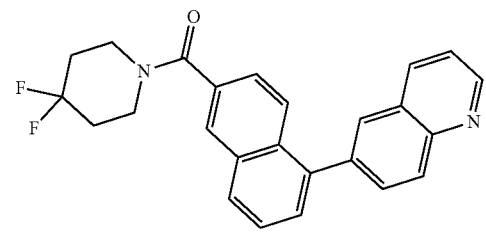
77
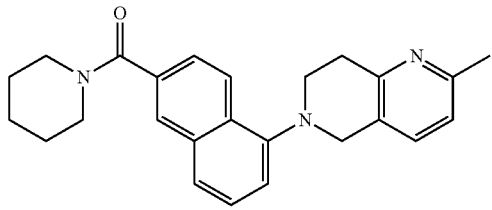
78
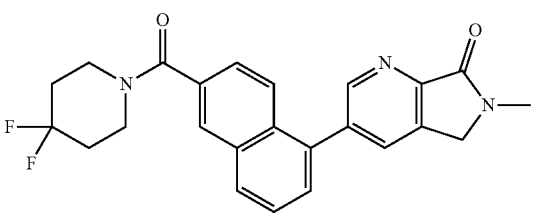
79
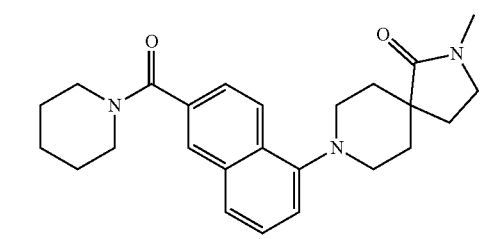
80
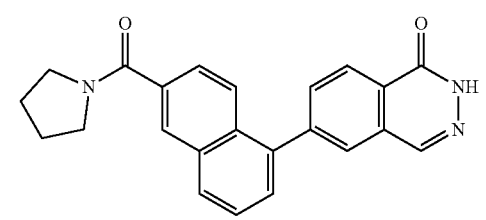
81
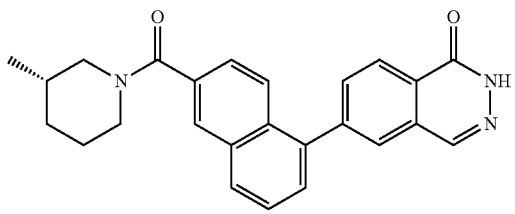
82
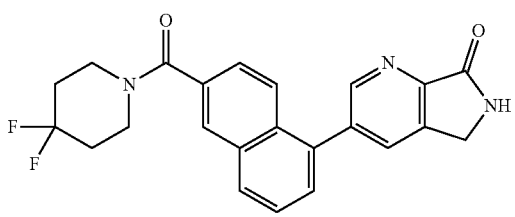
-continued
83
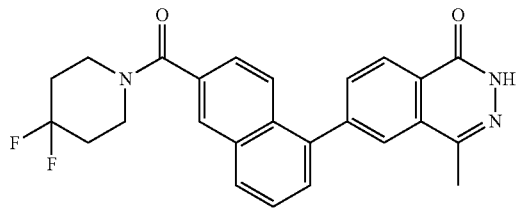
84
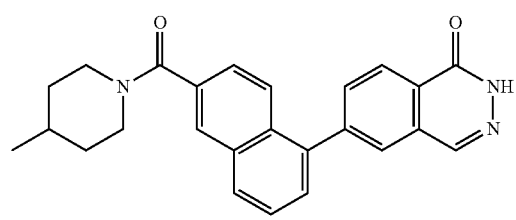
85
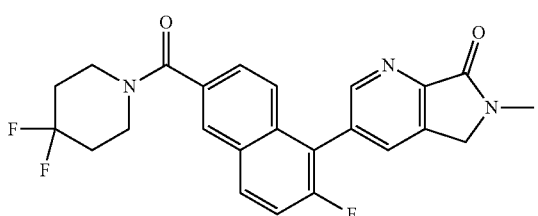
86
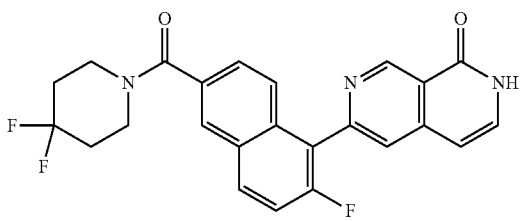
87
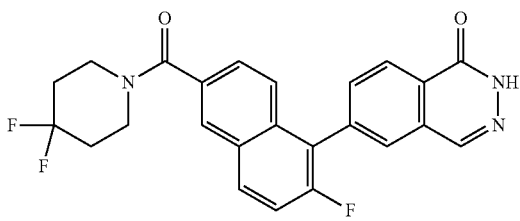
88
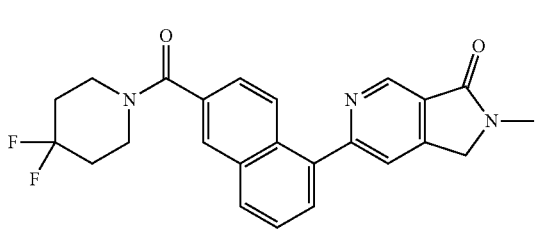
89
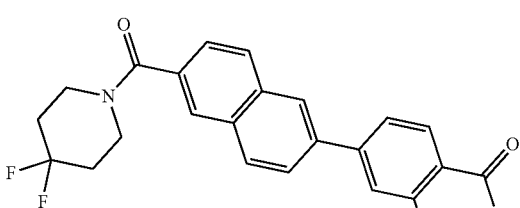

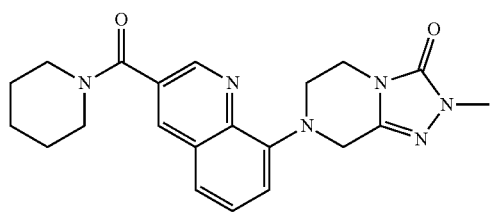
90
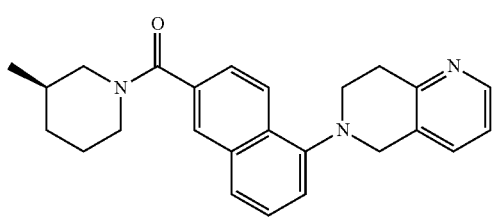
91
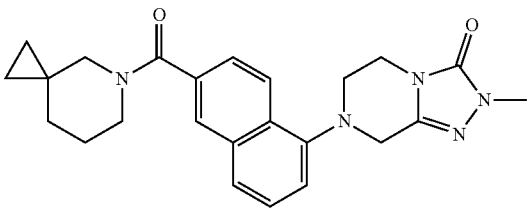
92
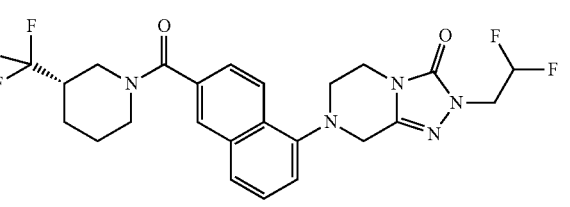
93
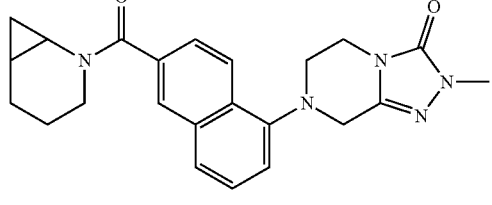
94
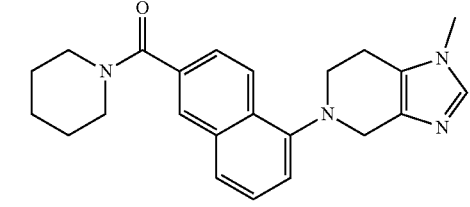
95
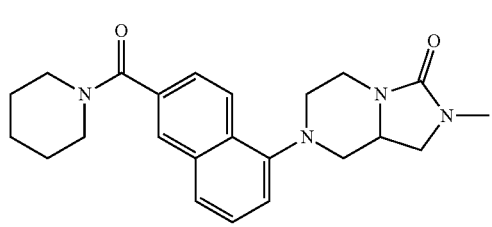
96
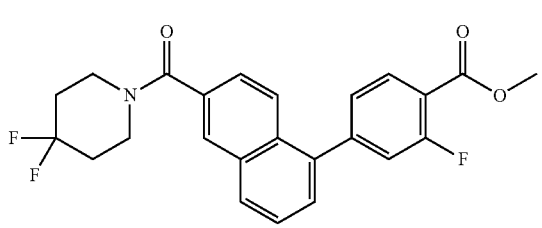
97
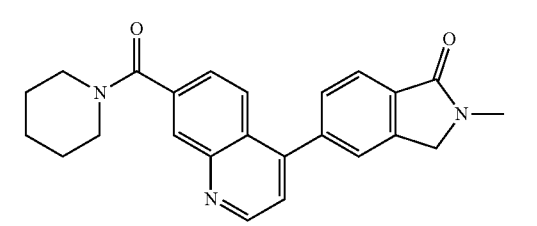
98
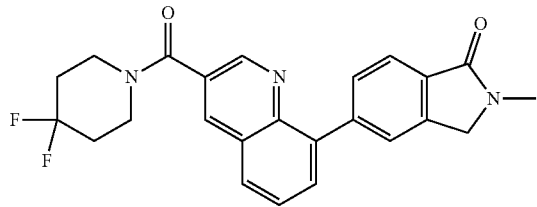
99
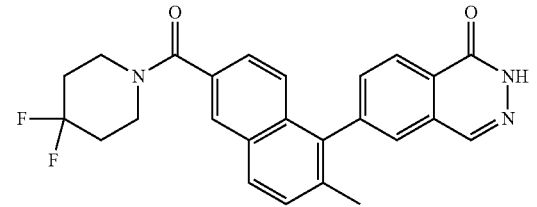
100
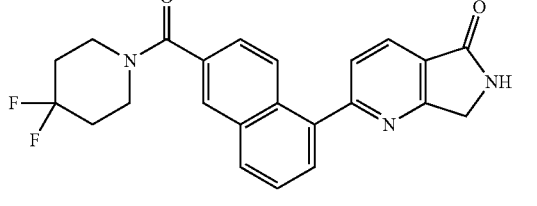
101
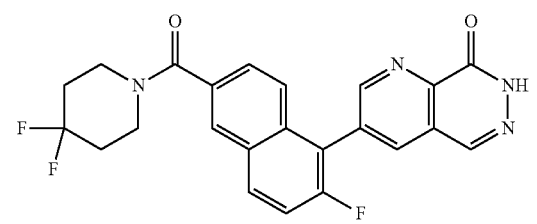
102
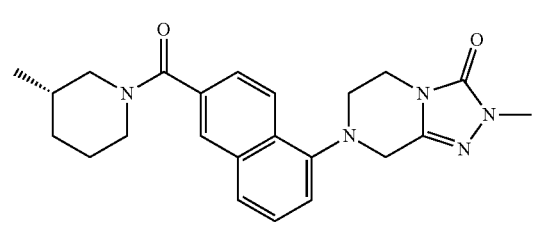
103

-continued
104
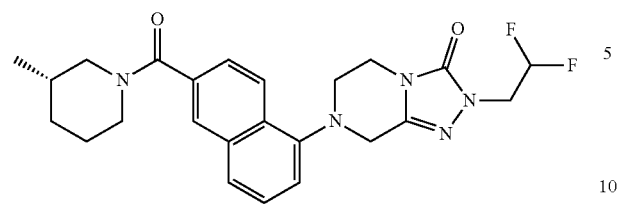
105
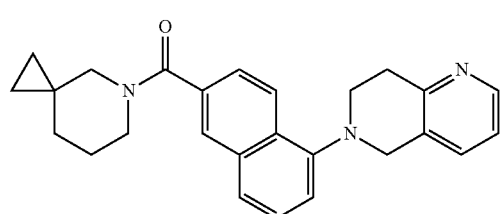
106
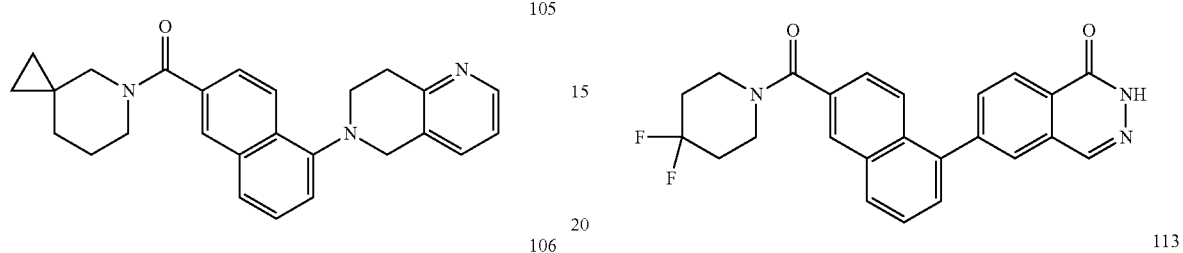
107
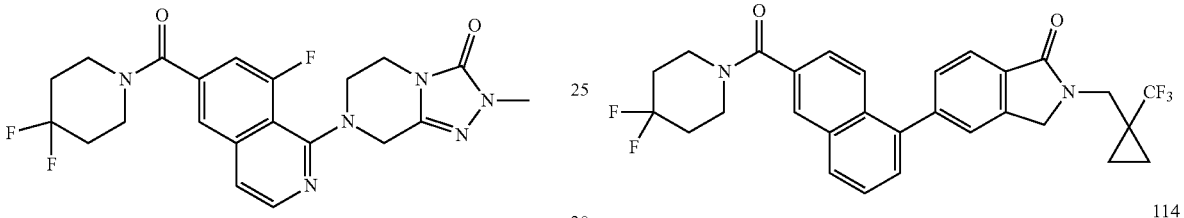
108
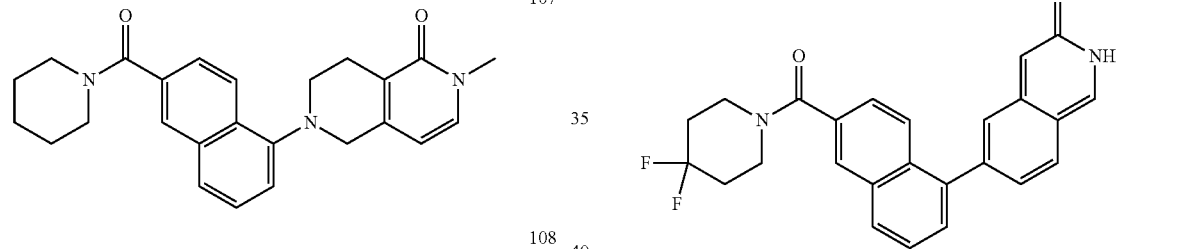
109
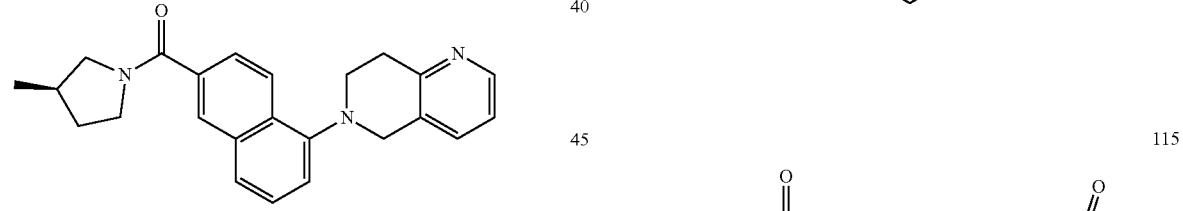
110
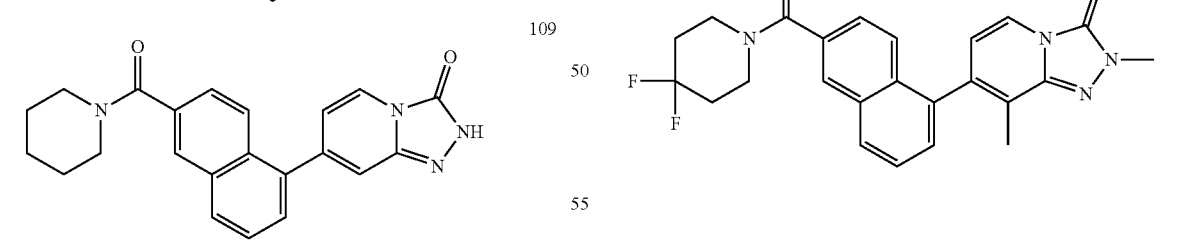
-continued
111
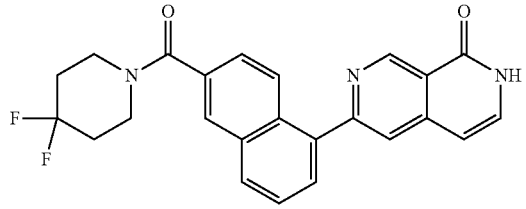
112
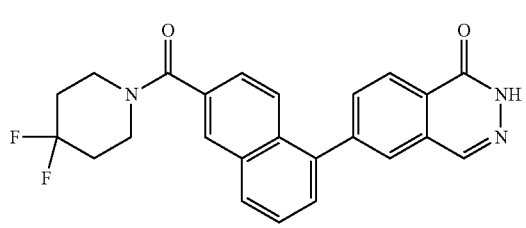
113
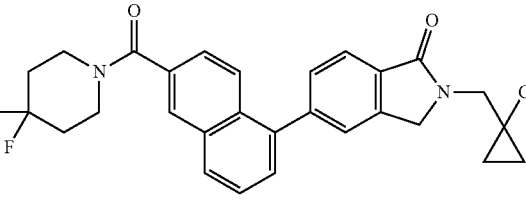
114
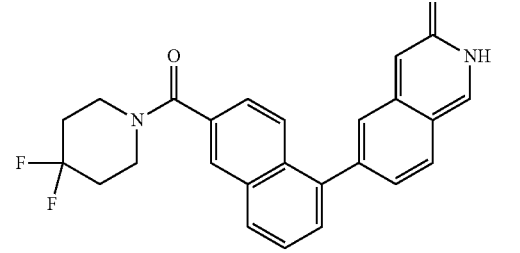
115
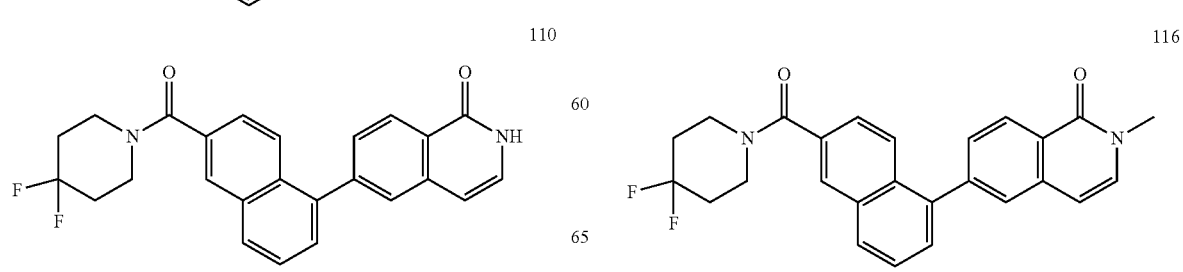
116
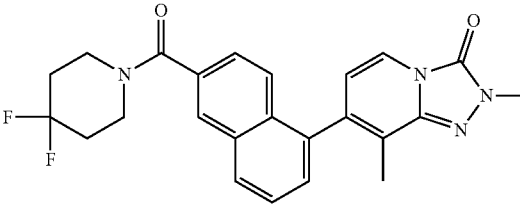

117
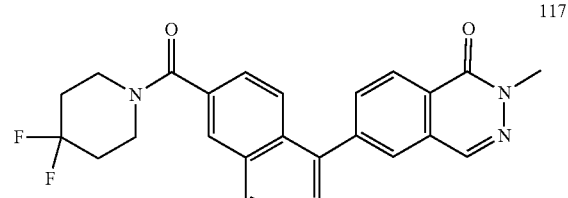
118
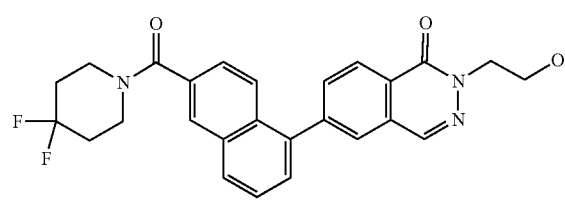
119
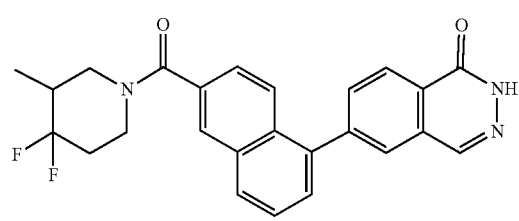
120
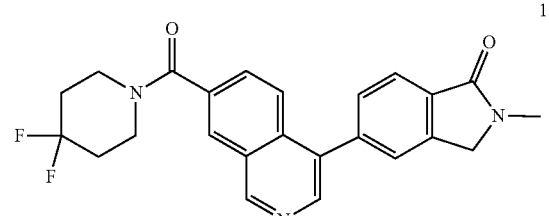
121
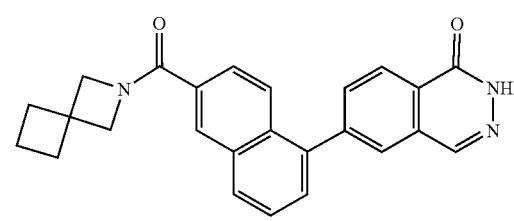
122
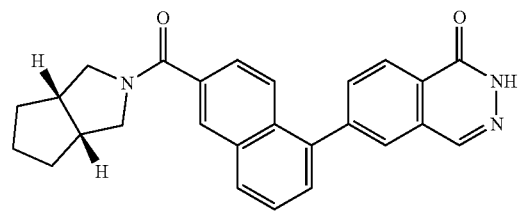
123
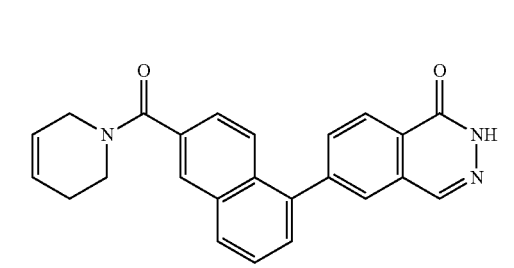
124
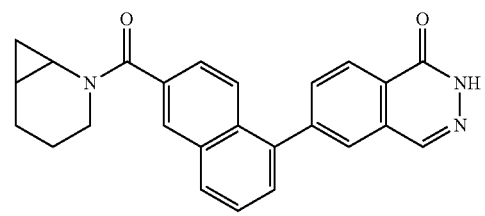
125
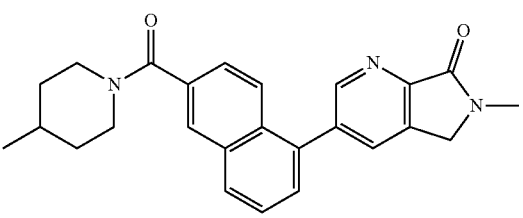
126
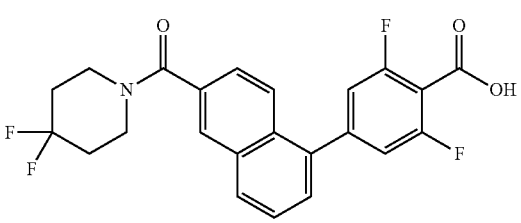
127
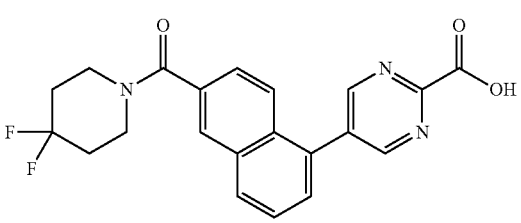
128
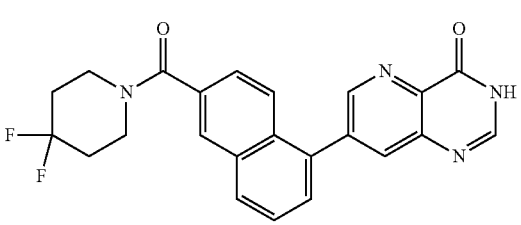
129
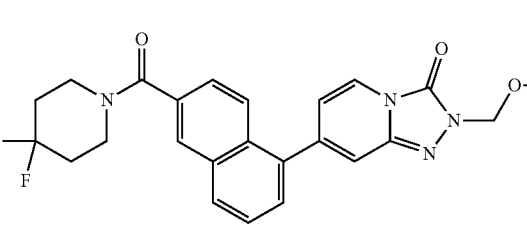
130
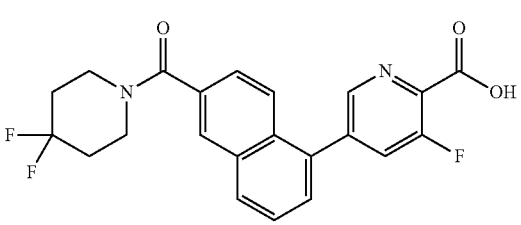

-continued
131
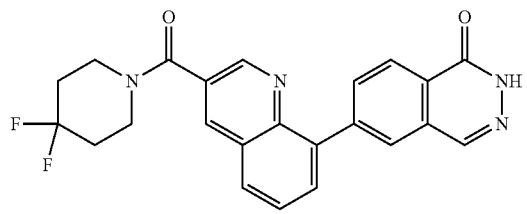
132
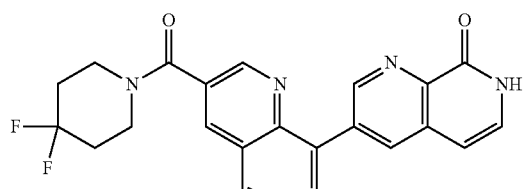
133
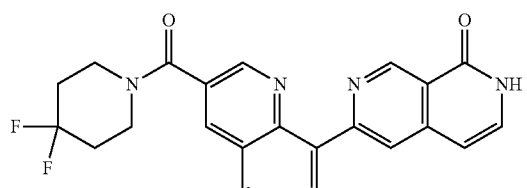
134
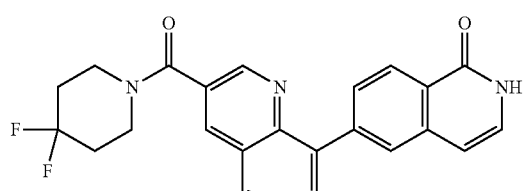
135
136
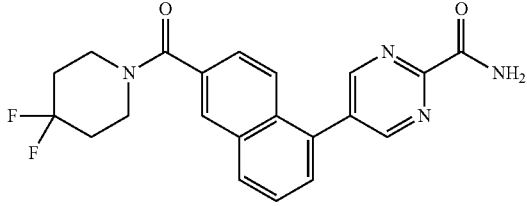
137
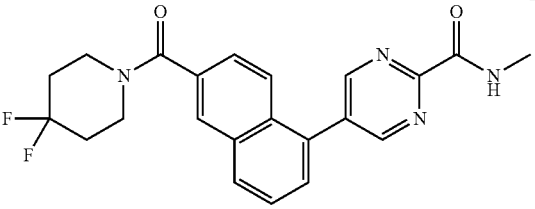
-continued
138
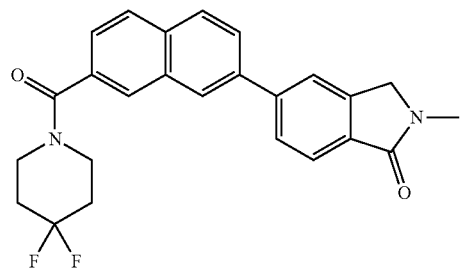
139
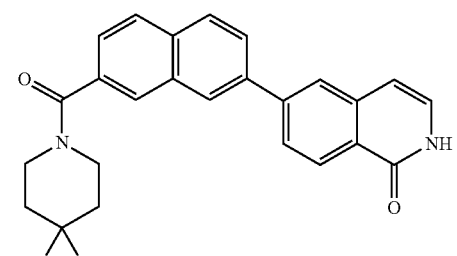
140
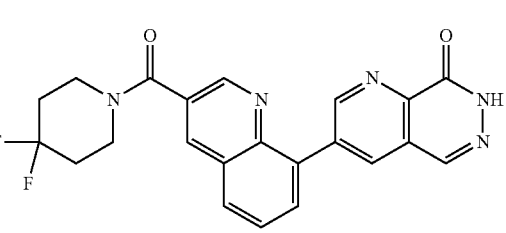
141
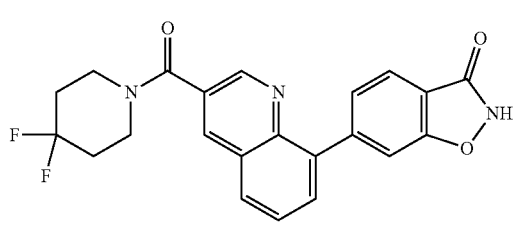
142
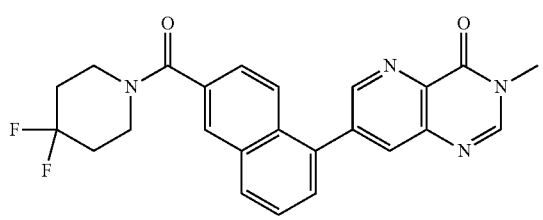
143
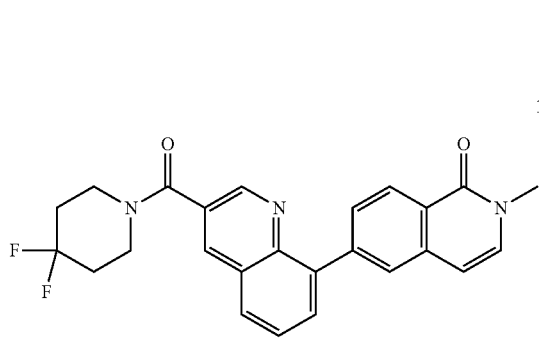

144
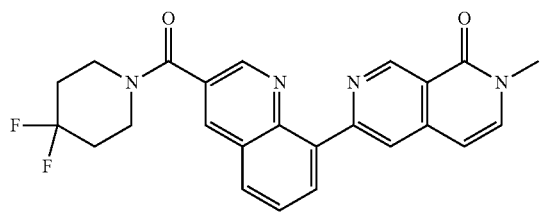
145
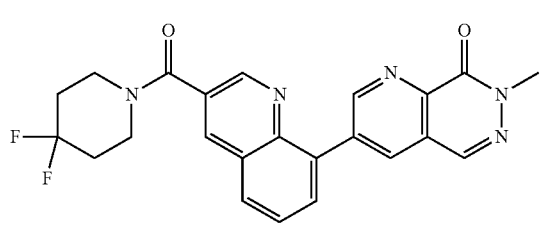
146
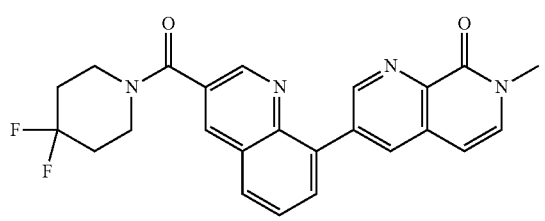
147
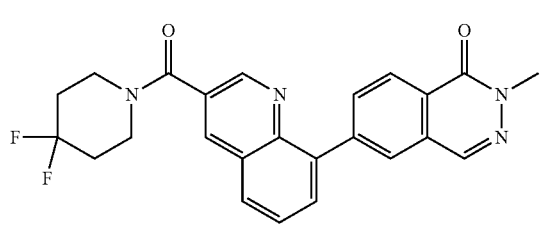
148
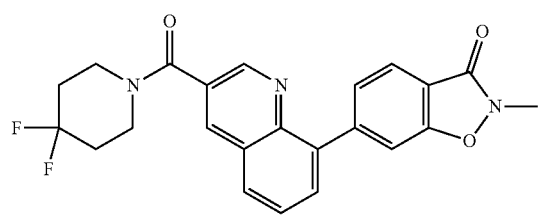
149
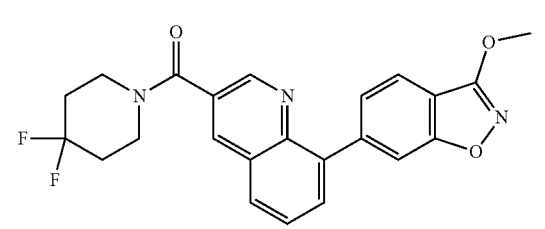
150
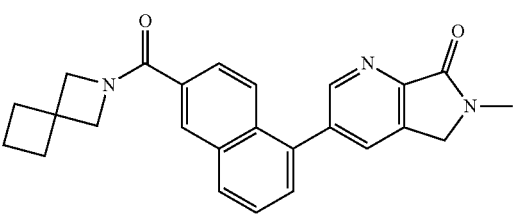
151
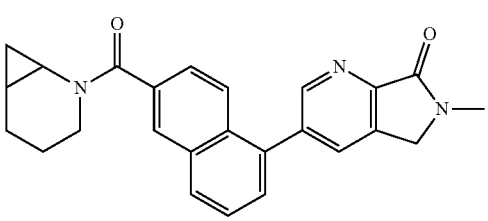
152
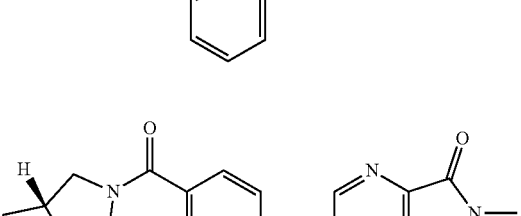
153
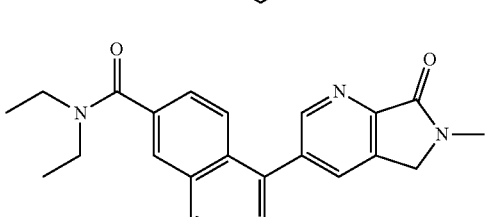
154
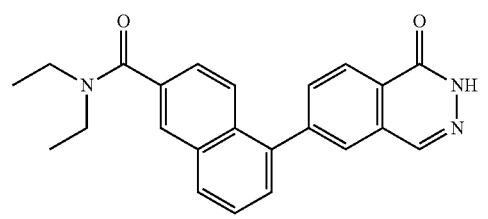
155
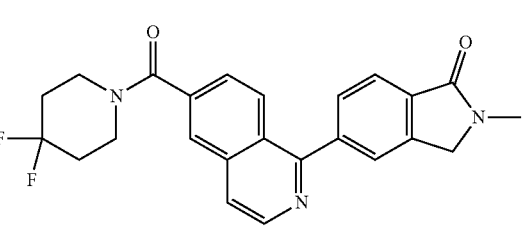
156

157
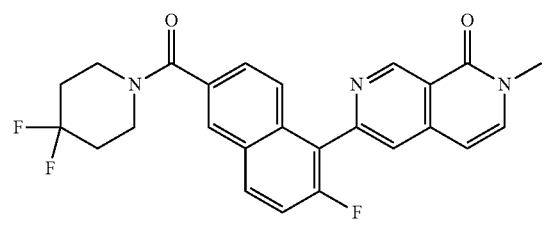
158
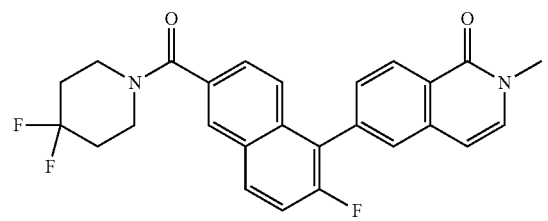
159
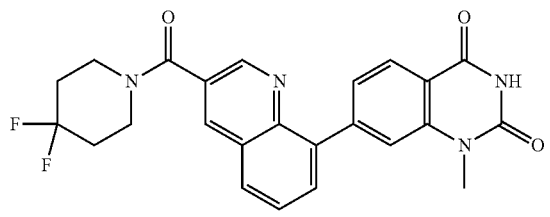
160
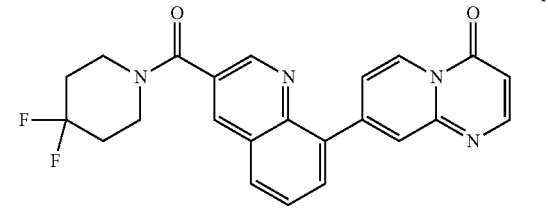
161
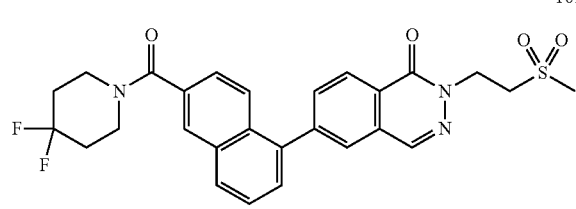
162
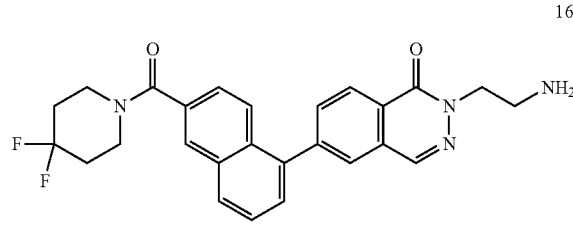
163
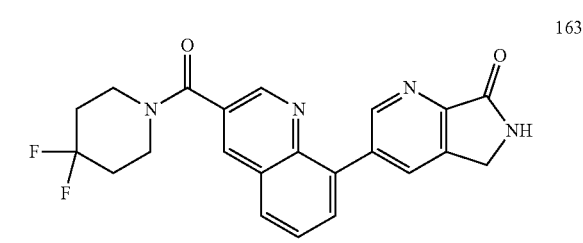
164
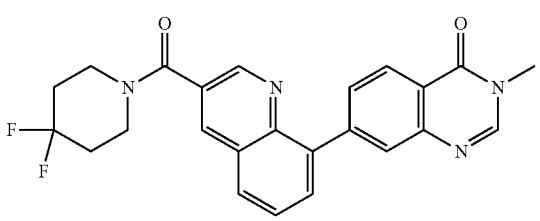
165
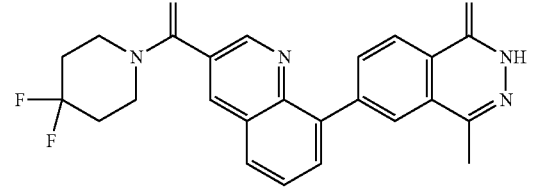
166
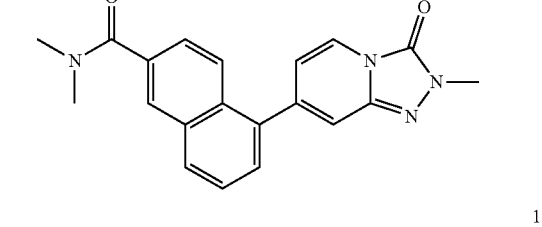
167
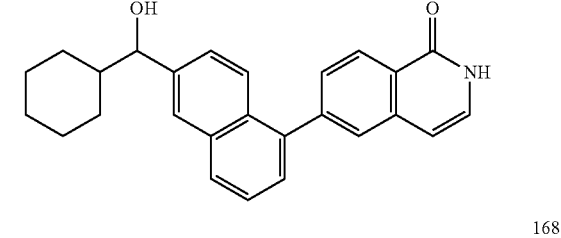
168
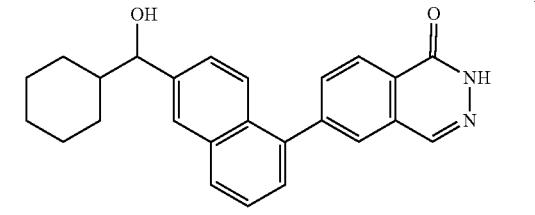
169
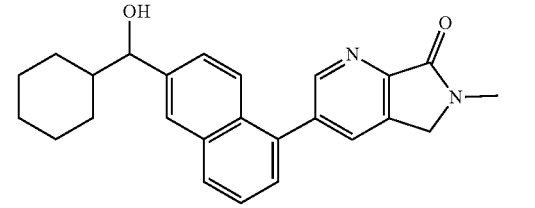
170
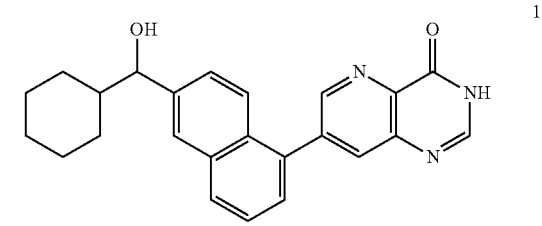

171
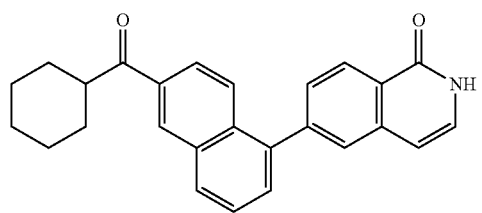
178
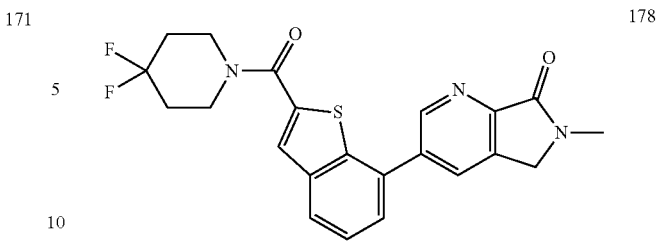
172
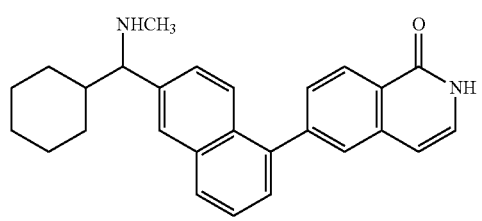
179
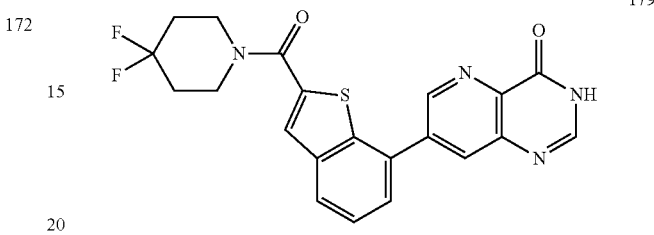
173
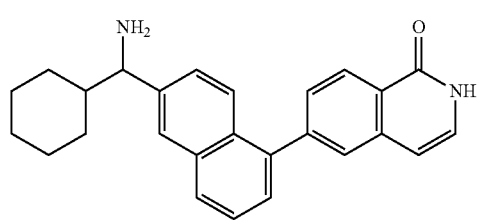
180
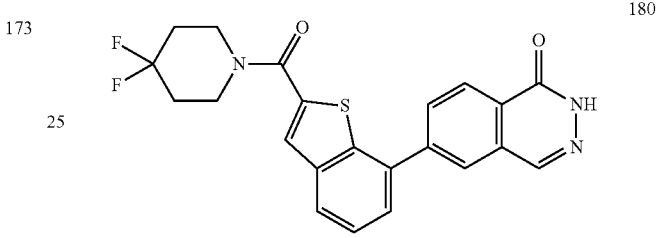
174
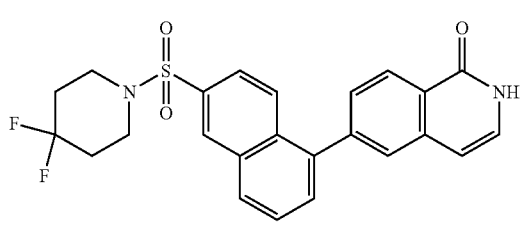
181
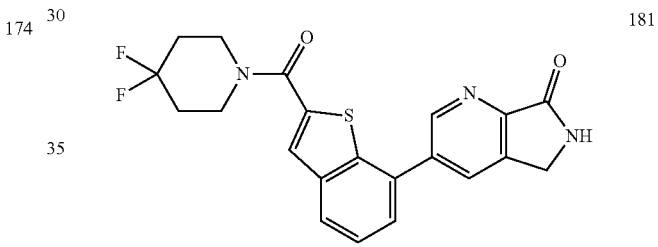
175
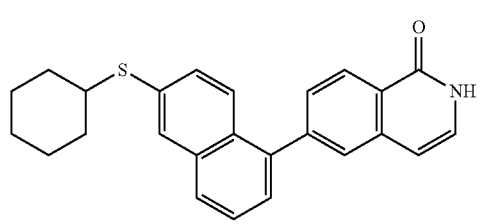
182
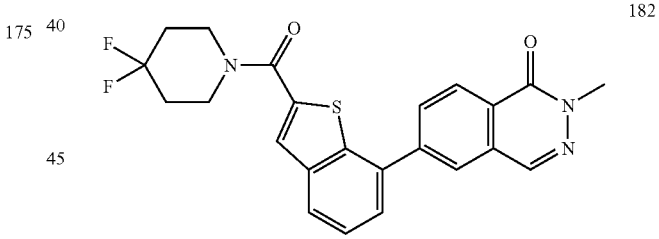
176
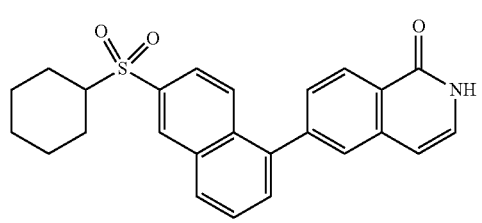
183
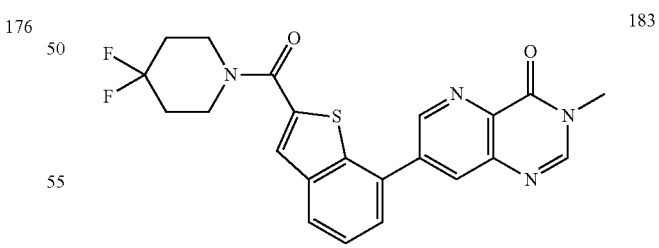
177
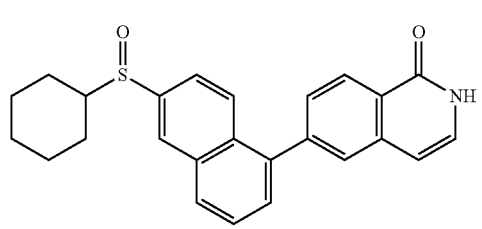
184
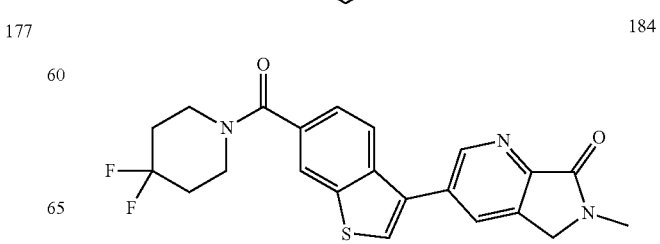

-continued

185

186

187

188

189

190

-continued

191

192

193

194

195

196

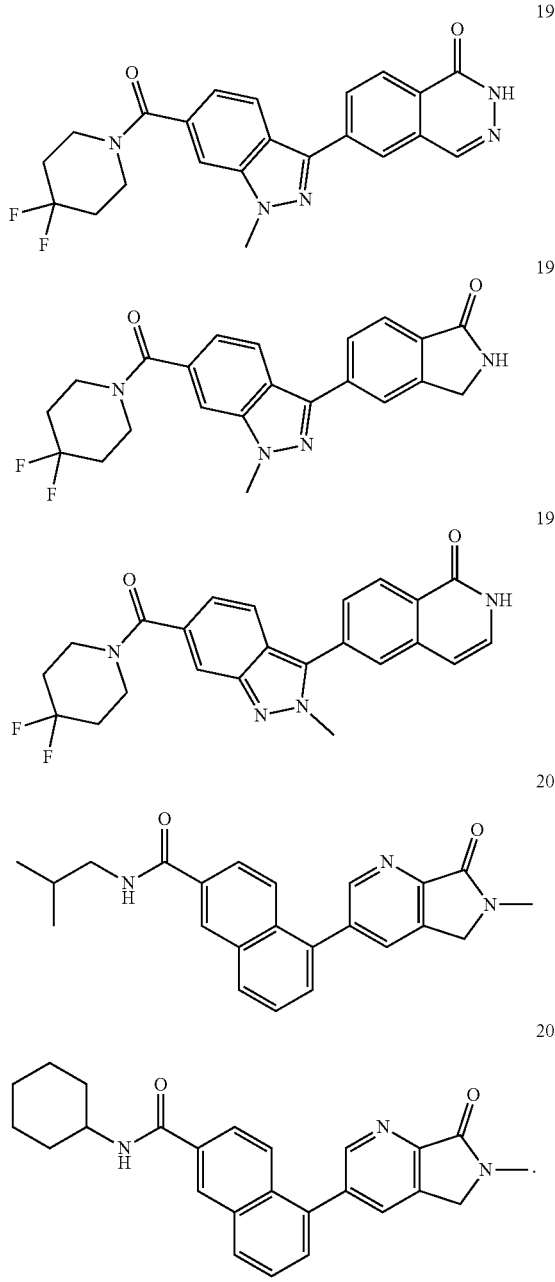

[26] A medicament including, as an active ingredient, the compound or a pharmacologically acceptable salt thereof described in any one of [1] to [25].

[27] A 15-PGDH inhibitor including, as an active ingredient, the compound or a pharmacologically acceptable salt thereof described in any one of [1] to [25].

[28] A method of treating or preventing Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening: includes administering the compound or a pharmacologically acceptable salt thereof described in any one of [1] to [25].

[29] Use of the compound or a pharmacologically acceptable salt thereof described in any one of [1] to [25] for manufacturing a medicament for treating or preventing Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening.

[30] A pharmaceutical composition for use in treating or preventing Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer, (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening, the composition including the compound or a pharmacologically acceptable salt thereof described in any one of [1] to [25]; and a pharmaceutically acceptable carrier.

DETAILED DESCRIPTION OF THE EMBODIMENTS

The present embodiments are described more in detail below.

The terms used herein are described.

The term "halogen" as used herein means fluorine, chlorine, bromine or iodine. The halogen is preferably fluorine or chlorine.

The term "5-membered heteroaromatic ring" as used herein means a 5-membered heteroaromatic ring containing 1 to 4 atoms selected from a sulfur atom, an oxygen atom, and a nitrogen atom. The nitrogen atom(s) in the aromatic ring may be N-oxide. Examples of the 5-membered heteroaromatic ring include furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, and thiadiazolyl.

The term "6-membered heteroaromatic ring" as used herein means a 6-membered heteroaromatic ring containing 1 to 4 nitrogen atoms. The nitrogen atom(s) in the aromatic ring may be N-oxide. Examples of the 6-membered heteroaromatic ring include pyridyl, pyridazinyl, pyrimidinyl, and pyrazinyl.

The term "bicyclic heteroaromatic ring consisting of 8 to 10 atoms" as used herein means a bicyclic heteroaromatic ring containing 8 to 10 atoms of which 1 to 4 are selected from a sulfur atom, an oxygen atom, and a nitrogen atom. The nitrogen atom(s) in the aromatic ring may be N-oxide. Examples of the bicyclic heteroaromatic ring consisting of 8 to 10 atoms include thienothiophenyl, thienofuranyl, thienoimidazolyl, furoimidazolyl, benzofuranyl, isobenzofuranyl, benzoxazolyl, benzoisoxazolyl, benzothiazolyl, benzoisothiazolyl, benzimidazolyl, benzothiophenyl, indolyl, isoindolyl, indazolyl, thiazolopyridyl, and oxazolopyrazinyl.

The term "fused heterocyclic ring consisting of 9 or 10 atoms" as used herein means a fused aromatic or non-aromatic ring constituted with 9 or 10 atoms of which 2 to 5 are heteroatoms and optionally containing 1 to 4 double bonds and 1 to 3 carbonyls. Examples of the fused heterocyclic ring consisting of 9 or 10 atoms include oxodihydrobenzisoxazolyl, oxotriazolopyridyl, oxopyridotriazinyl, oxopyrodotriazinyl, dioxopyrodotriazinyl, and dihydropyridotriazinyl.

The term "heterocyclic ring" as used herein means a 5- to 7-membered heterocyclic ring containing 1 to 4 atoms selected from a sulfur atom, an oxygen atom, and a nitrogen atom and optionally containing 1 to 3 carbonyls. Examples include heteroaromatic rings such as furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, and pyrazinyl; unsaturated heterocyclic rings such as pyrrolinyl, imidazolinyl, pyrazolinyl, dihydropyranyl, dihydrothiopyranyl, and dihydropyridyl; and saturated heterocyclic rings such as morpholinyl, thiomorpholinyl, pyrrolidinyl, imidazolidinyl, imidazolinyl, pyrazolidinyl, pyrazolinyl, piperidinyl, piperazinyl, tetrahydrofuranyl, oxathiolanyl, oxazinanyl, oxooxathiolanyl, dioxooxathiolanyl, oxothiazolidinyl, dioxothiazolidinyl, dithiepanyl, oxathiepanyl, and thiazepanyl.

It should be noted that the aforementioned "heterocyclic ring" may be fused with one or more other rings. Examples include isobenzofuranyl, benzoxazolyl, benzisoxazolyl, benzothiazolyl, benzisothiazolyl, chromenyl, chromanonyl, xanthenyl, phenoxathiinyl, indolizinyl, isoindolidinyl, indolyl, indazolyl, purinyl, quinolizinyl, isoquinolyl, quinolyl, phthalazinyl, naphthyridinyl, quinoxalinyl, quinazolinyl, carbazolyl, carbolinyl, acridinyl, and isoindolinyl.

The term "carbonyl" as used herein means a C=O group.

The term "formyl" as used herein means a —CHO group.

The term "aminocarbonyl" as used herein means a —C(=O)—NH$_2$ group.

The term "$C_1$-$C_6$ alkyl" as used herein means a straight- or branched-chain alkyl group having 1 to 6 carbon atoms. Examples include methyl, ethyl, propyl, isopropyl, butyl, isobutyl, sec-butyl, tert-butyl, pentyl, isopentyl, neopentyl, 1-methylbutyl, 2-methylbutyl, 1,2-dimethylpropyl, hexyl, and isohexyl.

The term "$C_1$-$C_6$ alkylcarbonyl" as used herein means a straight- or branched-chain alkylcarbonyl group derived from an aliphatic carboxylic acid having 1 to 6 carbon atoms; that is, a $C_1$-$C_6$ alkyl-C(=O)— group. Examples of the $C_1$-$C_6$ alkylcarbonyl include methylcarbonyl, ethylcarbonyl, propylcarbonyl, isopropylcarbonyl, butylcarbonyl, isobutylcarbonyl, sec-butylcarbonyl, t-butylcarbonyl, pentylcarbonyl, isopentylcarbonyl, neopentylcarbonyl, 1-methylbutylcarbonyl, 2-methylbutylcarbonyl, 1,2-dimethylpropylcarbonyl, hexylcarbonyl, and isohexylcarbonyl.

The term "$C_1$-$C_6$ alkoxy" as used herein means a straight- or branched-chain alkoxy group having 1 to 6 carbon atoms; that is, a $C_1$-$C_6$ alkyl-O— group. Examples include methoxy, ethoxy, propoxy, isopropoxy, isobutoxy, butoxy, sec-butoxy, tert-butoxy, pentyloxy, and hexyloxy.

The term "$C_1$-$C_6$ alkoxycarbonyl" as used herein means a straight- or branched-chain alkoxycarbonyl group having 1 to 6 carbon atoms; that is, a $C_1$-$C_6$ alkyl-O—C(=O)— group. Examples include methoxycarbonyl, ethoxycarbonyl, propoxycarbonyl, isopropoxycarbonyl, isobutoxycarbonyl, butoxycarbonyl, sec-butoxycarbonyl, tert-butoxycarbonyl, pentyloxycarbonyl, and hexyloxycarbonyl.

The term "$C_1$-$C_6$ alkylsulfonyl" as used herein means a straight- or branched-chain alkylsulfonyl group having 1 to 6 carbon atoms; that is, a $C_1$-$C_6$ alkyl-$SO_2$— group. Examples include methylsulfonyl, ethylsulfonyl, propylsulfonyl, isopropylsulfonyl, butylsulfonyl, isobutylsulfonyl, sec-butylsulfonyl, and tert-butylsulfonyl.

The term "$C_1$-$C_6$ alkylaminosulfonyl" as used herein means an amino-substituted sulfonyl group containing a straight- or branched-chain alkyl group having 1 to 6 carbon atoms; that is, a $C_1$-$C_6$ alkyl-$NHSO_2$— group. Examples include methylaminosulfonyl, ethylaminosulfonyl, propylaminosulfonyl, isopropylaminosulfonyl, butylaminosulfonyl, isobutylaminosulfonyl, sec-butylaminosulfonyl, and tert-butylaminosulfonyl.

The term "$C_1$-$C_6$ alkylsulfonylamino" as used herein means an amino group in which one hydrogen is substituted with the $C_1$-$C_6$ alkylsulfonyl mentioned above; that is, a $C_1$-$C_6$ alkyl-$SO_2$NH— group. Examples include methylsulfonylamino, ethylsulfonylamino, propylsulfonylamino, isopropylsulfonylamino, butylsulfonylamino, isobutylsulfonylamino, sec-butylsulfonylamino, and tert-butylsulfonylamino.

The term "$C_3$-$C_8$ cycloalkyl" as used herein means a monocyclic, saturated cycloalkyl group having 3 to 8 carbon atoms. Examples include cyclopropyl, cyclobutyl, cyclopentyl, cyclohexyl, cycloheptyl, and cyclooctyl.

The term "$C_3$-$C_8$ cycloalkylcarbonyl" as used herein means a cycloalkylcarbonyl group derived from a monocyclic cycloalkane carboxylic acid having 3 to 8 carbon atoms; that is, a $C_3$-$C_8$ cycloalkyl-C(=O)— group. Examples of the $C_3$-$C_8$ cycloalkylcarbonyl include cyclopropylcarbonyl, cyclobutylcarbonyl, cyclopentylcarbonyl, cyclohexylcarbonyl, cycloheptylcarbonyl, and cyclooctylcarbonyl.

The term "$C_3$-$C_8$ cycloalkylsulfonyl" as used herein means a cyclic alkylsulfonyl group having 3 to 8 carbon atoms; that is, a $C_3$-$C_8$ cycloalkyl-$SO_2$— group. Examples include cyclopropylsulfonyl, cyclobutylsulfonyl, cyclopentylsulfonyl, cyclohexylsulfonyl, cycloheptylsulfonyl, and cyclooctylsulfonyl.

The term "$C_3$-$C_8$ cycloalkylsulfonylamino" as used herein means an amino group in which one hydrogen is substituted with the cycloalkylsulfonyl having 3 to 8 carbon atoms mentioned above; that is, a $C_3$-$C_8$ cycloalkyl-$SO_2$NH— group. Examples include cyclopropylsulfonylamino, cyclobutylsulfonylamino, cyclopentylsulfonylamino, cyclohexylsulfonylamino, cycloheptylsulfonylamino, and cyclooctylsulfonylamino.

The term "3- to 10-membered nitrogen-containing heterocycloalkyl" as used herein means a monocyclic, bicyclic or tricyclic 3-, 4-, 5-, 6-, 7-, 8-, 9- or 10-membered saturated or non-aromatic, unsaturated heterocycloalkyl group containing at least one nitrogen atom and optionally containing one or more oxygen or sulfur atoms.

The 3- to 10-membered nitrogen-containing heterocycloalkyl group may be fused with one or more 6-membered aromatic hydrocarbon or 6-membered heteroaromatic rings. Furthermore, the 3- to 10-membered nitrogen-containing heterocycloalkyl group may have a bridged or spiro ring. Examples of the 3- to 10-membered nitrogen-containing heterocycloalkyl include aziridinyl, azetidinyl, imidazolidyl, pyrrolidinyl, piperidinyl, piperazinyl, morpholinyl, thiomorpholinyl, thiazepanyl, diazepanyl, oxazocanyl, octahydroindolyl, azaspiroheptyl, oxaazaspiroheptyl, oxaazaspirooctyl, oxaazaspirononyl, 5-azabicyclo[2,1,1]hexyl, 2-azabicyclo[2,1,1]hexyl, 6-azabicyclo[3,1,1]heptyl, 3-azabicyclo[3,1,1]heptyl, 3-azabicyclo[3,1,0]hexyl, 2-azabicyclo[2,2,1]heptyl, 3-azabicyclo[3,2,1]octyl, 8-azabicyclo[3,2,1]octyl, dihydropyrazolyl, dihydropyrrolyl, dihydroimidazolyl, dihydrooxadiazolyl, dihydropyranyl, pyranyl, tetrahydropyrazinyl, tetrahydrooxazepinyl, dihydrooxazepinyl, tetrahydrothiazepinyl, dihydrothiazepinyl, tetrahydrodiazepinyl, dihydrodiazepinyl, dihydropyridinyl, dihydropyrimidinyl, dihydropyridazinyl, and dihydropyrazinyl. Examples of the 3- to 10-membered nitrogen-containing heterocycloalkyl group that may be fused with one or more 6-membered aromatic hydrocarbon or 6-membered heteroaromatic rings include dihydroindole, tetrahydroquinoline, tetrahydroisoquinoline, tetrahydrobenzazepine, tetrahydrobenzodiazepine, tetrahydrobenzoxazepine, tetrahydrobenzothiazepine, and tetrahydronaphthyridine.

The term "3- to 8-membered heterocycloalkyl" as used herein means a monocyclic, bicyclic or tricyclic 3-, 4-, 5-, 6-, 7- or 8-membered heterocycloalkyl group containing 1 to 4 heteroatoms independently selected from the group consisting of N,N-oxide, O, S, SO, and $SO_2$ and optionally containing 1 to 3 carbonyls.

The 3- to 8-membered heterocycloalkyl group may be fused with one or more other 6-membered aromatic hydrocarbon or 6-membered heteroaromatic rings. Furthermore, the 3- to 8-membered heterocycloalkyl group may have a bridged or spiro ring. Examples of the 3- to 8-membered heterocycloalkyl include aziridinyl, azetidinyl, imidazolidyl, pyrrolidinyl, piperidinyl, piperazinyl, morpholinyl, thiomorpholinyl, thiazepanyl, diazepanyl, oxazocanyl, octahydroindolyl, azaspiroheptyl, oxaazaspiroheptyl, oxaazaspirooctyl, oxaazaspirononyl, 5-azabicyclo[2,1,1]hexyl, 2-azabicyclo[2,1,1]hexyl, 6-azabicyclo[3,1,1]heptyl, 3-azabicyclo[3,1,1]heptyl, 3-azabicyclo[3,1,0]hexyl, 2-azabicyclo[2,2,1]heptyl, 3-azabicyclo[3,2,1]octyl, 8-azabicyclo[3,2,1]octyl, dihydropyrazolyl, dihydropyrrolyl, dihydroimidazolyl, dihydrooxadiazolyl, dihydropyranyl, pyranyl, tetrahydropyrazinyl, tetrahydrooxazepinyl, dihydrooxazepinyl, tetrahydrothiazepinyl, dihydrothiazepinyl, tetrahydrodiazepinyl, dihydrodiazepinyl, dihydropyridinyl, dihydropyrimidinyl, dihydropyridazinyl, and dihydropyrazinyl. Examples of the 3- to 8-membered heterocycloalkyl group that may be fused with one or more 6-membered aromatic hydrocarbon or 6-membered heteroaromatic rings include dihydroindole, tetrahydroquinoline, tetrahydroisoquinoline, tetrahydrobenzazepine, tetrahydrobenzodiazepine, tetrahydrobenzoxazepine, tetrahydrobenzothiazepine, and tetrahydronaphthyridine.

The term "5- to 7-membered heterocycloalkyl" as used herein means a saturated or non-aromatic, unsaturated monocyclic 5-, 6- or 7-membered heterocycloalkyl group containing 1 to 4 heteroatoms independently selected from the group consisting of N,N-oxide, O, S, SO, and $SO_2$ and optionally containing 1 to 3 carbonyls. The 5- to 7-membered heterocycloalkyl group may be fused with one or more other 6-membered aromatic hydrocarbon or 6-membered heteroaromatic rings. Examples of the 5- to 7-membered heterocycloalkyl include imidazolidyl, thiazolidyl, pyrrolidinyl, piperidinyl, piperazinyl, morpholinyl, thiomorpholinyl, dihydropyrazolyl, dihydropyrrolyl, dihydroimidazolyl, dihydrooxadiazolyl, dihydropyranyl, pyranyl, tetrahydropyradinyl, azepanyl, diazepanyl, oxazepanyl, thiazepanyl, and tetrahydrodiazepinyl. Examples of 5- to 7-membered heterocycloalkyl group that may be fused with one or more 6-membered aromatic hydrocarbon or 6-membered heteroaromatic rings include dihydroindole, tetrahydroquinoline, and tetrahydroisoquinoline.

The term "5- to 7-membered heterocycloalkylcarbonyl" as used herein means a saturated or non-aromatic, unsaturated monocyclic 5-, 6- or 7-membered heterocycloalkylcarbonyl group containing 1 to 4 heteroatoms independently selected from the group consisting of N,N-oxide, O, S, SO, and $SO_2$ and optionally containing 1 to 3 carbonyls; that is, a 5- to 7-membered heterocycloalkyl-C(=O)— group. Examples of the 5- to 7-membered heterocycloalkylcarbonyl include imidazolidylcarbonyl, thiazolidylcarbonyl, pyrrolidinylcarbonyl, piperidinylcarbonyl, piperadinylcarbonyl, morpholinylcarbonyl, thiomorpholinylcarbonyl, dihydropyrazolylcarbonyl, dihydropyrrolylcarbonyl, dihydroimidazolylcarbonyl, dihydrooxadiazolylcarbonyl, dihydropyranylcarbonyl, pyranylcarbonyl, tetrahydropyrazinylcarbonyl, azepanylcarbonyl, diazepanylcarbonyl, oxazepanylcarbonyl, thiazepanylcarbonyl, and tetrahydrodiazepinylcarbonyl.

The term "5- to 7-membered heterocycloalkylamino" as used herein means a saturated or non-aromatic, unsaturated monocyclic 5-, 6- or 7-membered heterocycloalkylamino group containing 1 to 4 heteroatoms independently selected from the group consisting of N,N-oxide, O, S, SO, and $SO_2$ and optionally containing 1 to 3 carbonyls; that is a 5- to 7-membered heterocycloalkyl-NH— group. Examples of the 5- to 7-membered heterocycloalkylamino include imidazolidylamino, thiazolidylamino, pyrrolidinylamino, piperidinylamino, piperadinylamino, morpholinylamino, thiomorpholinylamino, dihydropyrazolylamino, dihydropyrrolylamino, dihydroimidazolylamino, dihydrooxadiazolylamino, dihydropyranylamino, pyranylamino, tetrahydropyrazinylamino, azepanylamino, diazepanylamino, oxazepanylamino, thiazepanylamino, and tetrahydrodiazepinylamino.

The term "5- to 7-membered heterocycloalkylaminocarbonyl" as used herein means a saturated or non-aromatic, unsaturated monocyclic 5-, 6- or 7-membered heterocycloalkylaminocarbonyl group containing 1 to 4 heteroatoms independently selected from the group consisting of N,N-oxide, O, S, SO, and $SO_2$ and optionally containing 1 to 3 carbonyls; that is, a 5- to 7-membered heterocycloalkyl-NHC(=O)— group. Examples of the 5- to 7-membered heterocycloalkylaminocarbonyl include imidazolidylaminocarbonyl, thiazolidylaminocarbonyl, pyrrolidinylaminocarbonyl, piperidinylaminocarbonyl, piperadinylaminocarbonyl, morpholinylaminocarbonyl, thiomorpholinylaminocarbonyl, dihydropyrazolylaminocarbonyl, dihydropyrrolylaminocarbonyl, dihydroimidazolylaminocarbonyl, dihydrooxadiazolylaminocarbonyl, dihydropyranylaminocarbonyl, pyranylaminocarbonyl, tetrahydropyrazinylaminocarbonyl, azepanylaminocarbonyl, diazepanylaminocarbonyl, oxazepanylaminocarbonyl, thiazepanylaminocarbonyl, and tetrahydrodiazepinylaminocarbonyl.

The term "$C_3$-$C_8$ cycloalkoxy" as used herein means a monocyclic, saturated cycloalkoxy group containing 3 to 8 carbon atoms; that is, a $C_3$-$C_8$ cycloalkyl-O— group. Examples include cyclopropyloxy, cyclobutyloxy, cyclopentyloxy, cyclohexyloxy, cycloheptyloxy, and cyclooctyloxy.

The term "halo($C_1$-$C_6$) alkyl" as used herein means a $C_1$-$C_6$ alkyl group substituted with 1 to 5 halogens which are the same or different. Examples of the halo($C_1$-$C_6$) alkyl include fluoromethyl, difluoromethyl, trifluoromethyl, 2-fluoroethyl, 2-chloroethyl, 2,2-difluoroethyl, 1,1-difluoroethyl, 1,2-difluoroethyl, 2,2,2-trifluoroethyl, 1,1,2,2,2-pentafluoroethyl, 2,2,2-trichloroethyl, 3-fluoropropyl, 2-fluoropropyl, 1-fluoropropyl, 3,3-difluoropropyl, 2,2-difluoropropyl, 1,1-difluoropropyl, 4-fluorobutyl, 5-fluoropentyl, and 6-fluorohexyl.

The term "halo($C_1$-$C_6$) alkoxy" as used herein means a $C_1$-$C_6$ alkoxy group substituted with 1 to 5 halogens which are the same or different. Examples of the halo($C_1$-$C_6$) alkoxy include fluoromethoxy, difluoromethoxy, trifluoromethoxy, 2-fluoroethoxy, 2-chloroethoxy, 2,2-difluoroethoxy, 1,1-difluoroethoxy, 1,2-difluoroethoxy, 2,2,2-trifluoroethoxy, 1,1,2,2,2-pentafluoroethoxy, 2,2,2-trichloroethoxy, 3-fluoropropoxy, 2-fluoropropoxy, 1-fluoropropoxy, 3,3-difluoropropoxy, 2,2-difluoropropoxy, 1,1-difluoropropoxy, 4-fluorobutoxy, 5-fluoropentoxy, and 6-fluorohexyloxy.

The term "hydroxy $C_1$-$C_6$ alkyl" as used herein means a $C_1$-$C_6$ alkyl group substituted with a hydroxyl group. Examples of the hydroxy $C_1$-$C_6$ alkyl include 2-hydroxyethyl, 1-hydroxyethyl, 3-hydroxypropyl, 2-hydroxypropyl, 1-hydroxypropyl, 4-hydroxybutyl, 3-hydroxybutyl, 2-hydroxybutyl, 1-hydroxybutyl, 5-hydroxypentyl, and 6-hydroxyhexyl.

The term "amino optionally containing 1 or 2 $C_1$-$C_6$ alkyl groups" as used herein means an amino group in which 1 or 2 hydrogens are optionally substituted with a straight- or branched-chain alkyl group having 1 to 6 carbon atoms. Examples include amino, methylamino, ethylamino, propylamino, isopropylamino, butylamino, isobutylamino, sec-butylamino, tert-butylamino, pentylamino, isopentylamino, neopentylamino, 1-methylbutylamino, 2-methylbutylamino, 1,2-dimethylpropylamino, hexylamino, isohexylamino, dimethylamino, diethylamino, N-ethyl-N-methylamino, and N—ethyl-N-propylamino.

The term "aminocarbonyl optionally containing 1 or 2 $C_1$-$C_6$ alkyl groups" as used herein means an aminocarbonyl group in which 1 or 2 hydrogens are optionally substituted with a straight- or branched-chain alkyl group having 1 to 6 carbon atoms. Examples include aminocarbonyl, methylaminocarbonyl, ethylaminocarbonyl, propylaminocarbonyl, isopropylaminocarbonyl, butylaminocarbonyl, isobutylaminocarbonyl, sec-butylaminocarbonyl, tert-butylaminocarbonyl, pentylaminocarbonyl, isopentylaminocarbonyl, neopentylaminocarbonyl, 1-methylbutylaminocarbonyl, 2-methylbutylaminocarbonyl, 1,2-dimethylpropylaminocarbonyl, hexylaminocarbonyl, isohexylaminocarbonyl, dimethylaminocarbonyl, diethylaminocarbonyl, N-ethyl-N-methylaminocarbonyl, and N—ethyl-N-propylaminocarbonyl.

The term "aminosulfonyl optionally containing 1 or 2 $C_1$-$C_6$ alkyl groups" as used herein means an aminosulfonyl group in which 1 or 2 hydrogens are optionally substituted with a straight- or branched-chain alkyl group having 1 to 6 carbon atoms. Examples include aminosulfonyl, methylaminosulfonyl, ethylaminosulfonyl, propylaminosulfonyl, isopropylaminosulfonyl, butylaminosulfonyl, isobutylaminosulfonyl, sec-butylaminosulfonyl, tert-butylaminosulfonyl, pentylaminosulfonyl, isopentylaminosulfonyl, neopentylaminosulfonyl, 1-methylbutylaminosulfonyl, 2-methylbutylaminosulfonyl, 1,2-dimethylpropylaminosulfonyl, hexylaminosulfonyl, isohexylaminosulfonyl, dimethylaminosulfonyl, diethylaminosulfonyl, N-ethyl-N-methylaminosulfonyl, and N—ethyl-N-propylaminosulfonyl.

The term "aryl" as used herein means an phenyl group or naphtyl group.

The term "heteroaryl" as used herein means an 5-membered heteroaromatic ring or 6-membered heteroaromatic ring or bicyclic heteroaromatic ring consisting of 8 to 10 atoms.

For the definitions of the functional groups present in each formula below, those described above may be referred to and descriptions thereof may be omitted. The referred definitions are for the terms described in the embodiments mentioned below.

The present embodiments relates to compounds represented by one of the following formulae (1), (2), (3) and (4) or pharmacologically acceptable salts thereof. Formula (1), (2), (3) and (4)

Chemical formula 26

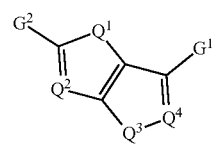 (1)

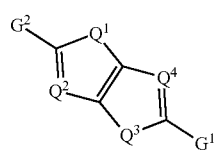 (2)

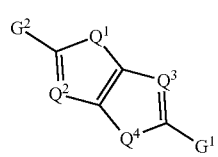 (3)

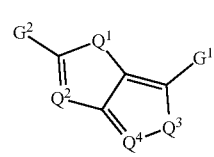 (4)

wherein $G^1$ is a phenyl group optionally having substituent(s) selected from the group A, a 5-membered aromatic heterocyclic group optionally having substituent(s) selected from the group A, a 6-membered aromatic heterocyclic group optionally having substituent(s) selected from the group A, a bicyclic aromatic heterocyclic group having 8 to 10 atoms and optionally having substituent(s) selected from the group A, a fused heterocyclic group having 9 or 10 atoms and optionally having substituent(s) selected from the group A, $C_3$-$C_8$ cycloalkyl group optionally having substituent(s) selected from the group A or 3 to 8-membered heterocycloalkyl group optionally having substituent(s) selected from the group A;

$G^2$ is a —C(=O)—X, —C(=O)—CHR$^1$R$^2$, —CH(OH)—CHR$^1$R$^2$, —CH(NY$_2$)—CHR$^1$R$^2$, —S—CHR$^1$R$^2$, —S(=O)$_2$—X, —S(=O)—CHR$^1$R$^2$ or —SO$_2$—CHR$^1$R$^2$ where X is —NR$^1$R$^2$;

$Q^1$ is —C(R$^3$)=C(R$^4$)—, —C(R$^5$)=N—, —N=C(R$^5$)—, —O— or —S—;

$Q^2$ is —C(R$^6$)= or —N=;

$Q^3$ is —C(R$^7$)=C(R$^8$)—, —C(R$^9$)=N—, —N=C(R$^9$)—, —NY—, —O— or —S—;

$Q^4$ is —C(R$^{10}$)= or —N=;

$R^1$ and $R^2$ are each independently selected from hydrogen, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

or $R^1$ and $R^2$ are taken together with the nitrogen atom to which they attached to form a 3 to 10-membered nitrogen atom containing heterocycloalkyl group optionally having substituent(s) selected from the group B; the 3 to 10-membered nitrogen atom containing heterocycloalkyl group optionally having unsaturated bond is a monocyclic ring or fused, bridged or spiro bicyclic ring; and the 3 to 10-membered nitrogen atom containing heterocycloalkyl group optionally contains silicon atom, oxygen atom or sulfur atom in substitution for a carbon atom;

$R^3$ and $R^4$ are each independently selected from hydrogen, halogen, —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^5$ is hydrogen, —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^6$ is hydrogen, halogen, —CN, —COOY, —NHC(O)Y, $C_1$-$C_6$alkyl optionally having substituent (s) selected from the group C, $C_1$-$C_6$alkoxy optionally having substituent(s) selected from the group C or $C_3$-$C_8$ cycloalkyl optionally having substituent(s) selected from the group C;

$R^7$ and $R^8$ are each independently selected from hydrogen, halogen, —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^9$ is hydrogen or —CN, —COOY, —NHC(O)Y, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

$R^{10}$ is hydrogen, halogen, —CN, —COOY, —NHC(O)Y, $C_1$-$C_6$ alkyl optionally having substituent (s) selected from the group C, $C_1$-$C_6$alkoxy optionally having substituent(s) selected from the group C or $C_3$-$C_8$ cycloalkyl optionally having substituent(s) selected from the group C;

Y is independently selected from hydrogen, $C_1$-$C_6$alkyl optionally having substituent(s) selected from the group C, $C_1$-$C_6$alkoxy optionally having substituent(s) selected from the group C or $C_3$-$C_8$ cycloalkyl optionally having substituent(s) selected from the group C;

A group is halogen, hydroxyl, carbonyl, nitrile, carboxyl, formyl, $C_1$-$C_6$alkyl optionally having substituent(s) selected from the group A1, $C_1$-$C_6$alkylcarbonyl optionally having substituent(s) selected from the group A1, $C_1$-$C_6$alkoxy optionally having substituent(s) selected from the group A1, $C_1$-$C_6$alkoxycarbonyl optionally having substituent(s) selected from the group A1, $C_1$-$C_6$alkylsulfonyl optionally having substituent(s) selected from the group A1, $C_1$-$C_6$ alkylsulfonylamino optionally having substituent(s) selected from the group A1, $C_3$-$C_8$ cycloalkyl optionally having substituent(s) selected from the group A1, $C_3$-$C_8$ cycloalkylcarbonyl optionally having substituent(s) selected from the group A1, $C_3$-$C_8$ cycloalkoxy optionally having substituent(s) selected from the group A1, $C_3$-$C_8$ cycloalkylsulfonyl optionally having substituent(s) selected from the group A1, $C_3$-$C_8$ cycloalkylsulfonylamino optionally having substituent(s) selected from the group A1, $C_5$-$C_7$ heterocycloalkyl optionally having substituent(s) selected from the group A1, $C_5$-$C_7$ heterocycloalkylcarbonyl optionally having substituent(s) selected from the group A1, $C_5$-$C_7$ heterocycloalkylamino optionally having substituent(s) selected from the group A1, $C_5$-$C_7$ heterocycloalkylaminocarbonyl optionally having substituent(s) selected from the group A1, aminocarbonyl optionally substituted with one or two $C_1$-$C_6$alkyl optionally having substituent(s) selected from the group A1, aminosulfonyl optionally substituted with one or two $C_1$-$C_6$alkyl optionally having substituent(s) selected from the group A1, amino optionally substituted with one or two $C_1$-$C_6$alkyl optionally having substituent(s) selected from the group A1, phenyl optionally having substituent(s) selected from the group B, 5-membered aromatic heterocyclic group optionally having substituent(s) selected from the group B, 6-membered aromatic heterocyclic group optionally having substituent(s) selected from the group B or heterocyclic group optionally having substituent(s) selected from the group B;

A1 group is halogen, hydroxyl, amino, carbonyl, nitrile, carboxyl, formyl, $C_1$-$C_6$alkyl optionally having substituent(s) selected from the group A2, $C_1$-$C_6$alkylcarbonyl optionally having substituent(s) selected from the group A2, $C_1$-$C_6$alkoxy optionally having substituent(s) selected from the group A2, $C_1$-$C_6$alkoxycarbonyl optionally having substituent(s) selected from the group A2, $C_1$-$C_6$alkylsulfonyl optionally having substituent(s) selected from the group A2, $C_1$-$C_6$ alkylsulfonylamino optionally having substituent(s) selected from the group A2, $C_3$-$C_8$ cycloalkyl optionally having substituent(s) selected from the group A2, $C_5$-$C_7$ heterocycloalkyl optionally having substituent(s) selected from the group A2, $C_5$-$C_7$ heterocycloalkylcarbonyl optionally having substituent(s) selected from the group A2, $C_5$-$C_7$ heterocycloalkylamino optionally having substituent(s) selected from the group A2, $C_5$-$C_7$ heterocycloalkylaminocarbonyl optionally having substituent(s) selected from the group A2, aminocarbonyl optionally substituted with one or two $C_1$-$C_6$alkyl optionally having substituent(s) selected from the group A2, amino optionally substituted with one or two $C_1$-$C_6$alkyl optionally having substituent(s) selected from the group A2, 5-membered aromatic heterocyclic group optionally having substituent(s) selected from the group B, 6-membered aromatic heterocyclic group optionally having substituent(s) selected from the group B or heterocyclic group optionally having substituent(s) selected from the group B;

A2 group is halogen, hydroxyl, nitrile, carboxyl, formyl, $C_1$-$C_6$alkyl, $C_1$-$C_6$ alkylcarbonyl, $C_1$-$C_6$ alkoxy, $C_1$-$C_6$alkoxycarbonyl, $C_1$-$C_6$alkylsulfonylamino, 5-membered aromatic heterocyclic group, 6-membered aromatic heterocyclic group, heterocyclic group or 5 to 7-membered heterocycloalkyl group;

B group is halogen, hydroxyl, carbonyl, carboxyl, $C_1$-$C_6$alkyl, halo-$C_1$-$C_6$alkyl, hydroxy-$C_1$-$C_6$alkyl, $C_1$-$C_6$ alkylcarbonyl, $C_1$-$C_6$ alkoxy, halo-$C_1$-$C_6$ alkoxy, $C_1$-$C_6$ alkoxycarbonyl, $C_1$-$C_6$ alkyl substituted with $C_1$-$C_6$ alkoxy, $C_1$-$C_6$alkyl substituted with $C_1$-$C_6$alkoxycarbonyl, $C_3$-$C_8$ cycloalkyl, $C_3$-$C_8$ cycloalkylcarbonyl, $C_3$-$C_8$ cycloalkoxy, aminocarbonyl optionally substituted with one or two $C_1$-$C_6$alkyl, $C_1$-$C_6$ alkylsulfonyl, aminosulfonyl optionally substituted with one or two $C_1$-$C_6$alkyl, $C_1$-$C_6$alkylsulfonylamino, amino optionally substituted with one or two $C_1$-$C_6$alkyl or 5 to 7-membered heterocycloalkyl group;

C group is halogen, hydroxyl, carboxyl, $C_1$-$C_6$ alkylcarbonyl, $C_1$-$C_6$ alkoxy, $C_1$-$C_6$ alkoxycarbonyl, aminocarbonyl optionally substituted with one or two $C_1$-$C_6$alkyl, amino optionally substituted with one or two $C_1$-$C_6$alkyl or 5 to 7-membered heterocycloalkyl group;

provided that wherein $Q^3$ is —N=C($R^9$)—, $R^9$ is methyl and $G^1$ is

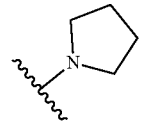 [SMILES: *N1CCCC1]

then $G^2$ is not

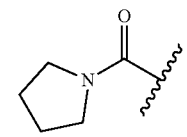

;

$Q^3$ is —N=C($R^9$)—, $R^9$ is hydrogen and $G^1$ is

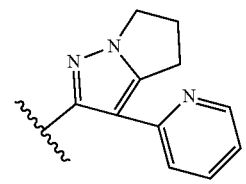 [SMILES: *c1nn2c(c1-c1ccccn1)CCC2]

then $G^2$ is not

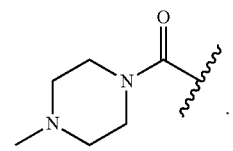 [SMILES: *C(=O)N1CCN(C)CC1]

.

In the compounds or their pharmacologically acceptable salts of the present embodiment, preferable substituents are as follows.

$Q^1$ is —C($R^3$)=C($R^4$)—, —C($R^5$)=N—, —N=C($R^5$)—, oxygen or sulfur; preferably, —C($R^3$)=C($R^4$)—, —C($R^5$)=N— or —N=C($R^5$)—; and more preferably, —C($R^3$)=C($R^4$)— or —C($R^5$)=N—.

$Q^2$ is C($R^6$) or nitrogen; and preferably, C($R^6$).

$Q^3$ is —C($R^7$)=C($R^8$)—, —C($R^9$)=N—, —N=C($R^9$)—, oxygen or sulfur; preferably, —C($R^3$)=C($R^4$)—, —C($R^5$)=N— or —N=C($R^5$)—; and more preferably, —C($R^3$)=C($R^4$)—.

$Q^4$ is C($R^{10}$) or nitrogen; and preferably, C($R^{10}$).

$G^1$ is a phenyl, a 5-membered heteroaromatic ring, a 6-membered heteroaromatic ring, a bicyclic heteroaromatic ring consisting of 8 to 10 atoms, a fused heterocyclic ring consisting of 9 or 10 atoms, a $C_3$-$C_8$ cycloalkyl group or a 3- to 8-membered heterocycloalkyl group, which are optionally substituted with one or more substituents selected from the group A; preferably, a group selected from the following C1) to C44); and more preferably, a group selected from the group consisting of C24) to C44).

$G^2$ is a —C(=O)—X, —C(=O)—CHR$^1$R$^2$, —CH(OH)—CHR$^1$R$^2$, —CH(NY$_2$)—CHR$^1$R$^2$, —S—CHR$^1$R$^2$, —S(=O)$_2$—X, —S(=O)—CHR$^1$R$^2$ or —SO$_2$—CHR$^1$R$^2$; and preferably, —C(=O)—X.

$R^1$ and $R^2$ are the same or different and are hydrogen or one selected from $C_1$-$C_6$ alkyl, $C_1$-$C_6$ alkoxy, and $C_3$-$C_8$ cycloalkyl, which are optionally substituted with one or more substituents selected from the group C; or $R^1$ and $R^2$, together with the nitrogen atom to which they are attached, form a 3- to 10-membered nitrogen-containing heterocycloalkyl group optionally substituted with one or more substituents selected from the group B. The nitrogen-containing heterocycloalkyl group has a monocyclic or bicyclic structure which may include fused bicyclic, bridged bicyclic and spiro bicyclic structures, and optionally contains a silicon atom, a nitrogen atom, and/or an oxygen atom. $R^1$ and $R^2$ preferably form, together with the nitrogen atom to which they are attached, a 3- to 10-membered nitrogen-containing heterocycloalkyl group optionally substituted with one or more substituents selected from the group B; and more preferably, 5- or 6-membered nitrogen-containing heterocycloalkyl group.

$R^3$ and $R^4$ are the same or different and are hydrogen, halogen, —CN, —COOY, —NHC(O)Y or one selected from $C_1$-$C_6$ alkyl, $C_1$-$C_6$ alkoxy, and $C_3$-$C_8$ cycloalkyl, which are optionally substituted with one or more substituents selected from the group C; and preferably, hydrogen, halogen or $C_1$-$C_6$ alkyl.

$R^5$ is hydrogen, —CN, —COOY, —NHC(O)Y or one selected from $C_1$-$C_6$ alkyl, $C_1$-$C_6$ alkoxy, and $C_3$-$C_8$ cycloalkyl, which are optionally substituted with one or more substituents selected from the group C; and preferably, hydrogen, halogen or $C_1$-$C_6$ alkyl.

$R^6$ is hydrogen, halogen, —CN, —COOY, —NHC(O)Y or one selected from $C_1$-$C_6$ alkyl, $C_1$-$C_6$ alkoxy, and $C_3$-$C_8$ cycloalkyl, which are optionally substituted with one or more substituents selected from the group C; and preferably, hydrogen, halogen or $C_1$-$C_6$ alkyl.

$R^7$ and $R^8$ are the same or different and are hydrogen, halogen, —CN, —COOY, —NHC(O)Y or one selected from $C_1$-$C_6$ alkyl, $C_1$-$C_6$ alkoxy, and $C_3$-$C_8$ cycloalkyl, which are optionally substituted with one or more substituents selected from the group C; and preferably, hydrogen, halogen or $C_1$-$C_6$ alkyl.

$R^9$ is hydrogen, —CN, —COOY, —NHC(O)Y, or one selected from $C_1$-$C_6$ alkyl, $C_1$-$C_6$ alkoxy, and $C_3$-$C_8$ cycloalkyl, which are optionally substituted with one or more substituents selected from the group C; and preferably, hydrogen, halogen or $C_1$-$C_6$ alkyl.

$R^{10}$ is hydrogen, halogen, —CN, —COOY, —NHC(O)Y or one selected from $C_1$-$C_6$ alkyl, $C_1$-$C_6$ alkoxy, and $C_3$-$C_8$ cycloalkyl, which are optionally substituted with one or more substituents selected from the group C; and preferably, hydrogen, halogen or $C_1$-$C_6$ alkyl.

Y is hydrogen or one selected from $C_1$-$C_6$ alkyl, $C_1$-$C_6$ alkoxy, and $C_3$-$C_8$ cycloalkyl, which are optionally substituted with one or more substituents selected from the group C.

$R^{11}$, $R^{12}$, and $R^{13}$ are the same or different and are hydrogen, halogen, $C_1$-$C_6$ alkyl, halo($C_1$-$C_6$) alkyl, $C_1$-$C_6$ alkoxy or halo($C_1$-$C_6$) alkoxy; preferably, hydrogen, halogen, $C_1$-$C_6$ alkyl or halo($C_1$-$C_6$) alkyl; and more preferably, hydrogen, fluorine, methyl or trifluoromethyl.

$R^{14}$, $R^{15}$, $R^{17}$, $R^{18}$, $R^{19}$, and $R^{20}$ are the same or different and are hydrogen, halogen, hydroxy, nitrile, carboxyl formyl, aminocarbonyl having an amino group which optionally contains one or more substituents selected from the group A1, and optionally containing 1 or 2 $C_1$-$C_6$ alkyl groups, or one selected from $C_1$-$C_6$ alkyl, amino, $C_1$-$C_6$ alkylcarbonyl, $C_1$-$C_6$ alkoxy, $C_1$-$C_6$ alkoxycarbonyl, $C_1$-$C_6$ alkylsulfonylamino, $C_1$-$C_6$ alkylsulfonyl, and $C_3$-$C_8$ cycloalkyl, which are optionally substituted with one or more substituents selected from the group A1; preferably, hydrogen, halogen, carboxyl, $C_1$-$C_6$ alkyl optionally substituted with one or more substituents selected from the group A1, or $C_1$-$C_6$ alkylsulfonylamino optionally substituted with one or more substituents selected from the group A1; and more preferably, hydrogen, fluorine, carboxyl, methyl, ethyl, difluoroethyl or dimethylamino.

$R^{16}$ is hydrogen, $C_1$-$C_6$ alkylaminosulfonyl, one selected from $C_1$-$C_6$ alkyl, $C_1$-$C_6$ alkylcarbonyl, $C_1$-$C_6$ alkoxycarbonyl, $C_1$-$C_6$ alkylsulfonyl, $C_3$-$C_8$ cycloalkyl, 5- to 7-membered heterocycloalkylcarbonyl, and 5- to 7-membered heterocycloalkylaminocarbonyl, which are optionally substituted with one or more substituents selected from the group A1, or aminocarbonyl optionally containing 1 or 2 $C_1$-$C_6$ alkyl groups optionally substituted with one or more substituents selected from the group A1, or a 5- or 6-membered heteroaromatic ring optionally substituted with one or more substituents selected from the group B; and preferably, hydrogen, methyl, acetyl, hydroxyethyl, aminoethyl or methylsulfonylethyl.

Examples of preferable compounds of the present embodiment are as follows.

Chemical formula 27

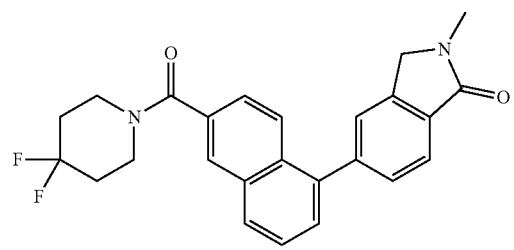

-continued

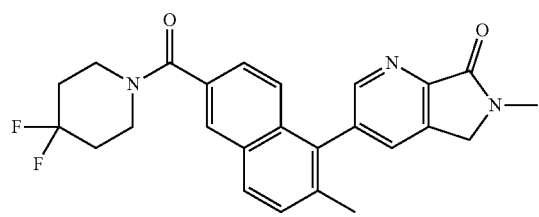
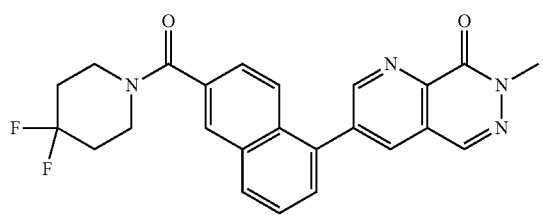
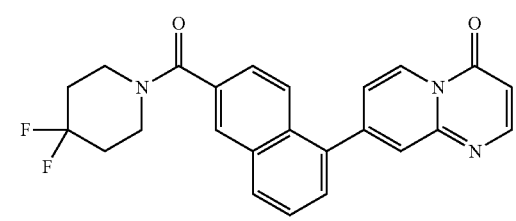
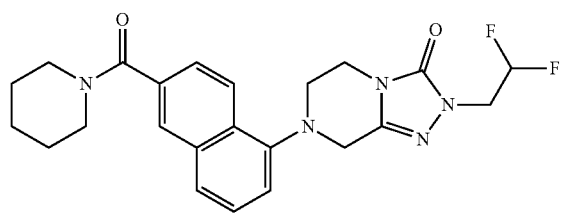
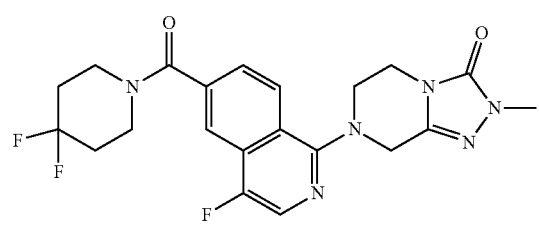
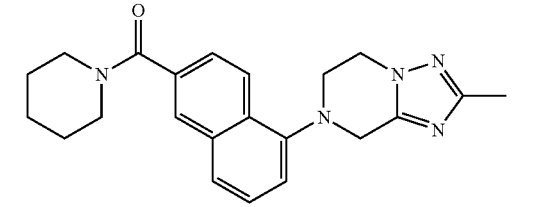
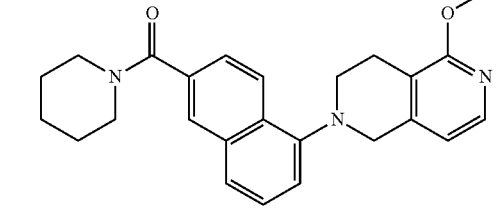
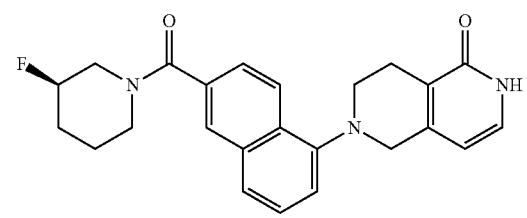
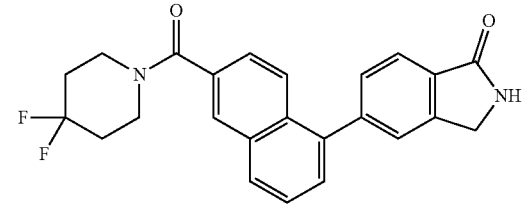
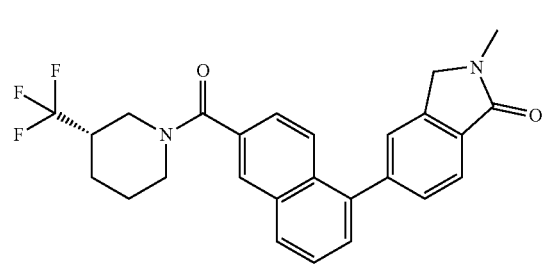
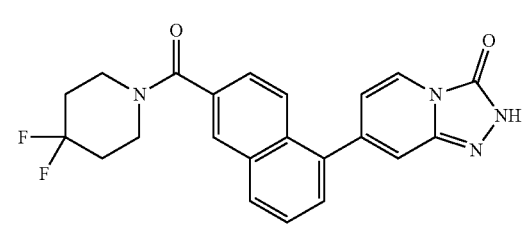
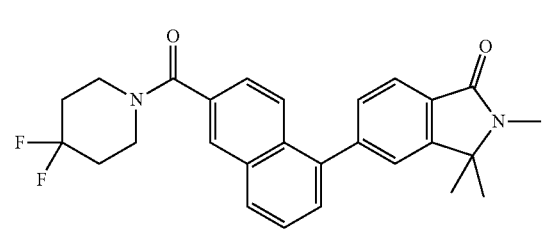
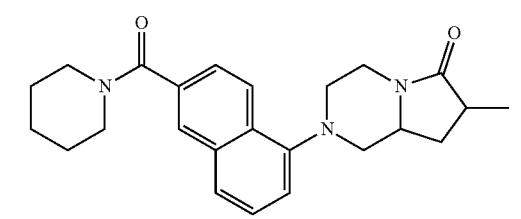
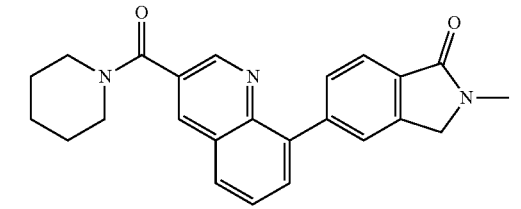

-continued

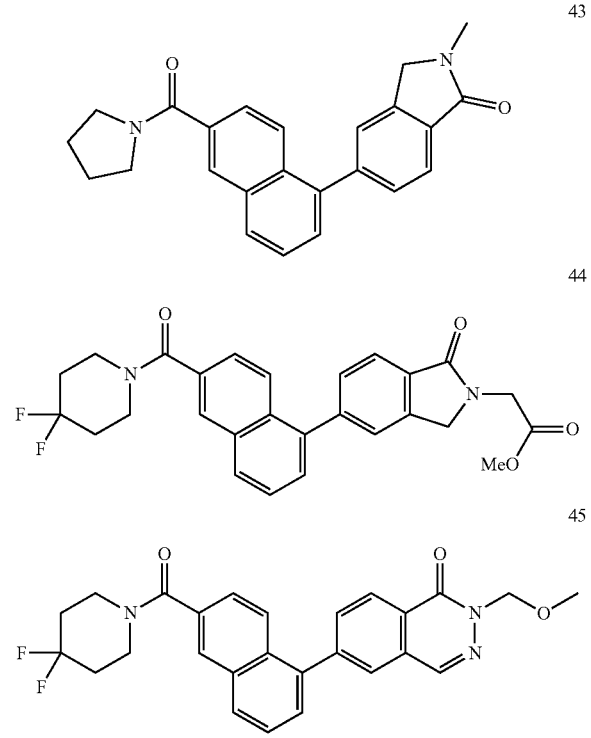

57
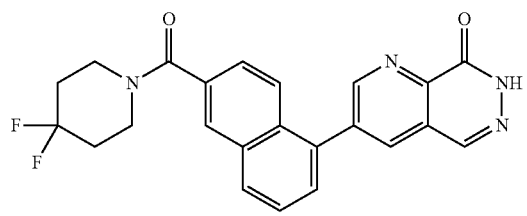
58
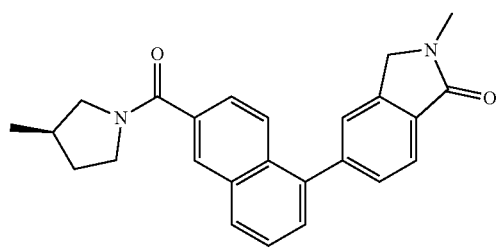
59
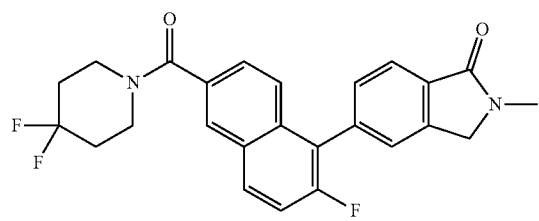
60
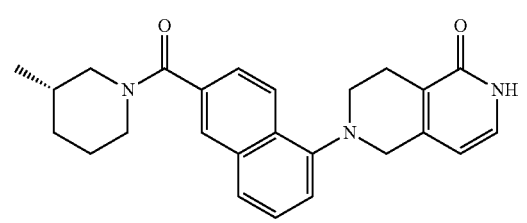
61
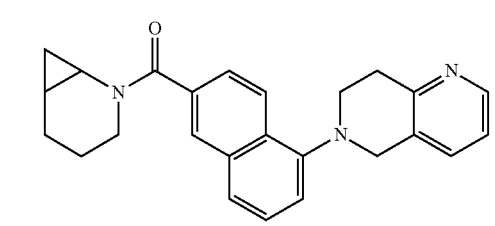
62
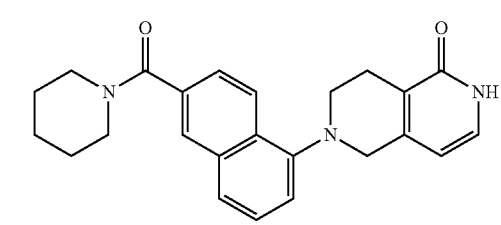
63
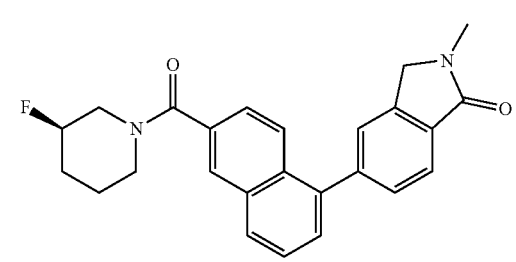
64
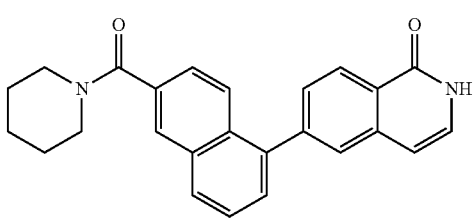
65
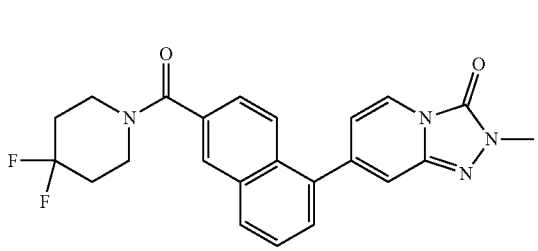
66
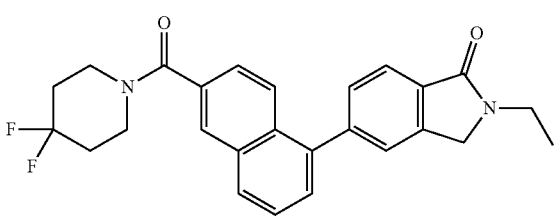
67
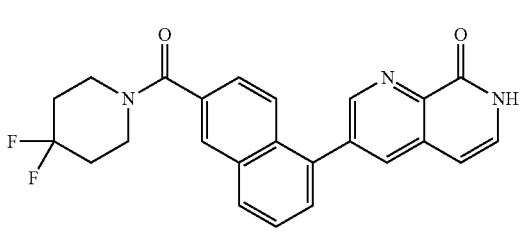
68
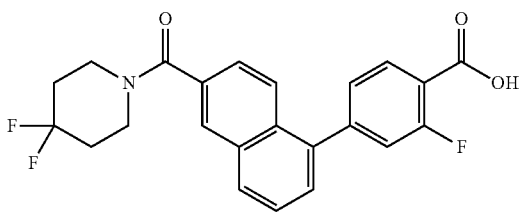
69
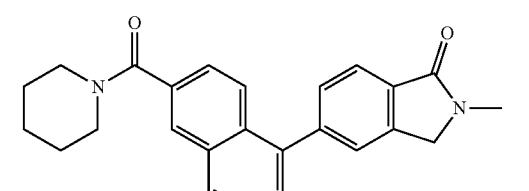
70
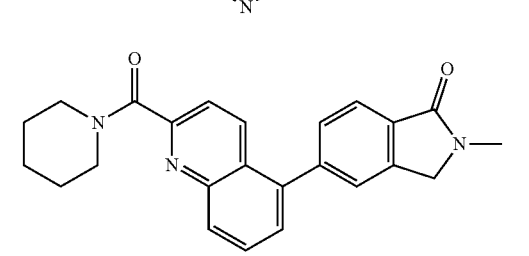

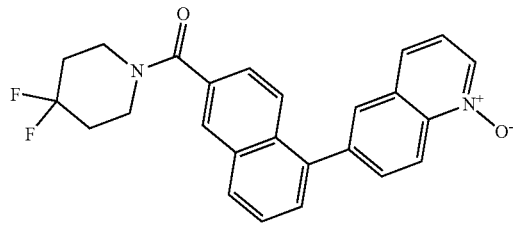
71
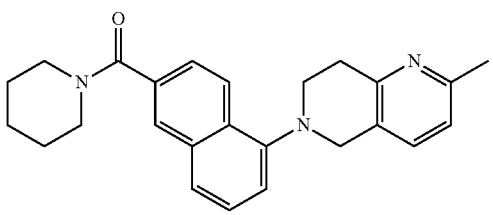
77
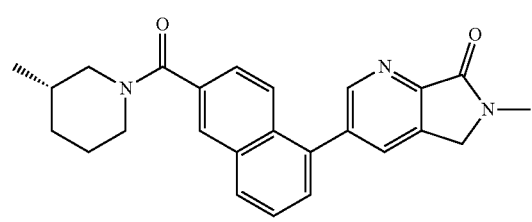
72
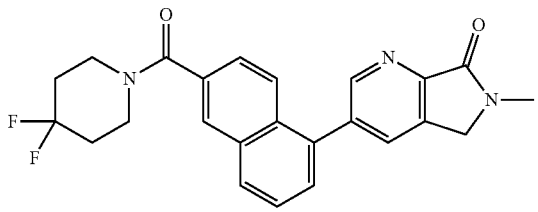
78
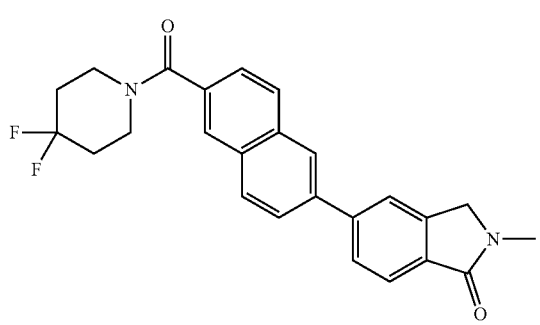
73
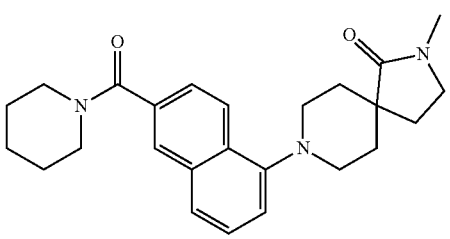
79
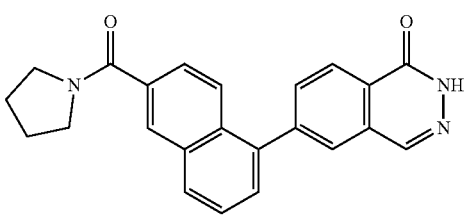
80
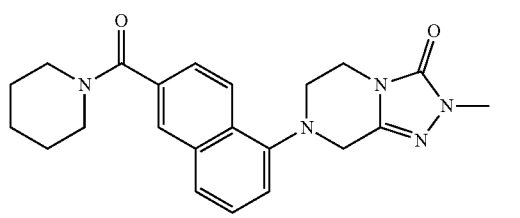
74
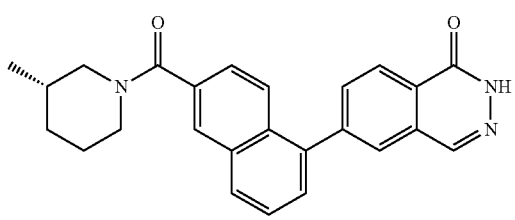
81
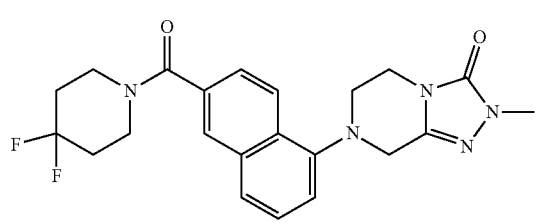
75
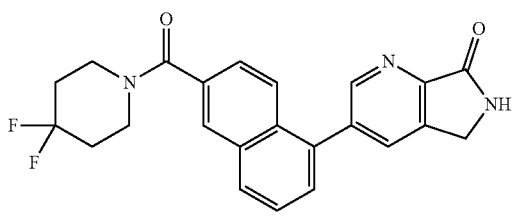
82
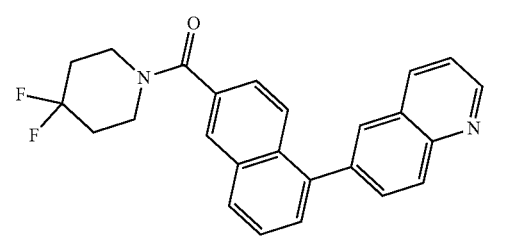
76
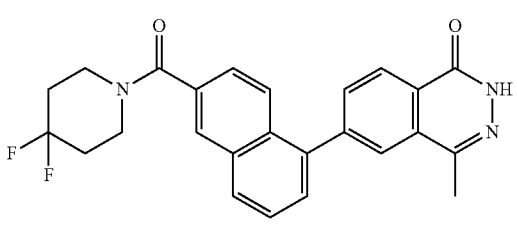
83

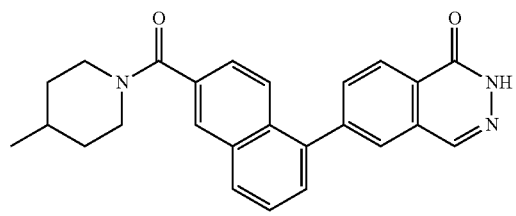
84
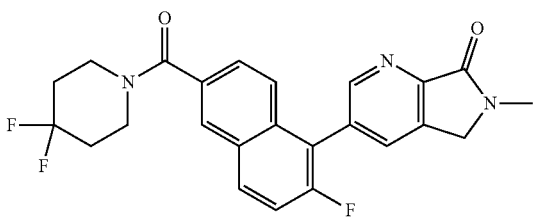
85
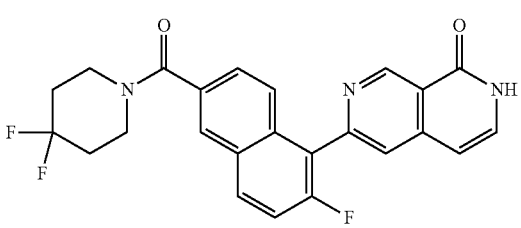
86
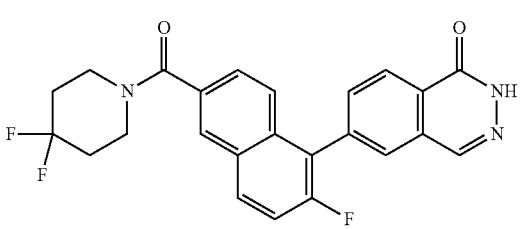
87
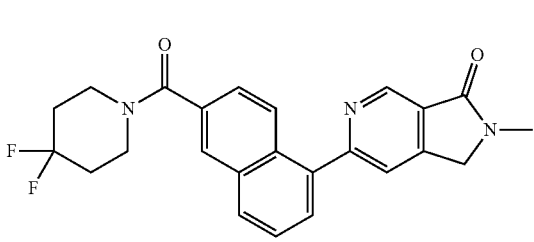
88
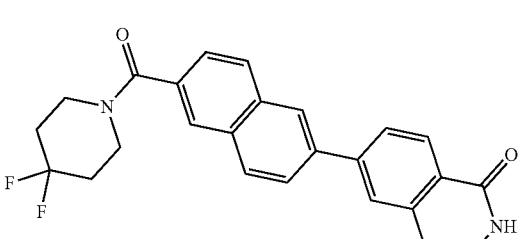
89
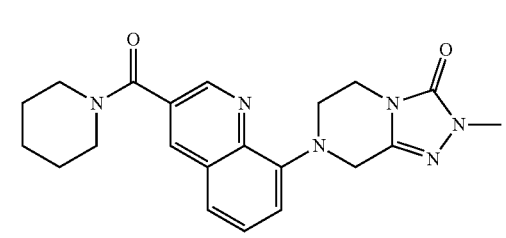
90
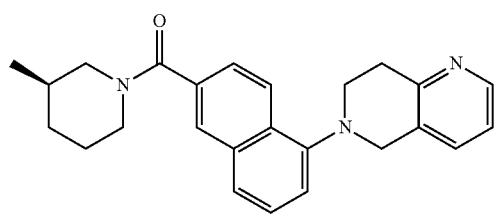
91
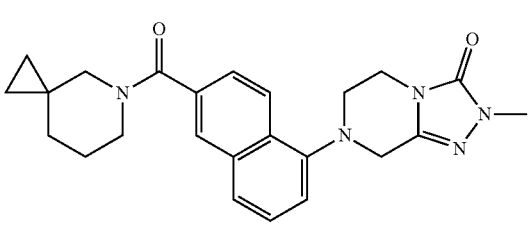
92
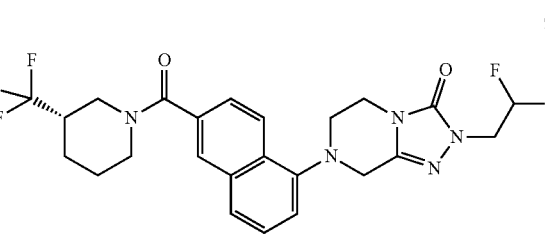
93
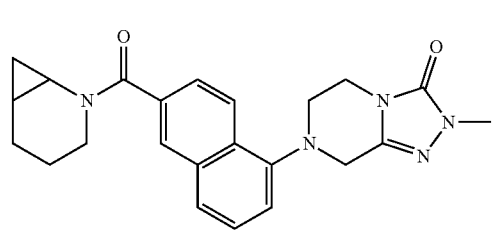
94
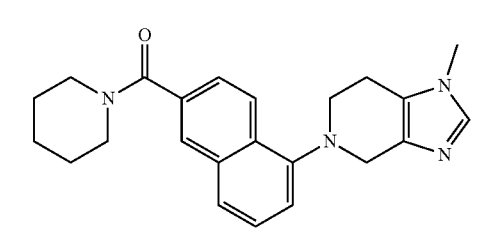
95
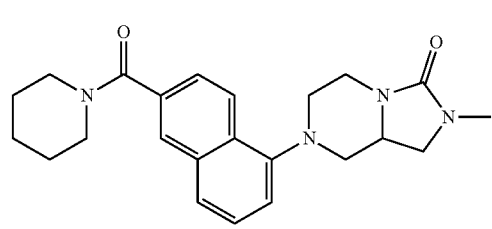
96
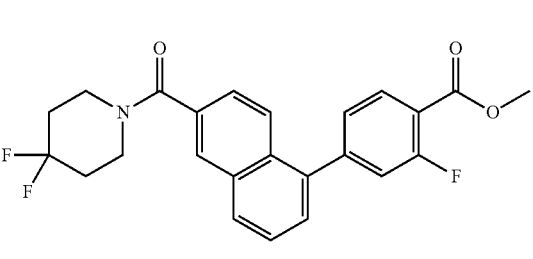
97

98
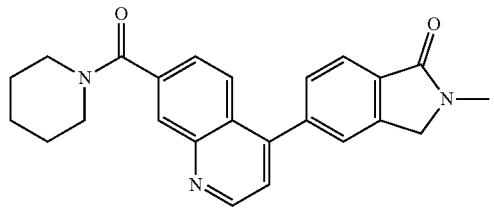
99
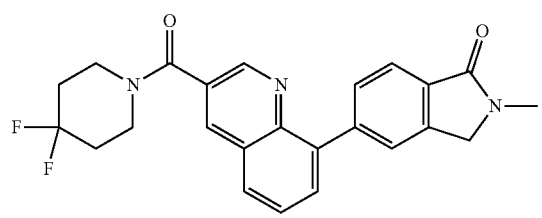
100
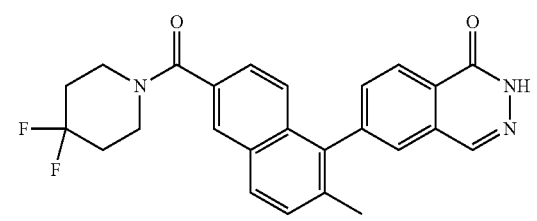
101
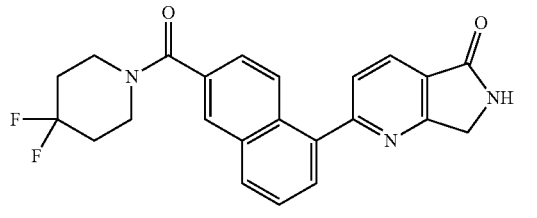
102
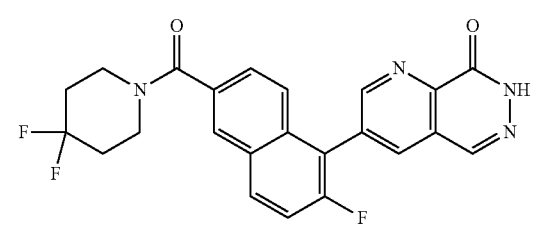
103
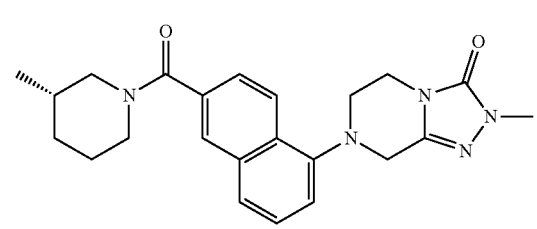
104
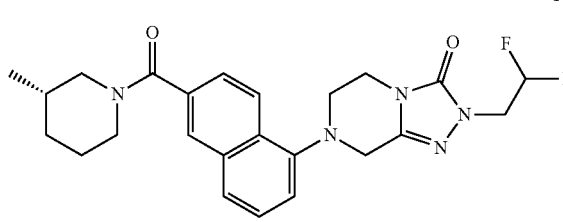
105
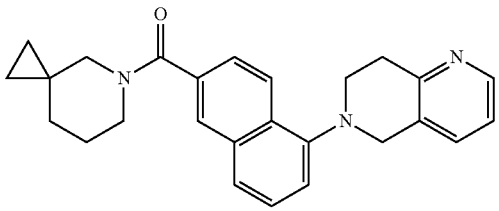
106
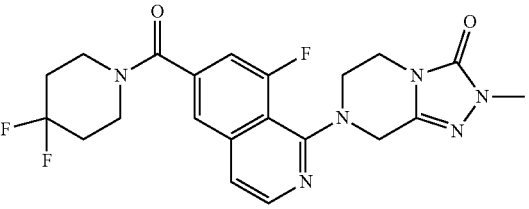
107
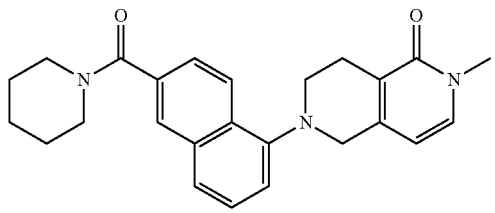
108
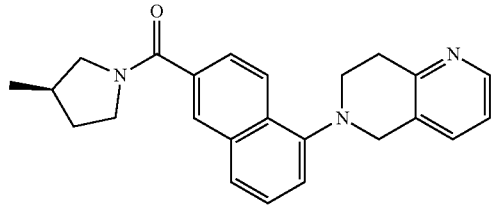
109
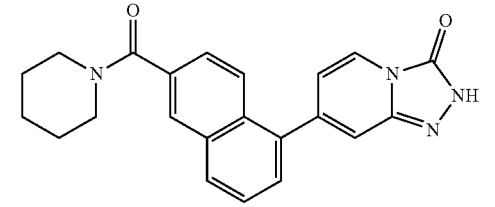
110
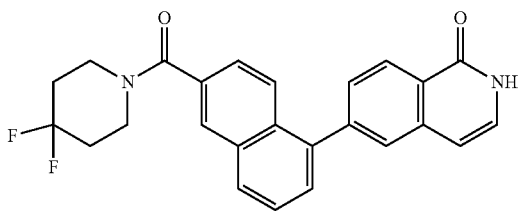
111
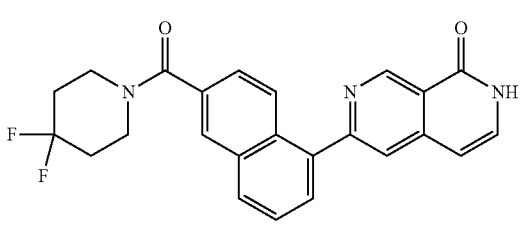

112 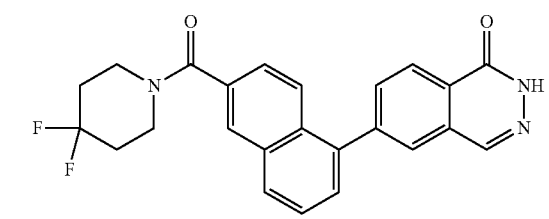
113 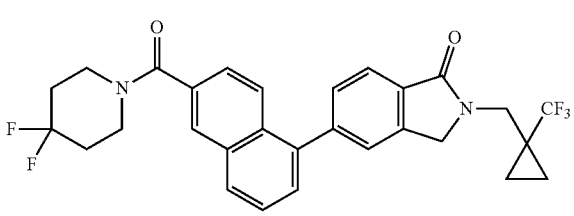
114 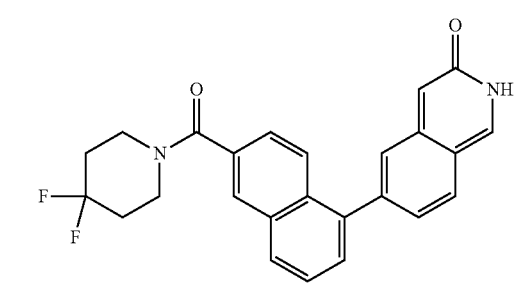
115 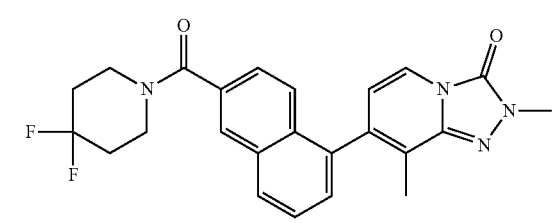
116 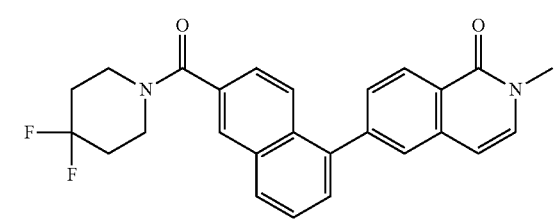
117 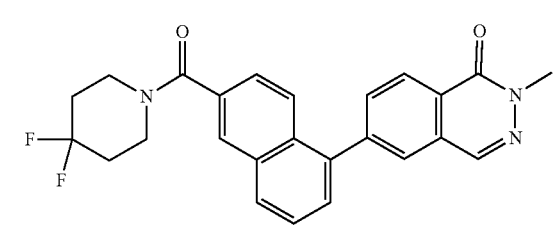
118 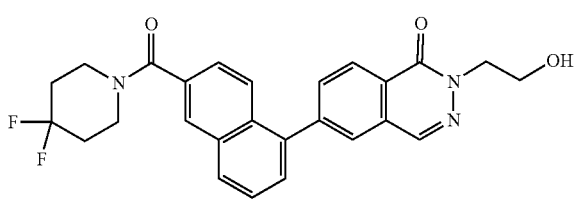
119 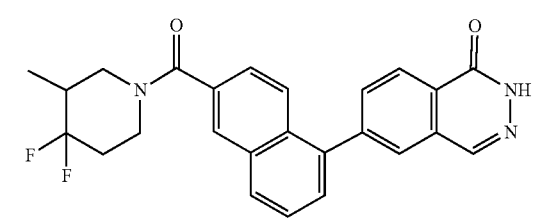
120 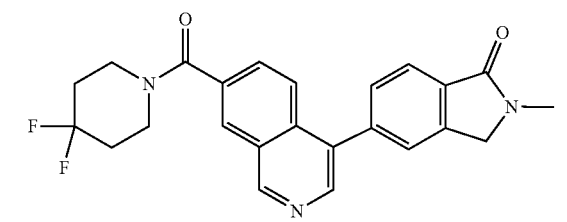
121 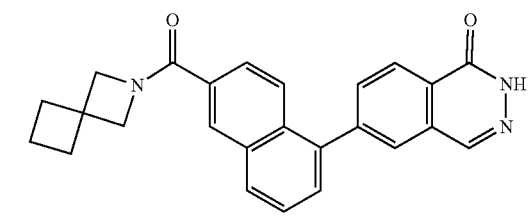
122 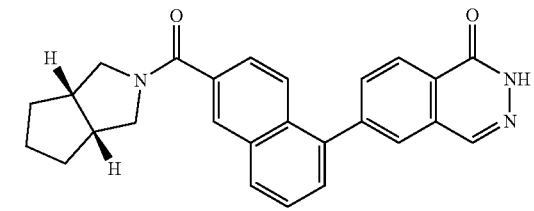
123 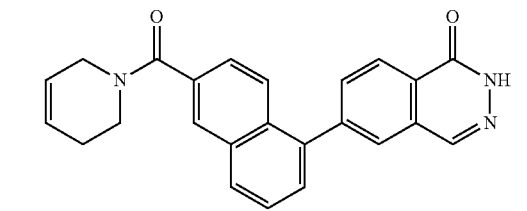
124 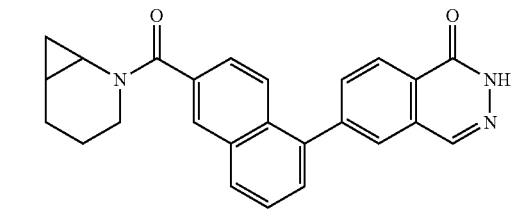

| 125 | 131 |
|---|---|
| 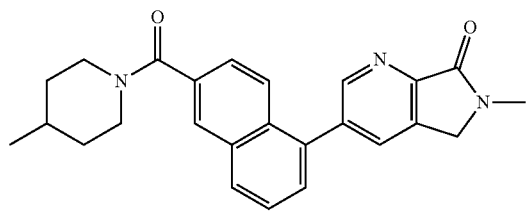 | 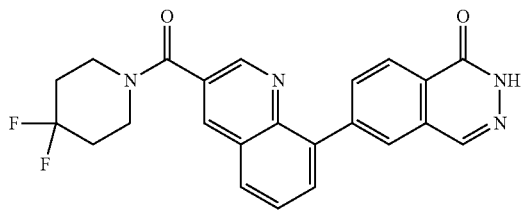 |
| 126 | 132 |
| 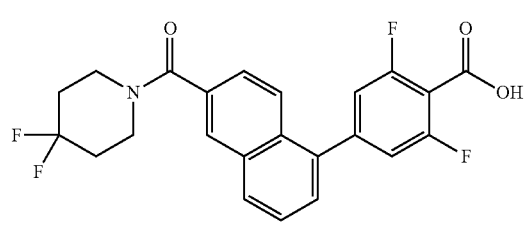 | 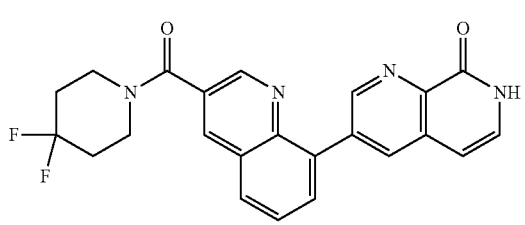 |
| 127 | 133 |
| 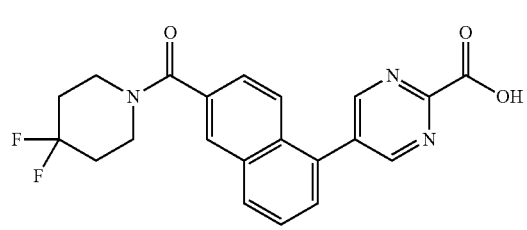 | 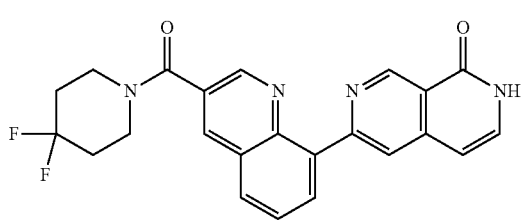 |
| 128 | 134 |
| 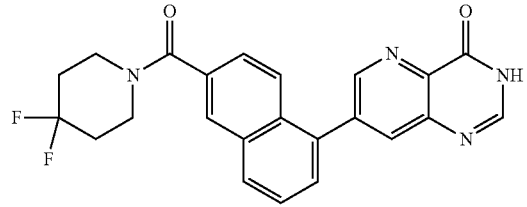 | 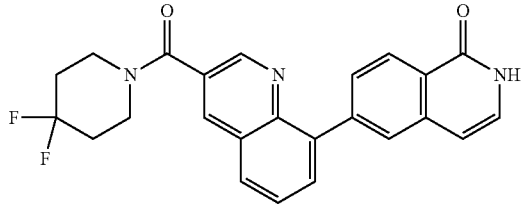 |
| 129 | 135 |
| 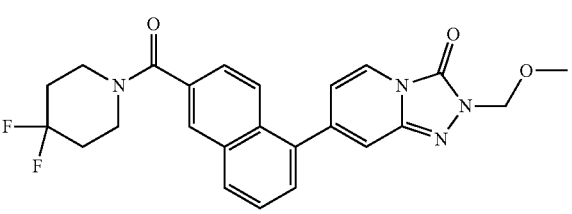 | 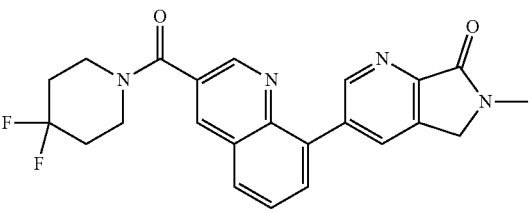 |
| 130 | 136 |
| 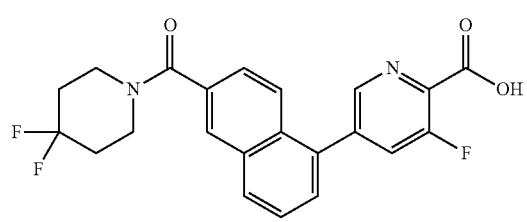 | 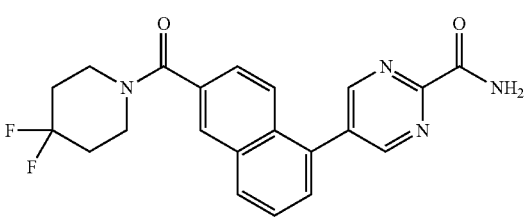 |

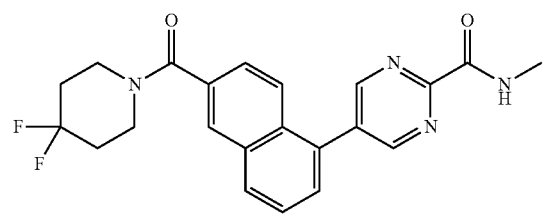
137
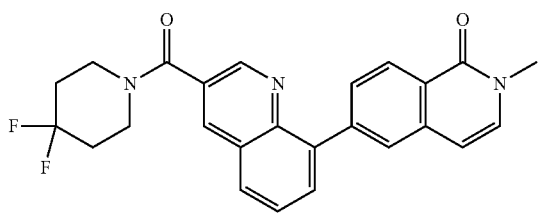
143
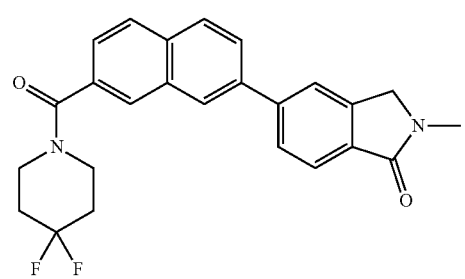
138
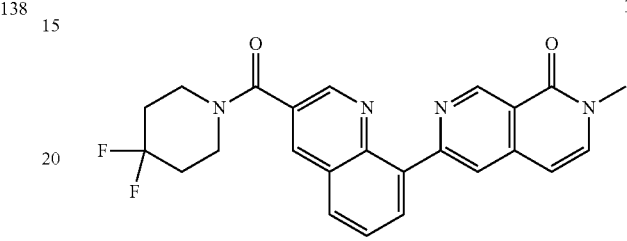
144
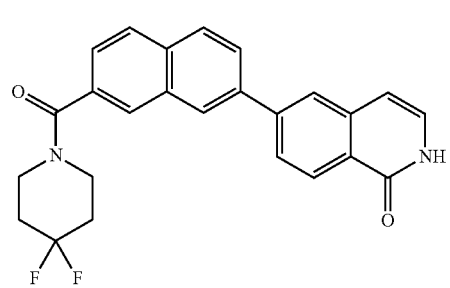
139
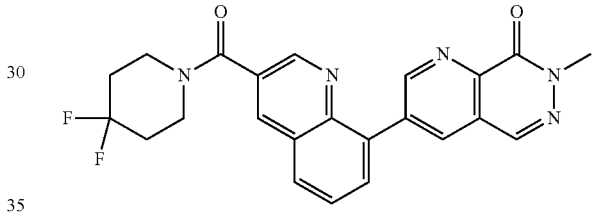
145
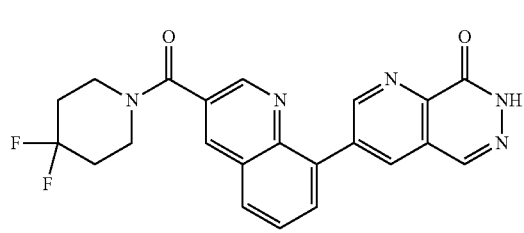
140
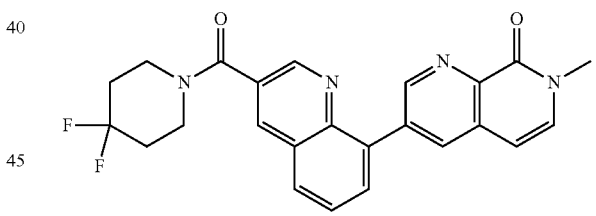
146
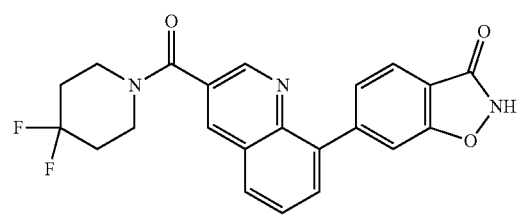
141
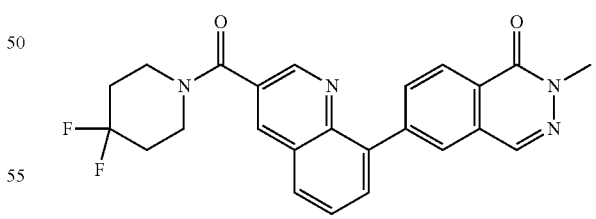
147
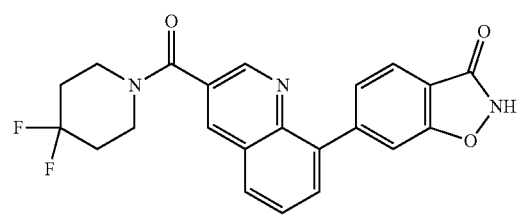
142
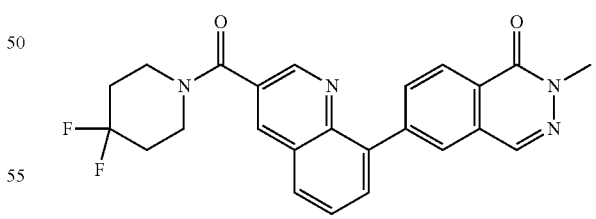
148

149 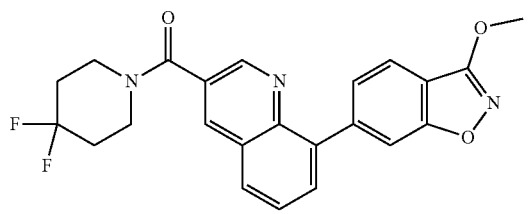
150 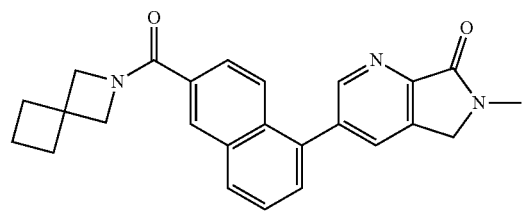
151 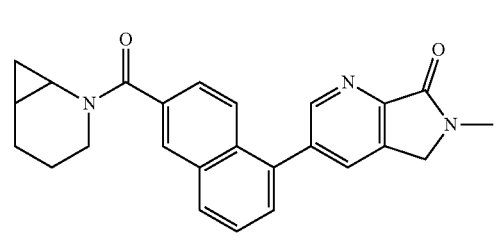
152 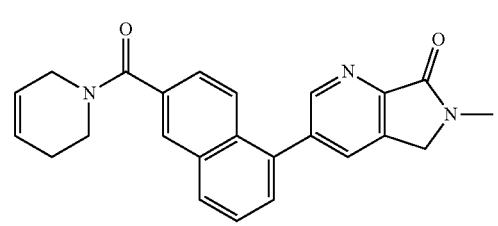
153 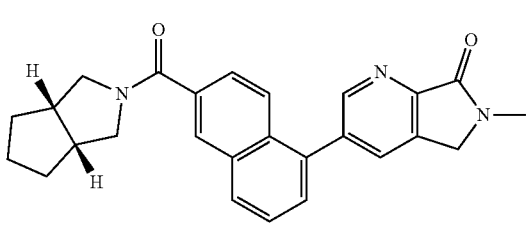
154 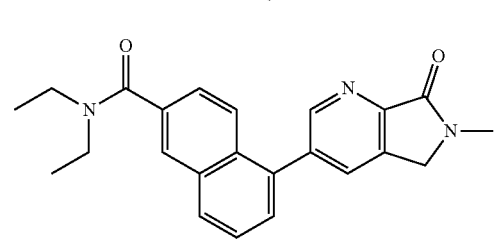
155 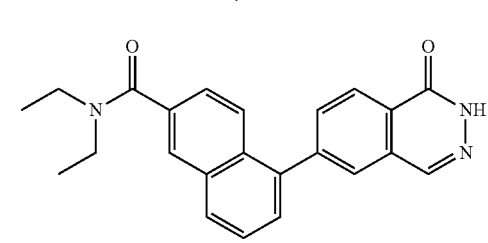
156 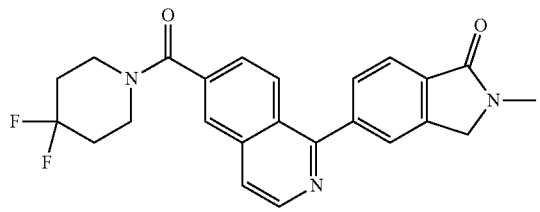
157 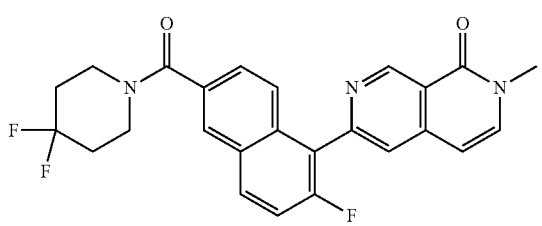
158 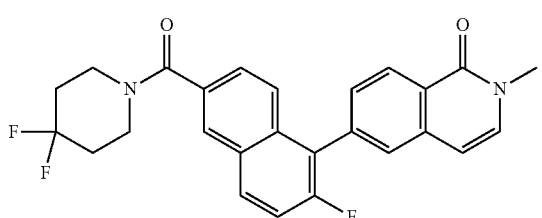
159 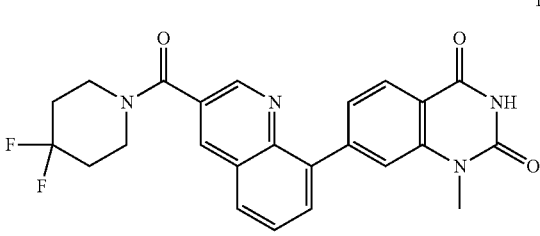
160 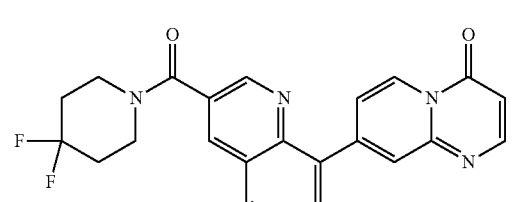
161 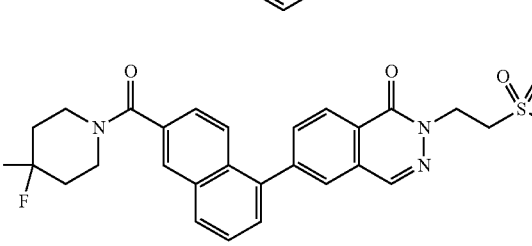
162 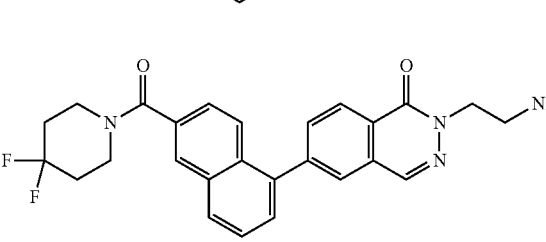

163
164
165
166
167
168
169

170
171
172
173
174
175
176

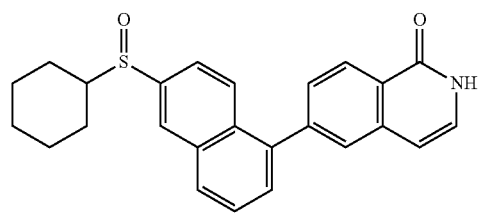 177
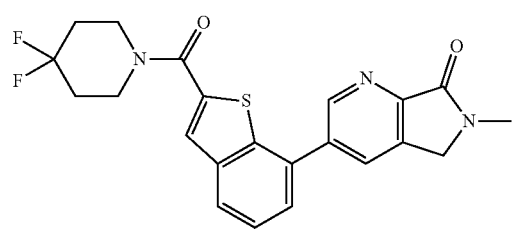 [SMILES: CN1Cc2cc(-c3cccc4cc(C(=O)N5CCC(F)(F)CC5)sc34)cnc2C1=O] 178
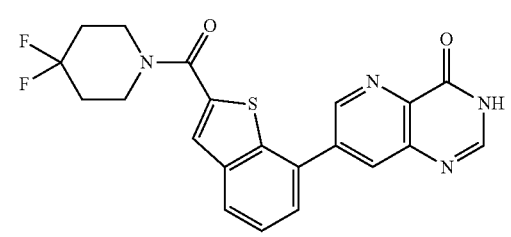 [SMILES: O=C(c1cc2cccc(-c3cnc4c(=O)[nH]cnc4c3)c2s1)N1CCC(F)(F)CC1] 179
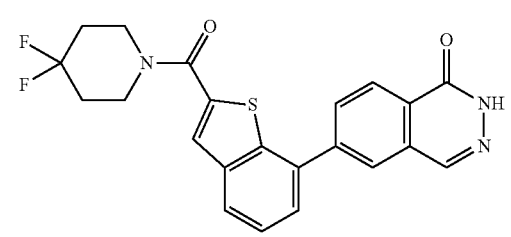 180
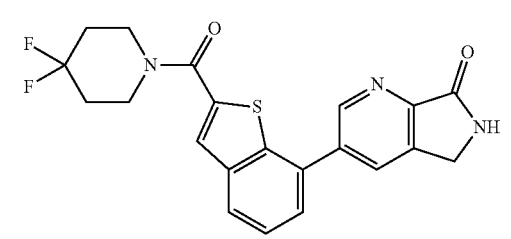 181
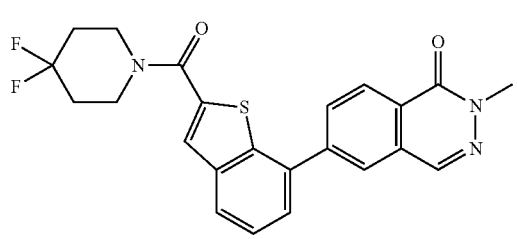 182
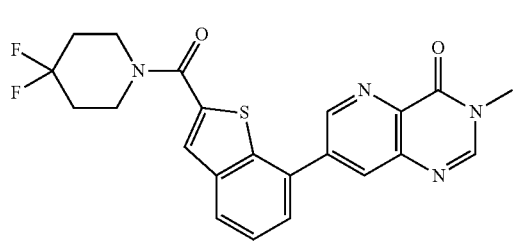 183
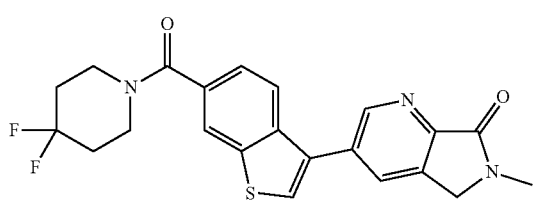 184
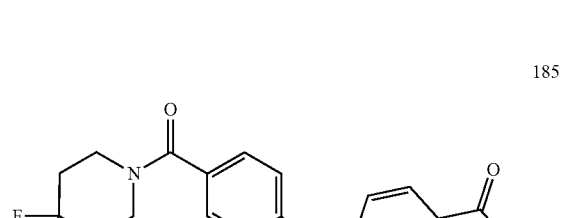 185
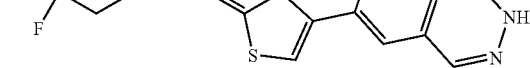 186
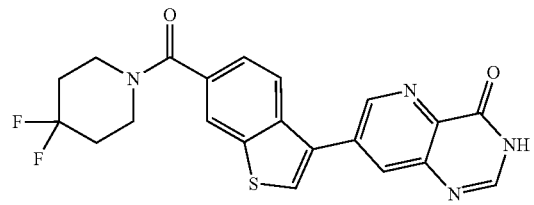 187
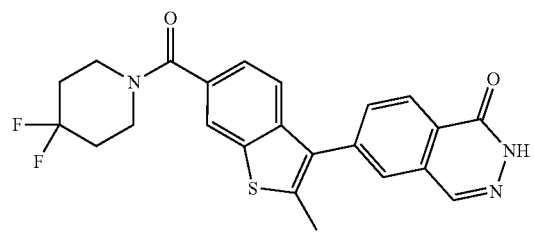 188
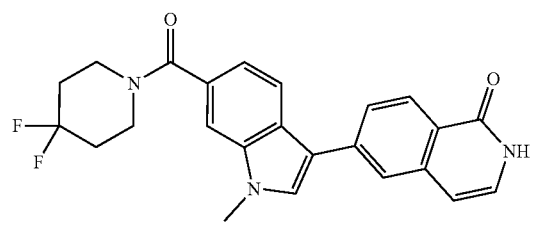 189
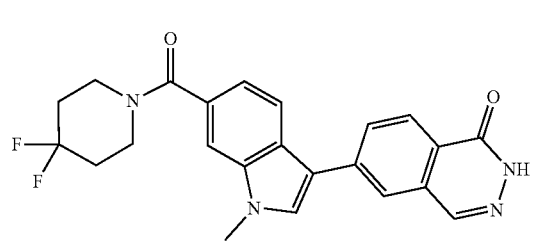

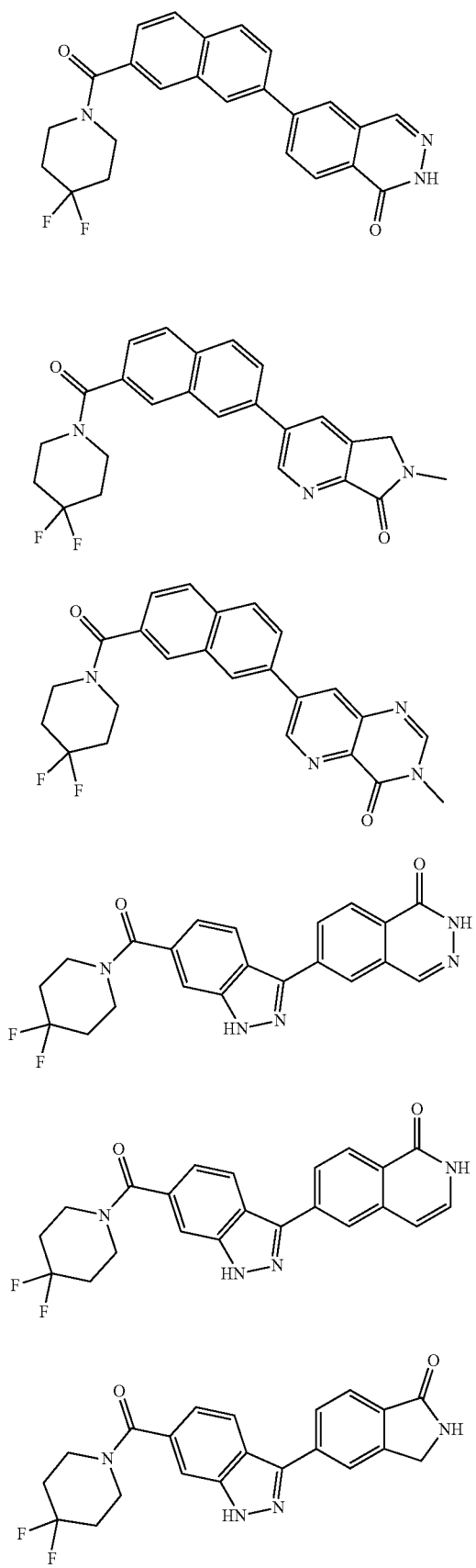
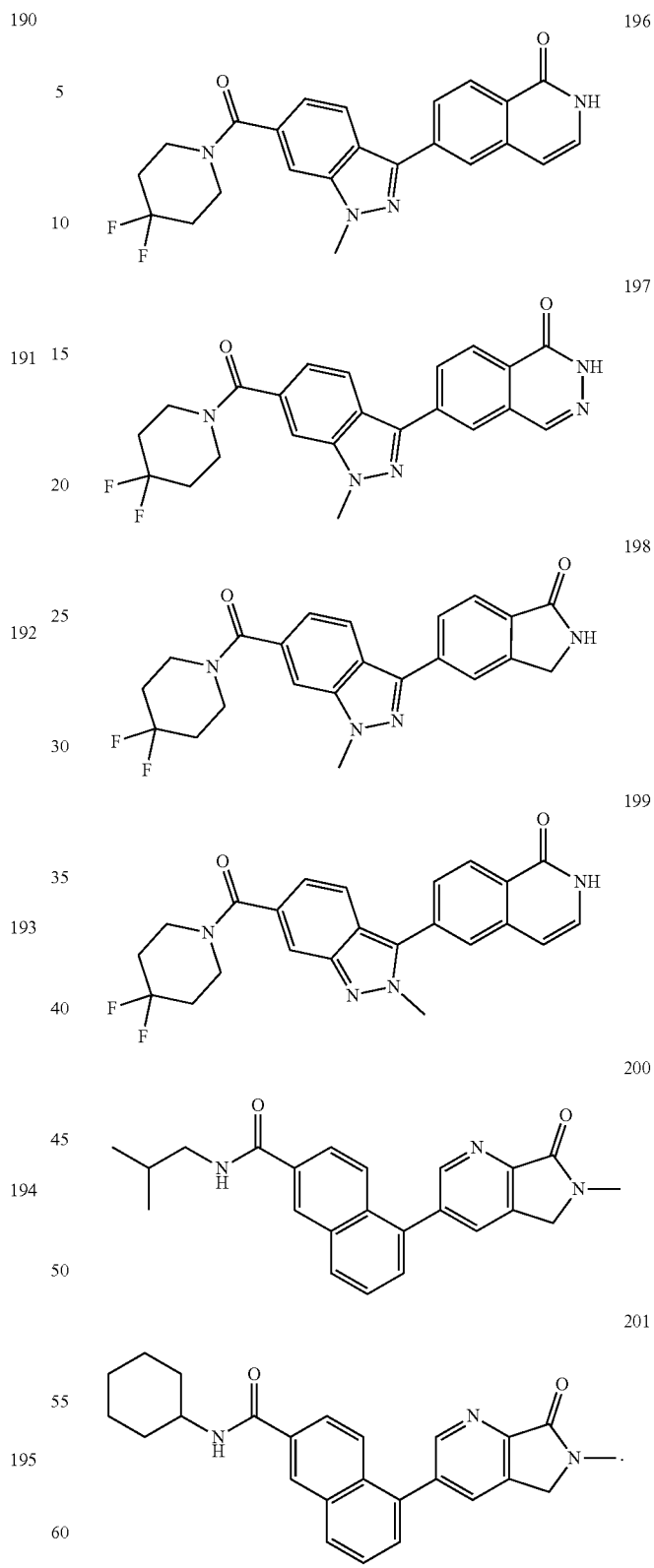
The compound (1), (2) and (3) of the present embodiment can be formulated into a pharmacologically acceptable salt thereof according to a routine method, if necessary. The term "pharmacologically acceptable salt" means a salt of a compound with a pharmaceutically acceptable non-toxic base or acid (e.g., with an inorganic or organic base or an inorganic or organic acid).

Examples of salts derived from a pharmaceutically acceptable non-toxic base include those with an inorganic base such as sodium salts, potassium salts, calcium salts, and magnesium salts and those with an organic base such as piperidine, morpholine, pyrrolidine, arginine, and lysine.

Examples of salts derived from a pharmaceutically acceptable non-toxic acid includes acid salts of a mineral acid such as hydrochloric acid, hydrobromic acid, sulfuric acid, and nitric acid and salts formed by the combination of a compound with an organic acid such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, and palmitic acid.

Furthermore, the compounds (1), (2), and (3) of the present embodiment and pharmacologically acceptable salts thereof may be present as a hydrate or solvate. Any hydrates and solvates formed from the derivatives represented by the formulas (1), (2), and (3) and salts thereof, including the preferred compounds specifically described above, are encompassed in the scope of the present invention. Examples of solvents that can solvate include methanol, ethanol, 2-propanol, acetone, ethyl acetate, dichloromethane, and diisopropyl ether.

The compounds (1), (2) and (3) of the present embodiment and pharmacologically acceptable salts thereof may be racemates, enantiomers/diastereomers, stereoisomers or rotational isomers.

When the compound (1), (2) or (3) of the present embodiment is an enantiomer having one or more asymmetric carbon atoms, the absolute configuration at each asymmetric carbon atom may be either the (S) configuration or the (R) configuration. These enantiomers as well as their mixtures are all encompassed in the present invention. Furthermore, as to the mixtures of enantiomers, their racemic modifications containing equal amounts of both enantiomers are also encompassed in the present invention. When the compound (1), (2) or (3) of the present invention is a solid or crystalline, racemic compounds, racemic mixtures, and racemic solid solutions are also encompassed in the present invention.

When one or more of the compounds (1), (2) and (3) of the present embodiment have their geometric isomer(s), the present invention encompasses all of them.

When one or more of the compounds (1), (2) and (3) of the present embodiment have their tautomer(s), the present invention encompasses all of them. In addition, the pharmacologically acceptable salts thereof include their prototropic tautomers.

For the compounds (1), (2) and (3) of the present embodiment and pharmacologically acceptable salts thereof, compounds labelled with a radioisotope (e.g., $^3$H, $^{14}$C, and $^{35}$S) etc. are included in the compounds of the present invention. In addition, their deuterated forms in which one or more $^1$H atoms have been replaced by $^2$H(D) are also encompassed in the present invention.

The names of the compounds (1), (2), and (3) of the present embodiment were created using ChemDraw Professional version 15.0.0.106 (PerkinElmer Informatics, Inc.®).

The term "15-PGDH inhibitory function" used in the present embodiment refers to a function of inhibiting 15-hydroxyprostaglandin dehydrogenase (15-PGDH), which is an important enzyme in the inactivation of active prostaglandins (e.g., $PGD_2$, $PGE_1$, $PGE_2$, $PGF_{2\alpha}$, and $PGI_2$), hydroxyeicosatetraenoic acids (HETEs), and pro-resolving lipid mediators (e.g., RvD1, RvD2, RvE1, MaR1, and $LXA_4$) (hereinafter, they are collectively referred to as substrates for 15-PGDH) For example, 15-PGDH converts $PGE_2$ into 15-keto $PGE_2$ by catalyzing the oxidation of the hydroxyl group at the C15 position.

The compounds (1), (2), and (3) of the present embodiment and pharmacologically acceptable salts thereof are shown to suppress degradation of $PGE_2$, for example, by inhibiting 15-PGDH. Consequently, the compound (1) of the present invention and pharmaceutically acceptable salts thereof can be applied to diseases in which the inactivation of substrates for 15-PGDH is involved. Thus, 15-PGDH inhibitors are useful as therapeutic and/or prophylactic agents for fibrosis (e.g., pulmonary fibrosis, idiopathic pulmonary fibrosis, liver fibrosis, sclerosis, and myelofibrosis), inflammatory diseases (e.g., aggravation of chronic obstructive pulmonary disease (COPD), acute lung injury, sepsis, asthma, and lung diseases, inflammatory bowel disease, gastrointestinal ulcer (NSAIDs causative ulcer, and the like), autoinflammatory diseases (Behcet's disease, and the like), vascular inflammatory syndrome, acute liver injury, acute kidney injury, and non-alcoholic steatohepatitis (NASH) atopic dermatitis, psoriasis, Interstitial cystitis, prostatitis syndrome (chronic premature gland inflammation/chronic pelvic pain syndrome, and the like)), cardiovascular diseases (e.g., pulmonary hypertension, angina pectoris, myocardial infarction, chronic kidney disease, cerebral apoplexy, renal failure, and peripheral circulatory disturbance), wound (e.g., diabetic ulcers, burn, and bedsore), autoimmune diseases (e.g., multiple sclerosis and rheumatoid arthritis), graft-versus-host disease, hair growth, bone marrow transplantations, organ transplantations, osteoporosis, otologic diseases (e.g., hearing loss, tinnitus, dizziness, and balance disorders), ophthalmologic diseases (e.g., glaucoma and dry eye), diabetes and/or underactive bladder.

Method of producing the compounds (1), (2), (3) and (4) of the present embodiment The compounds (1), (2), (3) and (4) of the present embodiment and pharmacologically acceptable salts thereof can be produced using any one of the methods described in detail in the following Schemes 1-15.

The compounds (1), (2), (3) and (4) of the present embodiment can be produced using one of various methods of synthesis. A representative method of producing the compound (1) of the present invention is described below.

Scheme 1

Step 1-1

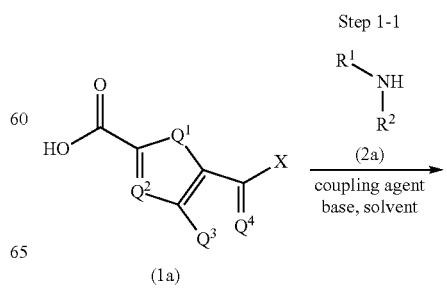

(1a)

-continued

Step 1-2

(3a) + bis(pinacolato)diboron → (4a)
Pd catalyst, base, solvent, heat

Step 1-3

(4a) + Ar—X (5a) → final compound
Pd catalyst, base, solvent, heat $Q^1$, $Q^2$, $Q^3$ and $Q^4$ are as described in claim [1]
X = I, Br, Cl, OTf
$R^1$ and $R^2$ are as described in claim [1]
Ar = (hetero)aryl Step 1-1

This step is a step of converting the carboxylic acid group of the compound (1a) to produce the compound (3a) by reaction with the amine (2a) in a solvent in the presence of a coupling agent and a base. The coupling agent used may include 1-[bis(dimethylamino)methylene]-1H-1,2,3-triazolo[4,5-b]pyridinium 3-oxid hexafluorophosphate (HATU), N-Ethyl-N'-(3-dimethylaminopropyl) carbodiimide hydrochloride (EDCI), 1-hydroxybenzotriazole (HOBt), dicyclohexylcarbodiimide (DCC), (benzotriazol-1-yl-oxytripyrrolidinophosphonium hexafluorophosphate (PyBOP) and the like. The base used may include triethylamine (TEA), N,N-Diisopropylethylamine (DIPEA) and the like. The amount of the amine (2a) used is about 1 to 2 molar equivalents with respect to 1 mole of the compound (1a). The reaction can be usually performed at r.t. in a solvent such as DMF, $CH_3CN$ and the like. The reaction time varies depending on the starting materials, the coupling agent, the base, the solvent used, and the reaction temperature.

Step 1-2

This step is a step of reacting the compound (3a) with bis(pinacolato)diboron in a solvent to produce the compound (4a) using a palladium catalyst system in the presence of a base such as potassium acetate (KOAc). Examples of palladium catalyst used may include [1,1-bis(diphenylphosphino)ferrocene]dichloropalladium(II) [Pd(dppf)Cl$_2$] and the like. Examples of solvent used may include 1,4-dioxane, toluene and the like. The amount of bis(pinacolato)diboron used is usually about 1 to 2 molar equivalents with respect to 1 mole of the compound (3a). The reaction can be usually performed at 90° C. to the reflux temperature of the solvent. The reaction time varies depending on the starting material, the catalyst system, the base, the solvent used, and the reaction temperature.

Step 1-3

This step is a step of reacting the compound (4a) with the compound (5a) to produce the final compound. The final compound can be produced by reacting the compound (4a) with the compound (5a) using a palladium catalyst in the presence of a base in mixed solvents such as 1,4-dioxane, DME and H$_2$O. The palladium catalyst used may include dichloro[1,1'-bis(diphenylphosphino)ferrocene]palladium (II)-DCM adduct [Pd(dppf)Cl$_2$-DCM], Tris(dibenzylideneacetone)dipalladium(0) [Pd$_2$(dba)$_3$] with 2-dicyclohexylphosphino-2',4',6'-triisopropylbiphenyl (XPhos), tetrakis(triphenylphosphine) palladium (0) [Pd(PPh$_3$)$_4$] and the like. Examples of base may include cesium carbonate (Cs$_2$CO$_3$), potassium carbonate (K$_2$CO$_3$) and the like. The amount of compound (5a) used is about 1 to 2 molar equivalents with respect to 1 mole of the compound (4a). The reaction can be usually performed at 90° C. to the reflux temperature of the solvent, and usually goes to completion in 1-8 hours.

Scheme 2

Step 2-1

(6a) boronic ester or (7a) boronic acid (3a) + (6a) or (7a) → final compound
Pd catalyst, base, solvent, heat $Q_1$, $Q^2$, $Q^3$ and $Q^4$ are as described in claim [1]
Ar = (hetero)aryl Step 2-1

This step is a step of reacting the compound (3a) with a boronic ester as compound (6a) or a boronic acid as compound (7a) to produce the final compound. Compound (3a) can be obtained using the appropriate starting materials under the conditions described in procedure 1, step 1-1. The final compound can be produced under Suzuki coupling conditions. The compound (6a) or (7a) used is usually about 1 to 2 molar equivalents with respect to 1 mole of the compound (3a). The reaction is generally performed in mixed solvents such as 1,4-dioxane and H$_2$O. Examples of base used may include Cs$_2$CO$_3$ or K$_2$CO$_3$. The reaction can be performed at 90° C. to the reflux temperature of the solvent. The reaction time varies depending on the starting materials, the Pd catalyst, the base, the solvent used, and the reaction temperature.

103

Scheme 3

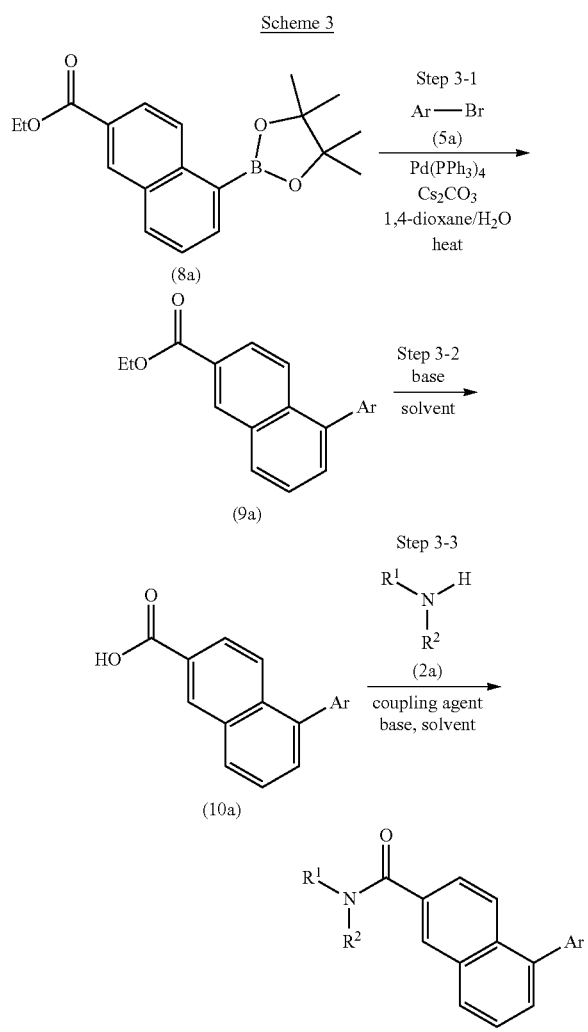

R¹ and R² are as described in claim [1]
Ar = (hetero)aryl

Step 3-1

This step is a step of reacting the compound (8a) with the compound (5a) to produce the compound (9a). The compound (9a) can be produced in accordance with the method described in step 1-3 for the preparation of 6-(6-(4,4-difluoropiperidine-1-carbonyl) naphthalen-1-yl) isoquinolin-1(2H)-one.

Compound (8a) can be produced from ethyl 5-bromo-2-naphthoate in accordance with the method described in step 1-2 for the preparation of the intermediate (4aa).

Step 3-2

This step is a step of hydrolyzing the ester moiety of the compound (9a) to produce the compound (10a). The compound (10a) can be produced by treating the compound (9a) with a base in mixed solvents such as MeOH and $H_2O$, followed by acidification using an acid such as HCl. Examples of base used may include KOH, LiOH, NaOH and the like. The reaction can be usually performed at r.t. to the reflux temperature of the solvent. The reaction time varies depending on the substrate, the base, the solvent used, and the reaction temperature.

104

Step 3-3

This step is a step of converting the carboxylic acid group of the compound (10a) to produce the final compound by the reaction with the amine (2a). The final compound can be produced in accordance with any method described in step 1-1 of procedure 1 or in the literature.

Scheme 4

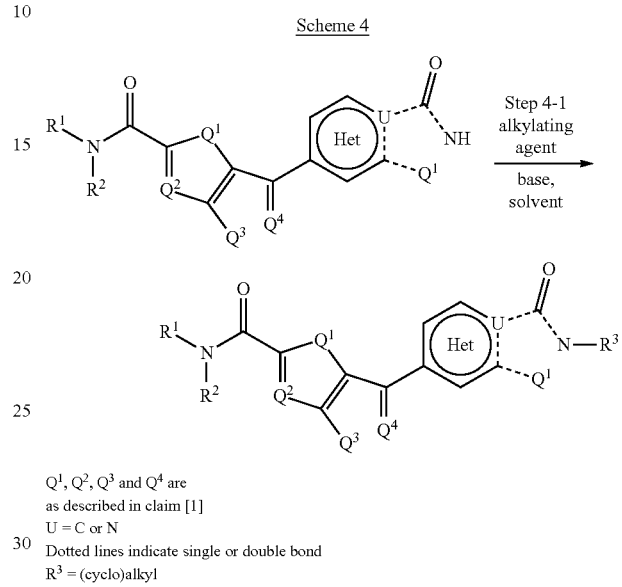

$Q^1$, $Q^2$, $Q^3$ and $Q^4$ are as described in claim [1]
U = C or N
Dotted lines indicate single or double bond
$R^3$ = (cyclo)alkyl

Step 4-1

This step is a step of N-alkylation using an alkylating agent such as an alkyl halide. The alkylated compound can be produced using a base such as sodium hydride (NaH), $Cs_2CO_3$, NaOtBu and the like in a solvent such as DMF, $CH_3CN$, 1,4-dioxane, THF and the like. The amount of the alkylating agent used is usually about 1 to 2 molar equivalents with respect to 1 mole of the starting material. The reaction time and temperature vary depending on the starting materials, the alkylating agent, the base and the solvent used.

Scheme 5

-continued

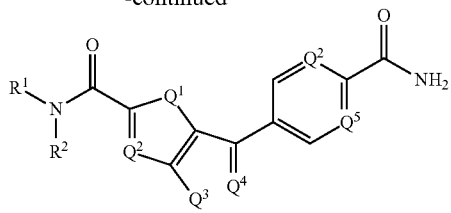

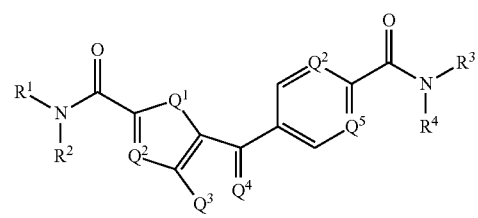

$Q^1$, $Q^2$, $Q^3$ and $Q^4$ are
as described in the claim [1]
$Q^5$ = C, N or CF
$R^3$ = (cyclo)alkyl
$R^4$ = H or (cyclo)alkyl Step 5-1

This step is a step of converting a carboxylic acid to the corresponding acid chloride (11a). The carboxylic acid (5-[6-(4,4-difluoropiperidine-1-carbonyl)-1-naphthyl]-3-fluoro-pyridine-2-carboxylic acid, 4-(6-(4,4-difluoropiperidine-1-carbonyl)naphthalen-1-yl)-2,6-difluorobenzoic acid, 4-(6-(4,4-difluoropiperidine-1-carbonyl)naphthalen-1-yl)-2-fluoro-6-methoxybenzoic acid, 5-(6-(4,4-difluoropiperidine-1-carbonyl)naphthalen-1-yl)pyrimidine-2-carboxylic acid) can be prepared by Suzuki-coupling in accordance with the methods described for step 1-3 of procedure 1, or (4-(6-(4,4-difluoropiperidine-1-carbonyl)naphthalen-1-yl)-2-fluorobenzoic acid) by hydrolysis of the corresponding methyl ester (methyl 4-(6-(4,4-difluoropiperidine-1-carbonyl)naphthalen-1-yl)-2-fluorobenzoate) under basic conditions.

Step 5-2

This step is a step of converting the acid chloride moiety of the compound (11a) to a primary amide to produce the final compound. The final compound can be produced by reaction with ammonia in a solvent such as MeOH.

Step 5-3

This step is a step of converting the acid chloride moiety of compound (11a) into an amide to produce the final compound. The final compound can be produced by reaction with an amine (12a) in the presence of a base such as DIPEA and TEA in a solvent such as 1,4-dioxane and THF. The reaction can be performed at ambient temperature.

Scheme 6

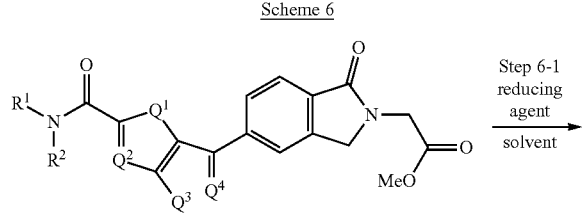

Step 6-1
reducing agent
solvent

-continued

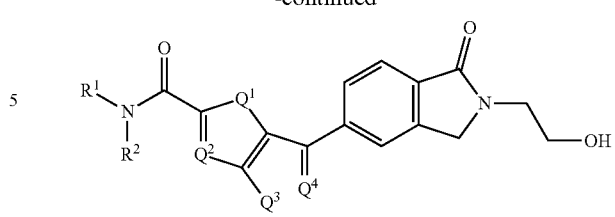

$Q^1$, $Q^2$, $Q^3$ and $Q^4$ are
as described in claim [1]
$R^1$ and $R^2$ are as described in claim [1]

Step 6-1

This step is a step of reducing the ester moiety of a compound produced according to the general procedure 1 or 2. The reduced compound can be produced by reaction with a reducing agent such as lithium borohydride (LiBH$_4$), lithium aluminum hydride (LiAlH$_4$) and the like in a solvent. Examples of the solvent used may include THF and the like. The reaction can be usually performed at −20° C. or r.t. The reaction time varies depending on the starting materials, the reducing agent, the solvent used, and the reaction temperature.

Scheme 7

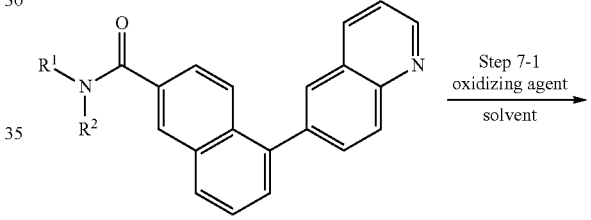

Step 7-1
oxidizing agent
solvent

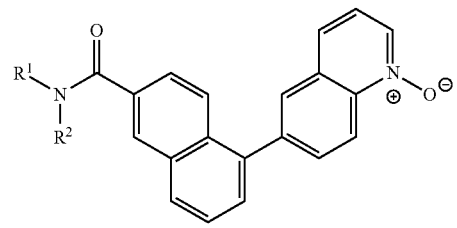

$R^1$ and $R^2$ are as described in claim [1]

Step 7-1

This step is a step of oxidizing the quinoline-N of a compound produced according to the general procedure 1 or 2. The expected N-oxide derivative can be produced by reaction with an oxidizing agent such as meta-chloroperoxybenzoic acid (mCPBA) in a solvent. Examples of the solvent used may include DCM and the like. The reaction can be usually performed at r.t. The reaction time varies depending on the starting material, the oxidizing agent, the solvent used, and the reaction temperature.

Scheme 8

Step 8-1

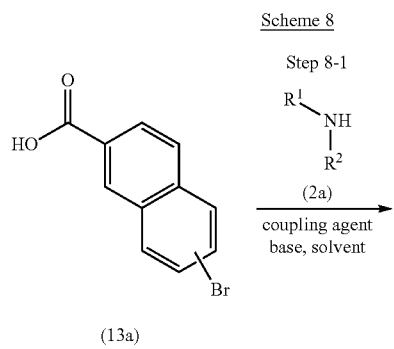

(13a)

Step 8-2

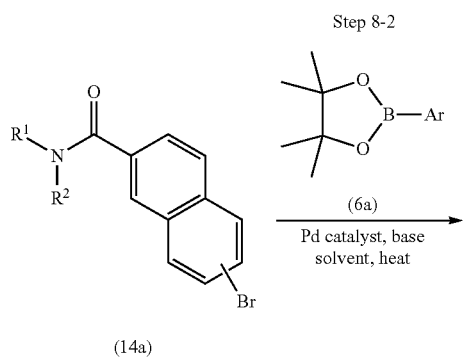

(14a)

$R^1$ and $R^2$ are as described in claim [1]
Ar = (hetero)aryl

Step 8-1

This step is a step of converting the carboxylic acid moiety of the compound (13a) to produce the compound (14a) by reaction with the amine (2a). The compound (14a) can be produced in accordance with the method described in step 1-1 of procedure 1, or other methods described in the literature.

Step 8-2

This step is a step of reacting the compound (14a) with the boronic ester (6a) to produce the final compound. The final compound can be produced in accordance with the methods described for step 2-1 of procedure 2, or other methods described in the literature.

Scheme 9

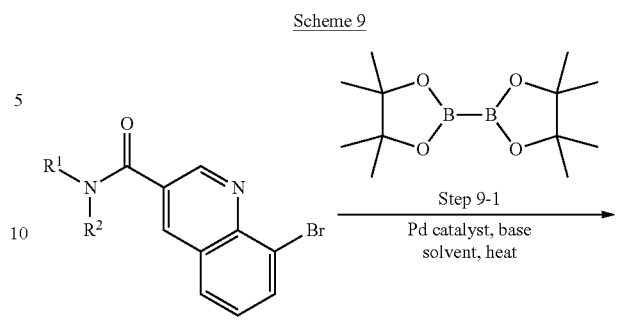

(3a)

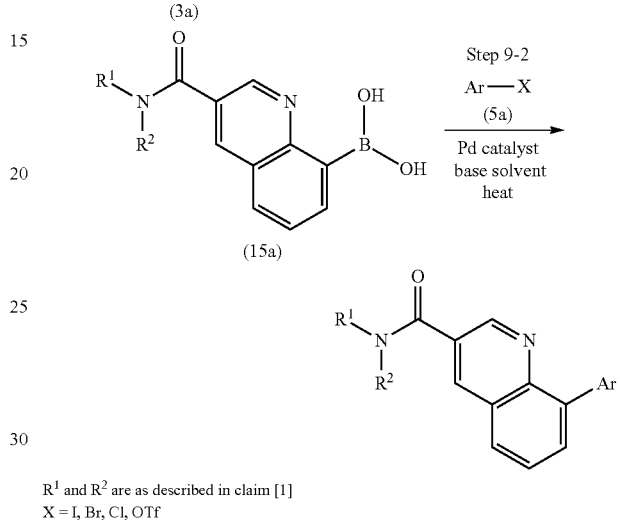

(15a)

$R^1$ and $R^2$ are as described in claim [1]
X = I, Br, Cl, OTf
Ar = (hetero)aryl Step 9-1

This step can be performed in accordance with the conditions described for step 1-2 of general procedure 1.

Step 9-2

This step can be performed in accordance with the conditions described for step 1-3 of general procedure 1

Scheme 10

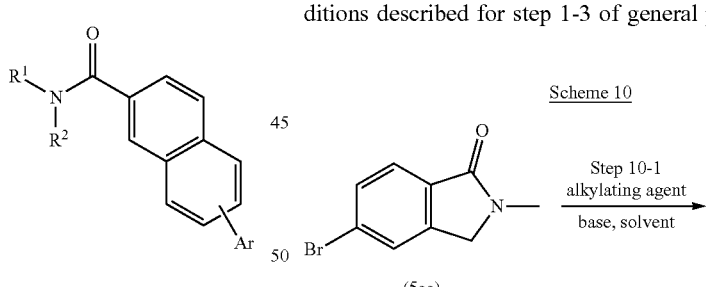

(5aa)

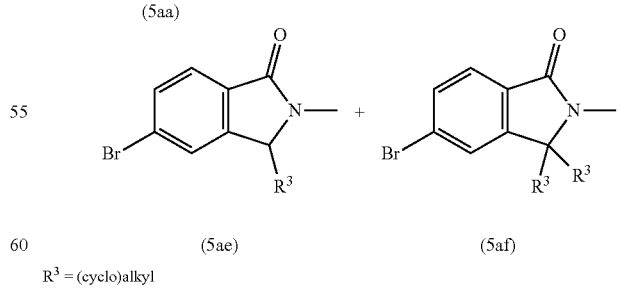

(5ae)    (5af)

$R^3$ = (cyclo)alkyl

Step 10-1

This step is a step of alkylating the compound (5aa) using an alkylating agent such as an alkyl halide in the presence of a base such as NaH and sodium hexamethyldisilylamide

[(Me₃Si)₂NH·Na] and the like in a solvent such as THF and the like. The reaction time varies depending on the starting material, the alkylating agent, the base, the solvent used, and the reaction temperature. The relative amount of the alkylated products (5ae and 5af) varies depending on the reaction conditions.

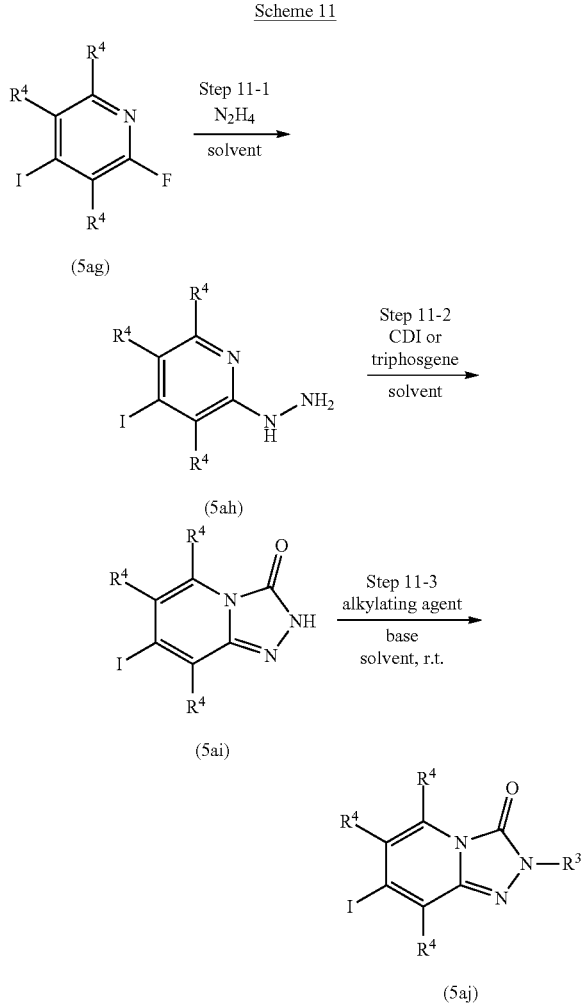

$R^3$ = (cyclo)alkyl
$R^4$ = H or (cyclo)alkyl

Step 11-1

This step is a step of converting the compound (5ag) to the hydrazine derivative (5ah). The compound (5ah) can be produced by reacting the compound (5ag) with hydrazine in the presence or absence of a base in a solvent. Examples of the base used may include DIPEA, pyridine and the like. The amount of hydrazine used may be about 2 to 5 molar equivalents with respect to 1 mole of the compound (5ag). Examples of the solvent used may include MeOH, EtOH and the like. The reaction can be performed at r.t. to the reflux temperature of the solvent used. The reaction time varies depending on the starting material, the solvent used, and the reaction temperature.

Step 11-2

This step is a step of converting the compound (5ah) to the compound (5ai). The compound (5ai) can be produced by reacting the compound (5ah) with CDI or triphosgene in the presence or absence of a base. Examples of solvent used may include THF, CH₃CN and the like. The amount of CDI or triphosgene used may be about 1 to 3 mole equivalents with respect to 1 molar of the compound (5ah). The reaction can be performed at r.t. to the reflux temperature of the solvent used.

Step 11-3

This step is a step of alkylating the compound (5ai) to provide the desired compound (5aj). The compound (5aj) can be produced by reacting the compound (5ai) with an alkyl halide in the presence of a base. Examples of the base used may include $K_2CO_3$, $Cs_2CO_3$ and the like. Examples of the solvent used may include DMF, THF and the like. The reaction can be usually performed at r.t.

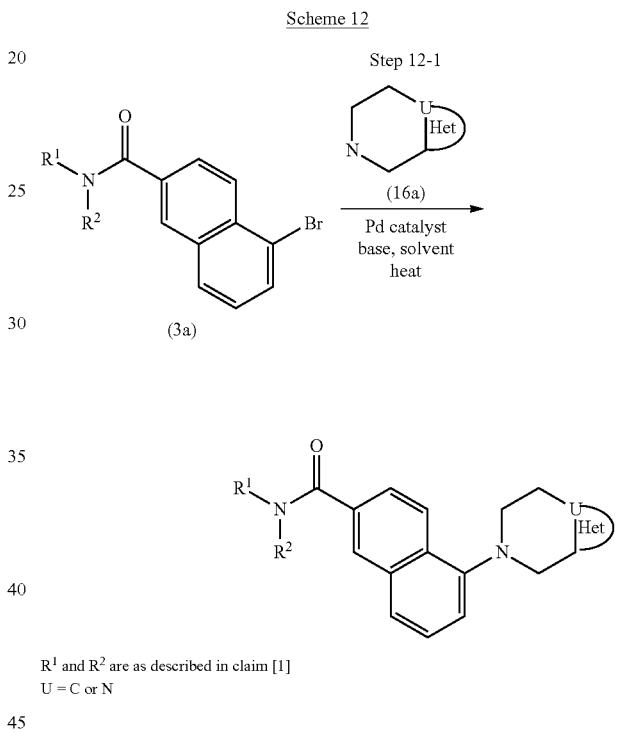

$R^1$ and $R^2$ are as described in claim [1]
U = C or N

Step 12-1

This step is a step of reacting the compound (3a) with the amine (16a) to produce the final compound via Buchwald-coupling using a catalyst system such as $Pd_2(dba)_3$ with XantPhos, in the presence of a base such as NaOtBu and $Cs_2CO_3$ in a solvent such as toluene and 1,4-dioxane under reflux conditions. The reaction time varies depending on the substrate, the catalyst system, the base and the solvent used.

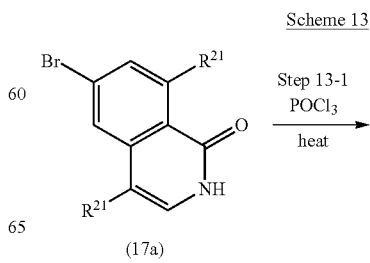

-continued

Step 13-2

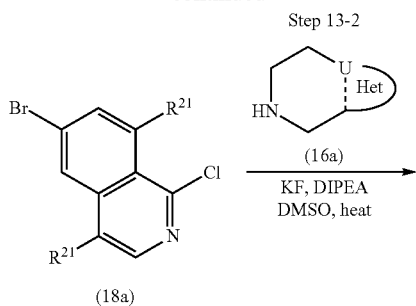

(18a)

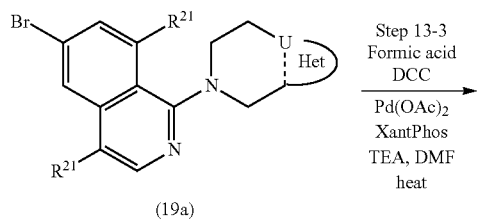

(19a)

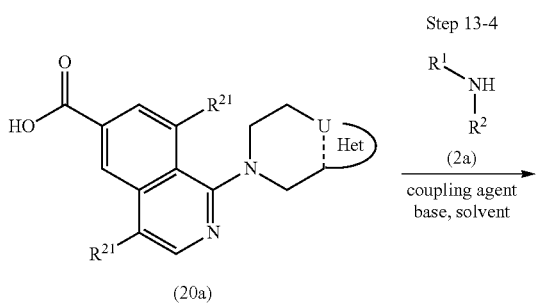

(20a)

-continued $R^{21}$ = H or F
U = C or N
$R^1$ and $R^2$ are as described in claim [1]

Step 13-1

This step is a step of converting the compound (17a) to the chloride derivative (18a). Compound (17a) may be commercially available, or can be produced in accordance with any method described in the literature. The compound (18a) can be produced by reacting the compound (17a) in phosphoryl chloride. The reaction can be usually performed under heated conditions in 1 hour.

Step 13-2

This step is a step of reacting the compound (18a) with the amine (16a) to produce the compound (19a). The compound (19a) can be produced by reacting the compound (18a) with the amine (16a), in the presence of potassium fluoride (KF) and DIPEA in DMSO. The amount of the compound (16a) used is usually about 1 to 2 molar equivalents with respect to 1 mole of the compound (18a). The reaction can be usually performed under heated conditions overnight.

Step 13-3

This step is a step of converting the bromide (19a) to the carboxylic acid (20a). The compound (20a) can be produced by reacting the compound (19a) with formic acid and DCC using Pd(OAc)$_2$ and XantPhos as catalyst system, in the presence of a base such as TEA in DMF. The amount of formic acid used is usually about 7 to 10 molar equivalents with respect to 1 mole of the compound (19a). The reaction can be usually performed at 100° C. overnight.

Step 13-4

This step is a step of converting the carboxylic acid group of the compound (20a) to produce the final compound by reaction with the amine (2a). The final compound can be produced using HATU as an activator in DMF in the presence of DIPEA as a base. The amount of the compound (2a) used is about 1 to 2 molar equivalents with respect to 1 mole of the compound (20a). The reaction can be usually performed at r.t.

Scheme 14

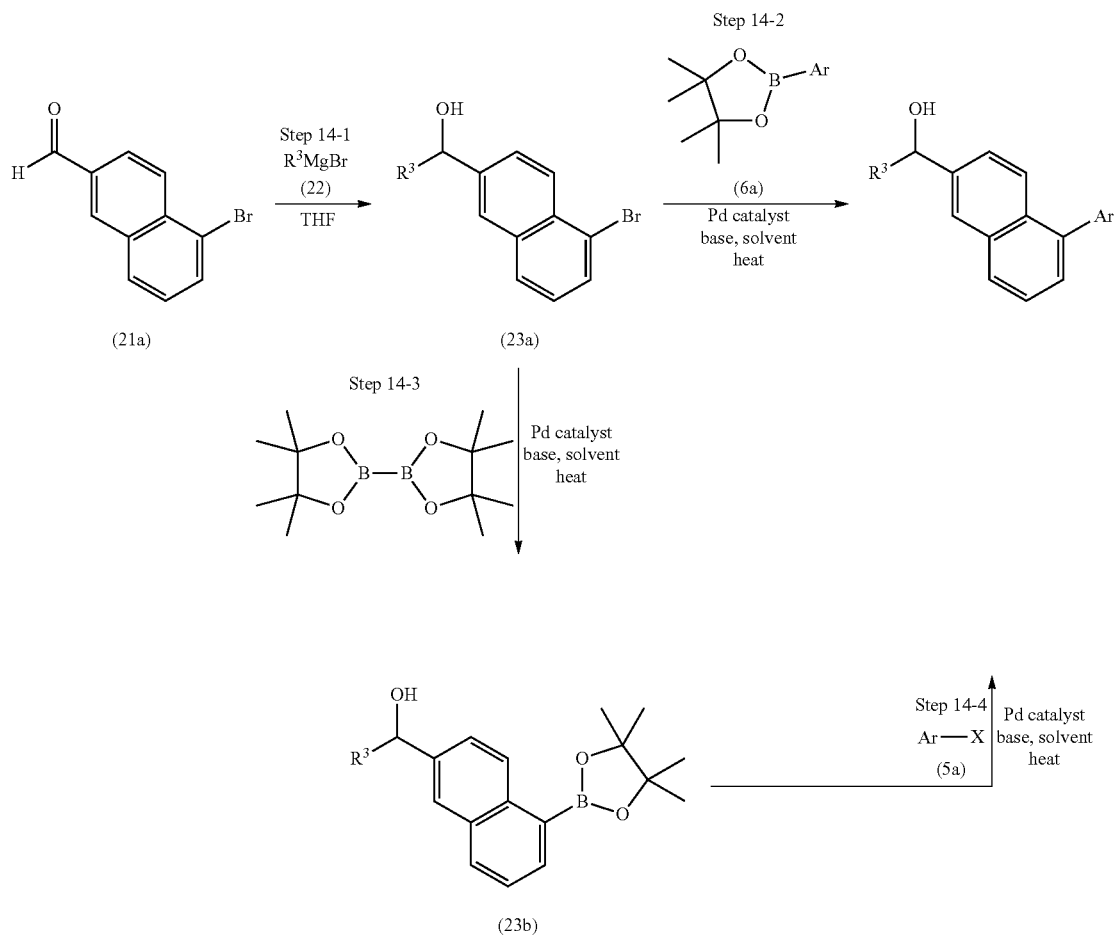

$R^3$ = (cyclo)alkyl
Ar = (hetero)aryl

Step 14-1

This step is a step of converting the aldehyde moiety of the compound (21a) to the corresponding alcohol (23a). The compound (23a) can be produced by reacting the compound (21a) with a Grignard reagent (22a) in a solvent such as THF and the like. The reaction is carried out preferentially at low temperature (0° C.) then allowed to warm up to r.t. overnight.

Step 14-2

This step is a step of reacting the compound (23a) with a boronic ester (6a) to provide the final compound. The final compound can be produced under Suzuki coupling conditions. using a Pd catalyst such as Pd(dppf)Cl$_2$-DCM in the presence of a base such as Cs$_2$CO$_3$ and K$_2$CO$_3$ in mixed solvents such as 1,4-dioxane and H$_2$O. The reaction can be performed at 90° C. to the reflux temperature of the solvent. The reaction time varies depending on the starting materials, the Pd catalyst, the base, the solvent used, and the reaction temperature.

Step 14-3

This step can be performed in accordance with the conditions described for Step 1-2 of general procedure 1.

Step 14-4

This step can be performed in accordance with the conditions described for Step 1-3 of general procedure 1.

Scheme 15

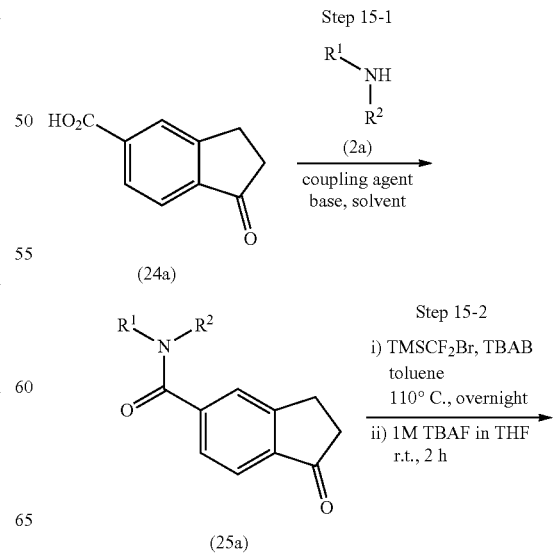

-continued

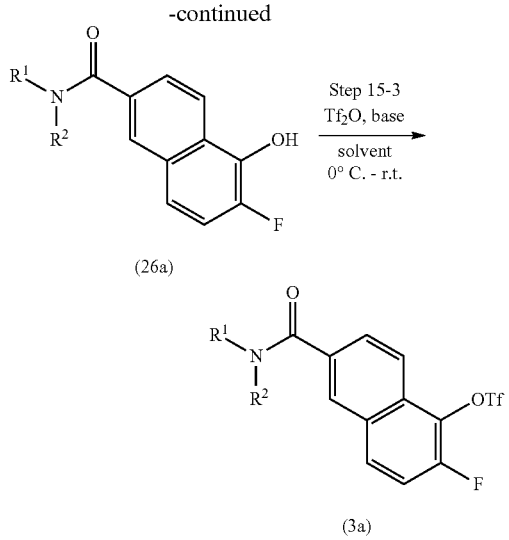

R¹ and R² are as described in claim [1]

Step 15-1

This step can be performed using similar conditions described for step 1-1 of procedure 1.

Step 15-2 (i, ii)

This step can be performed using similar conditions described in the literature (*Chem. Commun.* 2015, 51, 15362-15365)

Step 15-3

This step is a step of converting the hydroxy moiety of the compound (26a) to a triflate using triflic anhydride in the presence of a base such as TEA, DIPEA, pyridine and the like in a solvent such as DCM, THF and the like. The reaction can be usually performed at 0° C. to r.t., and goes to completion in 1-3 hours.

Scheme 16

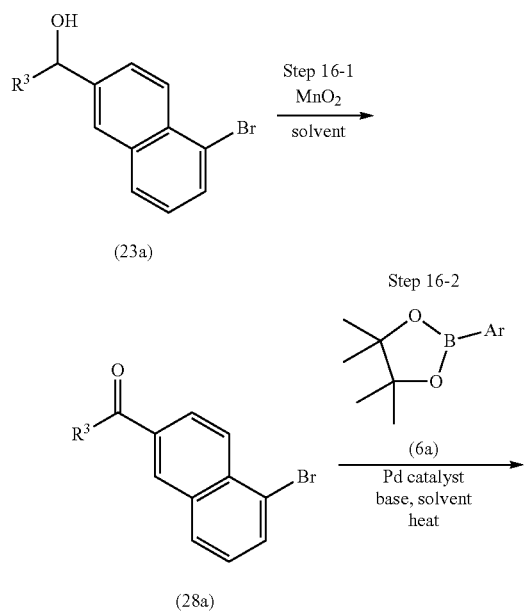

-continued

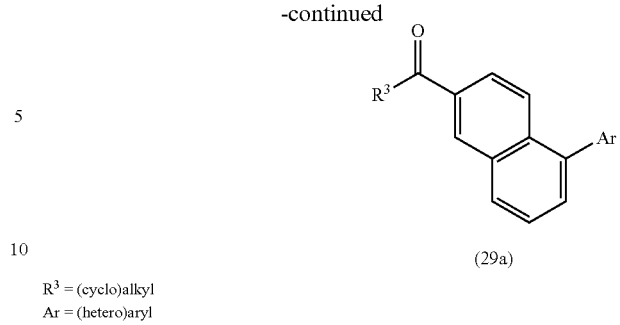

$R^3$ = (cyclo)alkyl
Ar = (hetero)aryl

Step 16-1

This step is a step of converting the alcohol moiety of the compound (23a) to the corresponding ketone (28a). The compound (28a) can be produced by reacting the compound (23a) with an oxidizing reagent such as $MnO_2$ in a solvent such as DCM, $CH_3CN$, $CHCl_3$ and the like. Reaction can be performed at r.t.–50° C. overnight. The reaction time varies depending on the starting materials, the solvent used, and the reaction temperature.

Step 16-2

This step is a step of reacting the compound (28a) with a boronic ester (6a) to provide the final compound (29a). The final compound can be produced under Suzuki coupling conditions. using a Pd catalyst such as $Pd(dppf)Cl_2$-DCM in the presence of a base such as $Cs_2CO_3$ and $K_2CO_3$ in mixed solvents such as 1,4-dioxane and $H_2O$. The reaction can be performed at 90° C. to the reflux temperature of the solvent. The reaction time varies depending on the starting materials, the Pd catalyst, the base, the solvent used, and the reaction temperature.

Scheme 17

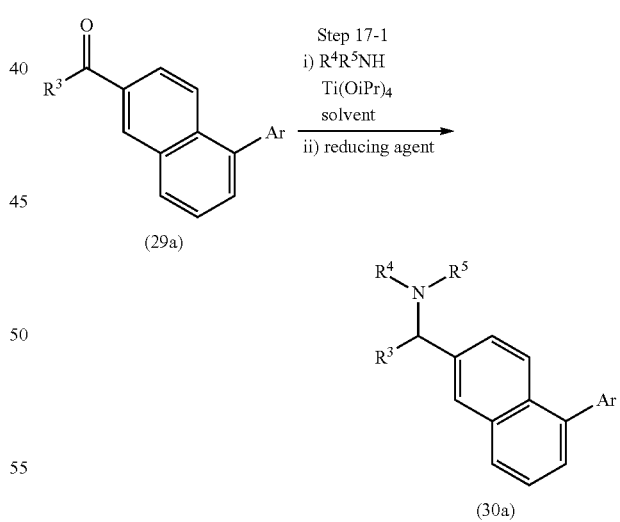

$R^3$ = (cyclo)alkyl
Ar = (hetero)aryl
$R^4, R^5$ = H, alkyl

Step 17-1

This step is a step of reacting the ketone (29a) with amines to provide the final compound (30a). The final compound can be produced under reductive amination conditions using $Ti(OiPr)_4$, in solvents such as MeOH, EtOH, THF followed by the addition of a reducing agent such as $NaBH_4$.

Scheme 18

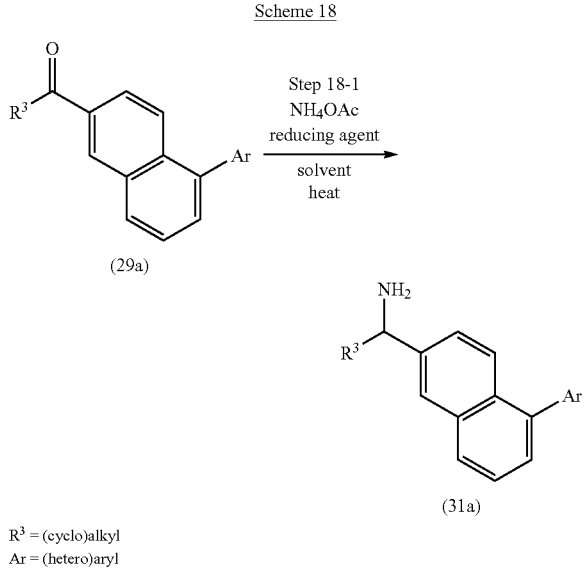

$R^3$ = (cyclo)alkyl
Ar = (hetero)aryl

Step 18-1

This step is a step of reacting the ketone (29a) with primary amine to provide the final compound (31a). The final compound can be produced under reductive amination conditions using reducing agents (NaCNBH$_3$) in mixed solvents such as MeOH and EtOH. The reaction can be performed at 65° C. over night.

Scheme 19

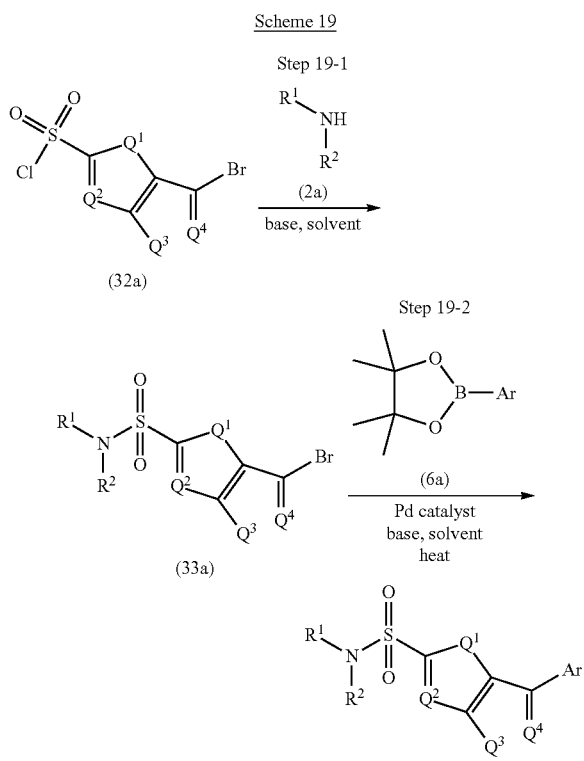

$Q^1$, $Q^2$, $Q^3$ and $Q^4$ are as described in claim [1]
$R^1$ and $R^2$ are as described in claim [1]
Ar = (hetero)aryl Step 19-1

This step is a step of converting the sulfonyl chloride group of the compound (32a) to produce the compound (33a) by reaction with the amine (2a) in a solvent in the presence of a base. The base used may be TEA, DIPEA and the like. The amount of the amine (2a) used is about 1 to 2 molar equivalents with respect to 1 mole of the compound (32a). The reaction can be usually performed at r.t. in a solvent such as DCM, THF, and the like.

Step 19-2

This step is a step of reacting the compound (33a) with a boronic ester as compound (6a) to produce the final compound. The final compound can be produced under Suzuki coupling conditions. The compound (6a) used is usually about 1 to 2 molar equivalents with respect to 1 mole of the compound (33a). The reaction is generally performed in mixed solvents such as 1,4-dioxane and H$_2$O. Examples of base used may include Cs$_2$CO$_3$ or K$_2$CO$_3$. The reaction can be performed at 90° C. to the reflux temperature of the solvent. The reaction time varies depending on the starting materials, the Pd catalyst, the base, the solvent and reaction temperature used.

Scheme 20

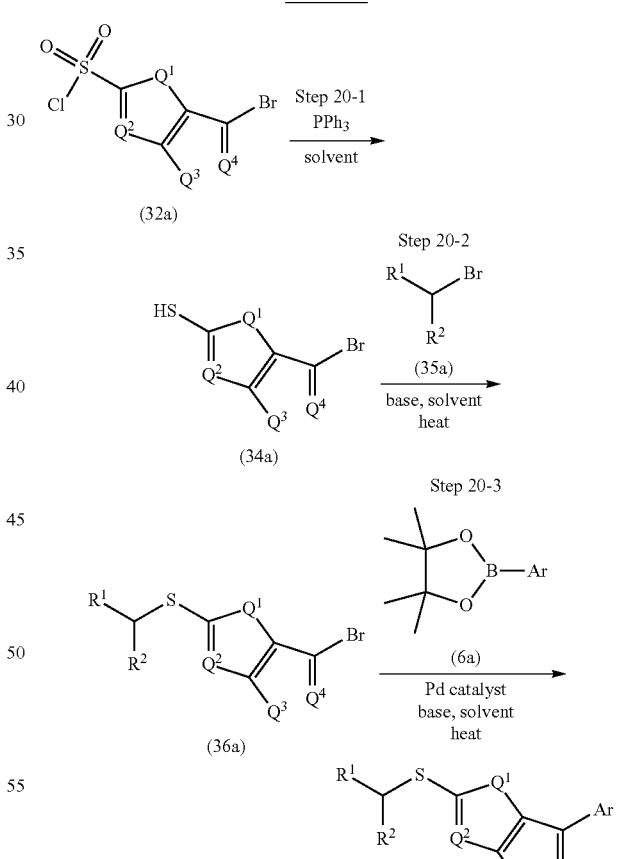

$Q^1$, $Q^2$, $Q^3$ and $Q^4$ are as described in claim [1]
$R^1$ and $R^2$ are as described in claim [1]
Ar = (hetero)aryl Step 20-1

This step is a step of reducing the sulfonyl chloride group of the compound (32a) to produce the compound (34a) by reaction with PPh₃ in the presence of a solvent such as toluene and the like. The reaction can be usually performed at r.t. and usually goes to completion in 1 h.

Step 20-2

This step is a step of reacting the compound (34a) with a cycloalkyl halide as compound (35a) to produce the compound (36a) in the presence of a base such as NaH, K₂CO₃, NaOEt and in a solvent such as DMF, acetone, DCM and the like. The reaction can be usually performed at 60° C. The reaction time varies depending on the starting material, the base, the solvent and the reaction temperature used.

Step 20-3

This step is a step of reacting the compound (36a) with a boronic ester as compound (6a) to produce the final compound. The final compound can be produced under Suzuki coupling conditions. The compound (6a) used is usually about 1 to 2 molar equivalents with respect to 1 mole of the compound (36a). The reaction is generally performed in mixed solvents such as 1,4-dioxane and H₂O. Examples of base used may include Cs₂CO₃ or K₂CO₃. The reaction can be performed at 90° C. to the reflux temperature of the solvent. The reaction time varies depending on the starting materials, the Pd catalyst, the base, the solvent used, and the reaction temperature.

Scheme 21

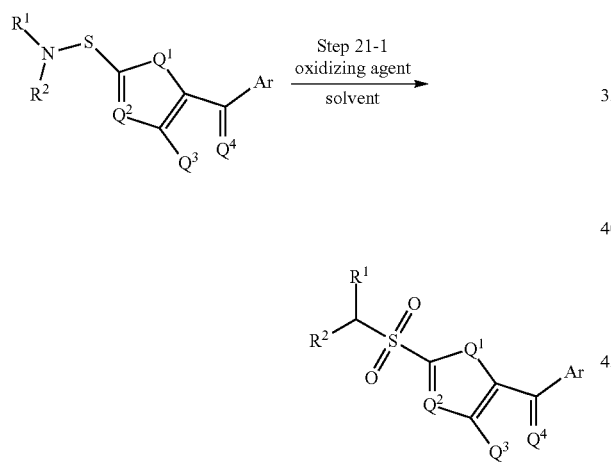

$Q^1, Q^2, Q^3$ and $Q^4$ are as described in claim [1]
$R^1$ and $R^2$ are as described in claim [1]
Ar = (hetero)aryl Step 21-1

This step is a step of oxidizing the thioether of a compound produced according to the general procedure 20. The expected sulfone derivative can be produced by reaction with an oxidizing agent such as mCPBA in a solvent. Examples of the solvent used may include DCM, CH₃CN and the like. The amount of the oxidizing agent used is about 2 molar equivalents with respect to 1 mole of the thioether compound. The reaction can be usually performed at r.t. The reaction time varies depending on the starting material, the oxidizing agent, the solvent used, and the reaction temperature.

Scheme 22

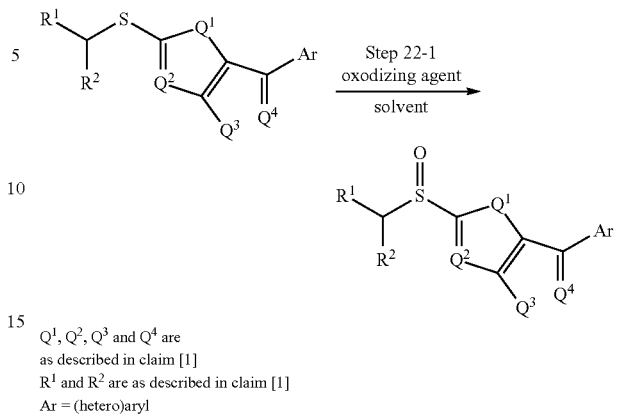

$Q^1, Q^2, Q^3$ and $Q^4$ are as described in claim [1]
$R^1$ and $R^2$ are as described in claim [1]
Ar = (hetero)aryl Step 22-1

This step is a step of oxidizing the thioether of a compound produced according to the general procedure 20. The expected sulfoxide derivative can be produced by reaction with an oxidizing agent such mCPBA in a solvent. Examples of the solvent used may include DCM, CHCl₃, CH₃CN and the like. The amount of the oxidizing agent used is about 1 molar equivalents with respect to 1 mole of the thioether compound. The reaction can be usually performed at r.t. The reaction time varies depending on the starting material, the oxidizing agent, the solvent used, and the reaction temperature.

Scheme 23

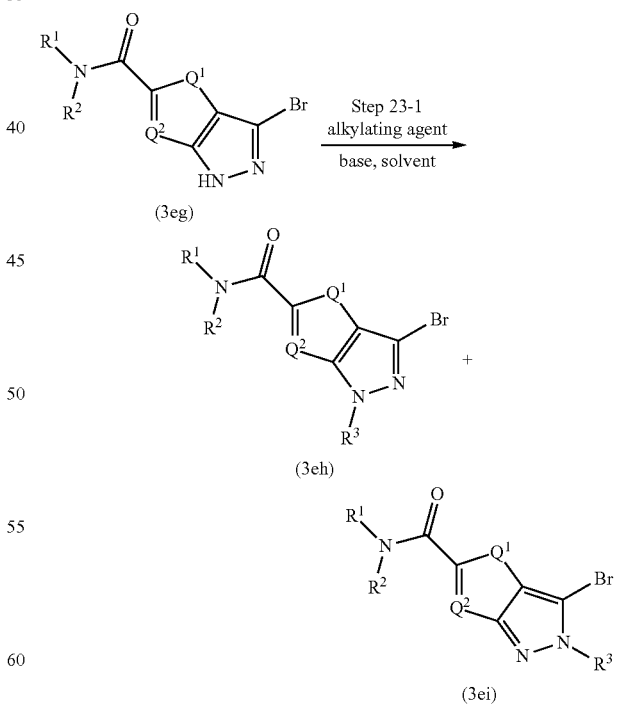

$Q^1, Q^2$, are as described in claim [1]
R1 and R2 are as described in claim [1]
$R^3$ = (cyclo)alkyl Step 23-1

This step is a step of alkylating the compound (3eg) using an alkylating agent such as an alkyl halide in the presence of a base such as NaH, $K_2CO_3$ and the like in a solvent such as DMF, $CH_3CN$, 1,4-dioxane, THF and the like. The reaction time varies depending on the starting material, the alkylating agent, the base, the solvent used, and the reaction temperature. The relative amount of the alkylated products (3eh and 3ei) varies depending on the reaction conditions.

Pharmaceutically acceptable salts of the compounds (1), (2), (3) and (4) of the present embodiment can be produced using the compounds (1), (2), (3) and (4) of the present embodiment, respectively, according to a routine method ("The fifth series of experimental chemistry" The Chemical Society of Japan, 2003, J. Pharma. Sci. 66, 2-19, 1997, and The Handbook of Pharmaceutical Salts; Properties, Selection, and Use. P. H. Stahl and C. G. Wermuth, Verlag, Zurich 2002, and the like).

The schemes mentioned above are illustrative examples of methods of producing the compounds (1), (2), (3) and (4) of the present embodiment and intermediate products thereof. They can be modified into various different schemes that can be readily understood and executed by those skilled in the art.

If one or more functional groups are of the kind that must be protected, introduction and removal of a protecting group can appropriately be combined according to a standard method. For the types of protecting groups as well as their introduction and removal, exemplified methods are described in Theodra W. Green & Peter G. M. Wuts, "*Greene's Protective Groups in Organic Synthesis*," fourth edition, Wiley-Interscience, 2006.

Intermediate products that are used for producing one of the compounds (1), (2), (3) and (4) of the present embodiment and pharmacologically acceptable salts thereof can be isolated and purified, if necessary, using an isolation and purification method widely known to a person skilled in the art, such as solvent extraction, crystallization, recrystallization, chromatography, and preparative high performance liquid chromatography.

The term "15-PGDH inhibitory function" in the present embodiment means to exhibit an inhibitory effect on 15-PGDH.

The compounds (1), (2), (3) and (4) of the present embodiment and pharmacologically acceptable salts thereof have a strong inhibitory activity in, for example, 15-PGDH enzyme inhibition tests and 15-PGDH inhibitory activity assays for mouse lung tissues. Accordingly, the compounds (1), (2), (3) and (4) of the present embodiment and pharmacologically acceptable salts thereof are useful as therapeutic and/or prophylactic agents for Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening.

They can be used for producing medicaments for treating and/or preventing Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer, (NSAIDs causative ulcer, and the like), autoinflammatory diseases (Behcet's disease, and the like), vascular inflammatory syndrome acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening.

Furthermore, medicaments containing the compound (1), (2), (3) or (4) of the present embodiment as an active ingredient can be used for prophylactic and/or therapeutic agents for various disease conditions (e.g., Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening) in which 15-PGDH is involved.

Medicaments containing the compound (1), (2), (3) or (4) of the present embodiment or a pharmacologically acceptable salt thereof Medicaments containing one of the compounds (1), (2), (3) and (4) of the present embodiment and pharmacologically acceptable salts thereof as an active ingredient can be formulated into various dosage forms depending on their use. Examples of such dosage forms include powders, granules, fine granules, dry syrups, tablets, capsules, injections, liquids, ointments, suppositories, patches, and sublinguals, which are administered orally or parenterally.

These medicaments can be formulated as pharmaceutical compositions containing, as an active ingredient, the compound (1), (2), (3) or (4) of the present invention or a pharmacologically acceptable salt thereof and pharmacologically acceptable additives using a known method, based on their dosage forms. Examples of additives contained in such pharmaceutical compositions include excipients, disintegrating agents, binders, lubricants, diluents, buffers, isotonizing agents, preservatives, wetting agents, emulsifying agents, dispersing agents, stabilizers, and solubilizing agents. The pharmaceutical compositions can be prepared by appropriately mixing the compound (1), (2), (3) or (4) of the present invention or a pharmacologically acceptable salt thereof with additives or by diluting it with additives or dissolving it in additives. Furthermore, when they are used in combination with a drug other than 15-PGDH inhibitors, active ingredients of the medicaments and the other drug can be formulated together or separately in a manner similar to those described above.

Medicaments according to the present embodiment can be administered systemically or locally and orally or parenterally (e.g., nasal, pulmonary, intravenous, rectal, subcutaneous, muscle or transdermal administration)

When a pharmaceutical composition containing the compound (1), (2), (3) or (4) of the present embodiment or a pharmacologically acceptable salt thereof as an active ingredient is used in actual therapies, the dosage of its active ingredient, that is, the compound (1), (2), (3) or (4) of the present embodiment or a pharmacologically acceptable salt thereof is appropriately determined depending on, for example, the age, gender and body weight of a patient, severity of disease, and level of treatment. For example, for oral administrations to adults (weighing 60 kg), the composition can be appropriately administered at a dosage of approximately 0.03-1000 mg/body per day as a single dose or as divided doses. Daily dosage for oral administration is preferably 0.06-540 mg/body, and more preferably 0.18-180 mg/body. For parenteral administrations to adults, it can be appropriately administered at a dosage of approximately 0.01-300 mg per person per day as a single dose or as divided doses. Daily dosage for parenteral administrations, is preferably 0.01-100 mg/body, and more preferably 0.06-60 mg/body. Furthermore, the dosage of the compound (1), (2), (3) or (4) of the present embodiment or a pharmacologically acceptable salt thereof can be decreased depending on the dosage(s) of drug(s) other than the 15-PGDH inhibitor.

EXAMPLES

The present invention is described more in detail below based on an Experimental example, Examples and Reference Examples. Methods of producing material compounds used for the production of the compounds (1), (2), (3) and (4) are also described in the Reference Examples because some of the material compounds are novel. The present invention is not limited to the compounds set forth in the following Examples, and may be modified to the extent that the modifications do not depart from the scope of the present invention.

Among the abbreviations and acronyms used in the Reference Examples, Examples, and Tables, $^1$H-NMR is for a spectrum obtained using proton nuclear magnetic resonance spectroscopy; CDCl$_3$ and DMSO-d$_6$ stand for chloroform-d and dimethyl sulfoxide-d$_6$, respectively; and MS (ESI$^+$) is for data obtained by mass spectrometry using electrospray ionization.

The solid wedges and dashed triangular shapes in the structural formulae denote relative positions of atoms in enantiomers, not their absolute place. The solid lines and dashed lines denote relative positions of atoms in racemic modifications and enantiomers obtained by the separation of a racemic modification.

Experimental Procedures

Synthesis of 5-(6-(4,4-difluoropiperidine-1-carbonyl)naphthalen-1-yl)-2-methylisoindolin-1-one

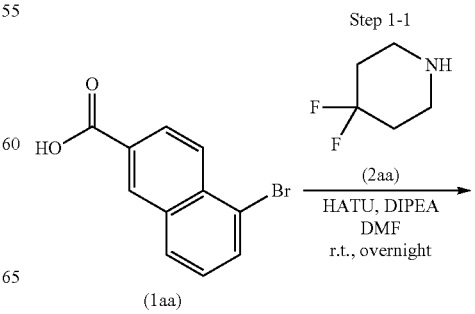

Step 1-2

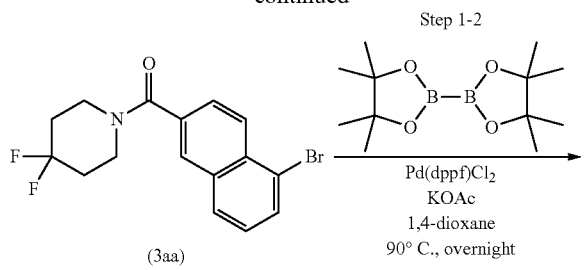

Step 1-3

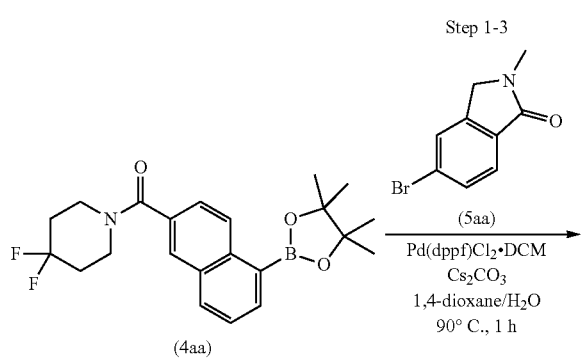

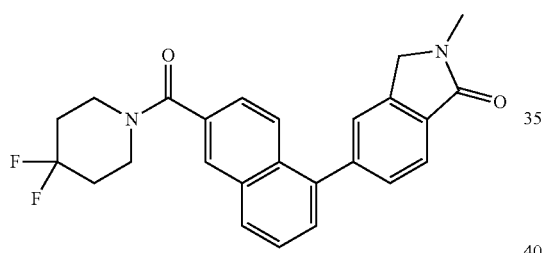

Step 1-1

A mixture of 5-bromonaphthalene-2-carboxylic acid (1aa) (2.5 g), 4,4-difluoropiperidine (2aa) (1.33 mL), HATU (5.68 g) and DIPEA (5.2 mL) in DMF (25 mL) was stirred at r.t. overnight. The mixture was partitioned between EtOAc and H₂O. The product was extracted with EtOAc from the aq. layer (×2). The combined organic layers were dried over Na₂SO₄ and concentrated. The residue was purified by silica gel column chromatography (0-40% EtOAc/Hexane) to give the expected product as a pale yellow solid (3.22 g, 91%); LRMS (ESI): m/z [M+H]⁺ 354, 356.

Step 1-2

A mixture of (5-bromo-2-naphthyl)-(4,4-difluoro-1-piperidyl)methanone (3aa) (1.5 g), KOAc (831.33 mg), bis(pinacolato)diboron (1.29 g) and Pd(dppf)Cl₂ (309.88 mg) was degassed and backfilled with nitrogen three times. After the addition of 1,4-dioxane (15 mL), the mixture was degassed again, backfilled with nitrogen three times, and heated at 90° C. overnight. After cooling to r.t., the mixture was filtered through celite, and the filtrate was concentrated. The residue was purified by silica gel column chromatography (0-40% EtOAc/Hexane) to give the expected product as a yellow oil (quantitative yield); LRMS (ESI): m/z [M+H]⁺ 402.

Step 1-3

A reaction vessel containing a mixture of (4,4-difluoro-1-piperidyl)-[5-(4,4,5,5-tetramethyl-1,3,2-dioxaborolan-2-yl)-2-naphthyl]methanone (4aa) (200 mg), 5-bromo-2-methylisoindolin-1-one (5aa) (124 mg), Cs₂CO₃ (325 mg) and Pd(dppf)Cl₂·DCM (89.5 mg) was degassed and backfilled with nitrogen three times. After the addition of 1,4-dioxane (4 mL) and H₂O (2 mL), the reaction mixture was degassed, and backfilled with nitrogen. The resulting mixture was stirred and heated at 100° C. for 1.5 h. After cooling to r.t., the mixture was filtered through celite, and the filtrate was concentrated. The residue was purified by prep HPLC (CH₃CN/0.1% TFA-H₂O/0.1% TFA) to give the expected product as a white solid (139.3 mg).

¹H NMR (400 MHz, CDCl₃) δ 1.91-2.25 (4H, m), 3.28 (3H, s), 3.54-4.05 (4H, m), 4.50 (2H, s), 7.47 (1H, dd, J=8.7, 1.7 Hz), 7.53-7.65 (4H, m), 7.89 (1H, d, J=8.7 Hz), 7.95 (1H, d, J=8.2 Hz), 7.99 (1H, d, J=7.8 Hz), 8.02 (1H, s); LRMS (ESI): m/z [M+H]⁺ 421.

The following compounds were synthesized using conditions analogous to 5-(6-(4,4-difluoropiperidine-1-carbonyl)naphthalen-1-yl)-2-methylisoindolin-1-one in accordance with the general procedure 1 (Scheme 1).

3-(2-(4,4-difluoropiperidine-1-carbonyl)benzo[b]thiophen-7-yl)-6-methyl-5,6-dihydro-7H-pyrrolo[3,4-b]pyridin-7-one

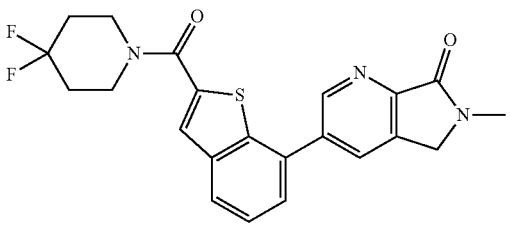

¹H NMR (400 MHz, DMSO-d₆) δ 2.05-2.17 (4H, m), 3.17 (3H, s), 3.75-3.81 (4H, m), 4.60 (2H, s), 7.65 (2H, d, J=4.6 Hz), 7.95 (1H, s), 8.06 (1H, t, J=4.6 Hz), 8.44 (1H, d, J=1.9 Hz), 9.01 (1H, d, J=1.9 Hz); LRMS (ESI): m/z [M+H]⁺ 428.

7-(2-(4,4-difluoropiperidine-1-carbonyl)benzo[b]thiophen-7-yl)pyrido[3,2-d]pyrimidin-4 (3H)-one

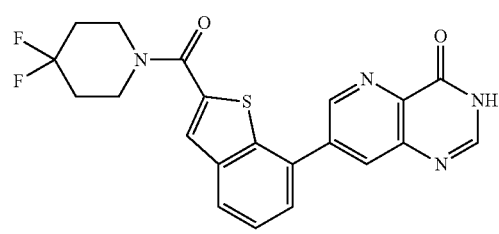

¹H NMR (400 MHz, DMSO-d₆) δ 2.06-2.17 (4H, m), 3.76-3.82 (4H, m), 7.65 (2H, d, J=4.6 Hz), 7.93 (1H, s), 8.01-8.06 (2H, m), 8.15 (1H, s), 8.77 (1H, s); LRMS (ESI): m/z [M+H]⁺ 427.

127

6-(2-(4,4-difluoropiperidine-1-carbonyl)benzo[b]thiophen-7-yl)phthalazin-1(2H)-one

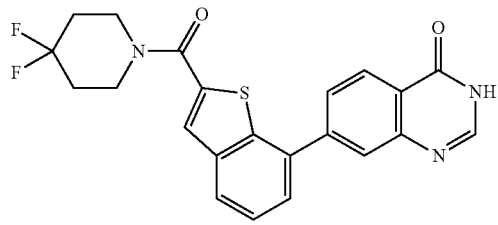 [SMILES: O=C(c1cc2cccc(-c3ccc4c(=O)[nH]cnc4c3)c2s1)N1CCC(F)(F)CC1]

$^1$H NMR (400 MHz, DMSO-d$_6$) δ 2.06-2.17 (4H, m), 3.75-3.81 (4H, m), 7.64-7.68 (2H, m), 7.95 (1H, s), 8.03-8.09 (1H, m), 8.19 (1H, d, J=8.1 Hz), 8.32 (1H, s), 8.39 (1H, d, J=8.1 Hz), 8.49 (1H, s), 12.80 (1H, br s); LRMS (ESI): m/z [M+H]$^+$ 426.

3-(2-(4,4-difluoropiperidine-1-carbonyl)benzo[b]thiophen-7-yl)-5,6-dihydro-7H-pyrrolo[3,4-b]pyridin-7-one

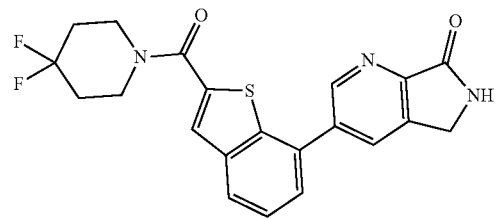 [SMILES: O=C1NCc2cc(-c3cccc4cc(C(=O)N5CCC(F)(F)CC5)sc34)cnc21]

$^1$H NMR (400 MHz, DMSO-d$_6$) δ 2.05-2.12 (4H, m), 3.77-3.81 (4H, m), 4.52 (2H, s), 7.63-7.69 (2H, m), 7.95 (1H, s), 8.03-8.09 (1H, m), 8.42 (1H, d, J=1.9 Hz), 9.03 (1H, d, J=1.9 Hz), 9.12 (1H, s); LRMS (ESI): m/z [M+H]$^+$ 414.

3-[6-(4,4-difluoropiperidine-1-carbonyl)benzothiophen-3-yl]-6-methyl-5H-pyrrolo[3,4-b]pyridin-7-one

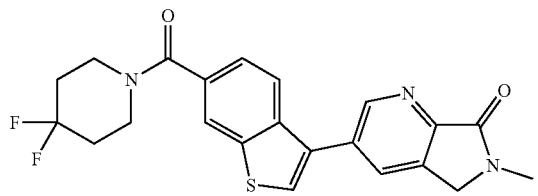 [SMILES: CN1Cc2cc(-c3csc4cc(C(=O)N5CCC(F)(F)CC5)ccc34)cnc2C1=O]

1H NMR (400 MHz, CDCl3) 2.08 (4H, br s), 3.34 (3H, s), 3.45-4.15 (4H, m), 4.54 (2H, s), 7.49 (1H, d, J=8.1 Hz), 7.70 (1H, s), 7.87 (1H, d, J=8.3 Hz), 8.01-8.08 (2H, m), 9.01 (1H, s); LRMS (ESI): m/z [M+H]+ 428.

128

6-(6-(4,4-difluoropiperidine-1-carbonyl)benzo[b]thiophen-3-yl)phthalazin-1(2H)-one

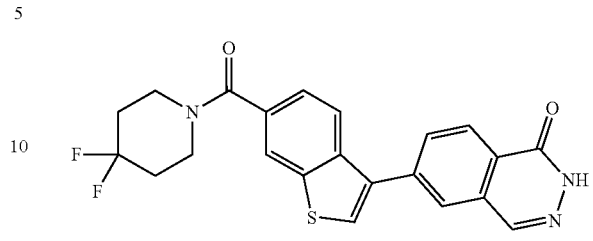

$^1$H NMR (400 MHz, DMSO-d$_6$) δ 2.07 (4H, br s), 3.57-3.85 (4H, m), 7.57 (1H, dd, J=8.4, 1.5 Hz), 8.05 (1H, d, J=8.3 Hz), 8.11 (1H, dd, J=8.2, 1.7 Hz), 8.24 (1H, d, J=1.7 Hz), 8.25 (1H, s), 8.27-8.29 (1H, m), 8.36 (1H, d, J=8.2 Hz), 8.48 (1H, s); LRMS (ESI): m/z [M+H]$^+$ 426.

7-(6-(4,4-difluoropiperidine-1-carbonyl)benzo[b]thiophen-3-yl)pyrido[3,2-d]pyrimidin-4 (3H)-one

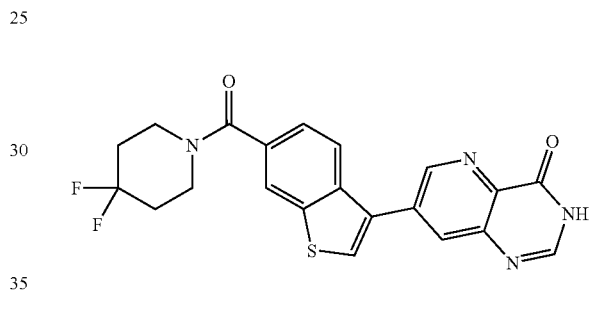

$^1$H NMR (400 MHz, DMSO-d$_6$) δ 2.08 (4H, br s), 3.28-3.86 (4H, m), 7.58 (1H, dd, J=8.4, 1.5 Hz), 8.03 (1H, d, J=8.4 Hz), 8.25 (1H, s), 8.28-8.36 (2H, m), 8.39 (1H, s), 9.07 (1H, d, J=2.1 Hz); LRMS (ESI): m/z [M+H]$^+$ 427.

6-(6-(4,4-difluoropiperidine-1-carbonyl)-2-methylbenzo[b]thiophen-3-yl)phthalazin-1 (2H)-one

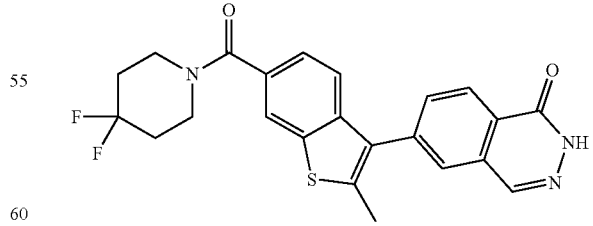

$^1$H NMR (400 MHz, CDCl$_3$) δ 2.02 (4H, br s), 2.57 (3H, s), 3.40-3.96 (4H, m), 7.36 (1H, d, J=8.3 Hz), 7.48 (1H, d, J=8.3 Hz), 7.77 (1H, s), 7.84 (1H, dd, J=8.1, 1.3 Hz), 7.93 (1H, s), 8.28 (1H, s), 8.57 (1H, d, J=8.3 Hz), 10.6 (1H, s); LRMS (ESI): m/z [M+H]$^+$ 440.

3-(7-(4,4-difluoropiperidine-1-carbonyl)naphthalen-2-yl)-6-methyl-5,6-dihydro-7H-pyrrolo[3,4-b]pyridin-7-one

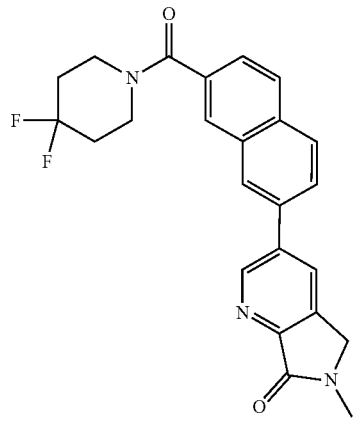 [SMILES: CN1Cc2cc(-c3ccc4ccc(C(=O)N5CCC(F)(F)CC5)cc4c3)cnc2C1=O]

¹H NMR (400 MHz, DMSO-d₆) δ 2.10 (4H, br s), 3.16 (3H, s), 3.51-3.82 (4H, m), 4.59 (2H, s), 7.63 (1H, d, J=8.6 Hz), 8.04-8.09 (2H, m), 8.16 (2H, d, J=8.3 Hz), 8.51 (2H, d, J=7.2 Hz), 9.18 (1H, s); LRMS (ESI): m/z [M+H]⁺ 422.

3-[6-(4,4-difluoropiperidine-1-carbonyl)-1-naphthyl]-6-methyl-5H-pyrrolo[3,4-b]pyridin-7-one

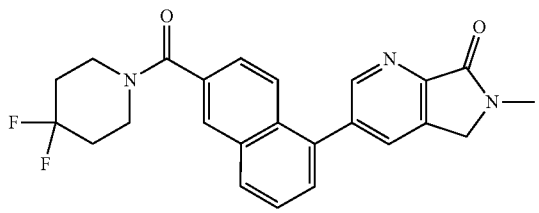 [SMILES: CN1Cc2cc(-c3cccc4cc(C(=O)N5CCC(F)(F)CC5)ccc34)cnc2C1=O]

¹H NMR (400 MHz, DMSO-d₆) δ 2.08 (4H, br s), 3.18 (3H, s), 3.45-3.84 (4H, m), 4.60 (2H, s), 7.59 (1H, dd, J=8.7, 1.7 Hz), 7.64 (1H, dd, J=7.1, 1.2 Hz), 7.71-7.75 (1H, m), 7.81 (1H, d, J=8.7 Hz), 8.15 (1H, d, J=7.9 Hz), 8.20 (1H, d, J=1.4 Hz), 8.22 (1H, d, J=1.9 Hz), 8.80 (1H, d, J=1.9 Hz); LRMS (ESI): m/z [M+H]⁺ 422.

7-(6-(4,4-difluoropiperidine-1-carbonyl)naphthalen-1-yl)-3-methylquinazolin-4 (3H)-one

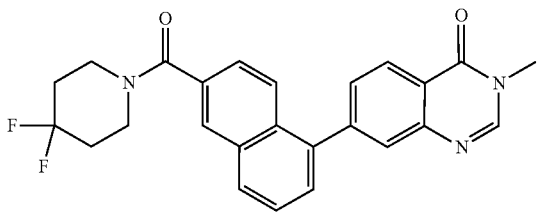 [SMILES: Cn1cnc2cc(-c3cccc4cc(C(=O)N5CCC(F)(F)CC5)ccc34)ccc2c1=O]

¹H NMR (400 MHz, CDCl₃) δ 1.85-2.31 (4H, m), 3.37-4.17 (7H, m), 7.45 (1H, d, J=8.7 Hz), 7.57 (1H, d, J=7.6 Hz), 7.61-7.68 (2H, m), 7.86 (1H, s), 7.92 (1H, d, J=8.7 Hz), 7.96 (1H, d, J=8.1 Hz), 8.02 (1H, s), 8.16 (1H, s), 8.45 (1H, d, J=8.1 Hz); LRMS (ESI): m/z [M+H]⁺ 434.

6-(6-(4,4-difluoropiperidine-1-carbonyl)naphthalen-1-yl)-2,7-naphthyridin-1 (2H)-one

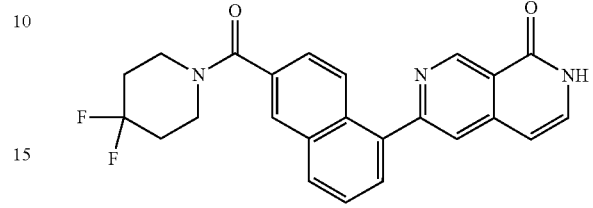

¹H NMR (400 MHz, CDCl₃) δ 1.86-2.28 (4H, m), 3.39-4.17 (4H, m), 6.61 (1H, d, J=7.0 Hz), 7.39-7.48 (1H, m), 7.52 (1H, d, J=8.3 Hz), 7.64-7.70 (1H, m), 7.73 (1H, s), 7.79 (1H, d, J=7.2 Hz), 7.97-8.07 (2H, m), 8.16 (1H, d, J=8.0 Hz), 9.77 (1H, s), 10.59 (NH, br s); LRMS (ESI): m/z [M+H]⁺ 420.

6-(6-(4,4-difluoropiperidine-1-carbonyl)naphthalen-1-yl)phthalazin-1(2H)-one

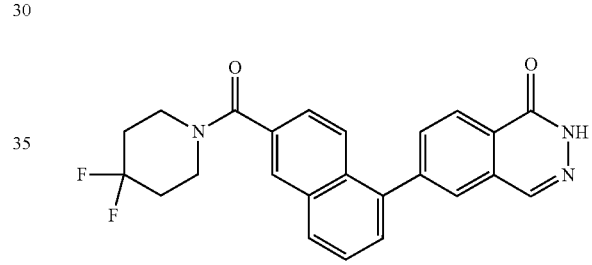

¹H NMR (400 MHz, CDCl₃) δ 2.06 (4H, br s), 3.41-4.15 (4H, m)), 7.48 (1H, dd, J=8.7, 1.6 Hz), 7.56 (1H, d, J=7.1 Hz), 7.65 (1H, dd, J=8.2, 7.1 Hz), 7.82-7.86 (2H, m), 7.92 (1H, dd, J=8.2, 1.6 Hz), 7.99 (1H, d, J=8.2 Hz), 8.04 (1H, d, J=1.6 Hz), 8.23 (1H, s), 8.56 (1H, d, J=8.2 Hz), 10.05 (NH, br s); LRMS (ESI): m/z [M+H]⁺ 420.

6-(6-(4,4-difluoropiperidine-1-carbonyl)naphthalen-1-yl)-1,2-dihydro-3H-pyrrolo[3,4-c]pyridin-3-one

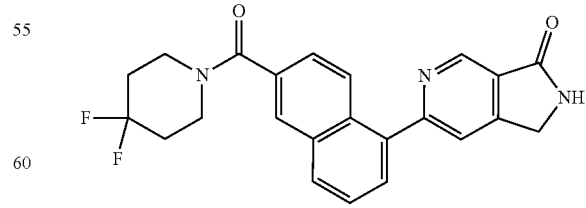

¹H NMR (400 MHz, DMSO-d₆) δ 2.08 (4H, br s), 3.43-3.84 (4H, m), 4.56 (2H, s), 7.57 (1H, d, J=8.4 Hz), 7.70-7.76 (2H, m), 7.96 (1H, s), 8.12-8.17 (3H, m), 8.84 (1H, s), 9.06 (1H, s); LRMS (ESI): m/z [M+H]⁺ 408.

Methyl 4-(6-(4,4-difluoropiperidine-1-carbonyl)naphthalen-1-yl)-2-fluorobenzoate

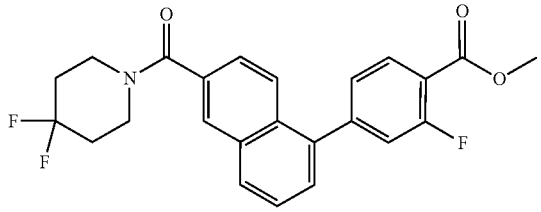 [SMILES: COC(=O)c1ccc(-c2cccc3cc(C(=O)N4CCC(F)(F)CC4)ccc23)cc1F]

$^1$H NMR (400 MHz, DMSO-d$_6$) δ 2.08 (4H, br s), 3.44-3.83 (4H, m), 3.91 (3H, s), 7.48 (1H, d, J=7.2 Hz), 7.53-7.61 (3H, m), 7.68-7.72 (1H, m), 7.85 (1H, d, J=7.9 Hz), 8.04-8.08 (1H, m), 8.12 (1H, d, J=7.4 Hz), 8.17 (1H, s); LRMS (ESI): m/z [M+H]$^+$ 428.

5-(6-(4,4-difluoropiperidine-1-carbonyl)naphthalen-1-yl)-2,3-dimethylisoindolin-1-one

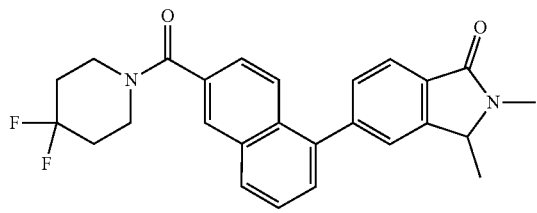 [SMILES: CC1c2cc(-c3cccc4cc(C(=O)N5CCC(F)(F)CC5)ccc34)ccc2C(=O)N1C]

Starting material 5-bromo-2,3-dimethylisoindolin-1-one (5ae-ai) was obtained using the method described in procedure 10.

$^1$H NMR (400 MHz, CDCl$_3$) δ 1.57 (3H, d, J=6.7 Hz), 1.95-2.18 (4H, m), 3.21 (3H, s), 3.56-4.02 (4H, m), 4.57 (1H, q, J=6.9 Hz), 7.48 (1H, dd, J=8.6, 1.8 Hz), 7.54-7.66 (4H, m), 7.90 (1H, d, J=8.5 Hz), 7.94-7.99 (2H, m), 8.03 (1H, s); LRMS (ESI): m/z [M+H]$^+$ 435.

5-(6-(4,4-difluoropiperidine-1-carbonyl)naphthalen-1-yl)-2,3,3-trimethylisoindolin-1-one

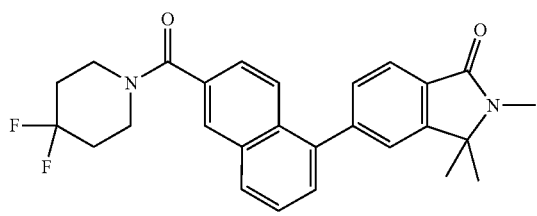 [SMILES: CN1C(=O)c2ccc(-c3cccc4cc(C(=O)N5CCC(F)(F)CC5)ccc34)cc2C1(C)C]

Starting material 5-bromo-2,3,3-trimethylisoindolin-1-one (5af-ai) was obtained was obtained using the method described in procedure 10.

$^1$H NMR (400 MHz, CDCl$_3$) δ 1.55 (6H, s), 1.96-2.19 (4H, m), 3.12 (3H, s), 3.53-4.04 (4H, m), 7.48 (1H, dd, J=8.7, 1.7 Hz), 7.54-7.59 (3H, m), 7.63-7.66 (1H, m), 7.91-7.99 (3H, m), 8.03 (1H, d, J=1.6 Hz); LRMS (ESI): m/z [M+H]$^+$ 449.

6-(6-(4,4-difluoropiperidine-1-carbonyl)naphthalen-1-yl) isoquinolin-3 (2H)-one

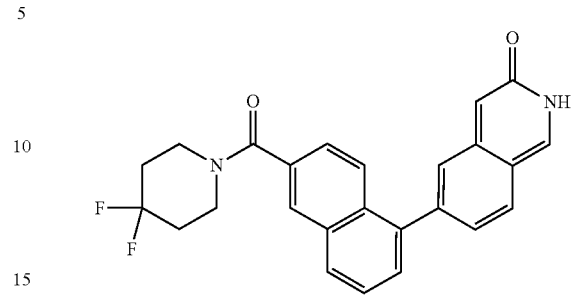

$^1$H NMR (400 MHz, CDCl$_3$) δ 1.85-2.24 (4H, m), 3.26-4.17 (4H, m), 7.13 (1H, s), 7.41-7.52 (2H, m), 7.56-7.69 (2H, m), 7.74 (1H, s), 7.91-8.00 (3H, m), 8.02 (1H, d, J=1.5 Hz), 8.86 (1H, s); LRMS (ESI): m/z [M+H]$^+$ 419.

3-(6-(4,4-difluoropiperidine-1-carbonyl)naphthalen-1-yl)-1,7-naphthyridin-8 (7H)-one

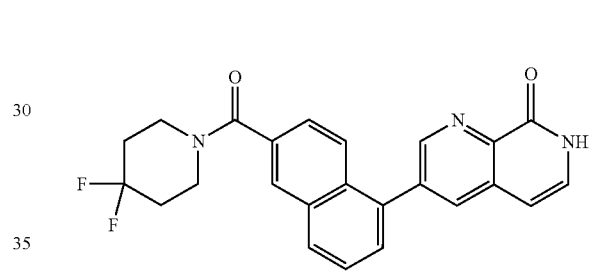

$^1$H NMR (400 MHz, CDCl$_3$) δ 2.05 (4H, br s), 3.35-4.17 (4H, m)), 6.64 (1H, d, J=7.0 Hz), 7.35-7.45 (1H, m), 7.51 (1H, dd, J=8.7, 1.6 Hz), 7.60 (1H, d, J=7.2 Hz), 7.68 (1H, dd, J=8.1, 7.2 Hz), 7.87 (1H, d, J=8.7 Hz), 8.01 (1H, d, J=8.1 Hz), 8.05 (1H, d, J=1.2 Hz), 8.07 (1H, d, J=1.6 Hz), 9.04 (1H, d, J=1.2 Hz), 12.09 (NH, br s); LRMS (ESI): m/z [M+H]$^+$ 420.

3-(6-(4,4-difluoropiperidine-1-carbonyl)naphthalen-1-yl)pyrido[2,3-d]pyridazin-8(7H)-one

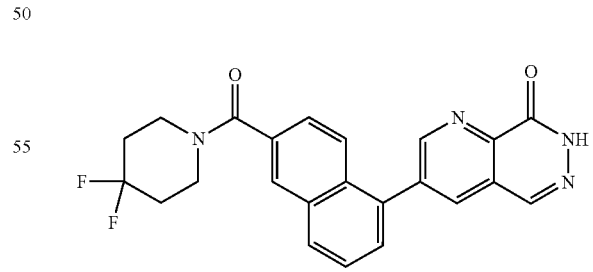

$^1$H NMR (400 MHz, CDCl$_3$) δ 2.05 (4H, br s), 3.35-4.16 (4H, m)), 7.53 (1H, dd, J=8.7, 1.5 Hz), 7.59 (1H, d, J=6.2 Hz), 7.70 (1H, dd, J=8.2, 6.2 Hz), 7.79 (1H, d, J=8.7 Hz), 8.02-8.09 (2H, m), 8.21 (1H, d, J=1.9 Hz), 8.27 (1H, s), 9.26 (1H, d, J=1.9 Hz), 10.36 (NH, br s); LRMS (ESI): m/z [M+H]$^+$ 421.

133

3-(6-(4,4-difluoropiperidine-1-carbonyl)naphthalen-1-yl)-5,6-dihydro-7H-pyrrolo[3,4-b]pyridin-7-one

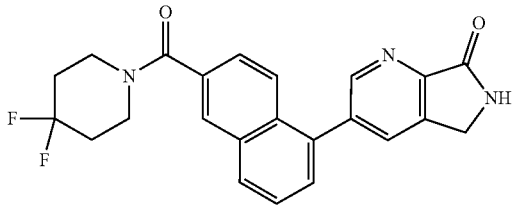 [SMILES: O=C1NCc2cc(-c3cccc4cc(C(=O)N5CCC(F)(F)CC5)ccc34)cnc21]

$^1$H NMR (400 MHz, DMSO-d$_6$) δ 2.02-2.13 (4H, m), 3.42-3.54 (2H, m), 3.72-3.84 (2H, m), 4.52 (2H, s), 7.59 (1H, dd, J=8.7, 1.8 Hz), 7.63-7.65 (1H, m), 7.71-7.75 (1H, m), 7.82 (1H, d, J=8.6 Hz), 8.16 (1H, d, J=8.9 Hz), 8.19-8.21 (2H, m), 8.82 (1H, d, J=1.8 Hz), 9.07 (1H, s); LRMS (ESI): m/z [M+H]$^+$ 408.

6-(6-(4,4-difluoropiperidine-1-carbonyl)naphthalen-1-yl)-4-methylphthalazin-1 (2H)-one

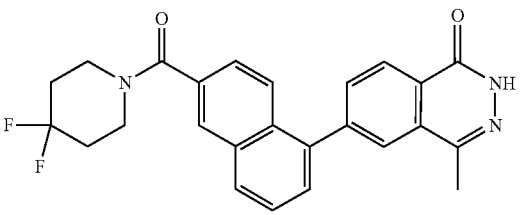 [SMILES: Cc1n[nH]c(=O)c2ccc(-c3cccc4cc(C(=O)N5CCC(F)(F)CC5)ccc34)cc12]

$^1$H NMR (400 MHz, CD$_3$OD) δ 2.09 (4H, br s), 2.62 (3H, s), 3.53-4.10 (4H, m), 7.55 (1H, dd, J=8.7, 1.7 Hz), 7.66 (1H, dd, J=7.1, 1.3 Hz), 7.71 (1H, dd, J=8.2, 7.1 Hz), 7.90 (1H, d, J=8.7 Hz), 7.99 (1H, dd, J=8.2, 1.5 Hz), 8.05 (1H, d, J=1.5 Hz), 8.10 (1H, d, J=8.2 Hz), 8.13 (1H, d, J=1.7 Hz), 8.51 (1H, d, J=8.2 Hz); LRMS (ESI): m/z [M+H]$^+$ 434.

8-(6-(4,4-difluoropiperidine-1-carbonyl)naphthalen-1-yl)-4H-pyrido[1,2-a]pyrimidin-4-one

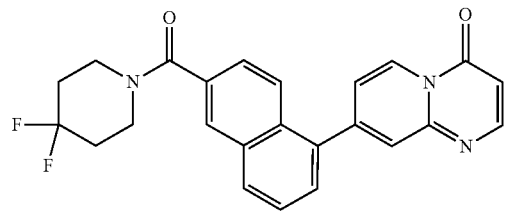 [SMILES: O=C(c1ccc2c(-c3ccn4c(=O)ccnc4c3)cccc2c1)N1CCC(F)(F)CC1]

$^1$H NMR (400 MHz, CDCl$_3$) δ 1.94-2.18 (4H, m), 3.57-3.75 (2H, m), 3.88-4.08 (2H, m), 6.58 (1H, d, J=6.4 Hz), 7.58-7.73 (5H, m), 7.92 (1H, d, J=8.1 Hz), 8.08-8.10 (2H, m), 8.33 (1H, d, J=6.4 Hz), 9.28 (1H, d, J=6.4 Hz); LRMS (ESI): m/z [M+H]$^+$ 420.

134

6-(6-(4,4-difluoropiperidine-1-carbonyl)naphthalen-1-yl)-2-methyl-1,2-dihydro-3H-pyrrolo[3,4-c]pyridin-3-one

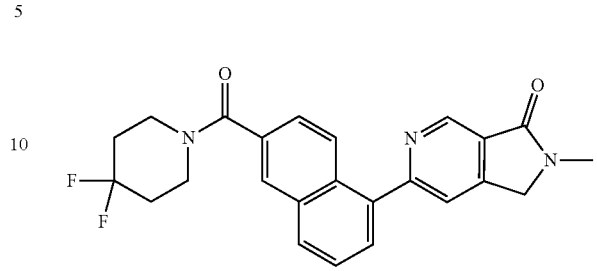

$^1$H NMR (400 MHz, DMSO-d$_6$) δ 2.03-2.13 (4H, m), 3.14 (3H, s), 3.44-3.56 (2H, m), 3.70-3.83 (2H, m), 4.66 (2H, s), 7.58 (1H, d, J=8.3 Hz), 7.71-7.77 (2H, m), 7.99 (1H, s), 8.11-8.17 (3H, m), 9.05 (1H, s); LRMS (ESI): m/z [M+H]$^+$ 422.

7-(6-(4,4-difluoropiperidine-1-carbonyl)naphthalen-1-yl)-1-methylquinazoline-2,4(1H,3H)-dione

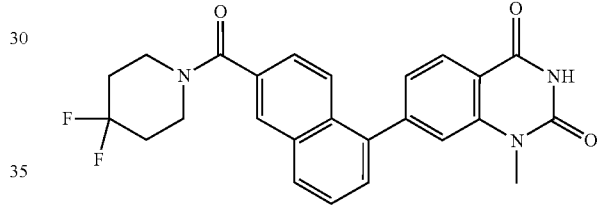

$^1$H NMR (400 MHz, DMSO-d$_6$) δ 2.07 (4H, br s), 3.45-3.56 (5H, m), 3.79 (2H, br s), 7.40 (1H, d, J=8.1 Hz), 7.51 (1H, s), 7.58 (1H, d, J=8.7 Hz), 7.64-7.65 (1H, m), 7.70-7.73 (1H, m), 7.88 (1H, d, J=8.1 Hz), 8.12-8.18 (3H, m), 11.66 (1H, s); LRMS (ESI): m/z [M+H]$^+$ 450.

4-(6-(4,4-difluoropiperidine-1-carbonyl)naphthalen-1-yl)-2,6-difluorobenzoic acid

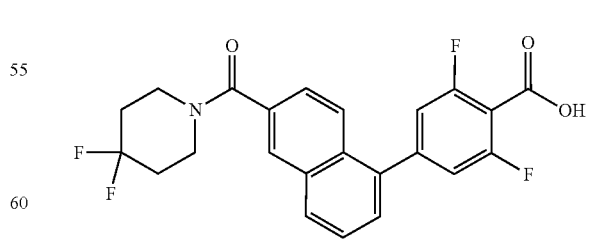

$^1$H NMR (400 MHz, CDCl$_3$) δ 1.96-2.23 (4H, m), 3.62-4.06 (4H, m), 7.17 (2H, d, J=8.8 Hz), 7.53 (2H, d, J=7.4 Hz), 7.63-7.67 (1H, m), 7.93 (1H, d, J=8.8 Hz), 8.00 (1H, d, J=8.2 Hz), 8.06 (1H, s); LRMS (ESI): m/z [M+H]$^+$ 432.

5-(6-(4,4-difluoropiperidine-1-carbonyl)naphthalen-1-yl)pyrimidine-2-carboxylic acid

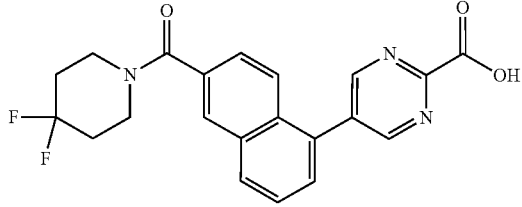 [SMILES: O=C(O)c1ncc(-c2cccc3cc(C(=O)N4CCC(F)(F)CC4)ccc23)cn1]

¹H NMR (400 MHz, CDCl₃) δ 1.96-2.22 (4H, m), 3.61-4.03 (4H, m), 7.58-7.60 (2H, m), 7.72-7.76 (1H, m), 7.80 (1H, d, J=8.0 Hz), 8.09-8.11 (2H, m), 9.15 (2H, s); LRMS (ESI): m/z [M+H]⁺ 398.

7-(6-(4,4-difluoropiperidine-1-carbonyl)naphthalen-1-yl)pyrido[3,2-d]pyrimidin-4(3H)-one

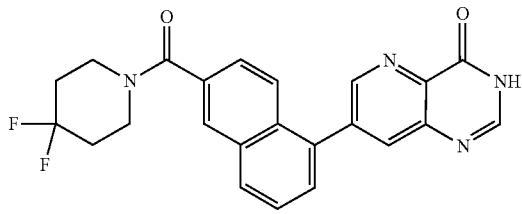 [SMILES: O=C(c1ccc2c(-c3cnc4c(=O)[nH]cnc4c3)cccc2c1)N1CCC(F)(F)CC1]

¹H NMR (400 MHz, CDCl₃) δ 1.88-2.36 (4H, m), 3.31-4.16 (4H, m), 7.53 (1H, d, J=8.7 Hz), 7.62 (1H, d, J=6.6 Hz), 7.69 (1H, dd, J=8.4, 6.6 Hz), 7.88 (1H, d, J=8.7 Hz), 8.04 (1H, d, J=8.4 Hz), 8.06 (1H, s), 8.29 (1H, s), 8.38 (1H, s), 9.08 (1H, s), 10.36 (NH, br s); LRMS (ESI): m/z [M+H]⁺ 421.

7-(6-(4,4-difluoropiperidine-1-carbonyl)naphthalen-1-yl)-3-methylpyrido[3,2-d]pyrimidin-4 (3H)-one

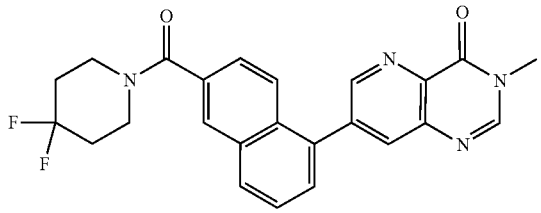 [SMILES: Cn1cnc2cc(-c3cccc4cc(C(=O)N5CCC(F)(F)CC5)ccc34)cnc2c1=O]

¹H NMR (400 MHz, CDCl₃) δ 1.86-2.27 (4H, m), 3.23-4.06 (7H, m), 7.51 (1H, dd, J=8.7, 1.5 Hz), 7.60 (1H, d, J=7.0 Hz), 7.68 (1H, dd, J=8.4, 7.0 Hz), 7.86 (1H, d, J=8.7 Hz), 8.02 (1H, d, J=8.4 Hz), 8.05 (1H, d, J=1.5 Hz), 8.22 (1H, d, J=2.0 Hz), 8.26 (1H, s), 9.03 (1H, d, J=2.0 Hz); LRMS (ESI): m/z [M+H]⁺ 435.

5-(6-(4,4-difluoropiperidine-1-carbonyl)naphthalen-1-yl)-3-fluoropicolinic acid

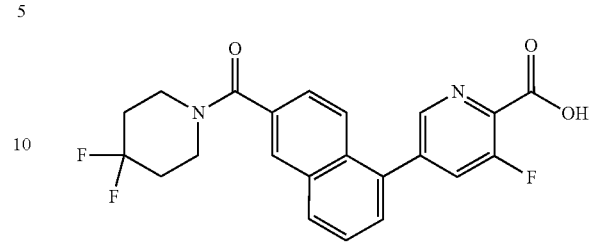

¹H NMR (400 MHz, CDCl₃) δ 1.96-2.23 (4H, m), 3.62-4.07 (4H, m), 7.55-7.60 (2H, m), 7.70-7.73 (1H, m), 7.83-7.86 (2H, m), 8.06-8.09 (2H, m), 8.64 (1H, s); LRMS (ESI): m/z [M+H]⁺ 415.

4-(6-(4,4-difluoropiperidine-1-carbonyl)naphthalen-1-yl)-2-fluoro-6-methoxybenzoic acid

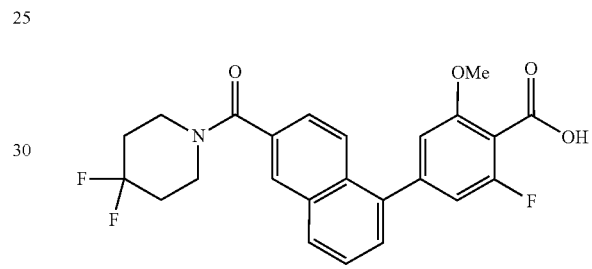

¹H NMR (400 MHz, DMSO-d₆) δ 2.08 (4H, br s), 3.45-3.81 (4H, m), 3.87 (3H, s), 7.02-7.05 (2H, m), 7.57-7.61 (2H, m), 7.66-7.70 (1H, m), 7.90 (1H, d, J=8.7 Hz), 8.10 (1H, d, J=8.3 Hz), 8.16 (1H, d, J=1.3 Hz); LRMS (ESI): m/z [M+H]⁺ 444.

The following compounds were synthesized in a similar manner using the appropriate tertiary amines in step 1-1 and heteroaryl bromides in step 1-3.

6-(6-(piperidine-1-carbonyl)naphthalen-1-yl)isoquinolin-1(2H)-one

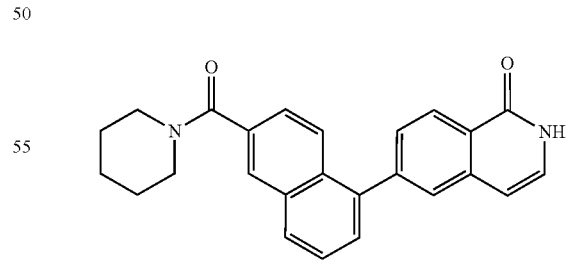

¹H NMR (400 MHz, CD₃OD) δ 1.50-1.81 (6H, m), 3.45 (2H, br s), 3.77 (2H, br s), 6.76 (1H, d, J=7.0 Hz), 7.26 (1H, d, J=7.0 Hz), 7.47 (1H, dd, J=8.7, 1.7 Hz), 7.59 (1H, dd, J=7.1, 1.2 Hz), 7.63-7.70 (2H, m), 7.78 (1H, d, J=1.7 Hz), 7.91 (1H, d, J=8.7 Hz), 8.02-8.09 (2H, m), 8.44 (1H, d, J=8.3 Hz); LRMS (ESI): m/z [M+H]⁺ 383.

(S)-6-(6-(3-methylpiperidine-1-carbonyl)naphthalen-1-yl) isoquinolin-1 (2H)-one

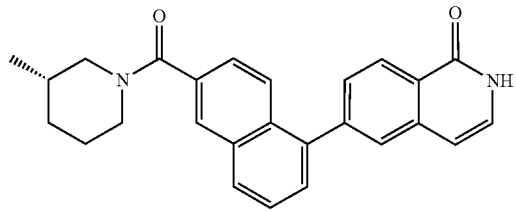 [SMILES: C[C@H]1CCCN(C(=O)c2ccc3c(-c4ccc5c(=O)[nH]ccc5c4)cccc3c2)C1]

¹H NMR (400 MHz, CDCl₃) δ 0.73-1.11 (3H, m), 1.13-1.29 (1H, m), 1.43-2.08 (4H, m), 2.44-3.12 (2H, m), 3.63-3.88 (1H, m), 4.64 (1H, br s), 6.62 (1H, d, J=7.1 Hz), 7.18-7.25 (1H, m), 7.45 (1H, dd, J=8.7, 1.6 Hz), 7.50-7.78 (4H, m), 7.90 (1H, d, J=8.7 Hz), 7.94 (1H, d, J=8.2 Hz), 7.98 (1H, d, J=1.6 Hz), 8.54 (1H, d, J=8.2 Hz), 10.39 (NH, br s); LRMS (ESI): m/z [M+H]⁺ 397.

(S)-3-(6-(3-methylpiperidine-1-carbonyl)naphthalen-1-yl)-1,7-naphthyridin-8 (7H)-one

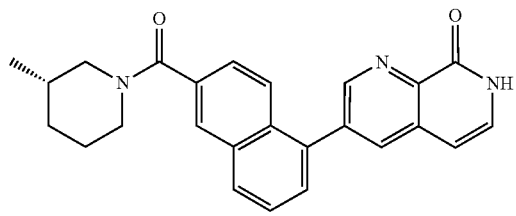 [SMILES: C[C@H]1CCCN(C(=O)c2ccc3c(-c4cnc5c(=O)[nH]ccc5c4)cccc3c2)C1]

¹H NMR (400 MHz, CDCl₃) δ 0.71-1.09 (3H, m), 1.12-1.33 (1H, m), 1.42-1.97 (4H, m), 2.43-2.80 (1H, m), 2.81-3.12 (1H, m), 3.59-3.83 (1H, m), 4.60 (1H, br s), 6.63 (1H, d, J=7.0 Hz), 7.35-7.42 (1H, m), 7.50 (1H, dd, J=8.6, 1.6 Hz), 7.57 (1H, d, J=6.5 Hz), 7.65 (1H, dd, J=8.2, 6.5 Hz), 7.84 (1H, d, J=8.6 Hz), 7.98-8.03 (2H, m), 8.06 (1H, d, J=1.8 Hz), 9.04 (1H, d, J=1.8 Hz), 11.86 (NH, br s); LRMS (ESI): m/z [M+H]⁺ 398.

(S)-6-(6-(3-methylpiperidine-1-carbonyl)naphthalen-1-yl)-2,7-naphthyridin-1 (2H)-one

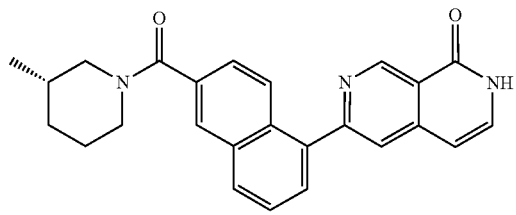

¹H NMR (400 MHz, CDCl₃) δ 0.72-1.10 (3H, m), 1.12-1.29 (1H, m), 1.38-2.00 (4H, m), 2.38-2.78 (1H, m), 2.79-3.08 (1H, m), 3.62-3.88 (1H, m), 4.47-4.73 (1H, m), 6.58 (1H, d, J=7.1 Hz), 7.33-7.40 (1H, m), 7.50 (1H, dd, J=8.7, 1.6 Hz), 7.63 (1H, dd, J=8.1, 7.2 Hz), 7.69 (1H, s), 7.72 (1H, d, J=7.2 Hz), 7.92-8.02 (2H, m), 8.15 (1H, d, J=8.7 Hz), 9.77 (1H, s), 10.18 (NH, br s); LRMS (ESI): m/z [M+H]⁺ 398.

(S)-6-(6-(3-methylpiperidine-1-carbonyl)naphthalen-1-yl)phthalazin-1(2H)-one

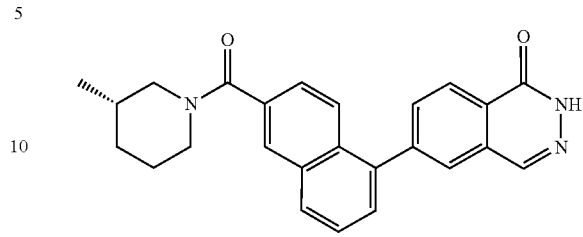

¹H NMR (400 MHz, CDCl₃) δ 0.72-1.11 (3H, m), 1.13-1.31 (1H, m), 1.42-2.00 (4H, m), 2.44-2.79 (1H, m), 2.81-3.13 (1H, m), 3.60-3.88 (1H, m), 4.62 (1H, br s), 7.47 (1H, dd, J=8.6, 1.6 Hz), 7.50 (1H, d, J=7.1 Hz), 7.65 (1H, dd, J=8.1, 7.1 Hz), 7.81 (1H, d, J=8.6 Hz), 7.85 (1H, s), 7.93 (1H, d, J=8.1 Hz), 7.97 (1H, d, J=8.1 Hz), 8.00 (1H, d, J=1.6 Hz), 8.22 (1H, s), 8.55 (1H, d, J=8.1 Hz), 10.00 (NH, br s); LRMS (ESI): m/z [M+H]⁺ 398.

(S)-6-methyl-3-(6-(3-methylpiperidine-1-carbonyl)naphthalen-1-yl)-5,6-dihydro-7H-pyrrolo[3,4-b]pyridin-7-one

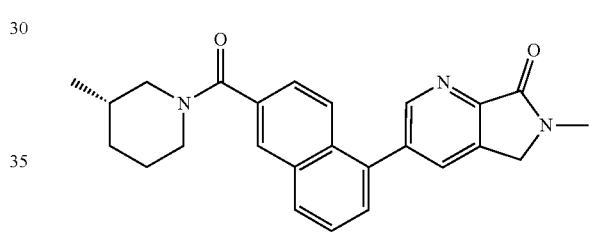

¹H NMR (400 MHz, CDCl₃) δ 0.70-1.10 (3H, m), 1.13-1.31 (1H, m), 1.39-2.00 (4H, m), 2.41-2.79 (1H, m), 2.80-3.10 (1H, m), 3.33 (3H, s), 3.57-3.86 (1H, m), 4.44-4.72 (3H, m), 7.44-7.55 (2H, m), 7.62 (1H, t, J=7.6 Hz), 7.77 (1H, d, J=8.6 Hz), 7.89-8.07 (3H, m), 8.90 (1H, s); LRMS (ESI): m/z [M+H]⁺ 400.

6-(6-(4-methylpiperidine-1-carbonyl)naphthalen-1-yl)phthalazin-1(2H)-one

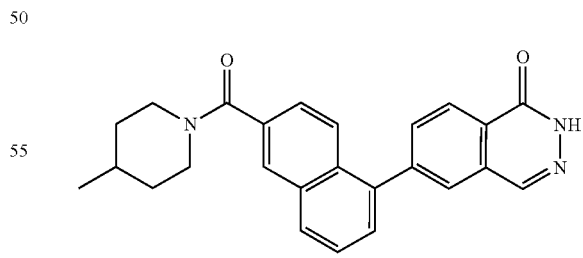

¹H NMR (400 MHz, CD₃OD) δ 1.02 (3H, d, J=6.5 Hz), 1.12-1.35 (2H, m), 1.60-1.88 (3H, m), 2.87-2.97 (1H, m), 3.13-3.24 (1H, m), 3.76-3.83 (1H, m), 4.65-4.73 (1H, m), 7.49 (1H, dd, J=8.7, 1.7 Hz), 7.63 (1H, d, J=7.1 Hz), 7.70 (1H, dd, J=8.2, 7.1 Hz), 7.89 (1H, d, J=8.7 Hz), 8.02 (1H, dd, J=8.2, 1.7 Hz), 8.06-8.10 (3H, m), 8.43 (1H, d, J=0.5 Hz), 8.49 (1H, d, J=8.2 Hz); LRMS (ESI): m/z [M+H]⁺ 398.

6-methyl-3-(6-(4-methylpiperidine-1-carbonyl)naphthalen-1-yl)-5,6-dihydro-7H-pyrrolo[3,4-b]pyridin-7-one

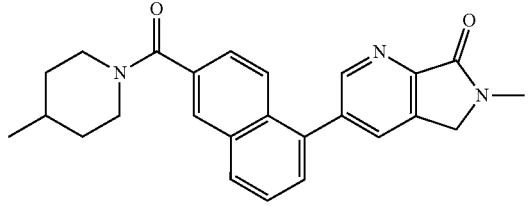

$^1$H NMR (400 MHz, CDCl$_3$) δ 0.99 (3H, d, J=6.5 Hz), 1.08-1.36 (2H, m), 1.50-1.87 (3H, m), 2.75-2.90 (1H, m), 2.98-3.12 (1H, m), 3.33 (3H, s), 3.72-3.83 (1H, m), 4.52 (2H, s), 4.68-4.79 (1H, m), 7.46-7.51 (2H, m), 7.62 (1H, dd, J=8.2, 7.1 Hz), 7.77 (1H, d, J=8.7 Hz), 7.92 (1H, d, J=1.9 Hz), 7.97 (1H, d, J=8.2 Hz), 7.99 (1H, d, J=1.6 Hz), 8.90 (1H, d, J=1.9 Hz); LRMS (ESI): m/z [M+H]$^+$ 400.

3-(6-(4,4-difluoropiperidine-1-carbonyl)-2-methylnaphthalen-1-yl)-6-methyl-5,6-dihydro-7H-pyrrolo[3,4-b]pyridin-7-one

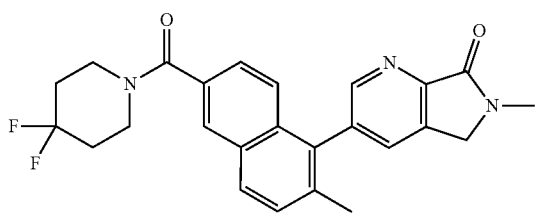 [SMILES: Cc1ccc2cc(C(=O)N3CCC(F)(F)CC3)ccc2c1-c1cnc2c(c1)CN(C)C2=O]

Starting material (4,4-difluoropiperidin-1-yl) (6-methyl-5-(4,4,5,5-tetramethyl-1,3,2-dioxaborolan-2-yl)naphthalen-2-yl)methanone for the preparation of 3-(6-(4,4-difluoropiperidine-1-carbonyl)-2-methylnaphthalen-1-yl)-6-methyl-5,6-dihydro-7H-pyrrolo[3,4-b]pyridin-7-one can be produced via bromination of commercially available 6-Methyl-2-naphthalenecarboxylic acid according to literature procedure (Tetrahedron: Asymmetry, 16, 2031-2038; 2005) to give 5-bromo-6-methyl-2-naphthoic acid, followed by amidation and Miyaura borylation according to general procedure 1 (Steps 1-1 and 1-2).

$^1$H NMR (400 MHz, CDCl$_3$) δ 1.92-2.16 (4H, m), 2.29 (3H, s), 3.38 (3H, s), 3.53-3.75 (2H, m), 3.86-4.00 (2H, m), 4.56 (2H, s), 7.31-7.40 (2H, m), 7.54 (1H, d, J=8.5 Hz), 7.77 (1H, d, J=1.7 Hz), 7.91 (1H, d, J=8.7 Hz), 7.98 (1H, d, J=1.4 Hz), 8.72 (1H, d, J=1.4 Hz); LRMS (ESI): m/z [M+H]$^+$ 436.

6-(6-(4,4-difluoropiperidine-1-carbonyl)-2-methylnaphthalen-1-yl)phthalazin-1(2H)-one

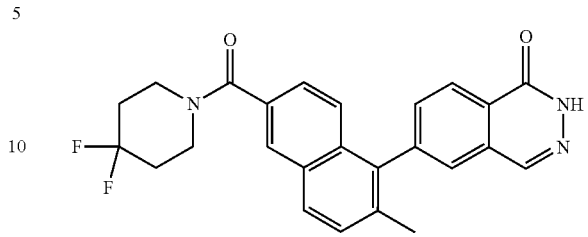

Starting material (4,4-difluoropiperidin-1-yl) (6-methyl-5-(4,4,5,5-tetramethyl-1,3,2-dioxaborolan-2-yl)naphthalen-2-yl)methanone for the preparation of 6-(6-(4,4-difluoropiperidine-1-carbonyl)-2-methylnaphthalen-1-yl)phthalazin-1(2H)-one can be produced from 6-methyl-2-naphthoic acid in accordance with any method described in the literature.

$^1$H NMR (400 MHz, CDCl$_3$) δ 1.94-2.16 (4H, m), 2.28 (3H, s), 3.52-4.05 (4H, m), 7.30-7.38 (2H, m), 7.55 (1H, d, J=8.4 Hz), 7.68 (1H, s), 7.74 (1H, dd, J=8.2, 1.3 Hz), 7.91 (1H, d, J=8.2 Hz), 7.99 (1H, s), 8.23 (1H, s), 8.60 (1H, d, J=8.3 Hz), 10.08 (NH, br s); LRMS (ESI): m/z [M+H]$^+$ 434.

6-(6-(4,4-difluoropiperidine-1-carbonyl)-2-fluoronaphthalen-1-yl) isoquinolin-1 (2H)-one

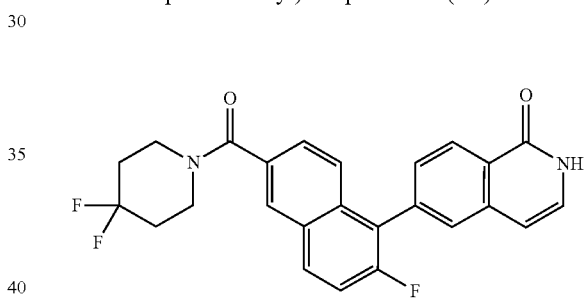

$^1$H NMR (400 MHz, CDCl$_3$) δ 2.04 (4H, br s), 3.40-4.20 (4H, m)), 6.62 (1H, d, J=7.1 Hz), 7.24 (1H, t, J=6.7 Hz), 7.48 (1H, t, J=9.0 Hz), 7.48 (1H, dd, J=8.7, 1.7 Hz), 7.59 (1H, dd, J=8.1, 1.3 Hz), 7.67 (1H, s), 7.71 (1H, d, J=8.7 Hz), 7.98 (1H, dd, J=9.1, 5.2 Hz), 8.03 (1H, d, J=1.5 Hz), 8.60 (1H, d, J=8.2 Hz), 10.16 (NH, br s); LRMS (ESI): m/z [M+H]$^+$ 437.

3-(6-(4,4-difluoropiperidine-1-carbonyl)-2-fluoronaphthalen-1-yl)-6-methyl-5,6-dihydro-7H-pyrrolo[3,4-b]pyridin-7-one

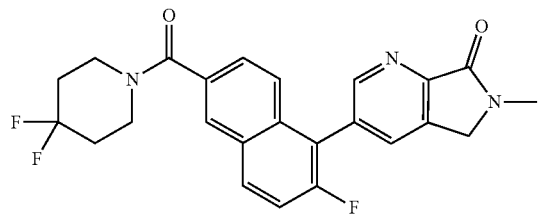 [SMILES: CN1Cc2cc(-c3c(F)ccc4cc(C(=O)N5CCC(F)(F)CC5)ccc34)cnc2C1=O]

$^1$H NMR (400 MHz, CDCl$_3$) δ 2.04 (4H, br s), 3.36 (3H, s), 3.45-4.10 (4H, m), 4.56 (2H, s), 7.49 (1H, t, J=9.0 Hz), 7.52 (1H, dd, J=8.8, 1.7 Hz), 7.64 (1H, t, J=8.6 Hz), 7.93

(1H, d, J=0.95 Hz), 8.02 (1H, dd, J=9.2, 5.5 Hz), 8.04 (1H, s), 8.85 (1H, d, J=1.8 Hz); LRMS (ESI): m/z [M+H]+ 440.

3-(6-(4,4-difluoropiperidine-1-carbonyl)-2-fluoronaphthalen-1-yl)pyrido[2,3-d]pyridazin-8(7H)-one

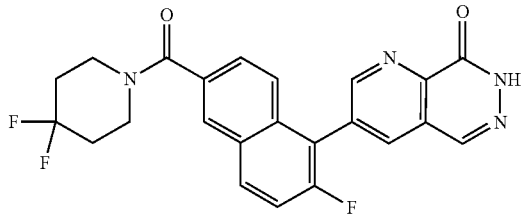 [SMILES: O=C(c1ccc2c(-c3cnc4c(=O)[nH]ncc4c3)c(F)ccc2c1)N1CCC(F)(F)CC1]

¹H NMR (400 MHz, CDCl₃) δ 2.06 (4H, br s), 3.45-4.10 (4H, m)), 7.53 (1H, t, J=9.1), 7.56 (1H, d, J=9.4 Hz), 7.63 (1H, d, J=8.5 Hz), 8.07 (1H, s), 8.07 (1H, dd, J=9.0, 5.5 Hz), 8.23 (1H, d, J=2.1 Hz), 8.28 (1H, s), 9.24 (1H, d, J=2.1 Hz), 10.25 (NH, br s); LRMS (ESI): m/z [M+H]+ 439.

6-(6-(4,4-difluoropiperidine-1-carbonyl)-2-fluoronaphthalen-1-yl)-2,7-naphthyridin-1 (2H)-one

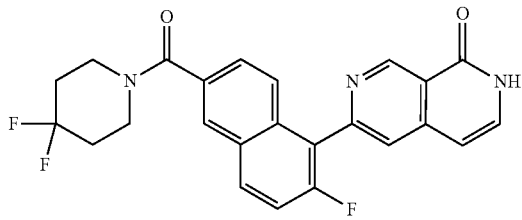 [SMILES: O=C(c1ccc2c(-c3cc4cc[nH]c(=O)c4cn3)c(F)ccc2c1)N1CCC(F)(F)CC1]

¹H NMR (400 MHz, CDCl₃) δ 2.04 (4H, br s), 3.45-4.10 (4H, m)), 6.60 (1H, d, J=7.3), 7.39 (1H, t, J=6.5 Hz), 7.48 (1H, t, J=9.2 Hz), 7.50 (1H, dd, J=8.8, 1.2 Hz), 7.71 (1H, s), 7.85 (1H, d, J=8.7 Hz), 8.02 (1H, dd, J=9.2, 5.2 Hz), 8.04 (1H, s), 9.81 (1H, s), 9.90 (NH, br s); LRMS (ESI): m/z [M+H]+ 438.

6-(6-(4,4-difluoropiperidine-1-carbonyl)-2-fluoronaphthalen-1-yl)phthalazin-1(2H)-one

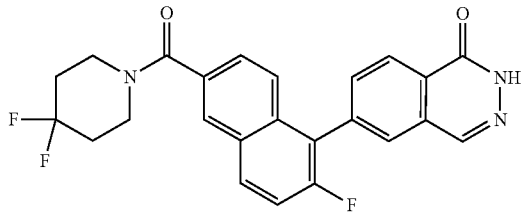 [SMILES: O=C(c1ccc2c(-c3ccc4c(=O)[nH]ncc4c3)c(F)ccc2c1)N1CCC(F)(F)CC1]

¹H NMR (400 MHz, CDCl₃) δ 2.06 (4H, br s), 3.45-4.10 (4H, m), 7.49 (1H, t, J=9.1), 7.50 (1H, dd, J=8.7, 1.5 Hz), 7.64 (1H, d, J=8.6 Hz), 7.84 (1H, d, J=0.7 Hz), 7.88 (1H, d, J=8.8 Hz), 8.02 (1H, dd, J=8.9, 5.3 Hz), 8.04 (1H, d, J=1.6 Hz), 8.24 (1H, s), 8.61 (1H, d, J=8.2 Hz), 10.03 (NH, br s); LRMS (ESI): m/z [M+H]+ 438.

5-(6-(4,4-difluoropiperidine-1-carbonyl)-2-fluoronaphthalen-1-yl)-2-methylisoindolin-1-one

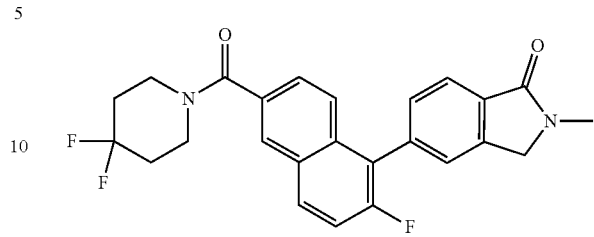

¹H NMR (400 MHz, CDCl₃) δ 2.05 (4H, br s), 3.67 (2H, br s), 3.69 (3H, s), 3.93 (2H, br s), 4.51 (2H, s), 7.46 (1H, t, J=9.0 Hz), 7.47 (1H, dd, J=9.0, 2.4 Hz), 7.52 (1H, s), 7.53 (1H, d, J=7.0 Hz), 7.67 (1H, d, J=8.7 Hz), 7.96 (1H, dd, J=8.9, 5.3 Hz), 8.02 (1H, d, J=1.5 Hz), 8.03 (1H, d, J=8.3 Hz); LRMS (ESI): m/z [M+H]+ 439.

The following compounds were synthesized in a similar manner using the appropriate heteroaryl iodides/chlorides in step 1-3.

7-(6-(4,4-difluoropiperidine-1-carbonyl)naphthalen-1-yl)-2,6-dimethyl-[1,2,4]triazolo[4,3-a]pyridin-3 (2H)-one

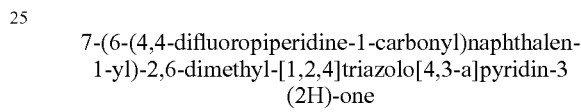
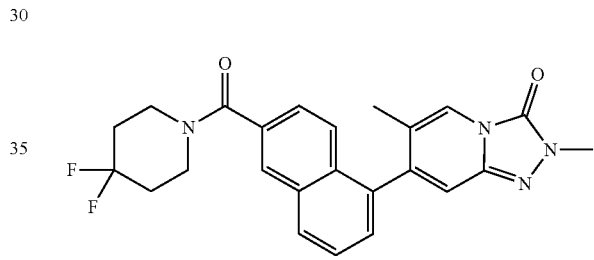

¹H NMR (400 MHz, CDCl₃) δ 1.80 (3H, d, J=1.1 Hz), 1.87-2.28 (4H, m), 3.36-4.13 (7H, m), 7.03 (1H, s), 7.41 (1H, d, J=7.0 Hz), 7.47 (1H, dd, J=8.6, 1.6 Hz), 7.56-7.65 (2H, m), 7.69-7.74 (1H, m), 7.96 (1H, d, J=8.3 Hz), 8.00 (1H, d, J=1.6 Hz); LRMS (ESI): m/z [M+H]+ 437.

7-(6-(4,4-difluoropiperidine-1-carbonyl)naphthalen-1-yl)-2,8-dimethyl-[1,2,4]triazolo[4,3-a]pyridin-3 (2H)-one

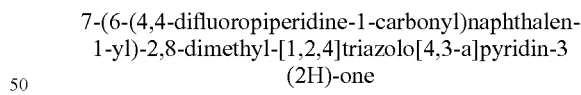
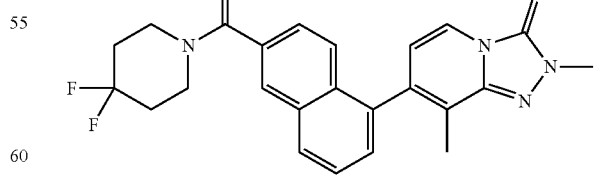

¹H NMR (400 MHz, CDCl₃) δ 1.85-2.28 (7H, m), 3.48-4.09 (7H, m), 6.46 (1H, d, J=7.1 Hz), 7.43 (1H, d, J=7.0 Hz), 7.46 (1H, dd, J=8.6, 1.6 Hz), 7.58-7.66 (2H, m), 7.75 (1H, d, J=7.1 Hz), 7.95 (1H, d, J=8.3 Hz), 8.00 (1H, d, J=1.6 Hz); LRMS (ESI): m/z [M+H] 437.

7-(6-(4,4-difluoropiperidine-1-carbonyl)naphthalen-1-yl)-2-methyl-[1,2,4]triazolo[4,3-a]pyridin-3(2H)-one

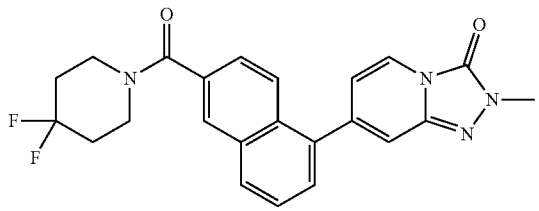 [SMILES: Cn1nc2cc(-c3cccc4cc(C(=O)N5CCC(F)(F)CC5)ccc34)ccn2c1=O]

Starting material 7-chloro-2-methyl-[1,2,4]triazolo[4,3-a]pyridin-3(2H)-one for the preparation of 7-(6-(4,4-difluoropiperidine-1-carbonyl)naphthalen-1-yl)-2-methyl-[1,2,4]triazolo[4,3-a]pyridin-3 (2H)-one was prepared by methylation of 7-chloro-2H-[1,2,4]triazolo[4,3-a]pyridin-3-one (5ab) according to the procedure described in Step 4-1.

$^1$H NMR (400 MHz, CDCl$_3$) δ 1.81-2.27 (4H, m), 3.31-4.11 (7H, m), 6.66 (1H, dd, J=7.2, 1.4 Hz), 7.18-7.20 (1H, m), 7.51 (1H, dd, J=8.6, 1.6 Hz), 7.54 (1H, d, J=7.1 Hz), 7.62 (1H, dd, J=8.1, 7.1), 7.88 (1H, dd, J=7.2, 0.9 Hz), 7.91-7.99 (2H, m), 8.01 (1H, d, J=1.6 Hz); LRMS (ESI): m/z [M+H]$^+$ 423.

7-(6-(4,4-difluoropiperidine-1-carbonyl)naphthalen-1-yl)-[1,2,4]triazolo[4,3-a]pyridin-3(2H)-one was prepared in accordance with the general procedure 1 using the method described below in detail.

Synthesis of 7-(6-(4,4-difluoropiperidine-1-carbonyl)naphthalen-1-yl)-[1,2,4]triazolo[4,3-a]pyridin-3 (2H)-one

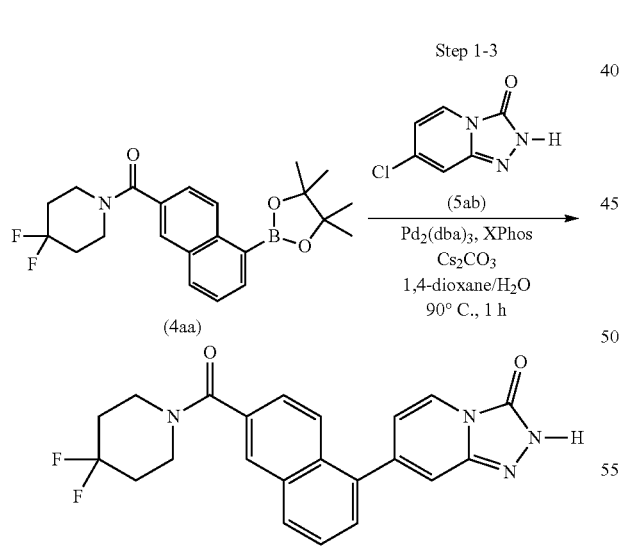

Step 1-3

A reaction vessel containing a mixture of (4,4-difluoro-1-piperidyl)-[5-(4,4,5,5-tetramethyl-1,3,2-dioxaborolan-2-yl)-2-naphthyl]methanone (4aa) (50.0 mg, 0.12 mmol), 7-chloro-2H-[1,2,4]triazolo[4,3-a]pyridin-3-one (5ab) (21.1 mg, 0.12 mmol), Cs$_2$CO$_3$ (121.8 mg, 0.37 mmol), Pd$_2$(dba)$_3$ (11.4 mg, 0.01 mmol) and XPhos (5.9 mg, 0.01 mmol) was degassed and backfilled with nitrogen three times. After the addition of 1,4-dioxane (2 mL) and H$_2$O (0.5 mL), the reaction mixture was degassed again, and backfilled with nitrogen. The resulting mixture was then stirred and heated at 90° C. for 1 h. After cooling to r.t., the mixture was filtered through celite, and the filtrate was concentrated. The residue was purified by prep HPLC (CH$_3$CN/0.1% TFA-H$_2$O/0.1% TFA) to give the expected product as a pale yellow solid (29.1 mg).

$^1$H NMR (400 MHz, CDCl$_3$) δ 1.84-2.30 (4H, m), 3.43-4.13 (4H, m), 6.68 (1H, dd, J=7.2, 1.3 Hz), 7.21-7.27 (1H, m), 7.48-7.67 (3H, m), 7.87-8.08 (4H, m), 10.54 (NH, br s); LRMS (ESI): m/z [M+H]$^+$ 409.

The following compounds were synthesized using conditions analogous to 7-(6-(4,4-difluoropiperidine-1-carbonyl)naphthalen-1-yl)-[1,2,4]triazolo[4,3-a]pyridin-3(2H)-one in accordance with the general procedure 1 (Scheme 1).

7-(6-(piperidine-1-carbonyl)naphthalen-1-yl)-[1,2,4]triazolo[4,3-a]pyridin-3 (2H)-one

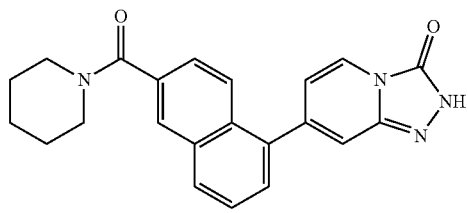 [SMILES: O=C(c1ccc2c(-c3ccn4c(=O)[nH]nc4c3)cccc2c1)N1CCCCC1]

$^1$H NMR (400 MHz, CDCl$_3$) δ 1.44-1.80 (6H, m), 3.40 (2H, br s), 3.77 (2H, br s), 6.68 (1H, d, J=7.1 Hz), 7.24 (1H, s), 7.47-7.54 (2H, m), 7.55-7.62 (1H, m), 7.85-8.01 (4H, m), 10.14 (NH, br s); LRMS (ESI): m/z [M+H]$^+$ 373.

2-(6-(4,4-difluoropiperidine-1-carbonyl)naphthalen-1-yl)-6,7-dihydro-5H-pyrrolo[3,4-b]pyridin-5-one

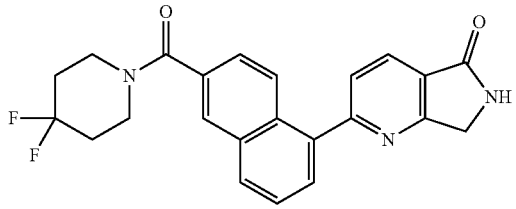 [SMILES: O=C1NCc2nc(-c3cccc4cc(C(=O)N5CCC(F)(F)CC5)ccc34)ccc21]

$^1$H NMR (400 MHz, DMSO-d$_6$) δ 2.07 (4H, br s), 3.44-3.56 (2H, m), 3.72-3.84 (2H, m), 4.55 (2H, s), 7.57 (1H, d, J=8.9 Hz), 7.70-7.77 (2H, m), 7.80 (1H, d, J=8.0 Hz) 8.14-8.17 (3H, m), 8.26 (1H, d, J=8.0 Hz), 8.89 (1H, s); LRMS (ESI): m/z [M+H]$^+$ 408.

6-(6-(4,4-difluoropiperidine-1-carbonyl)naphthalen-1-yl)isoquinolin-1(2H)-one was prepared in accordance with the general procedure 1 using the method described below in detail.

Synthesis of 6-(6-(4,4-difluoropiperidine-1-carbonyl) naphthalen-1-yl) isoquinolin-1 (2H)-one

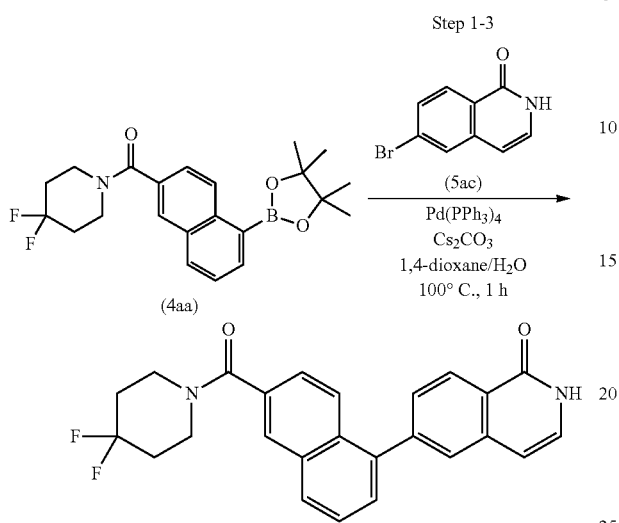

Step 1-3

A reaction vessel containing a mixture of (4,4-difluoro-1-piperidyl)-[5-(4,4,5,5-tetramethyl-1,3,2-dioxaborolan-2-yl)-2-naphthyl]methanone (4aa) (46.5 mg, 0.12 mmol), 6-bromo-2H-isoquinolin-1-one (5ac) (20.0 mg, 0.089 mmol), $Cs_2CO_3$ (87.2 mg, 0.27 mmol) $Pd(PPh_3)_4$ (25.8 mg, 0.02 mmol) was degassed and backfilled with nitrogen. After the addition of 1,4-dioxane (2.6 mL) and $H_2O$ (1.3 mL), the reaction mixture was degassed, and backfilled with nitrogen. The resulting mixture was then heated at 100° C. for 1 h. After cooling to r.t., the mixture was filtered through celite, and the filtrate was concentrated. The residue was purified by prep HPLC ($CH_3CN$/0.1% TFA-$H_2O$/0.1% TFA) to give the expected product (3.0 mg) as a white solid.

$^1$H NMR (400 MHz, $CD_3OD$) δ 2.09 (4H, br s), 3.52-4.09 (4H, m), 6.76 (1H, d, J=7.0 Hz), 7.26 (1H, d, J=7.0 Hz), 7.52 (1H, dd, J=8.7, 1.7 Hz), 7.61 (1H, d, J=7.1 Hz), 7.65 (1H, dd, J=8.2, 1.7 Hz), 7.68 (1H, dd, J=8.2, 7.1 Hz), 7.78 (1H, d, J=1.7 Hz), 7.92 (1H, d, J=8.7 Hz), 8.06 (1H, d, J=8.2 Hz), 8.11 (1H, d, J=1.7 Hz), 8.46 (1H, d, J=8.2 Hz); LRMS (ESI): m/z [M+H]$^+$ 419

The following compounds were synthesized using conditions analogous to 6-(6-(4,4-difluoropiperidine-1-carbonyl)naphthalen-1-yl)isoquinolin-1(2H)-one in accordance with the general procedure 1 (Scheme 1).

(4,4-difluoropiperidin-1-yl) (5-(7-methylquinolin-6-yl)naphthalen-2-yl)methanone

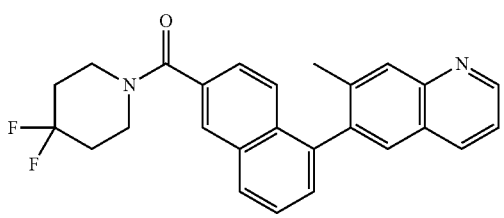 [SMILES: Cc1cc2ncccc2cc1-c1cccc2cc(C(=O)N3CCC(F)(F)CC3)ccc12]

$^1$H NMR (400 MHz, $CD_3OD$) δ 2.10 (4H, br s), 2.32 (3H, s), 3.53-4.06 (4H, m), 7.42 (1H, d, J=8.7 Hz), 7.49 (1H, dd, J=8.7, 1.7 Hz), 7.57 (1H, d, J=7.0 Hz), 7.74 (1H, dd, J=8.4, 7.1 Hz), 8.03 (1H, dd, J=8.3, 5.4 Hz), 8.12-8.46 (4H, m), 9.10 (1H, d, J=8.3 Hz), 9.19 (1H, dd, J=5.4, 1.5 Hz); LRMS (ESI): m/z [M+H]$^+$ 417.

6-(6-(pyrrolidine-1-carbonyl)naphthalen-1-yl)phthalazin-1(2H)-one

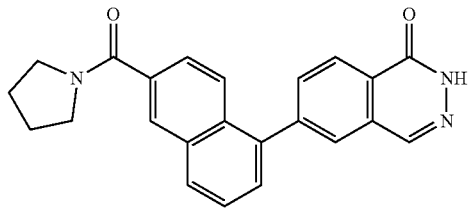 [SMILES: O=C(c1ccc2c(-c3ccc4c(=O)[nH]ncc4c3)cccc2c1)N1CCCC1]

$^1$H NMR (400 MHz, $CD_3OD$) δ 1.89-2.08 (4H, m), 3.55 (2H, t, J=6.6 Hz), 3.66 (2H, t, J=6.9 Hz), 7.59-7.66 (2H, m), 7.70 (1H, dd, J=8.2, 7.1 Hz), 7.88 (1H, d, J=8.7 Hz), 8.00 (1H, dd, J=8.2, 1.7 Hz), 8.05 (1H, d, J=1.7 Hz), 8.09 (1H, d, J=8.2 Hz), 8.19 (1H, d, J=1.7 Hz), 8.43 (1H, s), 8.49 (1H, d, J=8.2 Hz); LRMS (ESI): m/z [M+H]$^+$ 370.

(4,4-difluoropiperidin-1-yl) (5-(5-methylquinolin-6-yl)naphthalen-2-yl)methanone

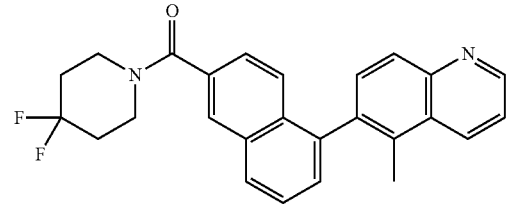 [SMILES: Cc1c(-c2cccc3cc(C(=O)N4CCC(F)(F)CC4)ccc23)ccc2ncccc12]

$^1$H NMR (400 MHz, $CD_3OD$) δ 2.11 (4H, br s), 2.52 (3H, s), 3.53-4.06 (4H, m), 7.44 (1H, d, J=8.7 Hz), 7.49 (1H, dd, J=8.7, 1.7 Hz), 7.56 (1H, dd, J=7.1, 1.2 Hz), 7.74 (1H, dd, J=8.3, 7.1 Hz), 7.99 (1H, d, J=8.7 Hz), 8.10-8.22 (4H, m), 9.22 (1H, dd, J=5.2, 1.5 Hz), 9.35 (1H, d, J=8.7 Hz); LRMS (ESI): m/z [M+H]$^+$ 417.

6-methyl-3-(6-(pyrrolidine-1-carbonyl)naphthalen-1-yl)-5,6-dihydro-7H-pyrrolo[3,4-b]pyridin-7-one

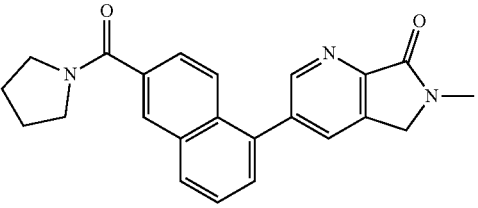 [SMILES: CN1Cc2cc(-c3cccc4cc(C(=O)N5CCCC5)ccc34)cnc2C1=O]

$^1$H NMR (400 MHz, $CD_3OD$) δ 1.88-2.08 (4H, m), 3.31 (3H, s), 3.55 (2H, t, J=6.6 Hz), 3.66 (2H, t, J=6.9 Hz), 4.65 (2H, s), 7.60-7.65 (2H, m), 7.70 (1H, dd, J=8.2, 7 h; 1 Hz), 7.86 (1H, d, J=8.8 Hz), 8.10 (1H, d, J=8.2 Hz), 8.18 (1H, d, J=1.9 Hz), 8.19 (1H, d, J=1.7 Hz), 8.80 (1H, d, J=1.9 Hz); LRMS (ESI): m/z [M+H]⁺ 372.

5-(6-(4,4-difluoropiperidine-1-carbonyl)naphthalen-1-yl)isoindolin-1-one was prepared in accordance with the general procedure 2 using the method described below in detail.

Synthesis of 5-(6-(4,4-difluoropiperidine-1-carbonyl) naphthalen-1-yl) isoindolin-1-one

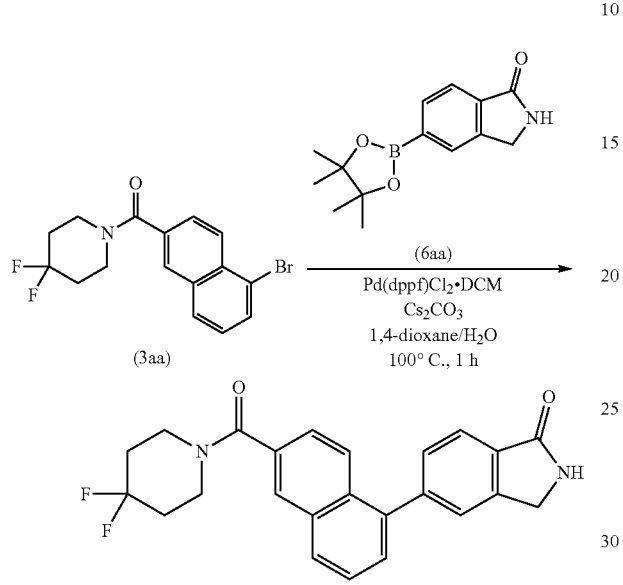

A reaction vessel containing a mixture of (5-bromonaphthalen-2-yl) (4,4-difluoropiperidin-1-yl)methanone (3aa) (16 mg, 0.045 mmol), 5-(4,4,5,5-tetramethyl-1,3,2-dioxaborolan-2-yl)isoindolin-1-one (6aa) (23.4 mg, 0.09 mmol), Cs₂CO₃ (50 mg, 0.15 mmol) and Pd(dppf)Cl₂-DCM (11 mg, 0.013 mmol) was degassed and backfilled with nitrogen three times. After the addition of 1,4-dioxane (0.4 mL) and H₂O (0.2 mL), the reaction mixture was degassed, and backfilled with nitrogen. The resulting mixture was heated at 100° C. for 1 h. After cooling to r.t., the mixture was filtered through celite, and the filtrate was concentrated. The residue was purified by prep HPLC (CH₃CN/0.1% TFA-H₂O/0.1% TFA) to give the expected product as a white solid (12.1 mg).
¹H NMR (400 MHz, DMSO-d₆) δ 2.09 (4H, br s), 3.44-3.84 (4H, m), 4.48 (2H, s), 7.55-7.60 (3H, m), 7.67-7.71 (2H, m), 7.83 (2H, d, J=8.0 Hz), 8.10 (1H, d, J=8.2 Hz), 8.17 (1H, s), 8.67 (1H, s); LRMS (ESI): m/z [M+H]⁺ 407.

The following compounds were synthesized in a similar manner using the appropriate starting materials.

4-(6-(4,4-difluoropiperidine-1-carbonyl)naphthalen-1-yl)-3-methylbenzamide

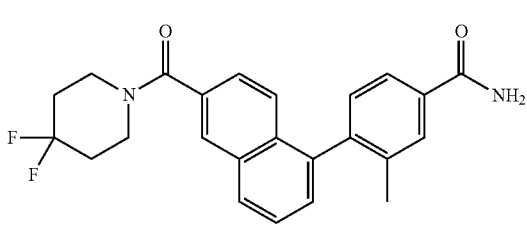 [SMILES: Cc1cc(C(N)=O)ccc1-c1cccc2cc(C(=O)N3CCC(F)(F)CC3)ccc12]

¹H NMR (400 MHz, DMSO-d₆) δ 2.01-2.14 (7H, m), 3.45-3.83 (4H, m), 7.30 (1H, d, J=7.9 Hz), 7.35 (1H, d, J=8.8 Hz), 7.43-7.52 (3H, m), 7.66-7.70 (1H, m), 7.83 (1H, d, J=8.5 Hz), 7.92 (1H, s), 8.05-8.09 (2H, m), 8.15 (1H, s); LRMS (ESI): m/z [M+H]⁺ 409.

(4,4-difluoropiperidin-1-yl) (5-(quinolin-6-yl)naphthalen-2-yl) methanone

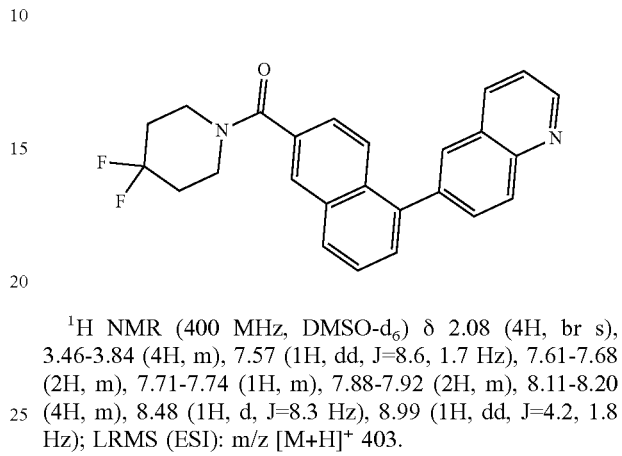

¹H NMR (400 MHz, DMSO-d₆) δ 2.08 (4H, br s), 3.46-3.84 (4H, m), 7.57 (1H, dd, J=8.6, 1.7 Hz), 7.61-7.68 (2H, m), 7.71-7.74 (1H, m), 7.88-7.92 (2H, m), 8.11-8.20 (4H, m), 8.48 (1H, d, J=8.3 Hz), 8.99 (1H, dd, J=4.2, 1.8 Hz); LRMS (ESI): m/z [M+H]⁺ 403.

5-(6-(3,3-dimethylpiperidine-1-carbonyl)naphthalen-1-yl)-2-methylisoindolin-1-one

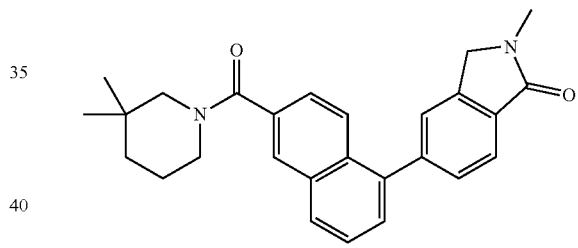

¹H NMR (400 MHz, DMSO-d₆) δ 0.75 (3H, s), 0.98 (3H, s), 1.38-1.62 (4H, m), 3.09-3.36 (6H, m), 3.57-3.66 (1H, m), 4.56 (2H, s), 7.47 (1H, s), 7.55 (1H, d, J=7.0 Hz), 7.59 (1H, d, J=7.2 Hz), 7.65-7.69 (1H, m), 7.71 (1H, s), 7.82 (2H, d, J=8.1 Hz), 8.03-8.09 (2H, m); LRMS (ESI): m/z [M+H]⁺ 413.

5-(6-(3,3-difluoropiperidine-1-carbonyl)naphthalen-1-yl)-2-methylisoindolin-1-one

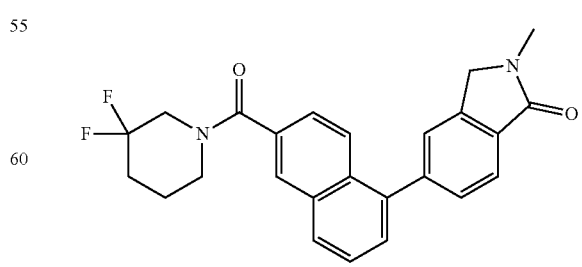

¹H NMR (400 MHz, DMSO-d₆) δ 1.66-1.78 (2H, m), 2.06-2.17 (2H, m), 3.12 (3H, s), 3.64-4.08 (4H, m), 4.56

(2H, s), 7.49 (1H, dd, J=8.7, 1.9 Hz), 7.56-7.60 (2H, m), 7.67-7.72 (2H, m), 7.81-7.85 (2H, m), 8.10-8.13 (2H, m); LRMS (ESI): m/z [M+H]⁺ 421.

(R)-5-(6-(3-fluoropiperidine-1-carbonyl)naphthalen-1-yl)-2-methylisoindolin-1-one

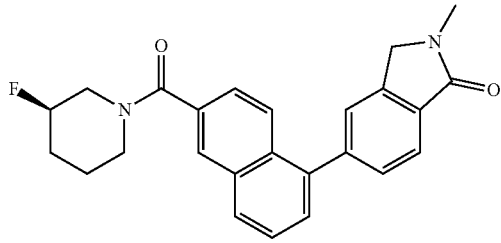 [SMILES: CN1Cc2cc(-c3cccc4cc(C(=O)N5CCC[C@@H](F)C5)ccc34)ccc2C1=O]

¹H NMR (400 MHz, DMSO-d₆) δ 1.45-1.91 (4H, m), 3.13 (3H, s), 3.36 (2H, br s), 3.52-3.71 (2H, m), 4.14-4.29 (1H, m), 4.56 (2H, s), 7.48 (1H, d, J=8.8 Hz), 7.55-7.59 (2H, m), 7.66-7.71 (2H, m), 7.81-7.83 (2H, m), 8.07-8.10 (2H, m); LRMS (ESI): m/z [M+H]⁺ 403.

(S)-2-methyl-5-(6-(3-(trifluoromethyl)piperidine-1-carbonyl) naphthalen-1-yl) isoindolin-1-one

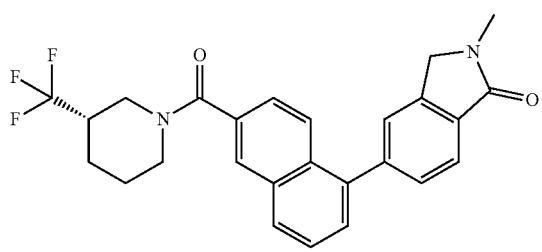

¹H NMR (400 MHz, CD₃OD) δ 1.52-2.01 (3H, m), 2.07-2.17 (1H, m), 2.47-2.64 (1H, m), 2.99-3.22 (2H, m), 3.26 (3H, s), 3.68-3.97 (1H, m), 4.61 (2H, br s), 4.70-4.83 (1H, m), 7.48 (1H, dd, J=8.7, 1.7 Hz), 7.56 (1H, dd, J=7.1, 1.2 Hz), 7.62 (1H, d, J=7.9 Hz), 7.64-7.71 (2H, m), 7.87-7.95 (2H, m), 8.03 (1H, d, J=8.3 Hz), 8.06 (1H, s); LRMS (ESI): m/z [M+H]⁺ 453.

5-(3-(4,4-difluoropiperidine-1-carbonyl)quinolin-8-yl)-2-methylisoindolin-1-one was prepared in accordance with the general procedure 2 using the method described below in detail.

Synthesis of 5-(3-(4,4-difluoropiperidine-1-carbonyl) quinolin-8-yl)-2-methylisoindolin-1-one

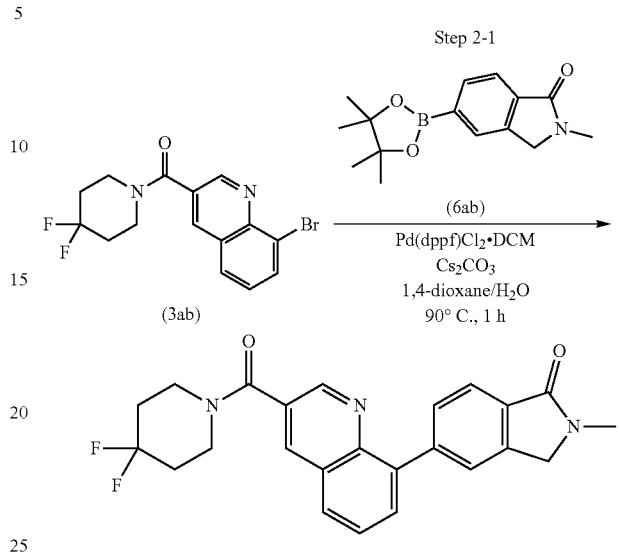

Step 2-1

To a mixture of (8-bromo-3-quinolyl)-(4,4-difluoro-1-piperidyl)methanone (3ab) (35.7 mg, 0.1 mmol), 2-methyl-5-(4,4,5,5-tetramethyl-1,3,2-dioxaborolan-2-yl)isoindolin-1-one (6ab) (32.9 mg, 0.12 mmol), Cs₂CO₃ (98.3 mg, 0.30 mmol) and Pd(dppf)Cl₂-DCM (4.0 mg, 0.005 mmol) were added 1,4-dioxane (0.6 mL) and H₂O (0.2 mL). The reaction mixture was degassed, backfilled with nitrogen, and stirred at 90° C. for 1 h. After cooling to r.t., the mixture was purified by prep HPLC (CH₃CN/0.1% TFA-H₂O/0.1% TFA) to provide the desired product as a white powder (14.6 mg).
¹H NMR (400 MHz, DMSO-d₆) δ 2.12 (4H, br s), 3.13 (3H, s), 3.53 (2H, br s), 3.81 (2H, br s), 4.55 (2H, s), 7.74 (1H, dd, J=9.2, 1.4 Hz), 7.77 (1H, dd, J=7.8, 0.77 Hz), 7.8 (1H, dd, J=7.3, 8.1 Hz), 7.84 (1H, s), 7.90 (1H, dd, J=7.2, 1.5 Hz), 8.14 (1H, dd, J=8.3, 1.5 Hz), 8.62 (1H, d, J=2.2 Hz), 8.96 (1H, d, J=2.2 Hz); LRMS (ESI): m/z [M+H]⁺ 422.

The following compounds were synthesized using conditions analogous to 5-(3-(4,4-difluoropiperidine-1-carbonyl)quinolin-8-yl)-2-methylisoindolin-1-one starting from the appropriate starting materials.

6-(6-(4,4-difluoropiperidine-1-carbonyl)-1-methyl-1H-indol-3-yl) isoquinolin-1 (2H)-one

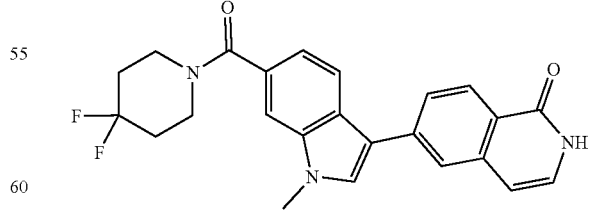

¹H NMR (400 MHz, CDCl₃) 2.07 (4H, br s), 3.79 (4H, br s), 3.93 (3H, s), 6.93 (1H, d, J=7.0 Hz), 7.23-7.34 (2H, m), 7.56 (1H, s), 7.61 (1H, s), 7.86-7.97 (2H, m), 8.03 (1H, d, J=8.4 Hz), 8.48 (1H, d, J=8.4 Hz), 12.21 (1H, s); LRMS (ESI): m/z [M+H]⁺ 422.

151
6-(6-(4,4-difluoropiperidine-1-carbonyl)-1-methyl-1H-indol-3-yl)phthalazin-1(2H)-one

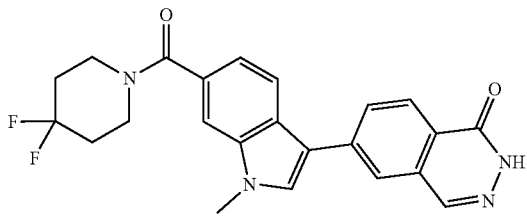 [SMILES: Cn1cc(-c2ccc3c(=O)[nH]ncc3c2)c2ccc(C(=O)N3CCC(F)(F)CC3)cc21]

$^1$H NMR (400 MHz, CDCl$_3$) δ 1.90-2.32 (4H, m), 3.75 (4H, br s), 3.92 (3H, s), 7.26 (1H, dd, J=8.2, 1.2 Hz), 7.53 (1H, s), 7.60 (1H, s), 7.94 (1H, J=1.5 Hz), 7.98 (1H, d, J=8.3 Hz), 8.05 (1H, dd, J=8.3, 1.6 Hz), 8.24 (1H, s), 8.44 (1H, d, J=8.3 Hz), 10.31 (1H, s); LRMS (ESI): m/z [M+H]$^+$ 423.

6-(6-(4,4-difluoropiperidine-1-carbonyl)-1H-indazol-3-yl)phthalazin-1(2H)-one

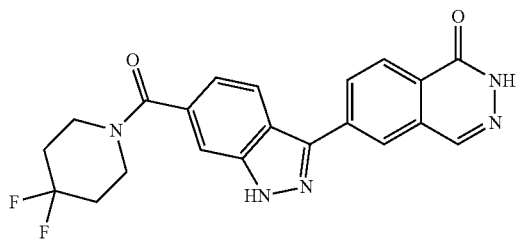 [SMILES: O=C(c1ccc2c(-c3ccc4c(=O)[nH]ncc4c3)n[nH]c2c1)N1CCC(F)(F)CC1]

$^1$H NMR (400 MHz, DMSO-d$_6$) δ 2.09 (4H, br s), 3.50-3.76 (4H, m), 7.33 (1H, d, J=7.6 Hz), 7.75 (1H, s), 8.32-8.37 (2H, m), 8.40 (1H, d, J=8.4 Hz), 8.56 (1H, s), 8.60 (1H, s), 12.68 (NH, br s); LRMS (ESI): m/z [M+H]$^+$ 410.

6-(6-(4,4-difluoropiperidine-1-carbonyl)-1H-indazol-3-yl) isoquinolin-1 (2H)-one

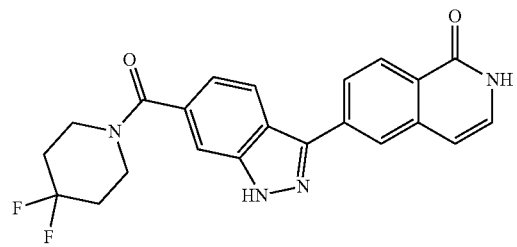 [SMILES: O=C(c1ccc2c(-c3ccc4c(=O)[nH]ccc4c3)n[nH]c2c1)N1CCC(F)(F)CC1]

$^1$H NMR (400 MHz, DMSO-d$_6$) δ 2.08 (4H, br s), 3.50-3.79 (4H, m), 6.76 (1H, d, J=6.8 Hz), 7.22-7.25 (1H, m), 7.32 (1H, d, J=8.4 Hz), 7.72 (1H, s), 8.15 (1H, d, J=8.4 Hz), 8.29-8.33 (3H, m), 11.29 (NH, br s), 13.69 (NH, br s); LRMS (ESI): m/z [M+H]$^+$ 409.

152
5-(6-(4,4-difluoropiperidine-1-carbonyl)-1H-indazol-3-yl)isoindolin-1-one

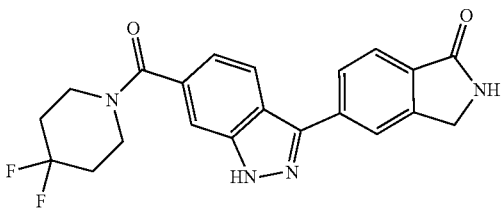 [SMILES: O=C1NCc2cc(-c3n[nH]c4cc(C(=O)N5CCC(F)(F)CC5)ccc34)ccc21]

$^1$H NMR (400 MHz, DMSO-d$_6$) δ 2.07 (4H, br s), 3.49-3.76 (4H, m), 4.48 (2H, s), 7.31 (1H, d, J=8.2 Hz), 7.71 (1H, s), 7.81 (1H, dd, J=8.1, 1.8 Hz), 8.14 (1H, d, J=7.6 Hz), 8.23-8.25 (2H, m), 8.62 (1H, s), 13.64 (1H, s); LRMS (ESI): m/z [M+H]$^+$ 397.

6-(6-(4,4-difluoropiperidine-1-carbonyl)-1-methyl-1H-indazol-3-yl) isoquinolin-1 (2H)-one

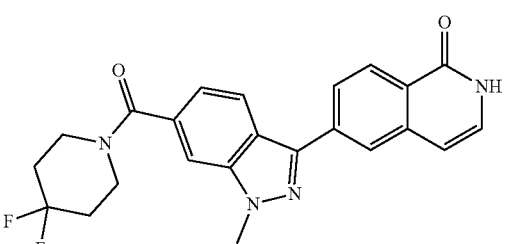

$^1$H NMR (400 MHz, DMSO-d$_6$) δ 2.10 (4H, br s), 3.47-3.79 (4H, m), 4.19 (3H, s), 6.76 (1H, d, J=7.3 Hz), 7.22-7.25 (1H, m), 7.35 (1H, d, J=8.3 Hz), 7.90 (1H, s), 8.12 (1H, dd, J=8.3, 1.7 Hz), 8.29-8.34 (3H, m), 11.30 (NH, br s); LRMS (ESI): m/z [M+H]$^+$ 423.

6-(6-(4,4-difluoropiperidine-1-carbonyl)-1-methyl-1H-indazol-3-yl)phthalazin-1(2H)-one

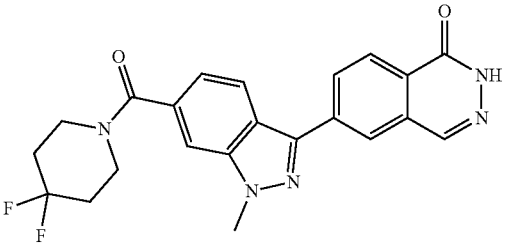 [SMILES: Cn1nc(-c2ccc3c(=O)[nH]ncc3c2)c2ccc(C(=O)N3CCC(F)(F)CC3)cc21]

$^1$H NMR (400 MHz, DMSO-d$_6$) δ 2.11 (4H, br s), 3.47-3.79 (4H, m), 4.21 (3H, s), 7.39 (1H, d, J=8.4 Hz), 7.93 (1H, s), 8.34 (1H, d, J=8.5 Hz), 8.38 (1H, d, J=8.5 Hz), 8.49 (1H, dd, J=8.3, 1.6 Hz), 8.57 (1H, s), 8.60 (1H, d, J=1.6 Hz), 12.70 (NH, br s); LRMS (ESI): m/z [M+H]$^+$ 424.

153

5-(6-(4,4-difluoropiperidine-1-carbonyl)-1-methyl-1H-indazol-3-yl)isoindolin-1-one

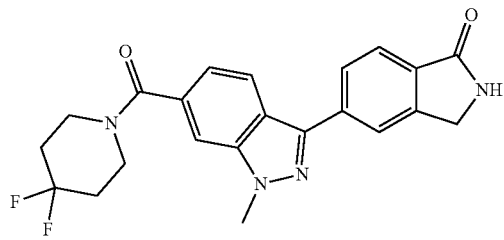 [SMILES: Cn1nc(-c2ccc3c(c2)CNC3=O)c2ccc(C(=O)N3CCC(F)(F)CC3)cc21]

¹H NMR (400 MHz, DMSO-d₆) δ 2.10 (4H, br s), 3.48-3.80 (4H, m), 4.18 (3H, s), 4.48 (2H, s), 7.33 (1H, d, J=8.2 Hz), 7.80 (1H, d, J=8.2 Hz), 7.89 (1H, s), 8.12 (1H, d, J=7.9 Hz), 8.21 (1H, s), 8.24 (1H, d, J=8.4 Hz), 8.63 (1H, s); LRMS (ESI): m/z [M+H]⁺ 411.

6-(6-(4,4-difluoropiperidine-1-carbonyl)-2-methyl-2H-indazol-3-yl) isoquinolin-1 (2H)-one

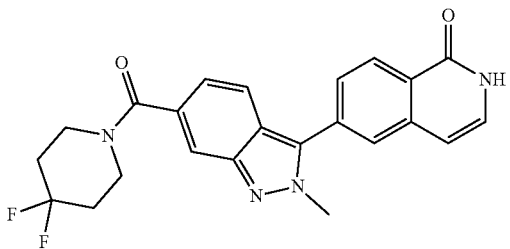 [SMILES: Cn1nc2cc(C(=O)N3CCC(F)(F)CC3)ccc2c1-c1ccc2c(=O)[nH]ccc2c1]

¹H NMR (400 MHz, DMSO-d₆) δ 2.05 (4H, br s), 3.47-3.76 (4H, m), 4.26 (3H, s), 6.70 (1H, d, J=7.5 Hz), 7.17 (1H, d, J=8.6 Hz), 7.27-7.31 (1H, m), 7.74 (1H, d, J=8.5 Hz), 7.79-7.80 (2H, m), 8.02 (1H, s), 8.37 (1H, d, J=8.4 Hz), 11.42 (NH, br s); LRMS (ESI): m/z [M+H]⁺ 423.

2-methyl-5-(3-(piperidine-1-carbonyl)quinolin-8-yl)isoindolin-1-one

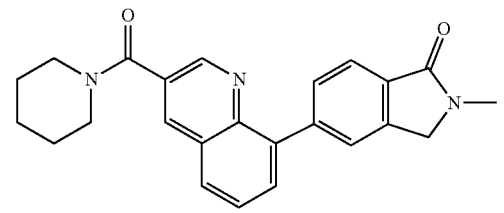 [SMILES: CN1Cc2cc(-c3cccc4cc(C(=O)N5CCCCC5)cnc34)ccc2C1=O]

¹H NMR (400 MHz, CDCl₃) δ 1.55 (2H, br s), 1.70 (4H, br s), 3.22 (3H, s), 3.41 (2H, br s), 3.76 (2H, br s), 4.46 (2H, s) 7.66 (1H, dd, J=8.9, 7.2 Hz), 7.71 (1H, dd, J=7.8, 1.4 Hz), 7.75-7.76 (1H, m), 7.78 (1H, dd, J=7.2, 1.5 Hz), 7.90 (1H, dd, J=8.3, 1.5 Hz), 7.93 (1H, d, J=8.1, 1.5 Hz), 8.29 (1H, d, J=2.2 Hz), 8.91 (1H, d, J=2.2 Hz); LRMS (ESI): m/z [M+H]⁺ 386.

154

5-(7-(4,4-difluoropiperidine-1-carbonyl)isoquinolin-4-yl)-2-methylisoindolin-1-one

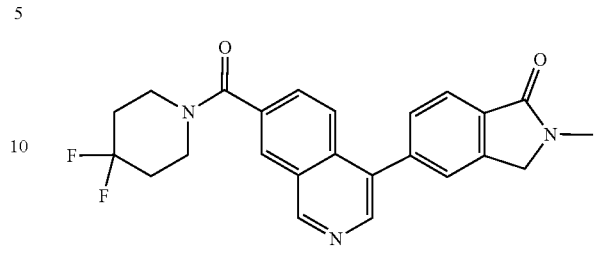

¹H NMR (400 MHz, CDCl₃) δ 2.10 (4H, br s), 3.26 (3H, s), 3.50-4.10 (4H, m), 4.53 (2H, s), 7.62 (1H, s), 7.68 (1H, d, J=7.7 Hz), 7.76 (1H, d, J=7.6 Hz), 7.95 (1H, d, J=7.9 Hz), 8.04 (1H, d, J=7.8 Hz), 8.22 (1H, s), 8.61 (1H, s), 9.40 (1H, s); LRMS (ESI): m/z [M+H]⁺ 422.

2-methyl-5-(7-(piperidine-1-carbonyl) isoquinolin-4-yl)isoindolin-1-one

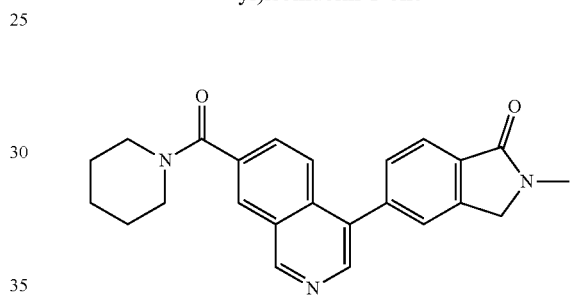

¹H NMR (400 MHz, DMSO-d₆) δ 1.48 (2H, br s), 1.63 (4H, br s), 3.14 (3H, s), 3.35 (2H, br s), 3.66 (2H, br s), 4.58 (2H, s) 7.59 (2H, m), 7.66 (1H, d, J=7.9 Hz), 7.81 (1H, s), 7.86 (1H, d, J=7.8 Hz), 7.89 (1H, d, J=8.7 Hz), 8.06 (1H, d, J=1.3 Hz), 9.04 (1H, s); LRMS (ESI): m/z [M+H]⁺ 386.

2-methyl-5-(2-(piperidine-1-carbonyl)quinolin-5-yl)isoindolin-1-one

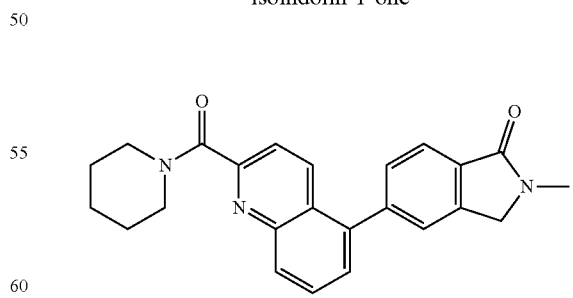

¹H NMR (400 MHz, DMSO-d₆) δ 1.38 (2H, br s), 1.54-1.60 (4H, m), 3.13 (3H, s), 3.42 (2H, t, J=5.2 Hz), 3.60 (2H, t, J=5.7 Hz), 4.53 (2H, s) 7.69-7.81 (5H, m), 7.87 (1H, d, J=7.0 Hz), 8.10 (1H, d, J=7.9 Hz), 8.58 (1H, d, J=8.3 Hz); LRMS (ESI): m/z [M+H]⁺ 386.

5-(7-(4,4-difluoropiperidine-1-carbonyl)quinolin-4-yl)-2-methylisoindolin-1-one

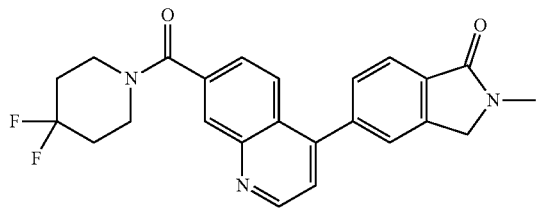 [SMILES: CN1Cc2cc(-c3ccnc4cc(C(=O)N5CCC(F)(F)CC5)ccc34)ccc2C1=O]

$^1$H NMR (400 MHz, CDCl$_3$) δ 2.17 (4H, br s), 3.30 (3H, s), 3.55-4.10 (4H, m), 4.54 (2H, s), 7.50 (1H, d, J=6.3 Hz), 7.59 (1H, d, J=0.6 Hz), 7.62 (1H, d, J=7.7 Hz), 7.63 (1H, dd, J=8.7, 1.7 Hz), 7.97 (1H, d, J=8.7 Hz), 8.05 (1H, d, J=7.8 Hz), 8.28 (1H, d, J=1.6 Hz), 9.09 (1H, d, J=4.8 Hz); LRMS (ESI): m/z [M+H]$^+$ 422.

2-methyl-5-(7-(piperidine-1-carbonyl)quinolin-4-yl)isoindolin-1-one

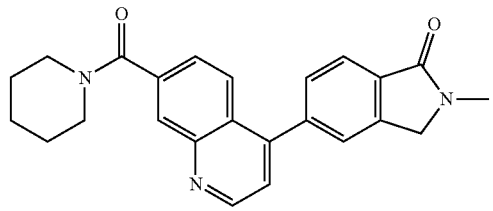 [SMILES: CN1Cc2cc(-c3ccnc4cc(C(=O)N5CCCCC5)ccc34)ccc2C1=O]

$^1$H NMR (400 MHz, DMSO-d$_6$) δ 1.48 (2H, br s), 1.63 (4H, br s), 3.14 (3H, s), 3.35 (2H, br s), 3.66 (2H, br s), 4.58 (2H, s) 7.59 (2H, m), 7.66 (1H, d, J=7.9 Hz), 7.81 (1H, s), 7.86 (1H, d, J=7.8 Hz), 7.89 (1H, d, J=8.7 Hz), 8.06 (1H, d, J=1.3 Hz), 9.04 (1H, d, J=4.5 Hz); LRMS (ESI): m/z [M+H]$^+$ 386.

5-[6-(4,4-difluoropiperidine-1-carbonyl)-1-isoquinolyl]-2-methyl-isoindolin-1-one

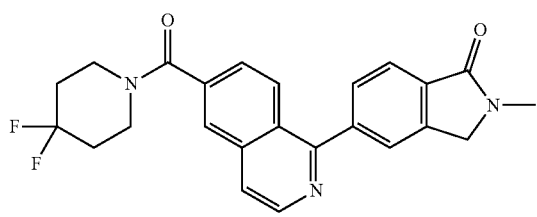 [SMILES: CN1Cc2cc(-c3nccc4cc(C(=O)N5CCC(F)(F)CC5)ccc34)ccc2C1=O]

$^1$H NMR (400 MHz, DMSO-d$_6$) S 2.08 (4H, br s), 3.66 (2H, br s), 3.80 (2H, br s), 3.94 (3H, s), 4.53 (2H, s), 7.60 (1H, s), 7.62 (1H, d, J=7.8 Hz), 7.76 (1H, dd, J=8.7, 1.7 Hz), 7.96 (1H, d, J=8.7 Hz), 8.04 (1H, d, J=7.8 Hz), 8.20 (1H, d, J=1.2 Hz), 8.61 (1H, s), 9.36 (1H, s); LRMS (ESI): m/z [M+H]$^+$ 422.

2-methyl-5-(6-(piperidine-1-carbonyl)benzofuran-3-yl)isoindolin-1-one was prepared in accordance with the general procedure 2 (Scheme 2) using the method described below in detail.

Synthesis of 2-methyl-5-(6-(piperidine-1-carbonyl)benzofuran-3-yl) isoindolin-1-one

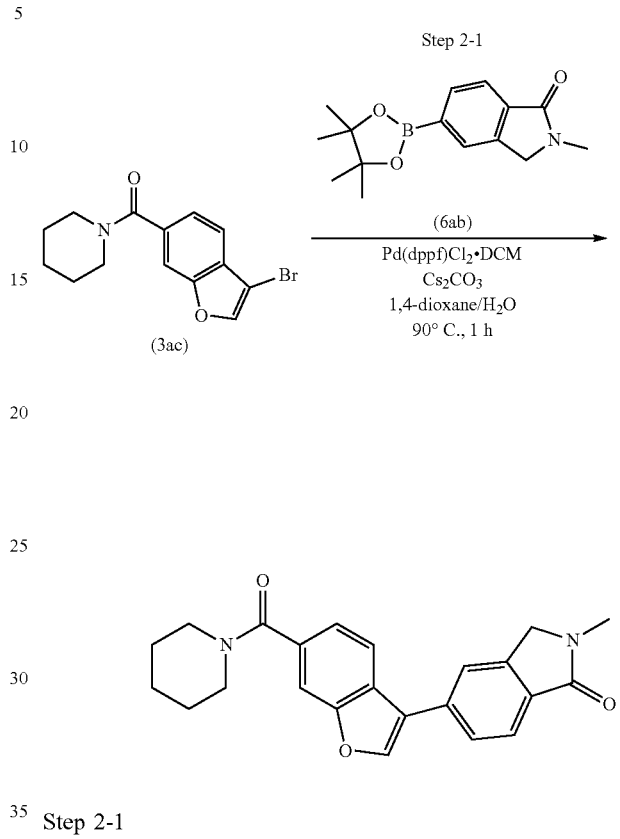

Step 2-1

Starting material (3ac) used for the preparation of 2-methyl-5-(6-(piperidine-1-carbonyl)benzofuran-3-yl)isoindolin-1-one was obtained from 3-bromobenzofuran-6-carboxylic acid which may be commercially available or can be obtained from benzofuran-6-carboxylic acid according to procedures reported in the literature (*J. Med. Chem.*, 2009, 52(20), 6270-6286; *J. Am. Chem. Soc.*, 2018, 140(20), 6432-6440).

A reaction vessel containing a mixture of (3-bromobenzofuran-6-yl)-(1-piperidyl)methanone (3ac) (12.0 mg, 0.04 mmol), 2-methyl-5-(4,4,5,5-tetramethyl-1,3,2-dioxaborolan-2-yl)isoindolin-1-one (6ab) (10.6 mg, 0.04 mmol), Cs$_2$CO$_3$ (38.1 mg, 0.12 mmol) and Pd(dppf)Cl$_2$-DCM (6.3 mg, 0.008 mmol) was degassed and backfilled with nitrogen three times. After the addition of 1,4-dioxane (0.6 mL) and H$_2$O (0.3 mL), the reaction mixture was degassed again, backfilled with nitrogen two times and immediately capped. The resulting mixture was heated at 90° C. for 1 h. After cooling to r.t., the mixture was filtered through celite, and the filtrate was concentrated. The residue was purified by prep HPLC to give the expected product as a pale yellow solid (8.7 mg).

$^1$H NMR (400 MHz, CDCl$_3$) δ 1.53-1.81 (6H, m), 3.24 (3H, s), 3.57 (4H, br s), 4.46 (2H, s), 7.39 (1H, dd, J=8.1, 1.3 Hz), 7.64 (1H, d, J=1.3 Hz), 7.70 (1H, s), 7.73 (1H, d, J=7.8 Hz), 7.85 (1H, d, J=8.1 Hz), 7.92 (1H, s), 7.95 (1H, d, J=7.8 Hz); LRMS (ESI): m/z [M+H]$^+$ 375.

2-methyl-5-(6-(piperidine-1-carbonyl)naphthalen-1-yl)isoindolin-1-one was prepared in accordance with the general procedure 2 using the method described below in detail.

Synthesis of 2-methyl-5-(6-(piperidine-1-carbonyl) naphthalen-1-yl) isoindolin-1-one

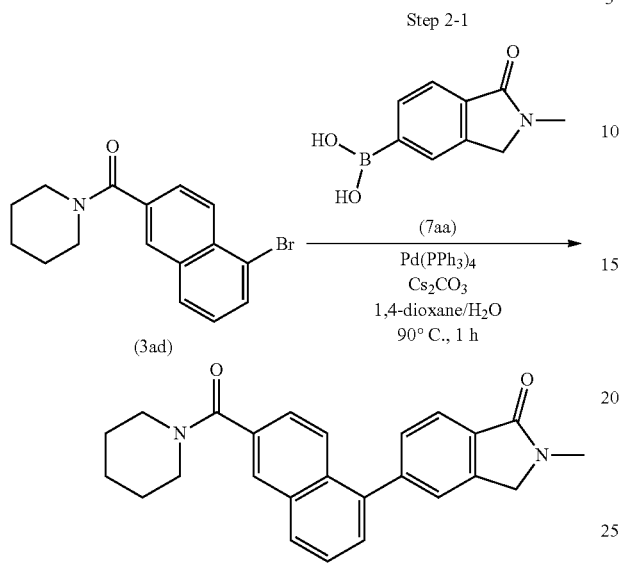

Step 2-1

A reaction vessel containing a mixture of (5-bromo-2-naphthyl)-(1-piperidyl)methanone (3ad) (15.0 mg, 0.05 mmol), (2-methyl-1-oxo-isoindolin-5-yl)boronic acid (7aa) (10.8 mg, 0.06 mmol), Cs$_2$CO$_3$ (46.1 mg, 0.14 mmol) and Pd(PPh$_3$)$_4$ (10.9 mg, 0.01 mmol) was degassed and backfilled with nitrogen three times. After the addition of 1,4-dioxane (0.75 mL) and H$_2$O (0.30 mL), the reaction mixture was degassed again, backfilled with nitrogen two times and immediately capped. The resulting mixture was heated at 90° C. for 1 h. After cooling to r.t., the mixture was filtered through celite, and the filtrate was concentrated. The residue was purified by prep HPLC to give the expected product as a white solid (14.9 mg).

$^1$H NMR (400 MHz, CDCl$_3$) δ 1.45-1.87 (6H, m), 3.26 (3H, s), 3.34-3.95 (4H, m), 4.48 (2H, s), 7.44 (1H, dd, J=8.7, 1.7 Hz), 7.48 (1H, d, J=7.1 Hz), 7.64-7.52 (3H, m), 7.84 (1H, d, J=8.7 Hz), 7.92 (1H, d, J=8.0 Hz), 7.95-7.98 (2H, m); LRMS (ESI): m/z [M+H]$^+$ 385.

The following compounds were synthesized using conditions analogous to 2-methyl-5-(6-(piperidine-1-carbonyl) naphthalen-1-yl)isoindolin-1-one in accordance with the general procedure 2 (Scheme 2).

2-methyl-5-(6-(pyrrolidine-1-carbonyl)naphthalen-1-yl)isoindolin-1-one

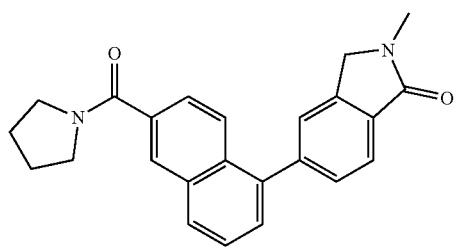 [SMILES: CN1Cc2cc(-c3cccc4cc(C(=O)N5CCCC5)ccc34)ccc2C1=O]

$^1$H NMR (400 MHz, CD$_3$OD) δ 1.89-2.08 (4H, m), 3.26 (3H, s), 3.55 (2H, t, J=6.5 Hz), 3.66 (2H, t, J=7.0 Hz), 4.61 (2H, s), 7.53-7.75 (5H, m), 7.86-7.96 (2H, m), 8.03 (1H, d, J=8.3 Hz), 8.15 (1H, d, J=1.7 Hz); LRMS (ESI): m/z [M+H]$^+$ 371.

(R)-2-methyl-5-(6-(3-methylpyrrolidine-1-carbonyl) naphthalen-1-yl) isoindolin-1-one

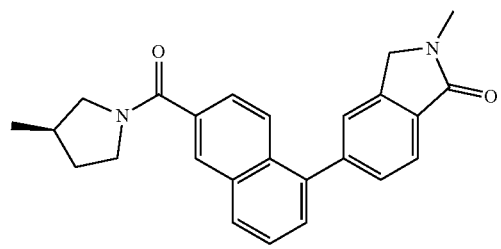 [SMILES: C[C@@H]1CCN(C(=O)c2ccc3c(-c4ccc5c(c4)CN(C)C5=O)cccc3c2)C1]

$^1$H NMR (400 MHz, CDCl$_3$) δ 0.98-1.20 (3H, m), 1.48-1.71 (1H, m), 1.96-2.44 (2H, m), 3.10 (1H, dd, J=10.2, 8.6 Hz), 3.26 (3H, s), 3.47-3.72 (2H, m), 3.76-3.92 (1H, m), 4.48 (2H, s), 7.48 (1H, d, J=7.0 Hz), 7.53-7.62 (4H, m), 7.84 (1H, d, J=8.7 Hz), 7.92 (1H, dd, J=8.2, 3.0 Hz), 7.96 (1H, d, J=7.8 Hz), 8.08 (1H, d, J=1.6 Hz); LRMS (ESI): m/z [M+H]$^+$ 385.

2-methyl-5-(6-(4-(trifluoromethyl)piperidine-1-carbonyl) naphthalen-1-yl) isoindolin-1-one

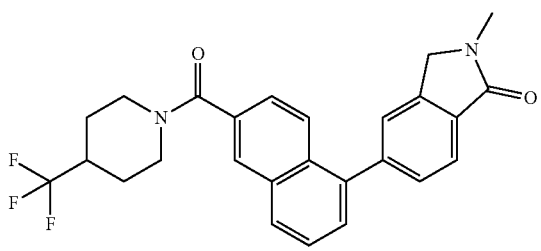 [SMILES: CN1Cc2cc(-c3cccc4cc(C(=O)N5CCC(C(F)(F)F)CC5)ccc34)ccc2C1=O]

$^1$H NMR (400 MHz, CDCl$_3$) δ 1.40-2.10 (4H, m), 2.25-2.38 (1H, m), 2.75-3.10 (2H, m), 3.26 (3H, s), 3.85-4.07 (1H, m), 4.48 (2H, s), 4.80-4.98 (1H, m), 7.43 (1H, dd, J=8.7, 1.7 Hz), 7.50 (1H, dd, J=7.1, 1.3 Hz), 7.53-7.62 (3H, m), 7.86 (1H, d, J=8.7 Hz), 7.93 (1H, d, J=8.2 Hz), 7.96 (1H, d, J=8.2 Hz), 7.98 (1H, d, J=1.7 Hz); LRMS (ESI): m/z [M+H]$^+$ 453.

6-(6-(4,4-difluoro-3-methylpiperidine-1-carbonyl)naphthalen-1-yl)phthalazin-1(2H)-one was prepared in accordance with the general procedure 3 (Scheme 3) using the method described below in detail.

Synthesis of 6-(6-(4,4-difluoro-3-methylpiperidine-1-carbonyl) naphthalen-1-yl) phthalazin-1 (2H)-one

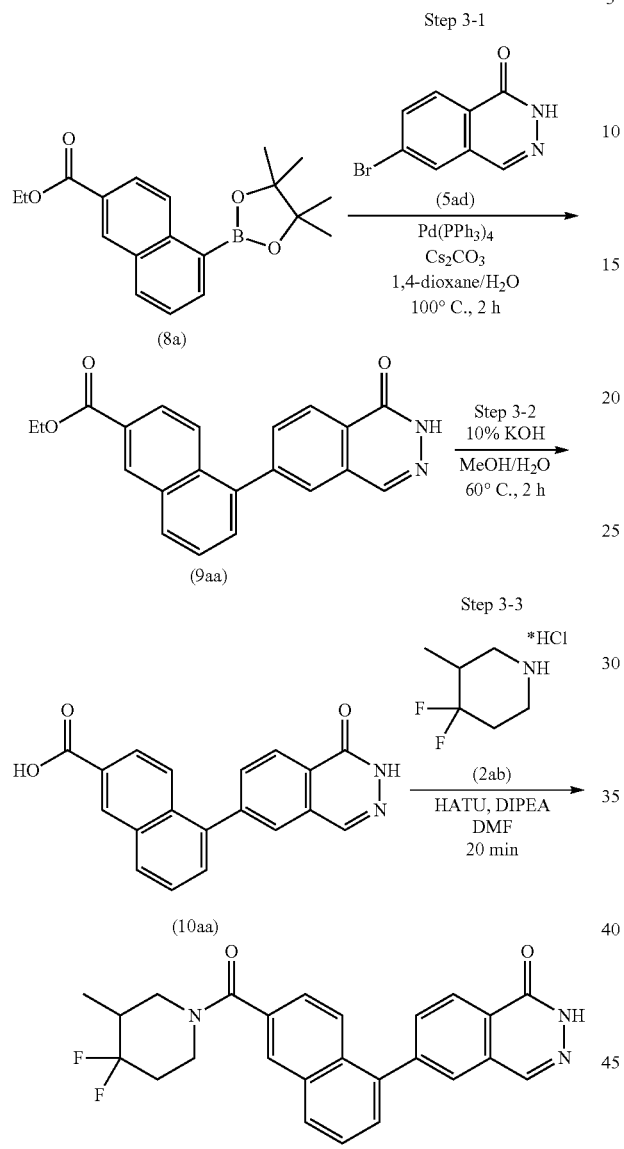

Step 3-1

A reaction vessel containing a mixture of 6-bromo-2H-phthalazin-1-one (5ad) (140.0 mg, 0.62 mmol), ethyl 5-(4,4,5,5-tetramethyl-1,3,2-dioxaborolan-2-yl)naphthalene-2-carboxylate (8a) (243.5 mg, 0.75 mmol), $Cs_2CO_3$ (506.7 mg, 1.55 mmol) and $Pd(PPh_3)_4$ (179.7 mg, 0.15 mmol) was degassed and backfilled with nitrogen three times. After the addition of 1,4-dioxane (6.0 mL) and $H_2O$ (3.0 mL) the reaction mixture was degassed again, backfilled with nitrogen two times and immediately capped. The resulting mixture was then stirred and heated at 100° C. for 2 h. After cooling to r.t., the mixture was filtered through celite, and the filtrate was concentrated. The mixture was partitioned between EtOAc and $H_2O$. The product was extracted with EtOAc from the aq. layer (×2). The combined organic layers were dried over $Na_2SO_4$ and concentrated. The residue was purified by prep HPLC to give the expected product as a dark green solid (120 mg); LRMS (ESI): m/z [M+H]⁺ 345.

Step 3-2

A reaction vessel containing a mixture of ethyl 5-(1-oxo-2H-phthalazin-6-yl)naphthalene-2-carboxylate (9aa) (39.5 mg, 0.11 mmol), 10% KOH (0.13 mL), $H_2O$ (2 mL) and MeOH (2 mL) was heated at 50° C. for 40 min. Additional 10% KOH (0.15 mL) was added, and the reaction was further heated at 60° C. for 1.5 h. After cooling to r.t., the solvents were evaporated in vacuo, and the residue was acidified with 2 M HCl. The formed precipitate was filtered to obtain the desired product as an off-white solid (24 mg); LRMS (ESI): m/z [M+H]⁺ 317.

Step 3-3

A mixture of 5-(1-oxo-2H-phthalazin-6-yl)naphthalene-2-carboxylic acid (10aa) (12.0 mg, 0.04 mmol), 4,4-difluoro-3-methyl-piperidine-HCl (2ab) (7.8 mg, 0.045 mmol), HATU (23.1 mg, 0.06 mmol) and DIPEA (0.016 mL, 0.095 mmol) in DMF (2 mL) was stirred at r.t. for 20 min. The crude mixture was purified by prep HPLC to obtain the desired product as a white solid (1.9 mg).

¹H NMR (400 MHz, $CD_3OD$) δ 0.82-1.22 (3H, m), 1.92-2.34 (3H, m), 3.08-3.51 (2H, m), 3.64-3.88 (1H, m), 4.30-4.55 (1H, m), 7.54 (1H, dd, J=8.7, 1.7 Hz), 7.65 (1H, dd, J=7.1, 1.3 Hz), 7.71 (1H, dd, J=8.2, 7.1 Hz), 7.90 (1H, d, J=8.7 Hz), 8.00 (1H, dd, J=8.2, 1.7 Hz), 8.05 (1H, d, J=1.7 Hz), 8.09 (1H, d, J=8.2 Hz), 8.12 (1H, d, J=1.7 Hz), 8.43 (1H, d, J=0.5 Hz), 8.49 (1H, d, J=8.2 Hz); LRMS (ESI): m/z [M+H]⁺ 434.

The following compounds were synthesized using conditions analogous to 6-(6-(4,4-difluoro-3-methylpiperidine-1-carbonyl)naphthalen-1-yl)phthalazin-1(2H)-one in accordance with the general procedure 3 (Scheme 3).

N-isobutyl-5-(6-methyl-7-oxo-6,7-dihydro-5H-pyrrolo[3,4-b]pyridin-3-yl)-2-naphthamide

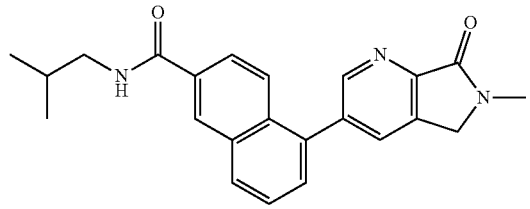 [SMILES: CC(C)CNC(=O)c1ccc2c(-c3cnc4c(c3)CN(C)C4=O)cccc2c1]

¹H NMR (400 MHz, DMSO-$d_6$) δ 0.92 (6H, d, J=6.6 Hz), 1.86-1.94 (1H, m), 3.13-3.18 (5H, m), 4.60 (2H, s), 7.65 (1H, d, J=7.1 Hz), 7.70-7.74 (1H, m), 7.81 (1H, d, J=8.8 Hz), 7.96 (1H, d, J=8.8 Hz), 8.17 (1H, d, J=8.4 Hz), 8.22 (1H, s), 8.58 (1H, s), 8.70-8.73 (1H, m), 8.80 (1H, s); LRMS (ESI): m/z [M+H]⁺ 374.

N-cyclohexyl-5-(6-methyl-7-oxo-6,7-dihydro-5H-pyrrolo[3,4-b]pyridin-3-yl)-2-naphthamide

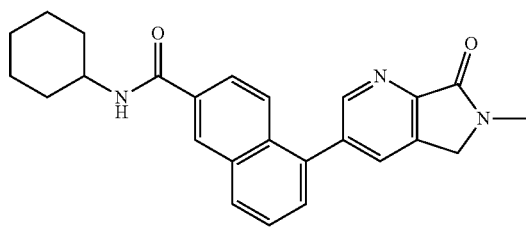 [SMILES: CN1Cc2cc(-c3cccc4cc(C(=O)NC5CCCCC5)ccc34)cnc2C1=O]

¹H NMR (400 MHz, DMSO-d₆) δ 1.29-1.39 (4H, m), 1.62-1.90 (6H, m), 3.17 (3H, s), 3.79-3.87 (1H, m), 4.60 (2H, s), 7.63-7.65 (1H, m), 7.70-7.74 (1H, m), 7.80 (1H, d, J=9.0 Hz), 7.95 (1H, dd, J=9.0, 1.8 Hz), 8.16 (1H, d, J=8.2 Hz), 8.21 (1H, s), 8.46 (1H, d, J=7.8 Hz), 8.57 (1H, s), 8.80 (1H, s); LRMS (ESI): m/z [M+H]⁺ 400.

6-(6-(2-azaspiro[3.3]heptane-2-carbonyl) naphthalen-1-yl)phthalazin-1(2H)-one

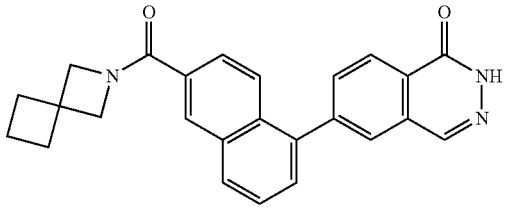 [SMILES: O=C(c1ccc2c(-c3ccc4c(=O)[nH]ncc4c3)cccc2c1)N1CC2(CCC2)C1]

¹H NMR (400 MHz, CD₃OD) δ 1.81-1.96 (2H, m), 2.21-2.31 (4H, m), 4.19 (2H, s), 4.42 (2H, s), 7.65 (1H, d, J=7.1 Hz), 7.67-7.74 (2H, m), 7.87 (1H, d, J=8.8 Hz), 7.99 (1H, dd, J=8.2, 1.4 Hz), 8.04 (1H, d, J=1.4 Hz), 8.11 (1H, d, J=8.2 Hz), 8.29 (1H, d, J=1.7 Hz), 8.42 (1H, d, J=0.5 Hz), 8.48 (1H, d, J=8.2 Hz); LRMS (ESI): m/z [M+H]⁺ 396.

Cis-rac-6-(6-((3aR,6aS)-octahydrocyclopenta[c]pyrrole-2-carbonyl) naphthalen-1-yl) phthalazin-1(2H)-one

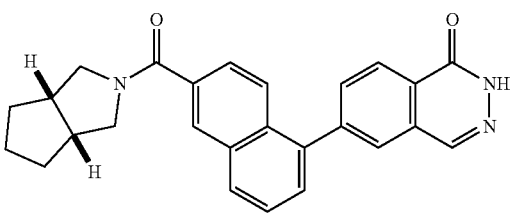 [SMILES: O=C(c1ccc2c(-c3ccc4c(=O)[nH]ncc4c3)cccc2c1)N1C[C@H]2CCC[C@H]2C1]

¹H NMR (400 MHz, CDCl₃) δ 1.31-1.46 (1H, m), 1.54-1.73 (2H, m), 1.74-2.02 (3H, m), 2.61-2.83 (2H, m), 3.29 (1H, dd, J=11.4, 4.5 Hz), 3.58 (1H, dd, J=13.0, 4.9 Hz), 3.71 (1H, dd, J=11.4, 8.1 Hz), 3.94 (1H, dd, J=13.0, 8.6 Hz), 7.54-7.63 (2H, m), 7.64 (1H, dd, J=8.2, 7.1 Hz), 7.81 (1H, d, J=8.8 Hz), 7.87 (1H, d, J=1.4 Hz), 7.95 (1H, dd, J=8.2, 1.4 Hz), 7.99 (1H, d, J=8.2 Hz), 8.09 (1H, d, J=1.6 Hz), 8.29 (1H, s), 8.56 (1H, d, J=8.2 Hz), 10.69 (1H, br s); LRMS (ESI): m/z [M+H]⁺ 410.

6-(6-(1,2,3,6-tetrahydropyridine-1-carbonyl)naphthalen-1-yl)phthalazin-1(2H)-one

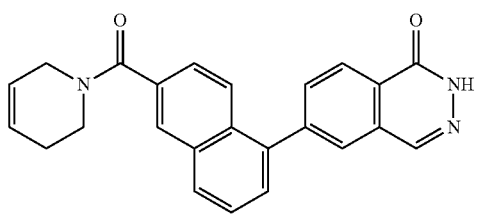 [SMILES: O=C(c1ccc2c(-c3ccc4c(=O)[nH]ncc4c3)cccc2c1)N1CC=CCC1]

¹H NMR (400 MHz, CD₃OD) δ 2.19-2.36 (2H, m), 3.53-3.60 (1H, m), 3.87-3.95 (1H, m), 4.02 (1H, br s), 4.24 (1H, br s), 5.56-6.00 (2H, m), 7.52 (1H, dd, J=8.7, 1.8 Hz), 7.64 (1H, d, J=7.1 Hz), 7.70 (1H, dd, J=8.2, 7.1 Hz), 7.90 (1H, d, J=8.7 Hz), 8.00 (1H, dd, J=8.2, 1.4 Hz), 8.05 (1H, d, J=1.4 Hz), 8.03-8.13 (2H, m), 8.43 (1H, d, J=0.6 Hz), 8.49 (1H, d, J=8.2 Hz); LRMS (ESI): m/z [M+H]⁺ 382.

6-(6-(2-azabicyclo[4.1.0]heptane-2-carbonyl)naphthalen-1-yl)phthalazin-1(2H)-one

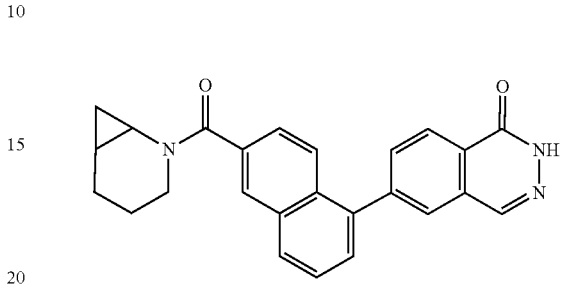

¹H NMR (400 MHz, CDCl₃) δ 0.58-0.65 (1H, m), 0.70-0.77 (1H, m), 1.13-1.62 (2H, m), 1.74-2.08 (3H, m), 2.64-2.84 (2H, m), 4.27-4.35 (1H, m), 7.54 (1H, d, J=7.1 Hz), 7.63 (1H, dd, J=8.1, 7.1 Hz), 7.68 (1H, dd, J=8.7, 1.6 Hz), 7.80 (1H, d, J=8.7 Hz), 7.89 (1H, d, J=1.5 Hz), 7.97 (1H, dd, J=8.0, 1.5 Hz), 8.00 (1H, d, J=8.0 Hz), 8.23 (1H, d, J=1.6 Hz), 8.33 (1H, s), 8.57 (1H, d, J=8.1 Hz); LRMS (ESI): m/z [M+H]⁺ 396, [M+Na]⁺ 418.

3-(6-(2-azaspiro[3.3]heptane-2-carbonyl)naphthalen-1-yl)-6-methyl-5,6-dihydro-7H-pyrrolo[3,4-b]pyridin-7-one

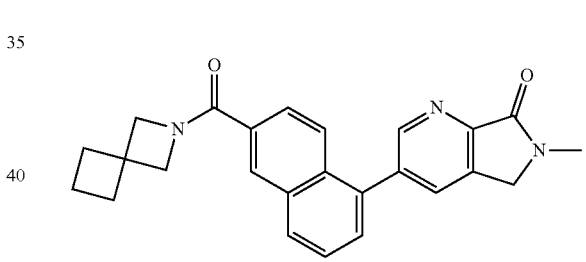

¹H NMR (400 MHz, CD₃OD) δ 1.81-1.95 (2H, m), 2.23-2.30 (4H, m), 3.31 (3H, s), 4.19 (2H, s), 4.42 (2H, s), 4.65 (2H, s), 7.64 (1H, d, J=7.1 Hz), 7.70 (1H, dd, J=8.3, 7.1 Hz), 7.73 (1H, dd, J=8.8, 1.8 Hz), 7.85 (1H, d, J=8.8 Hz), 8.13 (1H, d, J=8.3 Hz), 8.18 (1H, d, J=1.9 Hz), 8.30 (1H, d, J=1.8 Hz), 8.80 (1H, d, J=1.9 Hz); LRMS (ESI): m/z [M+H]⁺ 398.

3-(6-(2-azabicyclo[4.1.0]heptane-2-carbonyl)naphthalen-1-yl)-6-methyl-5,6-dihydro-7H-pyrrolo[3,4-b]pyridin-7-one

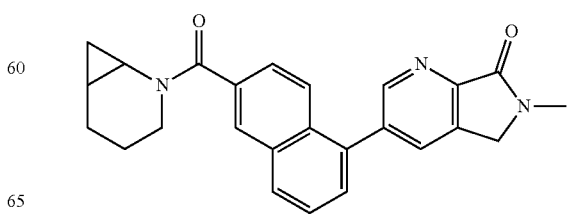

¹H NMR (400 MHz, CD₃OD) δ 0.60-0.71 (2H, m), 1.28-1.62 (2H, m), 1.71-1.83 (1H, m), 1.86-2.06 (2H, m), 2.69-2.82 (2H, m), 3.31 (3H, s), 4.19-4.30 (1H, m), 4.65 (2H, s), 7.51 (1H, dd, J=8.7, 1.6 Hz), 7.61 (1H, d, J=7.1 Hz), 7.68 (1H, dd, J=8.3, 7.1 Hz), 7.86 (1H, d, J=8.7 Hz), 8.10 (1H, d, J=8.3 Hz), 8.19 (1H, d, J=1.9 Hz), 8.24 (1H, d, J=1.6 Hz), 8.80 (1H, d, J=1.9 Hz); LRMS (ESI): m/z [M+H]⁺ 398.

6-methyl-3-(6-(1,2,3,6-tetrahydropyridine-1-carbonyl)naphthalen-1-yl)-5,6-dihydro-7H-pyrrolo[3,4-b]pyridin-7-one

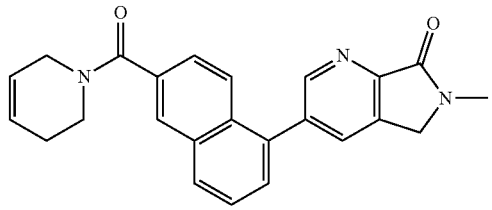 [SMILES: CN1Cc2cc(-c3cccc4cc(C(=O)N5CC=CCC5)ccc34)cnc2C1=O]

¹H NMR (400 MHz, CD₃OD) δ 2.18-2.36 (2H, m), 3.31 (3H, s), 3.52-3.60 (1H, m), 3.87-3.95 (1H, m), 4.01 (1H, br s), 4.24 (1H, br s), 4.66 (2H, s), 5.54-5.99 (2H, m), 7.53 (1H, dd, J=8.7, 1.5 Hz), 7.62 (1H, d, J=7.1 Hz), 7.70 (1H, dd, J=8.3, 7.1 Hz), 7.88 (1H, d, J=8.7 Hz), 8.07-8.12 (2H, m), 8.19 (1H, d, J=1.7 Hz), 8.81 (1H, d, J=1.7 Hz); LRMS (ESI): m/z [M+H]⁺ 384.

Cis-rac-6-methyl-3-(6-((3aR,6aS)-octahydrocyclopenta[c]pyrrole-2-carbonyl) naphthalen-1-yl)-5,6-dihydro-7H-pyrrolo[3,4-b]pyridin-7-one

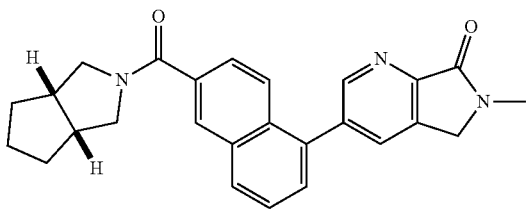 [SMILES: CN1Cc2cc(-c3cccc4cc(C(=O)N5C[C@H]6CCC[C@H]6C5)ccc34)cnc2C1=O]

¹H NMR (400 MHz, CD₃OD) δ 1.33-1.45 (1H, m), 1.53-1.70 (2H, m), 1.74-1.99 (3H, m), 2.65-2.85 (2H, m), 3.29-3.34 (4H, m), 3.55 (1H, dd, J=12.7, 4.5 Hz), 3.74 (1H, dd, J=11.2, 8.0 Hz), 3.86 (1H, dd, J=12.7, 8.5 Hz), 4.65 (2H, s), 7.57-7.63 (2H, m), 7.69 (1H, dd, J=8.2, 7.1 Hz), 7.85 (1H, d, J=8.8 Hz), 8.10 (1H, d, J=8.2 Hz), 8.14 (1H, d, J=1.7 Hz), 8.18 (1H, d, J=1.8 Hz), 8.80 (1H, d, J=1.7 Hz); LRMS (ESI): m/z [M+H]⁺ 412.

N,N-diethyl-5-(6-methyl-7-oxo-6,7-dihydro-5H-pyrrolo[3,4-b]pyridin-3-yl)-2-naphthamide

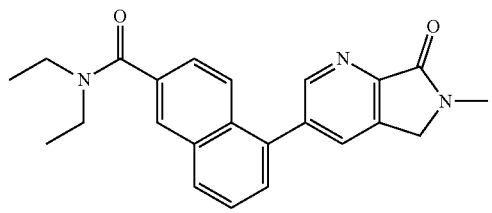 [SMILES: CCN(CC)C(=O)c1ccc2c(-c3cnc4c(c3)CN(C)C4=O)cccc2c1]

¹H NMR (400 MHz, CD₃OD) δ 1.16 (3H, t, J=6.8 Hz), 1.30 (3H, t, J=6.6 Hz), 3.27-3.43 (5H, m), 3.62 (2H, q, J=6.6 Hz), 4.65 (2H, s), 7.49 (1H, dd, J=8.7, 1.7 Hz), 7.61 (1H, d, J=7.1 Hz), 7.70 (1H, dd, J=8.3, 7.1 Hz), 7.87 (1H, d, J=8.7 Hz), 8.03 (1H, d, J=1.7 Hz), 8.09 (1H, d, J=8.3 Hz), 8.19 (1H, d, J=1.8 Hz), 8.81 (1H, d, J=1.8 Hz); LRMS (ESI): m/z [M+H]⁺ 374.

N,N-diethyl-5-(1-oxo-1,2-dihydrophthalazin-6-yl)-2-naphthamide

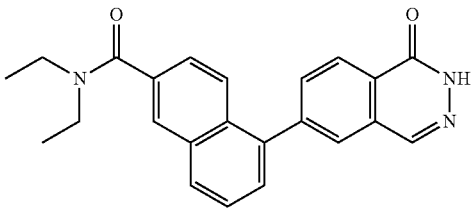 [SMILES: CCN(CC)C(=O)c1ccc2c(-c3ccc4c(=O)[nH]ncc4c3)cccc2c1]

¹H NMR (400 MHz, CD₃OD) δ 1.16 (3H, t, J=6.9 Hz), 1.30 (3H, t, J=6.9 Hz), 3.36 (2H, q, J=6.9 Hz), 3.61 (2H, q, J=6.9 Hz), 7.48 (1H, dd, J=8.7, 1.7 Hz), 7.62 (1H, d, J=7.1 Hz), 7.69 (1H, dd, J=8.2, 7.1 Hz), 7.89 (1H, d, J=8.7 Hz), 8.00 (1H, dd, J=8.2, 1.7 Hz), 8.03 (1H, d, J=1.7 Hz), 8.05 (1H, d, J=1.7 Hz), 8.07 (1H, d, J=8.2 Hz), 8.42 (1H, s), 8.48 (1H, d, J=8.2 Hz); LCMS (ESI): m/z [M+H]⁺ 372.

N,N-dimethyl-5-(2-methyl-3-oxo-2,3-dihydro-[1,2,4]triazolo[4,3-a]pyridin-7-yl)-2-naphthamide

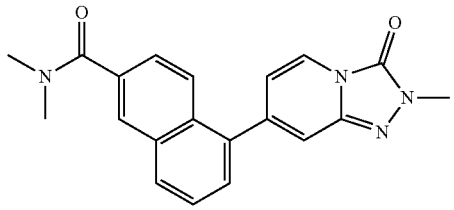

¹H NMR (400 MHz, CDCl₃) δ 3.12 (6H, br s), 3.74 (3H, s), 6.67 (1H, dd, J=7.2, 1.4 Hz), 7.19-7.20 (1H, m), 7.49-7.56 (2H, m), 7.59 (1H, dd, J=8.1, 7.2), 7.87 (1H, d, J=7.2 Hz), 7.91 (1H, d, J=8.6 Hz), 7.95 (1H, d, J=8.1 Hz), 8.01 (1H, d, J=1.4 Hz); LRMS (ESI): m/z [M+H]⁺ 347.

3-(6-(4,4-difluoropiperidine-1-carbonyl)naphthalen-1-yl)-7-methyl-1,7-naphthyridin-8 (7H)-one was prepared in accordance with the general procedure 4 (Scheme 4) using the method described below in detail.

Synthesis of 3-(6-(4,4-difluoropiperidine-1-carbonyl)naphthalen-1-yl)-7-methyl-1,7-naphthyridin-8 (7H)-one

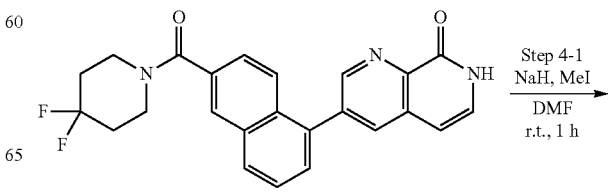

-continued

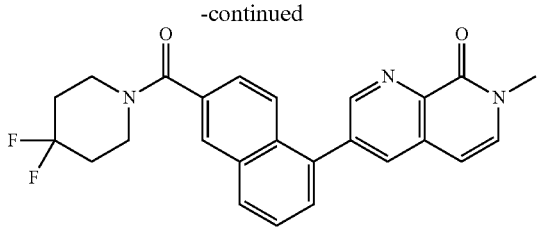

Step 4-1

To a solution of 3-[6-(4,4-difluoropiperidine-1-carbonyl)-1-naphthyl]-7H-1,7-naphthyridin-8-one (7.0 mg, 0.016 mmol) in DMF (0.5 mL) was added NaH, 60% dispersion in mineral oil (1.0 mg, 0.025 mmol) and the mixture was stirred at r.t. for 30 min. After the addition of MeI (2 μL, 0.03 mmol), the mixture was further stirred at r.t. for 1 h. The mixture was quenched with MeOH (0.5 mL) and purified by prep HPLC to give the expected product as a white solid (4.5 mg).

$^1$H NMR (400 MHz, CDCl$_3$) δ 1.87-2.29 (4H, m), 3.43-4.19 (7H, m), 6.52 (1H, d, J=7.2 Hz), 7.27 (1H, d, J=7.2 Hz), 7.49 (1H, dd, J=8.7, 1.6 Hz), 7.57 (1H, d, J=7.2 Hz), 7.66 (1H, dd, J=8.2, 7.2 Hz), 7.84 (1H, d, J=8.7 Hz), 7.97-8.02 (2H, m), 8.03 (1H, d, J=1.6 Hz), 9.00 (1H, d, J=2.1 Hz); LRMS (ESI): m/z [M+H]$^+$ 434.

The following compounds were synthesized using conditions analogous to 3-(6-(4,4-difluoropiperidine-1-carbonyl)naphthalen-1-yl)-7-methyl-1,7-naphthyridin-8 (7H)-one in accordance with the general procedure 4 (Scheme 4).

6-(2-(4,4-difluoropiperidine-1-carbonyl)benzo[b]thiophen-7-yl)-2-methylphthalazin-1 (2H)-one

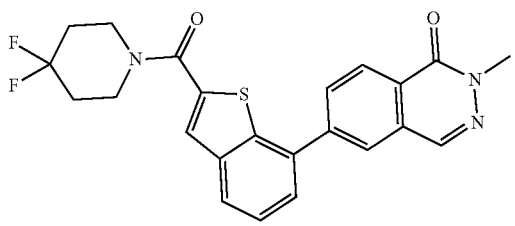 [SMILES: Cn1ncc2cc(-c3cccc4cc(C(=O)N5CCC(F)(F)CC5)sc34)ccc2c1=O]

$^1$H NMR (400 MHz, DMSO-d$_6$) δ 2.05-2.17 (4H, m), 3.76-3.81 (7H, m), 7.65 (2H, m), 7.93 (1H, s), 8.06 (1H, d, J=6.7 Hz), 8.15-8.26 (1H, m), 8.34 (1H, s), 8.42 (1H, d, J=8.2 Hz), 8.54 (1H, s); LRMS (ESI): m/z [M+H]$^+$ 440.

7-(2-(4,4-difluoropiperidine-1-carbonyl)benzo[b]thiophen-7-yl)-3-methylpyrido[3,2-d]pyrimidin-4 (3H)-one

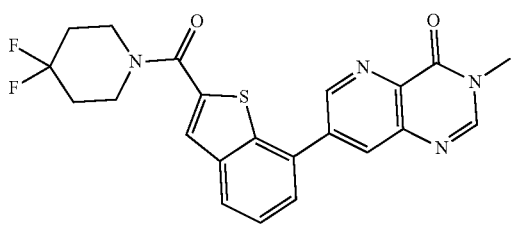 [SMILES: Cn1cnc2cc(-c3cccc4cc(C(=O)N5CCC(F)(F)CC5)sc34)cnc2c1=O]

$^1$H NMR (400 MHz, DMSO-d$_6$) δ 2.06-2.17 (4H, m), 3.57 (3H, s), 3.76-3.82 (4H, m), 7.68 (1H, t, J=7.6 Hz), 7.77 (1H, d, J=7.6 Hz), 7.97 (1H, s), 8.09 (1H, d, J=7.6 Hz), 8.43 (1H, d, J=2.1 Hz), 8.56 (1H, s), 9.14 (1H, d, J=2.1 Hz); LRMS (ESI): m/z [M+H]$^+$ 441.

7-(7-(4,4-difluoropiperidine-1-carbonyl)naphthalen-2-yl)-3-methylpyrido[3,2-d]pyrimidin-4 (3H)-one

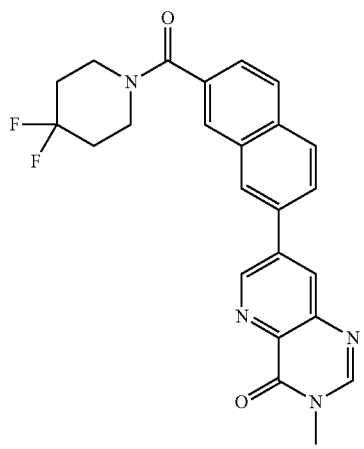 [SMILES: Cn1cnc2cc(-c3ccc4ccc(C(=O)N5CCC(F)(F)CC5)cc4c3)cnc2c1=O]

7-(7-(4,4-difluoropiperidine-1-carbonyl)naphthalen-2-yl)-3-methylpyrido[3,2-d]pyrimidin-4(3H)-one was obtained from 7-[7-(4,4-difluoropiperidine-1-carbonyl)-2-naphthyl]-3H-pyrido[3,2-d]pyrimidin-4-one (synthesized using conditions analogous to 5-(6-(4,4-difluoropiperidine-1-carbonyl)naphthalen-1-yl)-2-methylisoindolin-1-one in accordance with the general procedure 1, Scheme 1).

$^1$H NMR (400 MHz, DMSO-d$_6$) δ 2.11 (4H, br s), 3.50-3.80 (7H, m), 7.65 (1H, d, J=6.4 Hz), 8.10 (1H, d, J=8.7 Hz), 8.17-8.18 (3H, m), 8.52-8.55 (2H, m), 8.65 (1H, s), 9.32 (1H, s); LRMS (ESI): m/z [M+H]$^+$ 435.

6-(6-(4,4-difluoropiperidine-1-carbonyl)naphthalen-1-yl)-2-methylphthalazin-1 (2H)-one

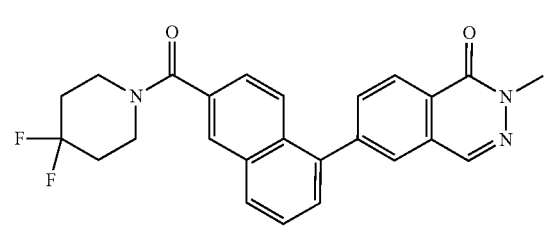 [SMILES: Cn1ncc2cc(-c3cccc4cc(C(=O)N5CCC(F)(F)CC5)ccc34)ccc2c1=O]

$^1$H NMR (400 MHz, CDCl$_3$) δ 1.85-2.29 (4H, m), 3.43-4.24 (7H, m), 7.47 (1H, dd, J=8.7, 1.6 Hz), 7.55 (1H, d, J=7.1 Hz), 7.65 (1H, dd, J=8.2, 7.1 Hz), 7.80 (1H, d, J=1.4 Hz), 7.83 (1H, d, J=8.7 Hz), 7.89 (1H, dd, J=8.2, 1.4 Hz), 7.98 (1H, d, J=8.2 Hz), 8.03 (1H, d, J=1.6 Hz), 8.21 (1H, s), 8.57 (1H, d, J=8.2 Hz); LRMS (ESI): m/z [M+H]$^+$ 434.

167

2-(6-(4,4-difluoropiperidine-1-carbonyl)naphthalen-1-yl)-6-methyl-6,7-dihydro-5H-pyrrolo[3,4-b]pyridin-5-one

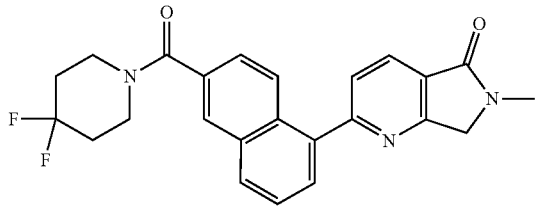 [SMILES: CN1Cc2nc(-c3cccc4cc(C(=O)N5CCC(F)(F)CC5)ccc34)ccc2C1=O]

$^1$H NMR (400 MHz, DMSO-d$_6$) δ 2.02-2.14 (4H, m), 3.16 (3H, s), 3.46-3.57 (2H, m), 3.72-3.83 (2H, m), 4.64 (2H, s), 7.58 (1H, dd, J=8.7, 1.8 Hz), 7.70-7.81 (3H, m), 8.12-8.17 (3H, m), 8.24 (1H, d, J=7.9 Hz); LRMS (ESI): m/z [M+H]$^+$ 422.

3-(6-(4,4-difluoropiperidine-1-carbonyl)naphthalen-1-yl)-7-methylpyrido[2,3-d]pyridazin-8 (7H)-one

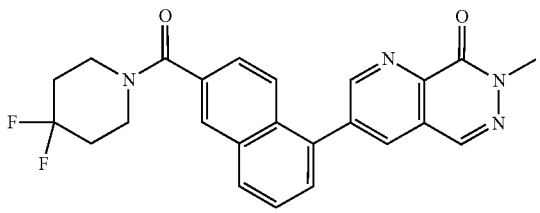 [SMILES: Cn1ncc2cc(-c3cccc4cc(C(=O)N5CCC(F)(F)CC5)ccc34)cnc2c1=O]

$^1$H NMR (400 MHz, CDCl$_3$) δ 2.06 (4H, br s), 3.43-4.15 (7H, m), 7.52 (1H, dd, J=8.7, 1.6 Hz), 7.58 (1H, d, J=6.1 Hz), 7.69 (1H, dd, J=8.3, 6.1 Hz), 7.78 (1H, d, J=8.7 Hz), 8.03 (1H, d, J=8.3 Hz), 8.05 (1H, d, J=1.6 Hz), 8.17 (1H, d, J=2.0 Hz), 8.24 (1H, s), 9.24 (1H, d, J=2.0 Hz); LRMS (ESI): m/z [M+H]$^+$ 435.

6-(6-(4,4-difluoropiperidine-1-carbonyl)naphthalen-1-yl)-2-methylisoquinolin-1 (2H)-one

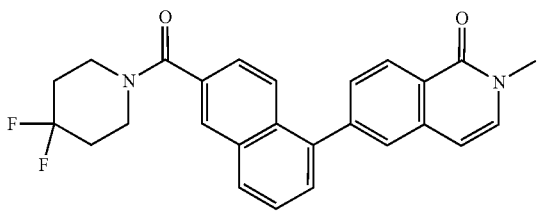 [SMILES: Cn1ccc2cc(-c3cccc4cc(C(=O)N5CCC(F)(F)CC5)ccc34)ccc2c1=O]

$^1$H NMR (400 MHz, CD$_3$OD) δ 2.09 (4H, br s), 3.53-4.03 (7H, m)), 6.77 (1H, d, J=7.3 Hz), 7.45 (1H, d, J=7.3 Hz), 7.52 (1H, dd, J=8.7, 1.6 Hz), 7.60 (1H, d, J=7.1 Hz), 7.65 (1H, dd, J=8.2, 1.6 Hz), 7.68 (1H, dd, J=8.2, 7.1 Hz), 7.76 (1H, d, J=1.6 Hz), 7.92 (1H, d, J=8.7 Hz), 8.05 (1H, d, J=8.2 Hz), 8.11 (1H, d, J=1.6 Hz), 8.46 (1H, d, J=8.2 Hz); LRMS (ESI): m/z [M+H]$^+$ 433.

168

6-(6-(4,4-difluoropiperidine-1-carbonyl)naphthalen-1-yl)-2-(2-(methylsulfonyl)ethyl)phthalazin-1 (2H)-one

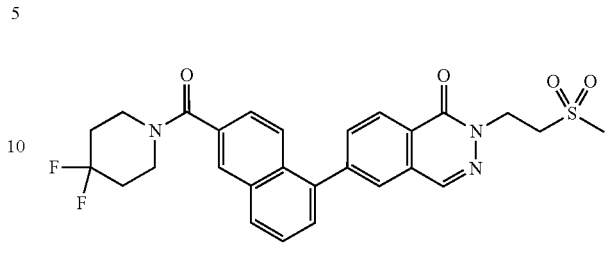

$^1$H NMR (400 MHz, CDCl$_3$) δ 1.81-2.27 (4H, m), 3.07 (3H, s), 3.37-4.11 (6H, m), 4.78 (2H, t, J=6.9 Hz), 7.48 (1H, dd, J=8.7, 1.6 Hz), 7.54 (1H, d, J=7.1 Hz), 7.65 (1H, dd, J=8.2, 7.1 Hz), 7.79-7.85 (2H, m), 7.92 (1H, dd, J=8.2, 1.6 Hz), 7.98 (1H, d, J=8.2 Hz), 8.03 (1H, d, J=1.6 Hz), 8.26 (1H, s), 8.55 (1H, d, J=8.2 Hz); LRMS (ESI): m/z [M+H]$^+$ 526.

2-(2-aminoethyl)-6-(6-(4,4-difluoropiperidine-1-carbonyl) naphthalen-1-yl) phthalazin-1 (2H)-one

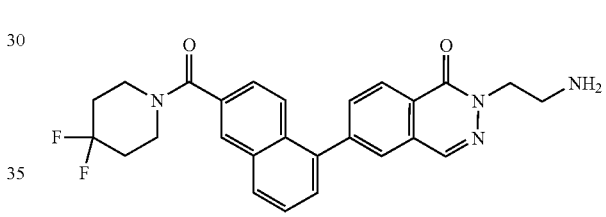

$^1$H NMR (400 MHz, DMSOd$_6$) δ 2.08 (4H, br s), 2.94 (2H, t, J=6.7 Hz), 3.41-4.89 (4H, m), 4.18 (2H, t, J=6.7 Hz), 7.57 (1H, dd, J=8.7, 1.6 Hz), 7.63 (1H, d, J=6.5 Hz), 7.65 (1H, dd, J=8.3, 6.5 Hz), 7.82 (1H, d, J=8.7 Hz), 7.98 (1H, dd, J=8.3, 1.6 Hz), 8.10 (1H, d, J=1.6 Hz), 8.14 (1H, d, J=8.3 Hz), 8.19 (1H, d, J=1.6 Hz), 8.40 (1H, d, J=8.3 Hz), 8.51 (1H, s); LRMS (ESI): m/z [M+H]$^+$ 463.

Methyl 2-(5-(6-(4,4-difluoropiperidine-1-carbonyl) naphthalen-1-yl)-1-oxoisoindolin-2-yl)acetate

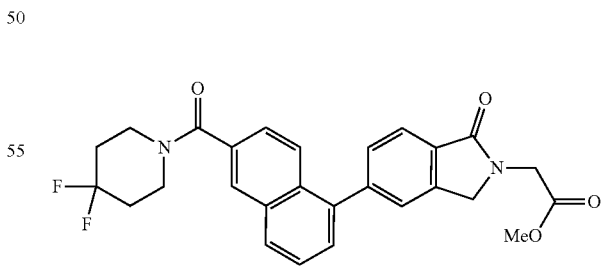

$^1$H NMR (400 MHz, DMSO-d$_6$) δ 2.09 (4H, br s), 3.44-3.55 (2H, m), 3.71 (3H, s), 3.75-3.84 (2H, m), 4.46 (2H, s), 4.64 (2H, s), 7.55-7.60 (2H, m), 7.63 (1H, dd, J=7.7, 1.4 Hz), 7.68-7.72 (1H, m), 7.77 (1H, s), 7.84-7.89 (2H, m), 8.11 (1H, d, J=8.3 Hz), 8.17 (1H, d, J=1.4 Hz); LRMS (ESI): m/z [M+H]$^+$ 479.

7-[6-(4,4-difluoropiperidine-1-carbonyl)-1-naphthyl]-2-(methoxymethyl)-[1,2,4]triazolo[4,3-a]pyridin-3-one

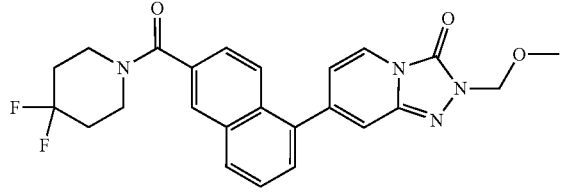 [SMILES: COCn1nc2cc(-c3cccc4cc(C(=O)N5CCC(F)(F)CC5)ccc34)ccn2c1=O]

$^1$H NMR (400 MHz, CDCl$_3$) δ 1.83-2.30 (4H, m), 3.51 (3H, s), 3.52-4.11 (4H, m), 5.39 (2H, s), 6.66 (1H, dd, J=7.2, 1.2 Hz), 7.20 (1H, t, J=1.2 Hz), 7.52 (1H, dd, J=8.7, 1.6 Hz), 7.54 (1H, d, J=7.2 Hz), 7.62 (1H, dd, J=8.3, 7.2), 7.88 (1H, dd, J=7.2, 1.2 Hz), 7.95 (1H, d, J=8.7 Hz), 7.97 (1H, d, J=8.3 Hz), 8.01 (1H, d, J=1.6 Hz); LRMS (ESI): m/z [M+H]$^+$ 453.

6-(6-(4,4-difluoropiperidine-1-carbonyl)naphthalen-1-yl)-2-(methoxymethyl)phthalazin-1 (2H)-one was obtained using a slightly modified method described for 3-(6-(4,4-difluoropiperidine-1-carbonyl)naphthalen-1-yl)-7-methyl-1,7-naphthyridin-8 (7H)-one.

6-(6-(4,4-difluoropiperidine-1-carbonyl)naphthalen-1-yl)-2-(methoxymethyl) phthalazin-1 (2H)-one

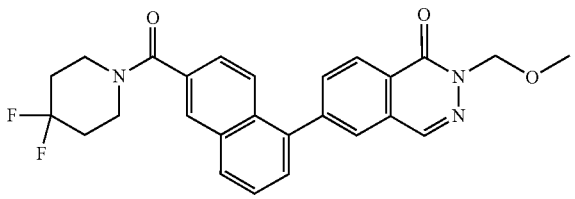 [SMILES: COCn1ncc2cc(-c3cccc4cc(C(=O)N5CCC(F)(F)CC5)ccc34)ccc2c1=O]

Step 4-1

To a solution of 6-[6-(4,4-difluoropiperidine-1-carbonyl)-1-naphthyl]-2H-phthalazin-1-one (7.0 mg, 0.02 mmol) in DMF (0.7 mL) was added NaH, 60% dispersion in mineral oil (1.0 mg, 0.025 mmol) and the mixture was stirred at r.t. for 30 min. After the addition of bromomethyl methyl ether (2.0 µL, 0.02 mmol), the mixture was stirred at r.t. for 1 h. Additional bromomethyl methyl ether (10 µL, 0.10 mmol) was added, and the mixture was further stirred at r.t. for 3 h. The mixture was quenched with MeOH and purified by prep HPLC to give the expected product as a white solid (5.7 mg).

$^1$H NMR (400 MHz, CDCl$_3$) δ 1.83-2.33 (4H, m), 3.40-4.15 (7H, m), 5.60 (2H, s), 7.48 (1H, dd, J=8.7, 1.6 Hz), 7.55 (1H, d, J=7.1 Hz), 7.65 (1H, dd, J=8.2, 7.1 Hz), 7.82 (1H, d, J=1.4 Hz), 7.84 (1H, d, J=8.7 Hz), 7.91 (1H, dd, J=8.2, 1.4 Hz), 7.98 (1H, d, J=8.2 Hz), 8.03 (1H, d, J=1.6 Hz), 8.25 (1H, s), 8.59 (1H, d, J=8.2 Hz); LRMS (ESI): m/z [M+H]$^+$ 464.

6-(6-(4,4-difluoropiperidine-1-carbonyl)naphthalen-1-yl)-2-(2-hydroxyethyl)phthalazin-1(2H)-one was obtained using a slightly modified method described for 3-(6-(4,4-difluoropiperidine-1-carbonyl)naphthalen-1-yl)-7-methyl-1,7-naphthyridin-8(7H)-one.

6-(6-(4,4-difluoropiperidine-1-carbonyl)naphthalen-1-yl)-2-(2-hydroxyethyl) phthalazin-1 (2H)-one

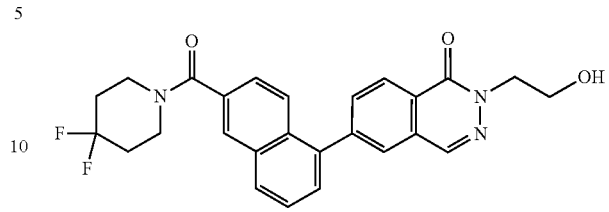

Step 4-1

To a solution of 6-[6-(4,4-difluoropiperidine-1-carbonyl)-1-naphthyl]-2H-phthalazin-1-one (7.0 mg, 0.017 mmol) in DMF (0.7 mL) was added NaH, 60% dispersion in mineral oil (2.0 mg, 0.05 mmol) and the mixture was stirred at r.t. for 30 min. After the addition of 2-iodoethanol (6.5 µL, 0.08 mmol), the mixture was further stirred at r.t. for 1 h. Additional 2-iodoethanol (65 µL, 0.8 mmol) was added and the mixture was further stirred at 50° C. overnight. After cooling to r.t., the mixture was quenched with MeOH, and purified by prep HPLC to give the expected product as a white solid (5.8 mg).

$^1$H NMR (400 MHz, CDCl$_3$) δ 1.83-2.27 (4H, m), 3.36-4.07 (4H, m), 4.12 (2H, t, J=4.9 Hz), 4.52 (2H, t, J=4.9 Hz), 7.48 (1H, dd, J=8.7, 1.6 Hz), 7.55 (1H, d, J=7.1 Hz), 7.65 (1H, dd, J=8.1, 7.1 Hz), 7.80-7.86 (2H, m), 7.92 (1H, dd, J=8.2, 1.6 Hz), 7.98 (1H, d, J=8.2 Hz), 8.03 (1H, d, J=1.6 Hz), 8.27 (1H, s), 8.57 (1H, d, J=8.1 Hz); LRMS (ESI): m/z [M+H]$^+$ 464.

6-(3-(4,4-difluoropiperidine-1-carbonyl)quinolin-8-yl)-2-methylisoquinolin-1(2H)-one was obtained using a slightly modified method described for 3-(6-(4,4-difluoropiperidine-1-carbonyl)naphthalen-1-yl)-7-methyl-1,7-naphthyridin-8 (7H)-one.

6-(3-(4,4-difluoropiperidine-1-carbonyl)quinolin-8-yl)-2-methylisoquinolin-1 (2H)-one

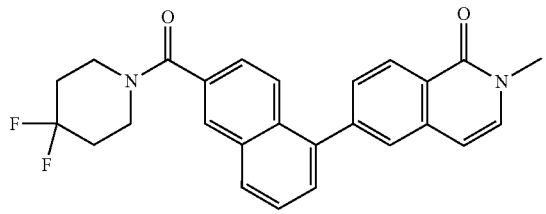 [SMILES: Cn1ccc2cc(-c3cccc4cc(C(=O)N5CCC(F)(F)CC5)ccc34)ccc2c1=O]

Step 4-1

To a solution of 6-[3-(4,4-difluoropiperidine-1-carbonyl)-8-quinolyl]-2H-isoquinolin-1-one (10.0 mg, 0.02 mmol) in DMF (0.5 mL) was added NaH, 60% dispersion in mineral oil (0.86 mg, 0.021 mmol) and the mixture was stirred at r.t. for 30 min. After the addition of MeI (1.5 µL, 0.024 mmol), the mixture was stirred at r.t. for additional 30 min. The mixture was quenched with MeOH (0.5 mL) and purified by prep HPLC to give the expected product as a white solid in quantitative yield.

$^1$H NMR (400 MHz, DMSO-d$_6$) δ 2.05-2.15 (4H, m), 3.50-3.58 (2H, m), 3.55 (3H, s), 3.75-3.85 (2H, m), 6.68 (1H, d, J=7.4 Hz), 7.53 (1H, d, J=7.4 Hz), 7.77 (1H, dd, J=7.5, 1.5 Hz), 7.82 (1H, d, J=7.9 Hz), 7.91 (1H, d, J=1.5

Hz), 7.95 (1H, dd, J=7.2, 1.4 Hz), 8.16 (1H, dd, J=8.2, 1.3 Hz), 8.30 (1H, d, J=8.3 Hz), 8.63 (1H, d, J=2.2 Hz), 8.97 (1H, d, J=2.2 Hz); LRMS (ESI): m/z [M+H]⁺ 434.

The following compounds were synthesized using conditions analogous to 6-(3-(4,4-difluoropiperidine-1-carbonyl)quinolin-8-yl)-2-methylisoquinolin-1(2H)-one in accordance with the general procedure 4 (Scheme 4).

6-[3-(4,4-difluoropiperidine-1-carbonyl)-8-quinolyl]-2-methyl-2,7-naphthyridin-1-one

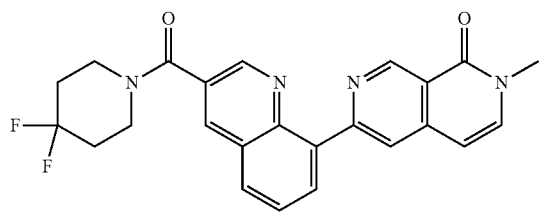 [SMILES: Cn1ccc2cc(-c3cccc4cc(C(=O)N5CCC(F)(F)CC5)cnc34)ncc2c1=O]

¹H NMR (400 MHz, DMSO-d₆) δ 2.11 (4H, br s), 3.53 (2H, br s), 3.58 (3H, s), 3.81 (2H, br s), 6.72 (1H, d, J=7.5 Hz), 7.79 (1H, d, J=7.3 Hz), 7.86 (1H, t, J=7.5 Hz), 8.21 (1H, d, J=7.3 Hz), 8.32 (1H, d, J=7.2 Hz), 8.34 (1H, s), 8.65 (1H, d, J=2.2 Hz), 9.03 (1H, d, J=2.3 Hz), 9.49 (1H, s); LRMS (ESI) m/z [M+H]⁺ 435.

3-[3-(4,4-difluoropiperidine-1-carbonyl)-8-quinolyl]-7-methyl-pyrido[2,3-d]pyridazin-8-one

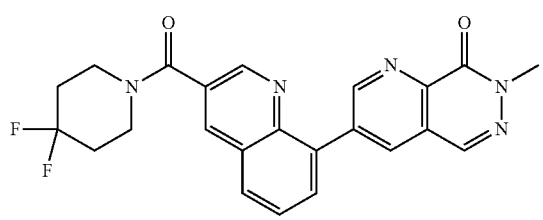 [SMILES: Cn1ncc2cc(-c3cccc4cc(C(=O)N5CCC(F)(F)CC5)cnc34)cnc2c1=O]

¹H NMR (400 MHz, DMSO-d₆) δ 2.05-2.15 (4H, m), 3.35-3.58 (4H, m), 3.81 (3H, s), 7.89 (1H, t, J=7.6 Hz), 8.11 (1H, dd, J=7.2, 1.4 Hz), 8.25 (1H, dd, J=8.2, 1.2 Hz), 8.53 (1H, s), 8.68 (1H, d, J=2.2 Hz), 8.70 (1H, d, J=2.2 Hz), 9.01 (1H, d, J=2.2 Hz), 9.39 (1H, d, J=2.1 Hz); LRMS (ESI): m/z [M+H]⁺ 436.

3-[3-(4,4-difluoropiperidine-1-carbonyl)-8-quinolyl]-7-methyl-1,7-naphthyridin-8-one

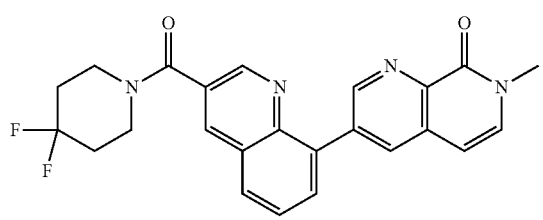 [SMILES: Cn1ccc2cc(-c3cccc4cc(C(=O)N5CCC(F)(F)CC5)cnc34)cnc2c1=O]

¹H NMR (400 MHz, CDCl₃) δ 1.95-2.24 (4H, m), 3.62-3.73 (2H, m), 3.75 (3H, s), 3.90-4.03 (2H, m), 6.56 (1H, d, J=7.3 Hz), 7.26 (1H, d, J=7.3 Hz), 7.78 (1H, dd, J=8.0, 7.2 Hz), 7.95 (1H, dd, J=7.2, 1.4 Hz), 8.02 (1H, dd, J=8.2, 1.4 Hz), 8.27 (1H, d, J=2.1 Hz), 8.39 (1H, d, J=2.2 Hz), 8.98 (1H, d, J=2.2 Hz), 9.19 (1H, d, J=2.1 Hz); LRMS (ESI): m/z [M+H]⁺ 435.

6-[3-(4,4-difluoropiperidine-1-carbonyl)-8-quinolyl]-2-methyl-phthalazin-1-one

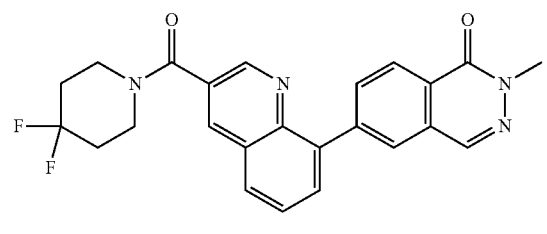 [SMILES: Cn1ncc2cc(-c3cccc4cc(C(=O)N5CCC(F)(F)CC5)cnc34)ccc2c1=O]

¹H NMR (400 MHz, DMSO-d₆) δ 2.05-2.15 (4H, m), 3.45-3.58 (2H, m), 3.78 (3H, s), 3.75-3.85 (2H, m), 7.84 (1H, d, J=7.4 Hz), 8.00 (1H, dd, J=7.2, 1.3 Hz), 8.17 (1H, dd, J=8.2, 1.7 Hz), 8.20 (1H, dd, J=8.2, 1.4 Hz), 8.23 (1H, d, J=1.4 Hz), 8.36 (1H, d, J=8.3 Hz), 8.50 (1H, s), 8.65 (1H, d, J=2.2 Hz), 8.98 (1H, d, J=2.2 Hz); LRMS (ESI): m/z [M+H]⁺ 435.

6-[3-(4,4-difluoropiperidine-1-carbonyl)-8-quinolyl]-2-methyl-1,2-benzoxazol-3-one

¹H NMR (400 MHz, DMSO-d₆) δ 2.05-2.18 (4H, m), 3.48-3.58 (2H, m), 3.64 (3H, s), 3.75-3.85 (2H, m), 7.62 (1H, dd, J=8.0, 1.2 Hz), 7.77 (1H, s), 7.81 (1H, t, J=7.7 Hz), 7.87 (1H, d, J=8.0 Hz), 7.96 (1H, dd, J=7.1, 1.3 Hz), 8.17 (1H, dd, J=8.2, 1.3 Hz), 8.63 (1H, d, J=2.1 Hz), 8.97 (1H, d, J=2.2 Hz); LRMS (ESI): m/z [M+H]⁺ 424.

(4,4-difluoro-1-piperidyl)-[8-(3-methoxy-1,2-benzoxazol-6-yl)-3-quinolyl]methanone

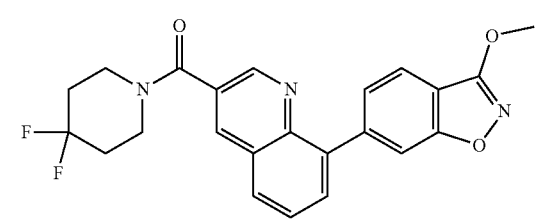 [SMILES: COc1noc2cc(-c3cccc4cc(C(=O)N5CCC(F)(F)CC5)cnc34)ccc12]

¹H NMR (400 MHz, DMSO-d₆) δ 2.08 (4H, br s), 3.66 (2H, br s), 3.69 (3H, s), 3.85 (2H, br s), 7.62 (1H, d, J=8.1 Hz), 7.77 (1H, s), 7.81 (1H, t, J=7.1 Hz), 7.87 (1H, d, J=8.1

Hz), 7.96 (1H, d, J=7.1 Hz), 8.17 (1H, d, J=7.8 Hz), 8.62 (1H, d, J=2.1 Hz), 8.97 (1H, d, J=2.1 Hz); LRMS (ESI): m/z [M+H]+ 424.

6-[6-(4,4-difluoropiperidine-1-carbonyl)-2-fluoro-1-naphthyl]-2-methyl-isoquinolin-1-one was obtained using a slightly modified method described for 3-(6-(4,4-difluoropiperidine-1-carbonyl)naphthalen-1-yl)-7-methyl-1,7-naphthyridin-8 (7H)-one.

6-[6-(4,4-difluoropiperidine-1-carbonyl)-2-fluoro-1-naphthyl]-2-methyl-isoquinolin-1-one

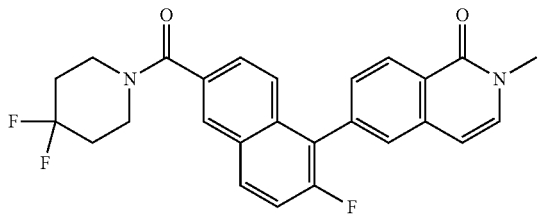 [SMILES: Cn1ccc2cc(-c3c(F)ccc4cc(C(=O)N5CCC(F)(F)CC5)ccc34)ccc2c1=O]

Step 4-1

To a solution of 6-[6-(4,4-difluoropiperidine-1-carbonyl)-2-fluoro-1-naphthyl]-2H-isoquinolin-1-one (4.0 mg, 0.009 mmol) (6-[6-(4,4-difluoropiperidine-1-carbonyl)-2-fluoro-1-naphthyl]-2H-isoquinolin-1-one) in DMF (0.5 mL) was added NaH, 60% dispersion in mineral oil (0.33 mg, 0.008 mmol) and the mixture was stirred at r.t. for 30 min. After the addition of MeI (0.6 µL, 0.009 mmol), the mixture was further stirred at r.t. for 30 min. The mixture was quenched with MeOH and purified by prep HPLC to give the expected product as a white solid (3.0 mg).

1H NMR (400 MHz, CDCl3) δ 2.05 (4H, br s), 3.67 (2H, br s), 3.69 (3H, s), 3.93 (2H, br s), 6.56 (1H, d, J=7.2 Hz), 7.18 (1H, d, J=7.3 Hz), 7.45-7.49 (2H, m), 7.55 (1H, d, J=8.7 Hz), 7.61 (1H, d, J=0.74 Hz), 7.70 (1H, d, J=8.7 Hz), 7.97 (1H, dd, J=8.9, 5.4 Hz), 8.02 (1H, d, J=1.6 Hz), 8.61 (1H, d, J=8.3 Hz); LRMS (ESI): m/z [M+H]+ 451.

6-[6-(4,4-difluoropiperidine-1-carbonyl)-2-fluoro-1-naphthyl]-2-methyl-2,7-naphthyridin-1-one was obtained from 6-[6-(4,4-difluoropiperidine-1-carbonyl)-2-fluoro-1-naphthyl]-2H-2,7-naphthyridin-1-one using the method described in step 4-1 for the preparation of 6-[6-(4,4-difluoropiperidine-1-carbonyl)-2-fluoro-1-naphthyl]-2-methyl-isoquinolin-1-one.

6-[6-(4,4-difluoropiperidine-1-carbonyl)-2-fluoro-1-naphthyl]-2-methyl-2,7-naphthyridin-1-one

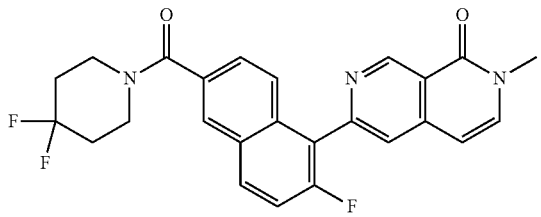 [SMILES: Cn1ccc2cc(-c3c(F)ccc4cc(C(=O)N5CCC(F)(F)CC5)ccc34)ncc2c1=O]

1H NMR (400 MHz, CDCl3) δ 2.04 (4H, br s), 3.33 (3H, s), 3.62 (2H, br s), 3.93 (2H, br s), 6.55 (1H, d, J=7.3 Hz), 7.38 (1H, d, J=7.3 Hz), 7.46 (1H, d, J=9.2 Hz), 7.48 (1H, d, J=9.1 Hz), 7.66-7.67 (1H, m,), 7.82 (1H, d, J=8.7 Hz), 8.01 (1H, dd, J=9.1, 5.4 Hz), 8.02 (1H, d, J=1.1 Hz), 9.83 (1H, s); LRMS (ESI): m/z [M+H]+ 452.

5-(6-(4,4-difluoropiperidine-1-carbonyl)naphthalen-1-yl)-2-((1-(trifluoromethyl)cyclopropyl)methyl) isoindolin-1-one was prepared in accordance with the general procedure 4 using the method described below in detail.

Synthesis of 5-(6-(4,4-difluoropiperidine-1-carbonyl)naphthalen-1-yl)-2-((1-(trifluoromethyl)cyclopropyl)methyl) isoindolin-1-one

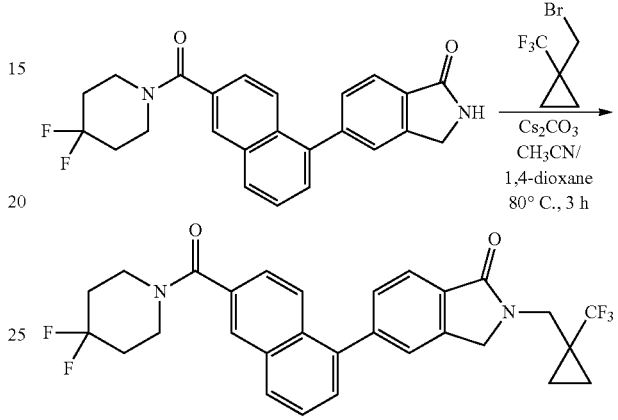

To a solution of 5-[6-(4,4-difluoropiperidine-1-carbonyl)-1-naphthyl]isoindolin-1-one (20.0 mg, 0.05 mmol) in CH3CN (0.12 mL) and 1,4-dioxane (0.12 mL) were added Cs2CO3 (54.5 mg, 0.17 mmol) and 1-(bromomethyl)-1-(trifluoromethyl)cyclopropane (9.4 µL, 0.07 mmol). The reaction mixture was heated at 80° C. for 2 h. Additional 1-(bromomethyl)-1-(trifluoromethyl)cyclopropane (18.8 µL) was added, and the mixture was further heated at 80° C. for another 1 h. After cooling to r.t., the solvent was evaporated in vacuo and the crude was purified by prep HPLC to obtain the expected product as a white solid (3.1 mg).

1H NMR (400 MHz, CDCl3) δ 1.03-1.06 (2H, m), 1.14-1.17 (2H, m), 1.93-2.18 (4H, m), 3.56-3.74 (2H, m), 3.90-4.00 (4H, m), 4.63 (2H, s), 7.47 (1H, dd, J=8.7, 1.7 Hz), 7.53-7.55 (1H, m), 7.58-7.66 (3H, m), 7.90 (1H, d, J=8.8 Hz), 7.96 (1H, d, J=8.1 Hz), 8.0 (1H, d, J=7.5 Hz), 8.03 (1H, d, J=1.6 Hz); LRMS (ESI): m/z [M+H]+ 529.

5-(6-(4,4-difluoropiperidine-1-carbonyl)naphthalen-1-yl)-2-ethylisoindolin-1-one was obtained using conditions analogous to 5-(6-(4,4-difluoropiperidine-1-carbonyl)naphthalen-1-yl)-2-((1-(trifluoromethyl)cyclopropyl)methyl) isoindolin-1-one in accordance with the general procedure 4 (Scheme 4).

5-(6-(4,4-difluoropiperidine-1-carbonyl)naphthalen-1-yl)-2-ethylisoindolin-1-one

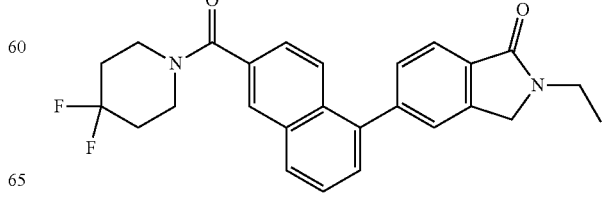

¹H NMR (400 MHz, CDCl₃) δ 1.34 (3H, t, J=7.3 Hz), 1.93-2.19 (4H, m), 3.57-3.70 (2H, m), 3.77 (2H, q, J=7.3 Hz), 3.87-4.01 (2H, m), 4.51 (2H, s), 7.47 (1H, dd, J=8.7, 1.8 Hz), 7.52-7.54 (1H, m), 7.58-7.66 (3H, m), 7.90 (1H, d, J=8.7 Hz), 7.95 (1H, d, J=8.2 Hz), 8.00 (1H, d, J=7.7 Hz), 8.02 (1H, d, J=1.7 Hz); LRMS (ESI): m/z [M+H]⁺ 435.

2-(cyclopropylmethyl)-5-(6-(4,4-difluoropiperidine-1-carbonyl)naphthalen-1-yl)isoindolin-1-one was prepared in accordance with the general procedure 4 (Scheme 4) using the method described below in detail.

Synthesis of 2-(cyclopropylmethyl)-5-(6-(4,4-difluoropiperidine-1-carbonyl) naphthalen-1-yl) isoindolin-1-one

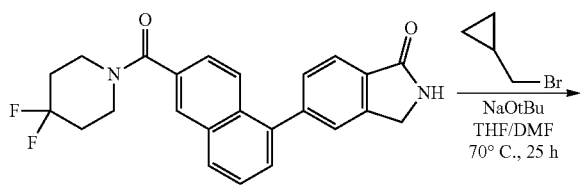

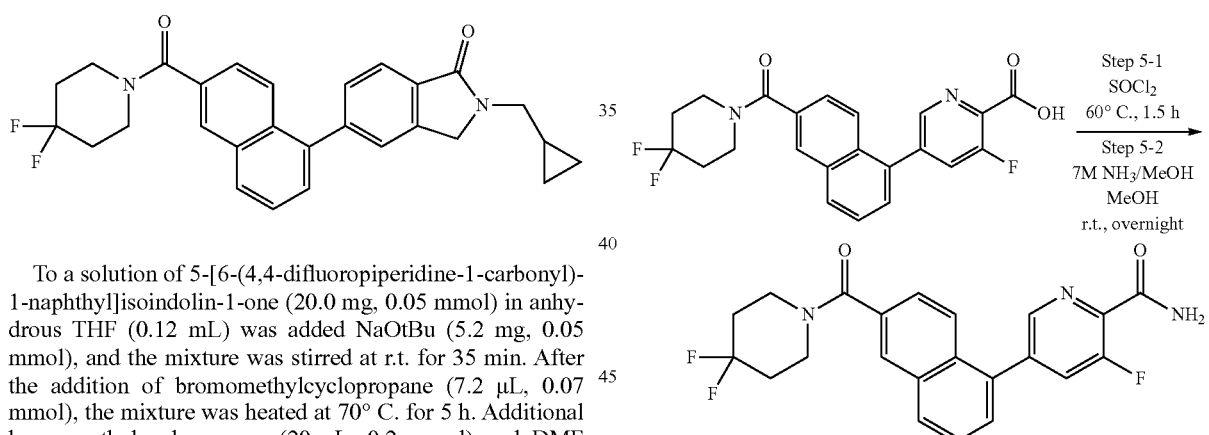

To a solution of 5-[6-(4,4-difluoropiperidine-1-carbonyl)-1-naphthyl]isoindolin-1-one (20.0 mg, 0.05 mmol) in anhydrous THF (0.12 mL) was added NaOtBu (5.2 mg, 0.05 mmol), and the mixture was stirred at r.t. for 35 min. After the addition of bromomethylcyclopropane (7.2 μL, 0.07 mmol), the mixture was heated at 70° C. for 5 h. Additional bromomethylcyclopropane (20 μL, 0.2 mmol) and DMF (0.12 mL) were added and the reaction mixture was heated at 70° C. overnight. Additional bromomethylcyclopropane (25 μL, 0.25 mmol) and NaOtBu (16 mg, 0.16 mmol) were added, and the reaction mixture was further heated at 70° C. for 5 h. After cooling to r.t., the solvent was evaporated in vacuo and the residue was purified by prep HPLC to obtain the desired product as a white solid (4.8 mg).

¹H NMR (400 MHz, DMSO-d₆) δ 0.32-0.36 (2H, m), 0.52-0.56 (2H, m), 1.07-1.11 (1H, m), 2.09 (4H, br s), 3.44-3.53 (4H, m), 3.70-3.88 (2H, m), 4.68 (2H, s), 7.55-7.61 (3H, m), 7.68-7.74 (2H, m), 7.83 (1H, s), 7.85 (1H, d, J=2.2 Hz), 8.10 (1H, d, J=8.1 Hz), 8.17 (1H, d, J=1.6 Hz); LRMS (ESI): m/z [M+H]⁺ 461.

2-((3,3-difluorocyclobutyl)methyl)-5-(6-(4,4-difluoropiperidine-1-carbonyl) naphthalen-1-yl) isoindolin-1-one was synthesized using conditions analogous to 2-(cyclopropylmethyl)-5-(6-(4,4-difluoropiperidine-1-carbonyl) naphthalen-1-yl) isoindolin-1-one in accordance with general procedure 4 (Scheme 4).

2-((3,3-difluorocyclobutyl)methyl)-5-(6-(4,4-difluoropiperidine-1-carbonyl) naphthalen-1-yl) isoindolin-1-one

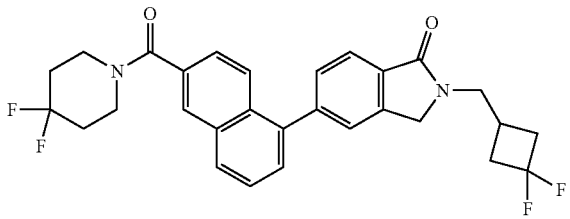 [SMILES: O=C(c1ccc2c(-c3ccc4c(c3)CN(CC3CC(F)(F)C3)C4=O)cccc2c1)N1CCC(F)(F)CC1]

¹H NMR (400 MHz, DMSO-d₆) δ 2.09 (4H, br s), 2.39-2.44 (2H, m), 2.67-2.78 (3H, m), 3.45-3.55 (2H, m), 3.72 (2H, d, J=7.3 Hz), 3.76-3.83 (2H, m), 4.60 (2H, s), 7.55-7.61 (3H, m), 7.67-7.72 (2H, m), 7.81-7.85 (2H, m), 8.10 (1H, d, J=7.9 Hz), 8.17 (1H, d, J=1.6 Hz); LRMS (ESI): m/z [M+H]⁺ 511.

5-[6-(4,4-difluoropiperidine-1-carbonyl)-1-naphthyl]-3-fluoro-pyridine-2-carboxamide was prepared in accordance with the steps 5-1 and 5-2 of general procedure 5 (Scheme 5) using the conditions described below in detail.

Synthesis of 5-[6-(4,4-difluoropiperidine-1-carbonyl)-1-naphthyl]-3-fluoro-pyridine-2-carboxamide Step 5-1
A reaction vial containing a mixture of 5-[6-(4,4-difluoropiperidine-1-carbonyl)-1-naphthyl]-3-fluoro-pyridine-2-carboxylic acid (10.4 mg, 0.03 mmol) and SOCl₂ (0.07 mL, 0.96 mmol) was heated at 60° C. for 1.5 h. After the removal of the excess SOCl₂, the residue was directly used in the next step without further purification.

Step 5-2
A mixture of 5-[6-(4,4-difluoropiperidine-1-carbonyl)-1-naphthyl]-3-fluoro-pyridine-2-carbonyl chloride (10.8 mg, 0.02 mmol) and 7M NH₃/MeOH (0.8 mL, 5.6 mmol) in MeOH (0.15 mL) was reacted at r.t. overnight. The volatiles were evaporated in vacuo, and the crude mixture was purified by prep HPLC to obtain the desired product as a white solid (2.5 mg).

¹H NMR (400 MHz, DMSO-d₆) δ 2.09 (4H, br s), 3.46-3.82 (4H, m), 7.62 (1H, dd, J=8.6, 1.8 Hz), 7.65-7.68 (1H, m), 7.71-7.75 (1H, m), 7.78 (1H, br s), 7.83-7.86 (1H, m), 8.07-8.11 (1H, m), 8.16-8.18 (2H, m), 8.20 (1H, d, J=1.5 Hz), 8.59-8.60 (1H, m); LRMS (ESI): m/z [M+H]$^+$ 414.

The following compounds were synthesized using conditions analogous to 5-[6-(4,4-difluoropiperidine-1-carbonyl)-1-naphthyl]-3-fluoro-pyridine-2-carboxamide in accordance with the general procedure 5 (Scheme 5).

5-[6-(4,4-difluoropiperidine-1-carbonyl)-1-naphthyl]pyrimidine-2-carboxamide

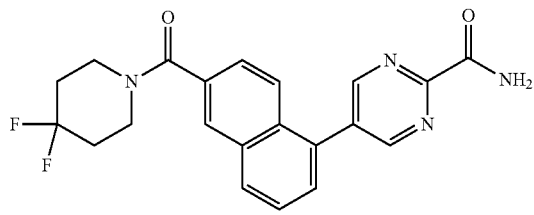 [SMILES: NC(=O)c1ncc(-c2cccc3cc(C(=O)N4CCC(F)(F)CC4)ccc23)cn1]

$^1$H NMR (400 MHz, CDCl$_3$) δ 1.95-2.20 (4H, m), 3.61-4.04 (4H, m), 6.00 (1H, s), 7.56-7.58 (2H, m), 7.69-7.73 (1H, m), 7.80 (1H, d, J=8.7 Hz), 7.91 (1H, br s), 8.05-8.07 (2H, m), 9.06 (2H, s); LRMS (ESI): m/z [M+H]$^+$ 397.

4-(6-(4,4-difluoropiperidine-1-carbonyl)naphthalen-1-yl)-2-fluorobenzamide

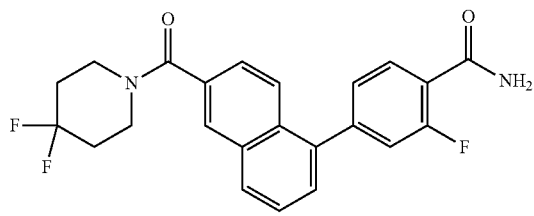 [SMILES: NC(=O)c1ccc(-c2cccc3cc(C(=O)N4CCC(F)(F)CC4)ccc23)cc1F]

$^1$H NMR (400 MHz, DMSO-d$_6$) δ 1.97-2.15 (4H, m), 3.49 (2H, br s), 3.77 (2H, br s), 7.41 (1H, dd, J=7.8, 1.7 Hz,), 7.44-7.47 (1H, m), 7.56-7.60 (2H, m), 7.67-7.71 (1H, m), 7.75 (1H, s), 7.80-7.85 (3H, m), 8.11 (1H, d, J=8.2 Hz), 8.17 (1H, s); LRMS (ESI): m/z [M+H]$^+$ 413.

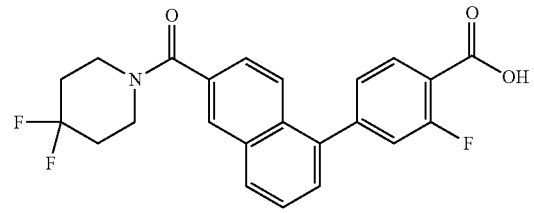 [SMILES: O=C(O)c1ccc(-c2cccc3cc(C(=O)N4CCC(F)(F)CC4)ccc23)cc1F]

$^1$H NMR (400 MHz, DMSO-d$_6$) δ 2.07 (4H, br s), 3.50 (2H, br s), 3.78 (2H, br s), 7.11-7.17 (2H, m), 7.53-7.68 (4H, m), 7.89 (1H, d, J=8.6 Hz), 8.06 (1H, d, J=8.1 Hz), 8.14 (1H, s); LRMS (ESI): m/z [M+H]$^+$ 414.

4-[6-(4,4-difluoropiperidine-1-carbonyl)-1-naphthyl]-2,6-difluoro-benzamide

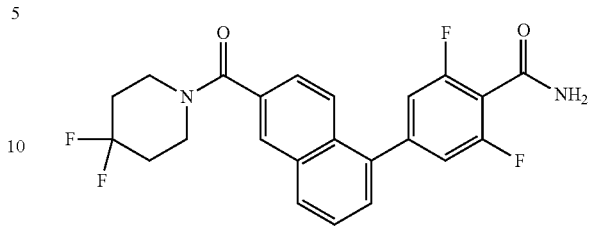

$^1$H NMR (400 MHz, DMSO-d$_6$) δ 2.08 (4H, br s), 3.46-3.83 (4H, m), 7.35 (2H, d, J=8.0 Hz), 7.57-7.63 (2H, m), 7.67-7.71 (1H, m), 7.83-7.86 (1H, m), 7.96 (1H, br s), 8.12 (1H, d, J=8.0 Hz), 8.18 (1H, s), 8.25 (1H, br s); LRMS (ESI): m/z [M+H]$^+$ 431.

4-[6-(4,4-difluoropiperidine-1-carbonyl)-1-naphthyl]-2-fluoro-6-methoxy-benzamide

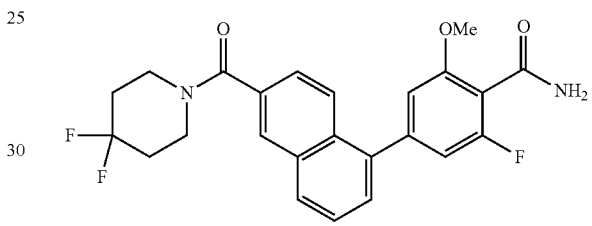

$^1$H NMR (400 MHz, DMSO-d$_6$) δ 2.10 (4H, br s), 3.45-3.55 (2H, m), 3.77-3.85 (5H, m), 6.97-7.00 (2H, m), 7.56-7.70 (4H, m), 7.89 (1H, d, J=8.8 Hz), 7.94 (1H, s), 8.09 (1H, d, J=8.5 Hz), 8.16 (1H, s); LRMS (ESI): m/z [M+H]$^+$ 443.2.

5-[6-(4,4-difluoropiperidine-1-carbonyl)-1-naphthyl]-N-methyl-pyrimidine-2-carboxamide was prepared as described in step 5-3 of general procedure 5 (Scheme 5) using the conditions described below in detail.

Synthesis of 5-[6-(4,4-difluoropiperidine-1-carbonyl)-1-naphthyl]-N-methyl-pyrimidine-2-carboxamide

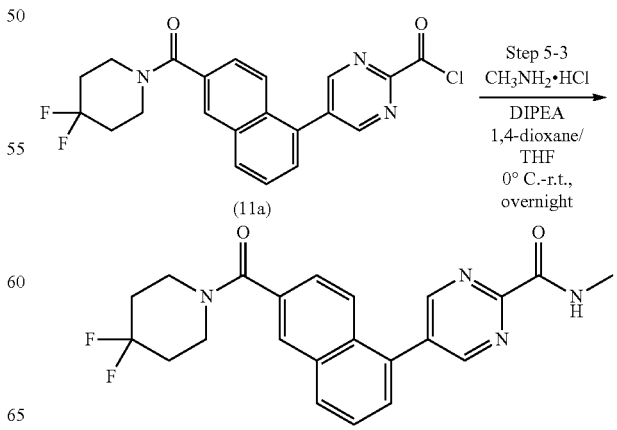

Step 5-3

To a solution of 5-[6-(4,4-difluoropiperidine-1-carbonyl)-1-naphthyl]pyrimidine-2-carbonyl chloride (11a) (7.33 mg, 0.02 mmol) in 1,4-dioxane (0.4 mL) and THF (0.4 mL) were added DIPEA (1.3 mL, 7.46 mmol) and $CH_3NH_2 \cdot HCl$ (29.0 mg, 0.43 mmol) at 0° C. The reaction mixture was stirred at r.t. overnight, then concentrated in vacuo. The crude was purified by prep HPLC to obtain the desired product as a pale brown solid (1 mg).

$^1$H NMR (400 MHz, $CDCl_3$) δ 1.94-2.20 (4H, m), 3.18 (3H, d, J=5.1 Hz), 3.60-4.00 (4H, m), 7.55-7.57 (2H, m), 7.68-7.72 (1H, m), 7.80 (1H, d, J=8.7 Hz), 8.04-8.07 (2H, m), 8.12 (1H, s), 9.03 (2H, s); LRMS (ESI): m/z $[M+H]^+$ 411.

The following compounds were synthesized using conditions analogous to 5-[6-(4,4-difluoropiperidine-1-carbonyl)-1-naphthyl]-N-methyl-pyrimidine-2-carboxamide in accordance with the general procedure 5 (Scheme 5).

4-(6-(4,4-difluoropiperidine-1-carbonyl)naphthalen-1-yl)-2-fluoro-N-methylbenzamide

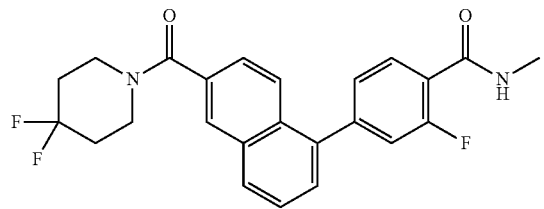 [SMILES: CNC(=O)c1ccc(-c2cccc3cc(C(=O)N4CCC(F)(F)CC4)ccc23)cc1F]

$^1$H NMR (400 MHz, DMSO-$d_6$) δ 2.07 (4H, br s), 2.83 (3H, d, J=4.5 Hz), 3.45-3.60 (2H, m), 3.73-3.82 (2H, m), 7.41 (1H, dd, J=7.9, 1.6 Hz), 7.45-7.48 (1H, m), 7.56-7.60 (2H, m), 7.67-7.71 (1H, m), 7.77-7.85 (2H, m), 8.11 (1H, d, J=8.5 Hz), 8.17 (1H, d, J=1.7 Hz), 8.37 (1H, br s); LRMS (ESI): m/z $[M+H]^+$ 427.

5-(6-(4,4-difluoropiperidine-1-carbonyl)naphthalen-1-yl)-2-(2-hydroxyethyl)isoindolin-1-one was prepared in accordance with the general procedure 6 (Scheme 6) using the method described below in detail.

Synthesis of 5-(6-(4,4-difluoropiperidine-1-carbonyl) naphthalen-1-yl)-2-(2-hydroxyethyl) isoindolin-1-one

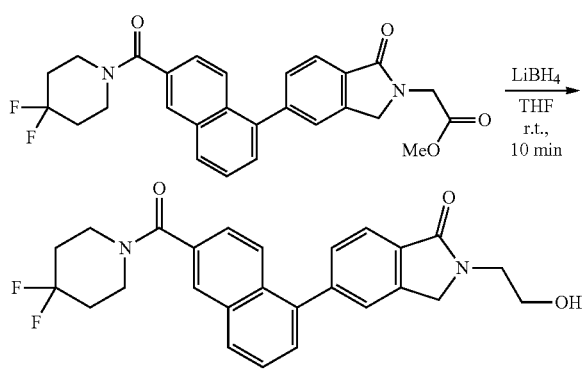

To a solution of methyl 2-[5-[6-(4,4-difluoropiperidine-1-carbonyl)-1-naphthyl]-1-oxo-isoindolin-2-yl]acetate (27.0 mg, 0.056 mmol) in anhydrous THF (1.4 mL) was added $LiBH_4$ (7.4 mg, 0.34 mmol) and the reaction mixture was stirred at r.t. for 10 min. The reaction mixture was quickly quenched with $H_2O$ and the solvent was evaporated in vacuo. The residue was dissolved in $H_2O$ and extracted with EtOAc (×2). The combined organic layers were dried in vacuo, and the residue was purified by prep HPLC to obtain the desired product as a white solid (9.5 mg).

$^1$H NMR (400 MHz, DMSO-$d_6$) δ 2.08 (4H, br s), 3.45-3.54 (2H, m), 3.63-3.67 (4H, m), 3.75-3.83 (2H, m), 4.66 (2H, s), 4.89 (1H, t, J=5.4 Hz), 7.55-7.60 (3H, m), 7.68-7.73 (2H, m), 7.82-7.85 (2H, m), 8.10 (1H, d, J=8.0 Hz), 8.17 (1H, d, J=1.6 Hz); LRMS (ESI): m/z $[M+H]^+$ 451.

6-(6-(4,4-difluoropiperidine-1-carbonyl)naphthalen-1-yl) quinoline 1-oxide was prepared in accordance with the general procedure 7 (Scheme 7) using the method described below in detail.

Synthesis of 6-(6-(4,4-difluoropiperidine-1-carbonyl) naphthalen-1-yl) quinoline 1-oxide

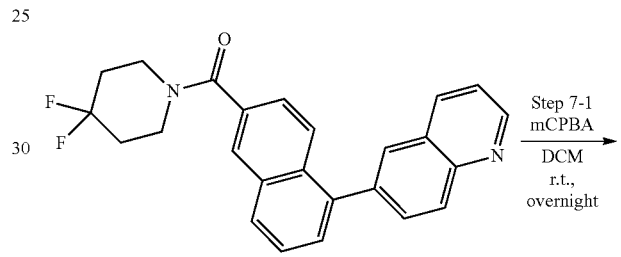

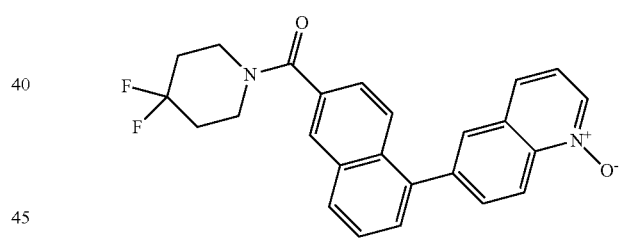

Step 7-1

A solution of (4,4-difluoro-1-piperidyl)-[5-(6-quinolyl)-2-naphthyl]methanone (72 mg, 0.18 mmol) in DCM (0.5 mL) was treated with mCPBA (40.1 mg, 0.23 mmol) and stirred at r.t. overnight. The solvent was evaporated under reduced pressure, and the residue was purified by prep HPLC to obtain the desired product as a white solid (1.22 mg, 2%).

$^1$H NMR (400 MHz, DMSO-$d_6$) δ 2.08 (4H, br s), 3.46-3.57 (2H, m), 3.71-3.83 (2H, m), 7.54-7.59 (2H, m), 7.66-7.68 (1H, m), 7.71-7.75 (1H, m), 7.85 (1H, d, J=8.2 Hz), 7.95 (1H, d, J=8.7 Hz), 8.04 (1H, d, J=8.4 Hz), 8.14 (1H, d, J=8.5 Hz), 8.19 (1H, s), 8.26 (1H, s), 8.66-8.69 (2H, m); LRMS (ESI): m/z $[M+H]^+$ 419.

5-[6-(4,4-difluoropiperidine-1-carbonyl)-2-naphthyl]-2-methyl-isoindolin-1-one was prepared in accordance with the general procedure 8 (Scheme 8) using the method described below in detail.

Synthesis of 5-[6-(4,4-difluoropiperidine-1-carbonyl)-2-naphthyl]-2-methyl-isoindolin-1-one

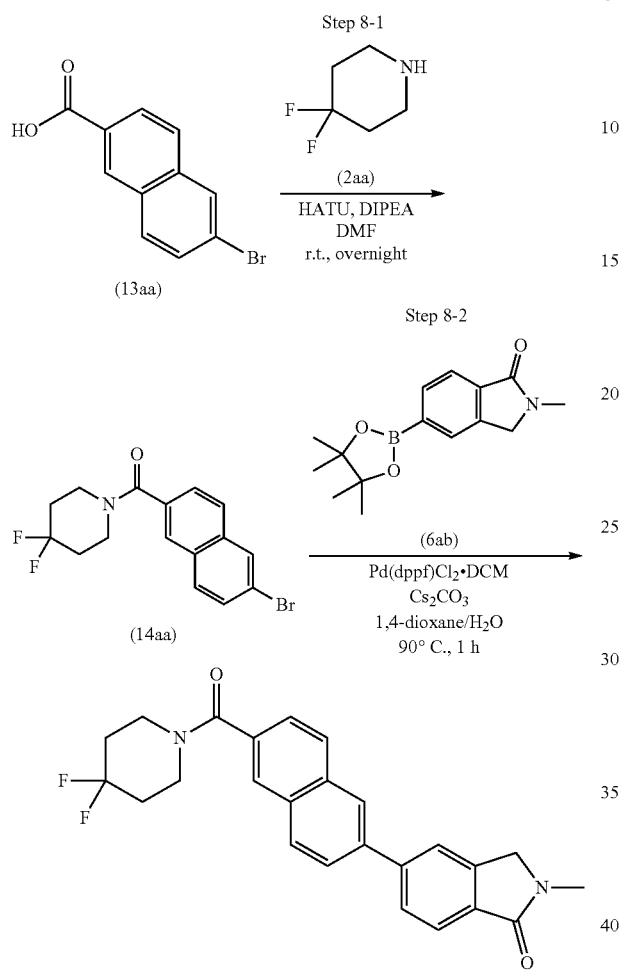

Step 8-1

A mixture of 6-bromonaphthalene-2-carboxylic acid (13aa) (250.0 mg, 1 mmol), 4,4-difluoropiperidine (2aa) (0.15 mL, 1.39 mmol), HATU (454.04 mg, 1.19 mmol) and DIPEA (0.52 mL, 2.99 mmol) in DMF (3.1 mL) was stirred at r.t. overnight. The mixture was partitioned between EtOAc and $H_2O$. The product was extracted with EtOAc from the aq. layer (×2). The combined organic layers were dried over $Na_2SO_4$ and concentrated. The residue was purified by silica gel column chromatography (0-20% EtOAc/Hexane) to give the expected product as a white solid (283.1 mg); LRMS (ESI): m/z [M+H]$^+$ 354, 356.

Step 8-2

A reaction vessel containing a mixture of (6-bromo-2-naphthyl)-(4,4-difluoro-1-piperidyl)methanone (14aa) (17.0 mg, 0.048 mmol), 2-methyl-5-(4,4,5,5-tetramethyl-1,3,2-dioxaborolan-2-yl)isoindolin-1-one (6ab) (26.2 mg, 0.1 mmol), $Cs_2CO_3$ (46.9 mg, 0.14 mmol) and Pd(dppf)Cl$_2$·DCM (7.8 mg, 0.01 mmol) was degassed and backfilled with nitrogen three times. After the addition of 1,4-dioxane (0.4 mL) and $H_2O$ (0.2 mL), the reaction mixture was degassed and backfilled with nitrogen. The resulting mixture was stirred and heated at 90° C. for 1 h. After cooling to r.t., the mixture was filtered through celite, and the filtrate was concentrated. The residue was purified by prep HPLC ($CH_3CN$/0.1% TFA-$H_2O$/0.1% TFA) to give the expected product as a white solid (15.5 mg).

$^1$H NMR (400 MHz, DMSO-d$_6$) δ 2.03-2.16 (4H, m), 3.13 (3H, s), 3.47-3.58 (2H, m), 3.70-3.83 (2H, m), 4.57 (2H, s), 7.62 (1H, d, J=8.4 Hz), 7.80 (1H, d, J=8.1 Hz), 7.94-8.01 (2H, m), 8.06-8.15 (4H, m), 8.39 (1H, s); LRMS (ESI): m/z [M+H]$^+$ 421.

The following compounds were synthesized using conditions analogous to 5-[6-(4,4-difluoropiperidine-1-carbonyl)-2-naphthyl]-2-methyl-isoindolin-1-one in accordance with the general procedure 8 (Scheme 8).

6-(7-(4,4-difluoropiperidine-1-carbonyl)naphthalen-2-yl)phthalazin-1(2H)-one

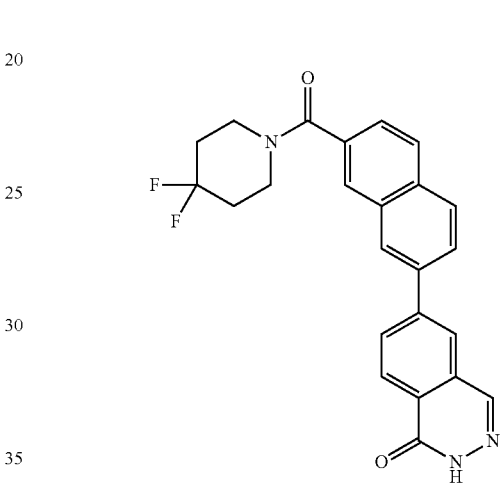

$^1$H NMR (400 MHz, DMSO-d$_6$) δ 2.10 (4H, br s), 3.79-3.53 (4H, m)), 7.64 (1H, dd, J=8.3, 1.5 Hz), 8.09 (2H, dd, J=8.5, 2.4 Hz), 8.16-8.18 (2H, m), 8.31-8.37 (2H, m), 8.42 (1H, s), 8.47 (1H, d, J=2.3 Hz), 8.53 (1H, s), 12.74 (NH, br s); LRMS (ESI): m/z [M+H]$^+$ 420.

6-[6-(4,4-difluoropiperidine-1-carbonyl)-2-naphthyl]-2H-isoquinolin-1-one

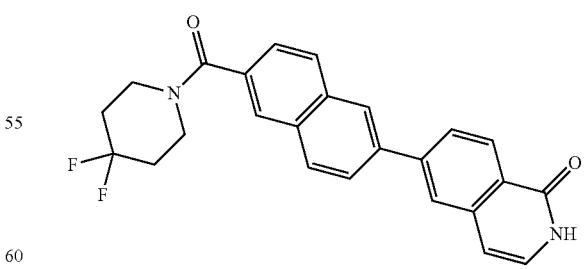

$^1$H NMR (400 MHz, DMSO-d$_6$) δ 2.04-2.16 (4H, m), 3.48-3.83 (4H, m), 6.68 (1H, d, J=7.2 Hz), 7.22-7.26 (1H, m), 7.63 (1H, d, J=8.4 Hz), 7.97 (1H, d, J=8.3 Hz), 8.04-8.06 (1H, m), 8.12-8.18 (4H, m), 8.31 (1H, d, J=8.4 Hz), 8.46 (1H, s), 11.31 (NH, br s); LRMS (ESI): m/z [M+H]$^+$ 419.

5-[7-(4,4-difluoropiperidine-1-carbonyl)-2-naphthyl]-2-methyl-isoindolin-1-one

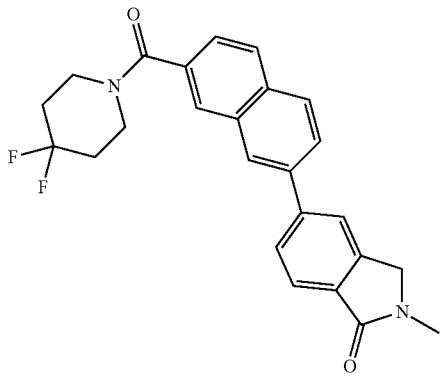 [SMILES: CN1Cc2cc(-c3ccc4ccc(C(=O)N5CCC(F)(F)CC5)cc4c3)ccc2C1=O]

¹H NMR (400 MHz, DMSO-d₆) δ 2.11 (4H, br s), 3.12 (3H, s), 3.48-3.84 (4H, m), 4.57 (2H, s), 7.61 (1H, d, J=8.1 Hz), 7.80 (1H, d, J=7.8 Hz), 7.94 (1H, d, J=7.8 Hz), 8.00 (1H, d, J=8.1 Hz), 8.05-8.07 (2H, m), 8.11-8.14 (2H, m), 8.42 (1H, s); LRMS (ESI): m/z [M+H]⁺ 421.

6-[7-(4,4-difluoropiperidine-1-carbonyl)-2-naphthyl]-2H-isoquinolin-1-one

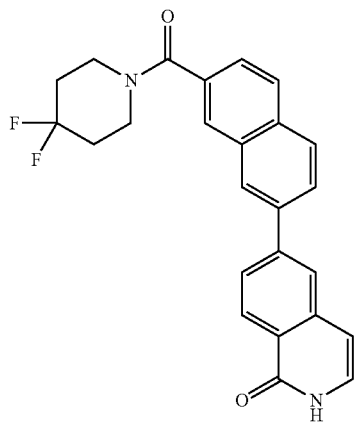 [SMILES: O=C(c1ccc2ccc(-c3ccc4c(=O)[nH]ccc4c3)cc2c1)N1CCC(F)(F)CC1]

¹H NMR (400 MHz, DMSO-d₆) δ 2.09 (4H, br s), 3.47-3.83 (4H, m), 6.67 (1H, d, J=7.6 Hz), 7.23-7.26 (1H, m), 7.61 (1H, d, J=8.4 Hz), 7.96 (1H, d, J=8.1 Hz), 8.05-8.08 (2H, m), 8.13-8.17 (3H, m), 8.31 (1H, d, J=8.3 Hz), 8.48 (1H, s), 11.30 (NH, br s); LRMS (ESI): m/z [M+H]⁺ 419.

6-(3-(4,4-difluoropiperidine-1-carbonyl)quinolin-8-yl) phthalazin-1(2H)-one was prepared in accordance with the procedure 9 (Scheme 9) using the method described below in detail.

Synthesis of 6-(3-(4,4-difluoropiperidine-1-carbonyl) quinolin-8-yl) phthalazin-1 (2H)-one

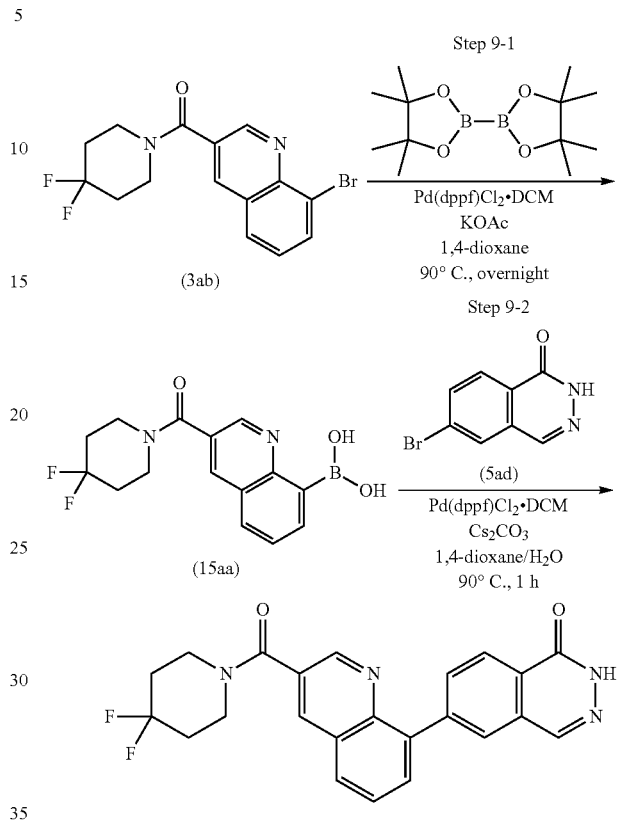

Step 9-1

A mixture of (8-bromoquinolin-3-yl) (4,4-difluoropiperidin-1-yl)methanone (3ab) (5.8 g, 16.6 mmol), KOAc (5.0 mg, 51 mmol), bis(pinacolato)diborate (6.3 g, 24.9 mmol) and Pd(dppf)Cl₂-DCM (678 mg, 5% mol) was degassed and backfilled with nitrogen three times. After the addition of 1,4-dioxane (15 mL), the mixture was degassed again by bubbling nitrogen through. The resulting mixture was heated at 90° C. overnight. After cooling to r.t., the mixture was filtered through celite, and the filtrate was concentrated. The residue was purified by silica gel column chromatography (0-20% MeOH/DCM) to give the expected product as a light brown oil (4.1 g); LRMS (ESI): m/z [M+H]⁺ 321.

Step 9-2

A reaction vessel containing a mixture of (3-(4,4-difluoropiperidine-1-carbonyl)quinolin-8-yl)boronic acid (15aa) (32 mg, 0.10 mmol), 6-bromophthalazin-1(2H)-one (5ad) (27 mg, 0.12 mmol), Cs₂CO₃ (97.7 mg, 0.3 mmol) and Pd(dppf)Cl₂-DCM (8.2 mg, 0.01 mmol) was degassed and backfilled with nitrogen three times. After the addition of 1,4-dioxane (0.6 mL) and H₂O (0.3 mL), the reaction mixture was degassed again by bubbling nitrogen through. The resulting mixture was heated at 100° C. for 1 h. After cooling to r.t., the mixture was filtered through celite, and the filtrate was concentrated. The residue was purified by prep HPLC to give the desired product as a white solid (18.8 mg).

¹H NMR (400 MHz, DMSO-d₆) δ 2.05-2.18 (4H, m), 3.48-3.58 (2H, m), 3.75-3.85 (2H, m), 7.84 (1H, t, J=7.6 Hz), 8.00 (1H, dd, J=7.2, 1.3 Hz), 8.14 (1H, dd, J=8.2, 1.7 Hz), 8.17-8.22 (2H, m), 8.32 (1H, d, J=8.2 Hz), 8.44 (1H, s), 8.64 (1H, d, J=2.2 Hz), 8.99 (1H, d, J=2.2 Hz), 12.71 (1H, s); LRMS (ESI): m/z [M+H]⁺ 421.

The following compounds were synthesized using conditions analogous to 6-(3-(4,4-difluoropiperidine-1-carbonyl)quinolin-8-yl)phthalazin-1 (2H)-one in accordance with the general procedure 9 (Scheme 9).

3-(3-(4,4-difluoropiperidine-1-carbonyl)quinolin-8-yl)-1,7-naphthyridin-8 (7H)-one

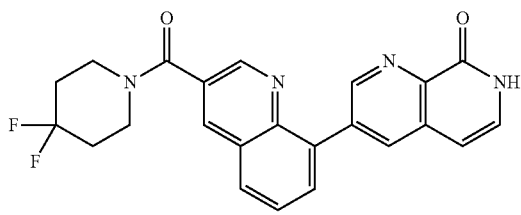 [SMILES: O=C(c1cnc2c(-c3cnc4c(=O)[nH]ccc4c3)cccc2c1)N1CCC(F)(F)CC1]

¹H NMR (400 MHz, DMSO-d₆) δ 2.12 (4H, br s), 3.54 (2H, br s), 3.81 (2H, br s), 6.63 (1H, d, J=7.2 Hz), 7.32 (1H, t, J=5.0 Hz)), 7.86 (1H, t, J=7.9 Hz), 8.15 (1H, d, J=8.0 Hz), 8.21 (1H, d, J=8.4 Hz), 8.39 (1H, d, J=2.1 Hz), 8.65 (1H, d, J=2.2 Hz), 9.00 (1H, d, J=2.2 Hz). 9.04 (1H, d, J=2.1 Hz), 11.58 (NH, br s); LRMS (ESI): m/z [M+H]⁺ 421.

6-(3-(4,4-difluoropiperidine-1-carbonyl)quinolin-8-yl)-2,7-naphthyridin-1 (2H)-one

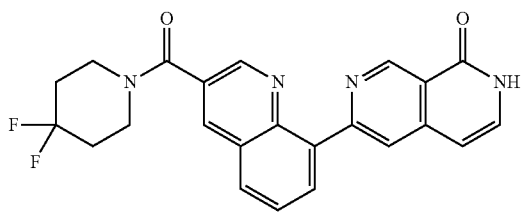 [SMILES: O=C(c1cnc2c(-c3cc4cc[nH]c(=O)c4cn3)cccc2c1)N1CCC(F)(F)CC1]

¹H NMR (400 MHz, DMSO-d₆) δ 2.12 (4H, br s), 3.54 (2H, br s), 3.81 (2H, br s), 6.65 (1H, d, J=7.2 Hz), 7.47 (1H, d, J=7.3 Hz)), 7.85 (1H, t, J=7.2 Hz), 8.22 (1H, d, J=8.0 Hz), 8.26 (1H, d, J=8.4 Hz), 8.31 (1H, s), 8.66 (1H, s), 9.03 (1H, s), 9.45 (1H, s), 11.65 (NH, br s); LRMS (ESI): m/z [M+H]⁺ 421.

6-(3-(4,4-difluoropiperidine-1-carbonyl)quinolin-8-yl) isoquinolin-1 (2H)-one

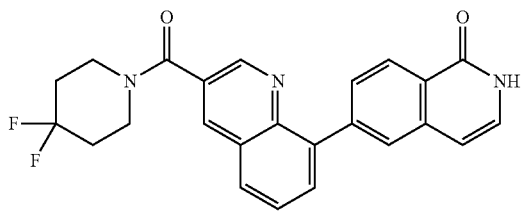 [SMILES: O=C(c1cnc2c(-c3ccc4c(=O)[nH]ccc4c3)cccc2c1)N1CCC(F)(F)CC1]

¹H NMR (400 MHz, DMSO-d₆) δ 2.05-2.18 (4H, m), 3.48-3.58 (2H, m), 3.75-3.85 (2H, m), 6.61 (1H, d, J=6.9 Hz), 7.21 (1H, t, J=6.4 Hz), 7.76 (1H, dd, J=8.1, 1.2 Hz), 7.81 (1H, t, J=7.6 Hz), 7.91 (1H, s), 7.94 (1H, d, J=7.1 Hz), 8.16 (1H, d, J=8.2 Hz), 8.26 (1H, d, J=8.3 Hz), 8.62 (1H, d, J=2.2 Hz), 8.97 (1H, d, J=2.2 Hz), 11.28 (1H, d, J=5.6 Hz); LRMS (ESI): m/z [M+H]⁺ 420.

3-(3-(4,4-difluoropiperidine-1-carbonyl)quinolin-8-yl)-6-methyl-5,6-dihydro-7H-pyrrolo[3,4-b]pyridin-7-one

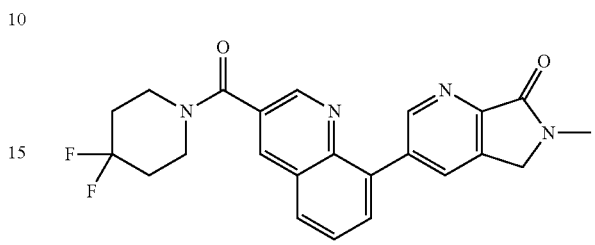

¹H NMR (400 MHz, DMSO-d₆) δ 2.05-2.18 (4H, m), 3.35 (3H, s), 3.48-3.58 (2H, m), 3.75-3.85 (2H, m), 4.59 (2H, s), 7.84 (1H, t, J=7.5 Hz), 8.00 (1H, dd, J=7.1, 1.3 Hz), 8.19 (1H, dd, J=8.3, 1.0 Hz), 8.34 (1H, m), 8.64 (1H, d, J=2.1 Hz), 8.96 (1H, d, J=1.8 Hz), 8.98 (1H, d, J=2.1 Hz); LRMS (ESI): m/z [M+H]⁺ 423.

3-(3-(4,4-difluoropiperidine-1-carbonyl)quinolin-8-yl)pyrido[2,3-d]pyridazin-8(7H)-one

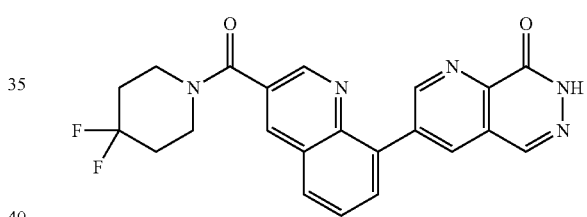

¹H NMR (400 MHz, DMSO-d₆) δ 2.05-2.18 (4H, m), 3.48-3.58 (2H, m), 3.75-3.85 (2H, m), 7.89 (1H, t, J=7.7 Hz), 8.11 (1H, dd, J=7.2, 1.3 Hz), 8.25 (1H, dd, J=8.3, 1.2 Hz), 8.49 (1H, s), 8.67-8.69 (2H, m), 9.01 (1H, d, J=2.2 Hz), 9.37 (1H, d, J=2.1 Hz), 12.99 (1H, s); LRMS (ESI): m/z [M+H]⁺ 422.

6-(3-(4,4-difluoropiperidine-1-carbonyl)quinolin-8-yl)benzo[d]isoxazol-3 (2H)-one

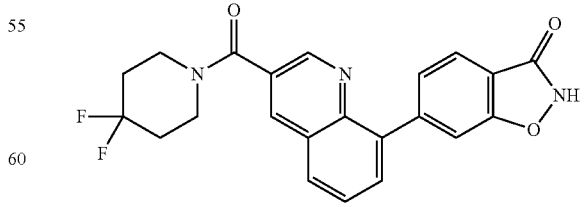

¹H NMR (400 MHz, DMSO-d₆) δ 2.05-2.18 (4H, m), 3.48-3.58 (2H, m), 3.75-3.85 (2H, m), 7.62 (1H, dd, J=8.0, 1.2 Hz), 7.70 (1H, s), 7.77 (1H, s), 7.81 (1H, t, J=7.7 Hz), 7.87 (1H, d, J=8.0 Hz), 7.96 (1H, dd, J=7.1, 1.3 Hz), 8.17

(1H, dd, J=8.2, 1.3 Hz), 8.63 (1H, d, J=2.1 Hz), 8.97 (1H, d, J=2.2 Hz); LRMS (ESI): m/z [M+H]⁺ 410.

7-[3-(4,4-difluoropiperidine-1-carbonyl)-8-quinolyl]-1-methyl-quinazoline-2,4-dione

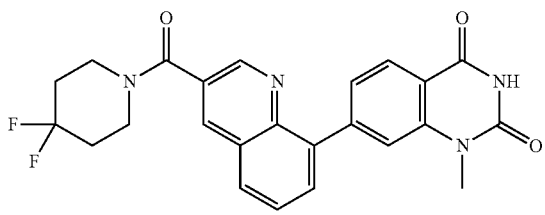 [SMILES: Cn1c(=O)[nH]c(=O)c2ccc(-c3cccc4cc(C(=O)N5CCC(F)(F)CC5)cnc34)cc21]

¹H NMR (400 MHz, DMSO-d₆) δ 2.12 (4H, br s), 3.52 (2H, br s), 3.49 (3H, s), 3.80 (2H, br s), 7.55 (1H, d, J=8.1 Hz), 7.63 (1H, s), 7.80 (1H, t, J=8.1 Hz), 7.99 (1H, d, J=7.2 Hz), 8.07 (1H, d, J=8.1 Hz), 8.17 (1H, d, J=8.2 Hz), 8.63 (1H, d, J=2.2 Hz), 8.97 (1H, d, J=2.2 Hz), 11.60 (1H, br s); LRMS (ESI): m/z [M+H]⁺ 451.

8-[3-(4,4-difluoropiperidine-1-carbonyl)-8-quinolyl]pyrido[1,2-a]pyrimidin-4-one

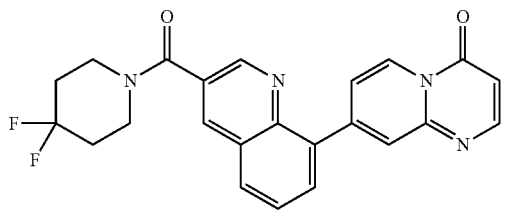 [SMILES: O=C(c1cnc2c(-c3ccn4c(=O)ccnc4c3)cccc2c1)N1CCC(F)(F)CC1]

¹H NMR (400 MHz, DMSO-d₆) δ 2.12 (4H, br s), 3.55 (2H, br s), 3.82 (2H, br s), 6.44 (1H, d, J=6.3 Hz), 7.78 (1H, d, J=7.4 Hz), 7.87 (1H, t, J=7.3 Hz), 8.04 (1H, d, J=1.9 Hz), 8.14 (1H, d, J=7.2 Hz), 8.25 (1H, d, J=8.3 Hz), 8.36 (1H, d, J=6.3 Hz), 8.67 (1H, d, J=2.1 Hz), 9.02 (1H, d, J=2.2 Hz), 9.06 (1H, d, J=7.3 Hz); LRMS (ESI): m/z [M+H]⁺ 421.

3-[3-(4,4-difluoropiperidine-1-carbonyl)-8-quinolyl]-5,6-dihydropyrrolo[3,4-b]pyridin-7-one

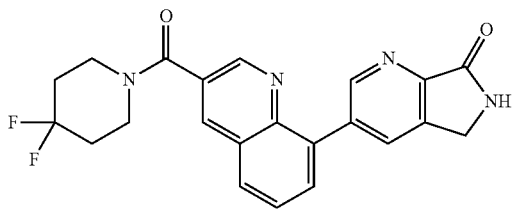 [SMILES: O=C1NCc2cc(-c3cccc4cc(C(=O)N5CCC(F)(F)CC5)cnc34)cnc21]

¹H NMR (400 MHz, DMSO-d₆) δ 2.12 (4H, br s), 3.53 (2H, br s), 3.81 (2H, br s), 4.50 (2H, s), 7.84 (1H, t, J=7.7 Hz), 7.99 (1H, d, J=7.7 Hz), 8.19 (1H, d, J=7.7 Hz), 8.33 (1H, d, J=1.6 Hz), 8.65 (1H, d, J=7.1, 2.2 Hz), 8.97-8.98 (2H, m,), 9.04 (1H, s); LRMS (ESI): m/z [M+H]⁺ 409.

7-[3-(4,4-difluoropiperidine-1-carbonyl)-8-quinolyl]-3-methyl-quinazolin-4-one

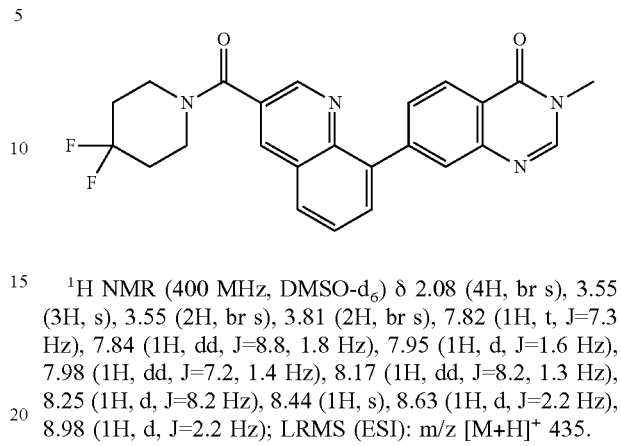

¹H NMR (400 MHz, DMSO-d₆) δ 2.08 (4H, br s), 3.55 (3H, s), 3.55 (2H, br s), 3.81 (2H, br s), 7.82 (1H, t, J=7.3 Hz), 7.84 (1H, dd, J=8.8, 1.8 Hz), 7.95 (1H, d, J=1.6 Hz), 7.98 (1H, dd, J=7.2, 1.4 Hz), 8.17 (1H, dd, J=8.2, 1.3 Hz), 8.25 (1H, d, J=8.2 Hz), 8.44 (1H, s), 8.63 (1H, d, J=2.2 Hz), 8.98 (1H, d, J=2.2 Hz); LRMS (ESI): m/z [M+H]⁺ 435.

6-[3-(4,4-difluoropiperidine-1-carbonyl)-8-quinolyl]-4-methyl-2H-phthalazin-1-one

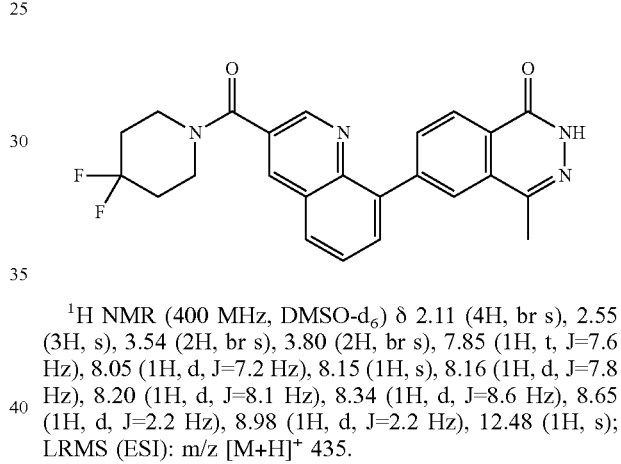

¹H NMR (400 MHz, DMSO-d₆) δ 2.11 (4H, br s), 2.55 (3H, s), 3.54 (2H, br s), 3.80 (2H, br s), 7.85 (1H, t, J=7.6 Hz), 8.05 (1H, d, J=7.2 Hz), 8.15 (1H, s), 8.16 (1H, d, J=7.8 Hz), 8.20 (1H, d, J=8.1 Hz), 8.34 (1H, d, J=8.6 Hz), 8.65 (1H, d, J=2.2 Hz), 8.98 (1H, d, J=2.2 Hz), 12.48 (1H, s); LRMS (ESI): m/z [M+H]⁺ 435.

Intermediates 5-bromo-2,3-dimethylisoindolin-1-one (5ae-ai) and 5-bromo-2,3,3-trimethylisoindolin-1-one (5af-ai) were prepared in accordance with the general procedure 10 (Scheme 10) using the method described below in detail.

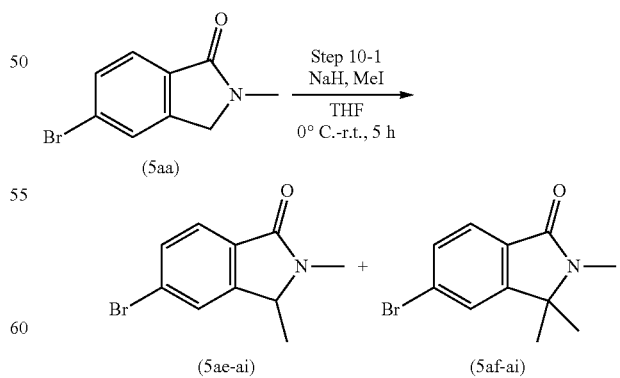

Step 10-1

To a solution of 5-bromo-2-methyl-isoindolin-1-one (5aa) (200.0 mg, 0.88 mmol) in anhydrous THF (3 mL) was added NaH, 60% dispersion in mineral oil (90.5 mg, 2.26 mmol) at 0° C., and the mixture was stirred at 0° C. for 20 min. After the addition of MeI (0.17 mL, 2.65 mmol), the mixture was further stirred at r.t. for 5 h. The mixture was quenched with H₂O and concentrated under reduced pressure. The residue was partitioned between EtOAc and H₂O. The product was extracted with EtOAc from the aq. layer (×2). The combined organic layers were dried over Na₂SO₄ and concentrated. The residue was purified by prep HPLC to obtain 5-bromo-2,3-dimethylisoindolin-1-one as a yellow oil (5ae-ai) (42.5 mg) and 5-bromo-2,3,3-trimethylisoindolin-1-one as a clear oil (5af-ai) (7.8 mg).

5-bromo-2,3-dimethylisoindolin-1-one (5ae-ai): ¹H NMR (400 MHz, DMSO-d₆) δ 1.42 (3H, d, J=6.7 Hz), 2.99 (3H, s), 4.57 (1H, q, J=6.7 Hz), 7.58-7.68 (2H, m), 7.93 (1H, s); LRMS (ESI): m/z [M+H]⁺ 240, 242

5-bromo-2,3,3-trimethylisoindolin-1-one (5af-ai): ¹H NMR (400 MHz, DMSO-d₆) δ 1.43 (6H, s), 2.91 (3H, s), 7.57-7.67 (2H, m), 8.04 (1H, d, J=1.6 Hz); LRMS (ESI): m/z [M+H]⁺ 254, 256.

Intermediate 7-iodo-2,6-dimethyl-[1,2,4]triazolo[4,3-a]pyridin-3(2H)-one (5aj-ai) was prepared in accordance with the general procedure 11 (Scheme 11) using the method described below in detail.

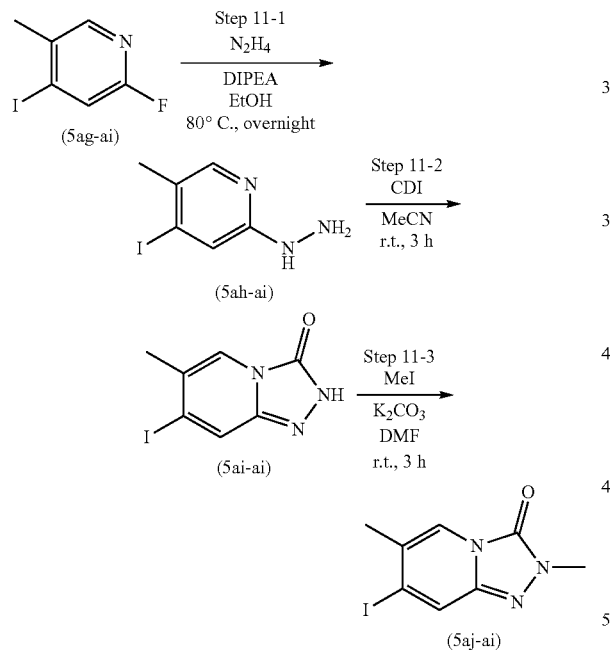

Step 11-1

To a solution of 2-fluoro-4-iodo-5-methyl-pyridine (5ag-ai) (500 mg, 2.11 mmol) in EtOH (7 mL) was added anhydrous hydrazine (1 mL, 31.86 mmol) and the mixture was heated at 50° C. overnight. To the reaction mixture, DIPEA (0.55 mL, 3.16 mmol) was added, and the resulting mixture was stirred at 70° C. overnight (22% conversion was observed by LCMS). Additional anhydrous hydrazine (2 mL) was added and the mixture was stirred at 80° C. overnight. After cooling to r.t., H₂O (~5 mL) was added, and the mixture was stirred for 10 min. The formed precipitate was collected by filtration, washed with H₂O, and dried under vacuum to give the expected product as a white solid (352 mg); LRMS (ESI): m/z [M+H]⁺ 250.

Step 11-2

To a suspension of (4-iodo-5-methyl-2-pyridyl)hydrazine (5ah-ai) (352 mg, 1.41 mmol) in CH₃CN (6 mL) was added CDI (275 mg, 1.7 mmol). The mixture was stirred at r.t. for 3 h. The formed precipitate was collected by filtration, washed with CH₃CN, and dried under house vacuum overnight to give the expected product as a pale yellow solid (299 mg); LRMS (ESI): m/z [M+H]⁺ 276.

Step 11-3

To a solution of 7-iodo-6-methyl-[1,2,4]triazolo[4,3-a]pyridin-3-ol (5ai-ai) (100 mg, 0.36 mmol) in DMF (2 mL) was added K₂CO₃ (100 mg, 0.73 mmol) and MeI (0.05 mL, 0.73 mmol). After stirring at r.t. for 3 h, the mixture was partitioned between EtOAc and H₂O. The product was extracted with EtOAc from the aq. layer (×2). The combined organic layers were dried over Na₂SO₄ and concentrated. The residue was purified by silica gel column chromatography (0-50% EtOAc/Hexane) to give the expected product as an off-white solid (87.6 mg); LRMS (ESI): m/z [M+H]⁺ 290.

Intermediate 7-iodo-2,8-dimethyl-[1,2,4]triazolo[4,3-a]pyridin-3 (2H)-one (5aj-aii) was synthesized from 2-fluoro-4-iodo-3-methylpyridine in accordance with the methods described in the procedure 11 for the synthesis of 7-iodo-2,6-dimethyl-[1,2,4]triazolo[4,3-a]pyridin-3 (2H)-one (5aj-ai).

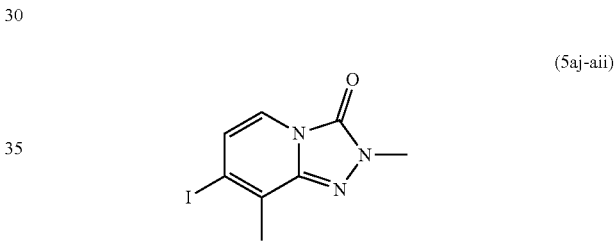

7-(6-(4,4-difluoropiperidine-1-carbonyl)naphthalen-1-yl)-2-methyl-5,6,7,8-tetrahydro-[1,2,4]triazolo[4,3-a]pyrazin-3(2H)-one was prepared in accordance with the general procedure 12 (Scheme 12) using the method described below in detail.

Synthesis of 7-(6-(4,4-difluoropiperidine-1-carbonyl)naphthalen-1-yl)-2-methyl-5,6,7,8-tetrahydro-[1,2,4]triazolo[4,3-a]pyrazin-3 (2H)-one

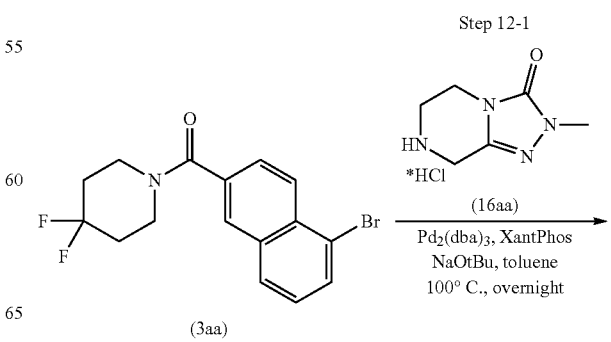

-continued

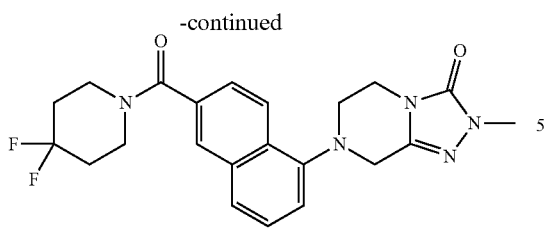

A reaction vessel containing a mixture of (5-bromo-2-naphthyl)-(4,4-difluoro-1-piperidyl)methanone (3aa) (35.0 mg, 0.099 mmol), Pd$_2$(dba)$_3$ (4.5 mg, 0.005 mmol) and XantPhos (5.7 mg, 0.010 mmol) was degassed and charged with nitrogen three times. After the addition of toluene (1 mL), the reaction mixture was degassed, backfilled with nitrogen, and stirred at r.t. for 15 min. To this, 2-methyl-5,6,7,8-tetrahydro-[1,2,4]triazolo[4,3-a]pyrazin-3-one HCl (16aa) (22.6 mg, 0.118 mmol) and NaOtBu (19.0 mg, 0.198 mmol) were added, and the mixture was then heated at 100° C. overnight. After cooling to r.t., the mixture was filtered through celite, and the filtrate was concentrated. The residue was purified by prep HPLC (CH$_3$CN/0.1% TFA-H$_2$O/0.1% TFA) to give the expected product as a white solid (20.0 mg).

$^1$H NMR (400 MHz, CD$_3$OD) δ 2.08 (4H, br s), 3.46 (3H, s), 3.52-3.72 (4H, m), 3.81-4.02 (4H, m), 4.24 (2H, s), 7.35 (1H, d, J=7.5 Hz), 7.54 (1H, dd, J=8.2, 7.5 Hz), 7.59 (1H, dd, J=8.7, 1.7 Hz), 7.76 (1H, d, J=8.2 Hz), 8.01 (1H, d, J=1.7 Hz), 8.30 (1H, d, J=8.7 Hz); LRMS (ESI): m/z [M+H]$^+$ 428, [M+Na]$^+$ 450.

The following compounds were synthesized using conditions analogous to 7-(6-(4,4-difluoropiperidine-1-carbonyl)naphthalen-1-yl)-2-methyl-5,6,7,8-tetrahydro-[1,2,4]triazolo[4,3-a]pyrazin-3(2H)-one in accordance with the general procedure 12.

2-methyl-7-(6-(piperidine-1-carbonyl)naphthalen-1-yl)-5,6,7,8-tetrahydro-[1,2,4]triazolo[4,3-a]pyrazin-3 (2H)-one

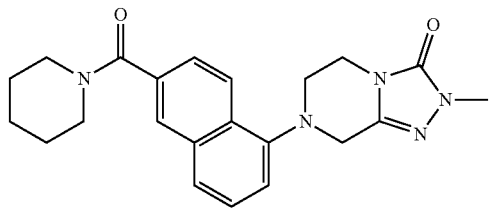 [SMILES: Cn1nc2n(c1=O)CCN(c1cccc3cc(C(=O)N4CCCCC4)ccc13)C2]

$^1$H NMR (400 MHz, CD$_3$OD) δ 1.50-1.80 (6H, m), 3.39-3.50 (5H, m), 3.56 (2H, br s), 3.76 (2H, br s), 3.86 (2H, t, J=5.6 Hz), 4.24 (2H, s), 7.33 (1H, dd, J=7.5, 1.0 Hz), 7.50-7.55 (2H, m), 7.74 (1H, d, J=8.5 Hz), 7.93 (1H, d, J=1.7 Hz), 8.28 (1H, d, J=8.7 Hz); LRMS (ESI): m/z [M+H]$^+$ 392.

(5-(7,8-dihydro-1,6-naphthyridin-6 (5H)-yl)naphthalen-2-yl) (piperidin-1-yl)methanone

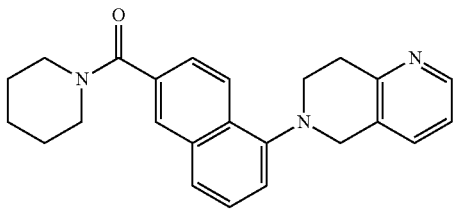 [SMILES: O=C(c1ccc2c(N3CCc4ncccc4C3)cccc2c1)N1CCCCC1]

$^1$H NMR (400 MHz, CD$_3$OD) δ 1.58 (2H, br s), 1.74 (4H, br s), 3.38-3.56 (4H, m), 3.62 (2H, br s), 3.77 (2H, br s), 4.52 (2H, s), 7.40 (1H, d, J=7.9 Hz), 7.51 (1H, dd, J=8.7, 1.6 Hz), 7.56 (1H, t, J=7.9 Hz), 7.75 (1H, d, J=7.9 Hz), 7.90 (1H, dd, J=7.8, 5.8 Hz), 7.95 (1H, d, J=1.6 Hz), 8.28 (1H, d, J=8.7 Hz), 8.41 (1H, d, J=7.8 Hz), 8.70 (1H, d, J=5.8 Hz); LRMS (ESI): m/z [M+H]$^+$ 372.

2-(2,2-difluoroethyl)-7-(6-(piperidine-1-carbonyl) naphthalen-1-yl)-5,6,7,8-tetrahydro-[1,2,4]triazolo[4,3-a]pyrazin-3 (2H)-one

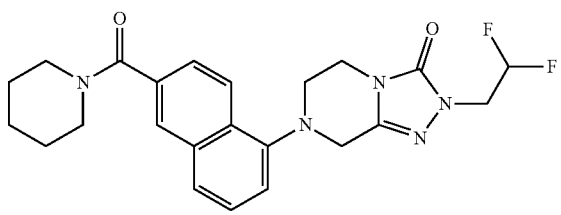 [SMILES: O=C(c1ccc2c(N3CCn4c(nn(CC(F)F)c4=O)C3)cccc2c1)N1CCCCC1]

$^1$H NMR (400 MHz, CDCl$_3$) δ 1.61-1.73 (6H, m), 3.52-3.61 (6H, m), 3.91 (2H, t, J=5.6 Hz), 4.17-4.25 (4H, m), 6.12 (1H, tt, J=55.5, 4.3 Hz), 7.19 (1H, dd, J=7.4, 1.0 Hz), 7.48-7.50 (1H, m), 7.56 (1H, dd, J=8.6, 1.7 Hz), 7.71 (1H, d, J=8.2 Hz), 7.94 (1H, d, J=1.6 Hz), 8.20 (1H, d, J=8.7 Hz); LRMS (ESI): m/z [M+H]$^+$ 442.

(R)-2-methyl-7-(6-(3-methylpiperidine-1-carbonyl) naphthalen-1-yl)-5,6,7,8-tetrahydro-[1,2,4]triazolo[4,3-a]pyrazin-3 (2H)-one $^1$H NMR (400 MHz, CDCl$_3$) δ 0.62-1.08 (3H, m), 1.10-1.27 (1H, m), 1.42-1.94 (4H, m), 2.35-2.78 (1H, m), 2.79-3.07 (1H, m), 3.50-3.75 (6H, m), 3.86 (2H, t, J=5.5 Hz), 4.20 (2H, s), 4.59 (1H, br s), 7.17 (1H, d, J=7.4 Hz), 7.47 (1H, dd, J=8.2, 7.4 Hz), 7.52 (1H, dd, J=8.7, 1.3 Hz), 7.68 (1H, d, J=8.2 Hz), 7.90 (1H, d, J=1.3 Hz), 8.18 (1H, d, J=8.7 Hz); LRMS (ESI): m/z [M+H]+ 406, [M+Na]$^+$ 428.

193

(R)-(5-(7,8-dihydro-1,6-naphthyridin-6 (5H)-yl) naphthalen-2-yl) (3-methylpiperidin-1-yl)methanone

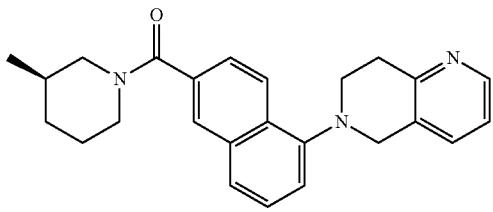 [SMILES: C[C@@H]1CCCN(C(=O)c2ccc3c(N4CCc5ncccc5C4)cccc3c2)C1]

¹H NMR (400 MHz, CDCl₃) δ 0.62-1.08 (3H, m), 1.10-1.27 (1H, m), 1.36-1.93 (4H, m), 2.39-2.76 (1H, m), 2.77-3.04 (1H, m), 3.34 (2H, br s), 3.44-3.82 (3H, m), 4.32 (2H, s), 4.59 (1H, br s), 7.15-7.25 (2H, m), 7.40-7.51 (3H, m), 7.62 (1H, d, J=8.2 Hz), 7.89 (1H, d, J=1.4 Hz), 8.24 (1H, d, J=8.7 Hz), 8.52 (1H, d, J=4.6 Hz); LRMS (ESI): m/z [M+H]⁺ 386.

(R)-6-(6-(3-methylpiperidine-1-carbonyl)naphthalen-1-yl)-5,6,7,8-tetrahydro-2,6-naphthyridin-1 (2H)-one

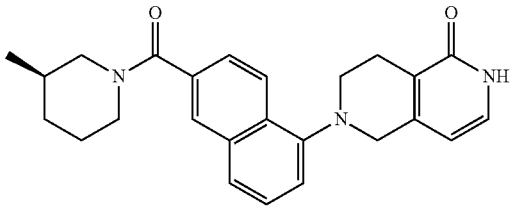 [SMILES: C[C@@H]1CCCN(C(=O)c2ccc3c(N4CCc5c(cc[nH]c5=O)C4)cccc3c2)C1]

¹H NMR (400 MHz, CDCl₃) δ 0.63-1.09 (3H, m), 1.10-1.28 (1H, m), 1.40-1.91 (4H, m), 2.39-2.77 (1H, m), 2.80-3.06 (3H, m), 3.44 (2H, br s), 3.57-3.83 (1H, m), 4.13 (2H, s), 4.61 (1H, br s), 6.08 (1H, d, J=6.4 Hz), 7.19 (1H, d, J=7.3 Hz), 7.25 (1H, d, J=6.4 Hz), 7.44-7.52 (2H, m), 7.61 (1H, d, J=8.2 Hz), 7.88 (1H, d, J=1.5 Hz), 8.23 (1H, d, J=8.6 Hz), 11.70 (NH, br s); LRMS (ESI): m/z [M+H]⁺ 402.

(S)-(5-(7,8-dihydro-1,6-naphthyridin-6 (5H)-yl) naphthalen-2-yl) (3-methylpiperidin-1-yl)methanone

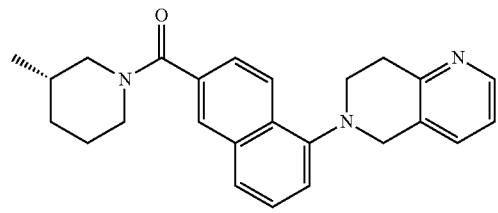 [SMILES: C[C@H]1CCCN(C(=O)c2ccc3c(N4CCc5ncccc5C4)cccc3c2)C1]

¹H NMR (400 MHz, CDCl₃) δ 0.61-1.07 (3H, m), 1.11-1.28 (1H, m), 1.40-1.93 (4H, m), 2.41-2.77 (1H, m), 2.78-3.05 (1H, m), 3.30 (2H, br s), 3.47-3.82 (3H, m), 4.31 (2H, s), 4.60 (1H, br s), 7.15 (1H, dd, J=7.7, 4.4 Hz), 7.22 (1H, d, J=7.4 Hz), 7.40-7.51 (3H, m), 7.62 (1H, d, J=8.2 Hz), 7.89 (1H, d, J=1.4 Hz), 8.25 (1H, d, J=8.7 Hz), 8.50 (1H, d, J=4.4 Hz); LRMS (ESI): m/z [M+H]⁺ 386.

194

(S)-6-(6-(3-methylpiperidine-1-carbonyl)naphthalen-1-yl)-5,6,7,8-tetrahydro-2,6-naphthyridin-1 (2H)-one

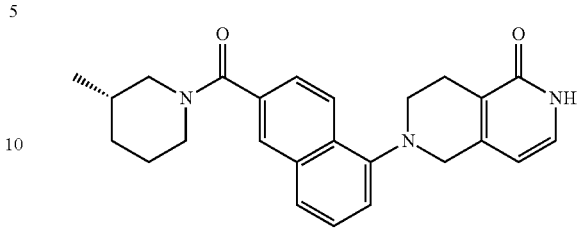

¹H NMR (400 MHz, CDCl₃) δ 0.67-1.08 (3H, m), 1.11-1.28 (1H, m), 1.35-1.95 (4H, m), 2.43-2.78 (1H, m), 2.80-3.05 (3H, m), 3.32-3.58 (2H, m), 3.59-3.82 (1H, m), 4.13 (2H, s), 4.60 (1H, br s), 6.12 (1H, d, J=6.8 Hz), 7.19 (1H, d, J=7.4 Hz), 7.24 (1H, d, J=6.8 Hz), 7.47 (1H, dd, J=8.4, 7.4 Hz), 7.49 (1H, dd, J=8.6, 1.6 Hz), 7.62 (1H, d, J=8.4 Hz), 7.89 (1H, d, J=1.6 Hz), 8.23 (1H, d, J=8.6 Hz), 10.80 (NH, br s); LRMS (ESI): m/z [M+H]⁺ 402.

(S)-2-methyl-7-(6-(3-methylpiperidine-1-carbonyl) naphthalen-1-yl)-5,6,7,8-tetrahydro-[1,2,4]triazolo[4,3-a]pyrazin-3 (2H)-one

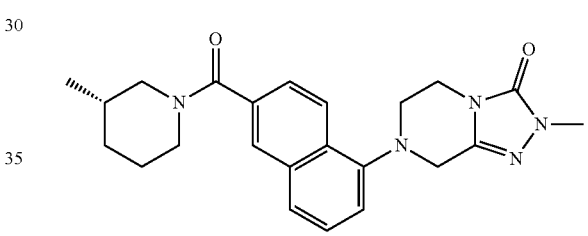

¹H NMR (400 MHz, CDCl₃) δ 0.68-1.07 (3H, m), 1.12-1.27 (1H, m), 1.34-1.94 (4H, m), 2.38-2.76 (1H, m), 2.77-3.07 (1H, m), 3.41-3.76 (6H, m), 3.86 (2H, t, J=5.5 Hz), 4.21 (2H, s), 4.59 (1H, br s), 7.17 (1H, d, J=7.4 Hz), 7.47 (1H, dd, J=8.2, 7.4 Hz), 7.52 (1H, dd, J=8.7, 1.5 Hz), 7.68 (1H, d, J=8.2 Hz), 7.91 (1H, d, J=1.5 Hz), 8.18 (1H, d, J=8.7 Hz); LRMS (ESI): m/z [M+H]+ 406, [M+Na]⁺ 428.

(S)-2-(2,2-difluoroethyl)-7-(6-(3-methylpiperidine-1-carbonyl)naphthalen-1-yl)-5,6,7,8-tetrahydro-[1,2,4]triazolo[4,3-a]pyrazin-3 (2H)-one ¹H NMR (400 MHz, CDCl₃) δ 0.69-1.10 (3H, m), 1.12-1.29 (1H, m), 1.40-1.96 (4H, m), 2.40-2.78 (1H, m), 2.79-3.07 (1H, m), 3.41-3.77 (3H, m), 3.88 (2H, t, J=5.5 Hz), 4.13-4.35 (4H, m), 4.59 (1H, br s), 6.10 (1H, tt, J=55.4, 4.5 Hz), 7.17 (1H, d, J=7.3 Hz), 7.48 (1H, dd, J=8.2, 7.3 Hz), 7.53 (1H, dd, J=8.7, 1.6 Hz), 7.69 (1H, d, J=8.2 Hz), 7.91 (1H, d, J=1.6 Hz), 8.18 (1H, d, J=8.7 Hz); LRMS (ESI): m/z [M+H]+ 456, [M+Na]+ 478.

7-(6-(5-azaspiro[2.5]octane-5-carbonyl)naphthalen-1-yl)-2-methyl-5,6,7,8-tetrahydro-[1,2,4]triazolo[4,3-a]pyrazin-3 (2H)-one

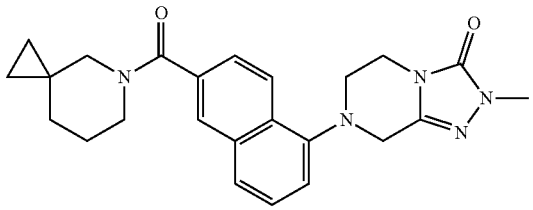 [SMILES: Cn1nc2n(c1=O)CCN(c1cccc3cc(C(=O)N4CCCC5(CC5)C4)ccc13)C2]

$^1$H NMR (400 MHz, CDCl$_3$) δ 0.03-0.75 (4H, m), 1.47-1.72 (3H, m), 1.73-1.88 (1H, m), 3.16 (1H, br s), 3.34-3.66 (7H, m), 3.75-3.90 (3H, m), 4.20 (2H, s), 7.17 (1H, dd, J=7.4, 0.8 Hz), 7.42-7.58 (2H, m), 7.67 (1H, d, J=6.0 Hz), 7.85-7.97 (1H, m), 8.17 (1H, d, J=7.9 Hz); LRMS (ESI): m/z [M+H]+ 418, [M+Na]+ 440.

(5-(7,8-dihydro-1,6-naphthyridin-6 (5H)-yl)naphthalen-2-yl) (5-azaspiro[2.5]octan-5-yl)methanone

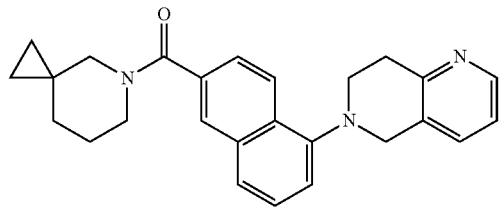 [SMILES: O=C(c1ccc2c(N3CCc4ncccc4C3)cccc2c1)N1CCCC2(CC2)C1]

$^1$H NMR (400 MHz, CDCl$_3$) δ 0.03-0.76 (4H, m), 1.45-1.88 (4H, m), 3.17 (1H, br s), 3.30 (2H, br s), 3.39-3.66 (4H, m), 3.82 (1H, br s), 4.31 (2H, s), 7.15 (1H, dd, J=7.6, 4.8 Hz), 7.22 (1H, d, J=7.4 Hz), 7.37-7.55 (3H, m), 7.56-7.66 (1H, m), 7.82-7.94 (1H, m), 8.24 (1H, d, J=8.0 Hz), 8.50 (1H, d, J=4.8 Hz); LRMS (ESI): m/z [M+H]+ 398.

(S)-2-methyl-7-(6-(3-(trifluoromethyl)piperidine-1-carbonyl)naphthalen-1-yl)-5,6,7,8-tetrahydro-[1,2,4]triazolo[4,3-a]pyrazin-3 (2H)-one

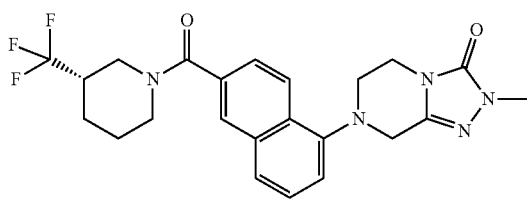 [SMILES: Cn1nc2n(c1=O)CCN(c1cccc3cc(C(=O)N4CCC[C@H](C(F)(F)F)C4)ccc13)C2]

$^1$H NMR (400 MHz, CD$_3$OD) δ 1.52-1.87 (3H, m), 2.06-2.16 (1H, m), 2.54 (1H, br s), 2.99-3.34 (2H, m), 3.46 (3H, s), 3.56 (2H, br s), 3.65-4.00 (3H, m), 4.24 (2H, s), 4.44-4.80 (1H, m), 7.34 (1H, dd, J=7.5, 0.9 Hz), 7.52-7.58 (2H, m), 7.75 (1H, d, J=8.4 Hz), 7.98 (1H, d, J=1.4 Hz), 8.30 (1H, d, J=8.7 Hz); LRMS (ESI): m/z [M+H]+ 460, [M+Na]+ 482.

(S)-2-(2,2-difluoroethyl)-7-(6-(3-(trifluoromethyl)piperidine-1-carbonyl)naphthalen-1-yl)-5,6,7,8-tetrahydro-[1,2,4]triazolo[4,3-a]pyrazin-3(2H)-one

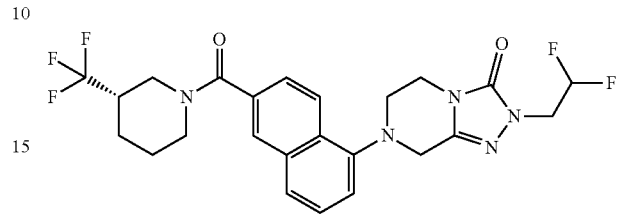

$^1$H NMR (400 MHz, CD$_3$OD) δ 1.44-1.95 (3H, m), 2.06-2.19 (1H, m), 2.48-2.62 (1H, m), 2.99-3.34 (2H, m), 3.58 (2H, br s), 3.68-3.82 (1H, m), 3.89 (2H, t, J=5.1 Hz), 4.14-4.24 (1H, m), 4.26 (2H, br s), 4.30 (1H, br s), 4.43-4.83 (1H, m), 6.01-6.34 (1H, m), 7.32-7.39 (1H, m), 7.50-7.61 (2H, m), 7.76 (1H, d, J=8.3 Hz), 7.98 (1H, s), 8.31 (1H, d, J=8.7 Hz); LRMS (ESI): m/z [M+H]+ 510, [M+Na]+ 532.

(S)-(5-(7,8-dihydro-1,6-naphthyridin-6 (5H)-yl)naphthalen-2-yl) (3-(trifluoromethyl)piperidin-1-yl)methanone

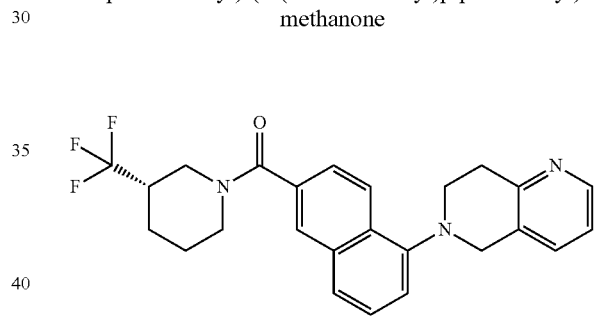

$^1$H NMR (400 MHz, CD$_3$OD) δ 1.50-1.94 (3H, m), 2.06-2.17 (1H, m), 2.47-2.63 (1H, m), 2.94-3.32 (4H, m), 3.54 (2H, br s), 3.69-3.83 (1H, m), 4.35 (2H, s), 4.45-4.84 (1H, m), 7.29 (1H, dd, J=7.7, 4.9 Hz), 7.36 (1H, dd, J=7.4, 0.8 Hz), 7.48-7.57 (2H, m), 7.65 (1H, dd, J=7.7, 1.6 Hz), 7.70 (1H, d, J=8.3 Hz), 7.96 (1H, d, J=1.6 Hz), 8.31 (1H, d, J=8.6 Hz), 8.40 (1H, dd, J=4.9, 1.6 Hz); LRMS (ESI): m/z [M+H]+ 440.

7-(6-(2-azabicyclo[4.1.0]heptane-2-carbonyl)naphthalen-1-yl)-2-methyl-5,6,7,8-tetrahydro-[1,2,4]triazolo[4,3-a]pyrazin-3 (2H)-one

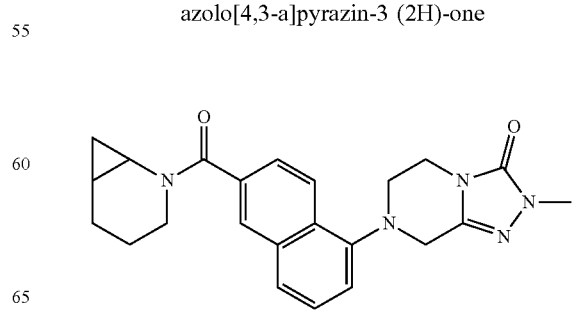

¹H NMR (400 MHz, CDCl₃) δ 0.53-0.60 (1H, m), 0.65-0.73 (1H, m), 1.19-2.05 (6H, m), 2.63-2.78 (2H, m), 3.44-3.64 (5H, m), 3.83-3.88 (2H, m), 4.14-4.34 (2H, m), 7.17 (1H, d, J=7.4 Hz), 7.46 (1H, dd, J=8.4, 7.4 Hz), 7.69 (1H, d, J=8.4 Hz), 7.73 (1H, dd, J=8.7, 1.5 Hz), 8.12 (1H, d, J=1.5 Hz), 8.17 (1H, d, J=8.7 Hz); LRMS (ESI): m/z [M+H]⁺ 404, [M+Na]⁺ 426.

(2-azabicyclo[4.1.0]heptan-2-yl) (5-(7,8-dihydro-1,6-naphthyridin-6 (5H)-yl)naphthalen-2-yl)methanone

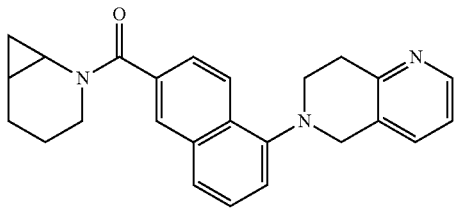 [SMILES: O=C(c1ccc2c(N3CCc4ncccc4C3)cccc2c1)N1CCCC2CC21]

¹H NMR (400 MHz, CDCl₃) δ 0.54-0.60 (1H, m), 0.65-0.73 (1H, m), 1.07-2.05 (6H, m), 2.64-2.78 (1H, m), 3.20-3.39 (2H, m), 3.46-3.64 (3H, m), 4.31 (2H, s), 7.15 (1H, dd, J=7.4, 4.8 Hz), 7.22 (1H, d, J=7.4 Hz), 7.43 (1H, dd, J=7.4, 1.5 Hz), 7.47 (1H, dd, J=8.4, 7.4 Hz), 7.62 (1H, d, J=8.4 Hz), 7.70 (1H, dd, J=8.7, 1.5 Hz), 8.11 (1H, d, J=1.5 Hz), 8.24 (1H, d, J=8.7 Hz), 8.52 (1H, dd, J=4.8, 1.5 Hz); LRMS (ESI): m/z [M+H]⁺ 384.

7-(6-(2-azabicyclo[4.1.0]heptane-2-carbonyl)naphthalen-1-yl)-2-(2,2-difluoroethyl)-5,6,7,8-tetrahydro-[1,2,4]triazolo[4,3-a]pyrazin-3 (2H)-one

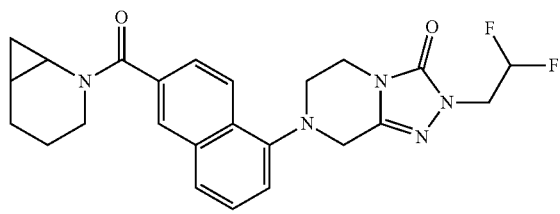 [SMILES: O=C(c1ccc2c(N3CCn4c(nn(CC(F)F)c4=O)C3)cccc2c1)N1CCCC2CC21]

¹H NMR (400 MHz, CDCl₃) δ 0.53-0.60 (1H, m), 0.65-0.73 (1H, m), 0.82-0.93 (1H, m), 1.08-2.06 (5H, m), 2.63-2.74 (1H, m), 2.92-3.01 (1H, m), 3.40-3.65 (3H, m), 3.85-3.93 (2H, m), 4.19 (2H, td, J=13.5, 4.3 Hz), 4.27-4.34 (1H, m), 6.09 (1H, tt, J=55.2, 4.2 Hz), 7.17 (1H, d, J=7.4 Hz), 7.47 (1H, dd, J=8.5, 7.4 Hz), 7.70 (1H, d, J=8.5 Hz), 7.75 (1H, dd, J=8.7, 1.5 Hz), 8.13 (1H, d, J=1.5 Hz), 8.17 (1H, d, J=8.7 Hz); LRMS (ESI): m/z [M+H]⁺ 454, [M+Na]⁺ 476.

(R)-(5-(7,8-dihydro-1,6-naphthyridin-6 (5H)-yl)naphthalen-2-yl) (3-methylpyrrolidin-1-yl)methanone

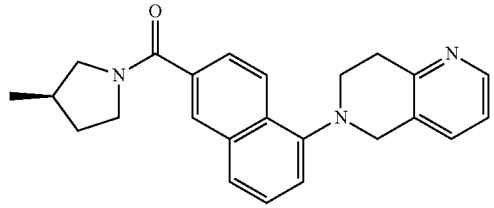 [SMILES: C[C@@H]1CCN(C(=O)c2ccc3c(N4CCc5ncccc5C4)cccc3c2)C1]

¹H NMR (400 MHz, CD₃OD) δ 1.00-1.19 (3H, m), 1.50-1.73 (1H, m), 1.99-2.49 (2H, m), 3.05-3.21 (2H, m), 3.43-3.67 (4H, m), 3.72-3.90 (1H, m), 4.34 (2H, s), 4.63 (1H, br s), 7.28 (1H, dd, J=7.5, 4.9 Hz), 7.34 (1H, d, J=7.5 Hz), 7.48-7.56 (1H, m), 7.59-7.64 (1H, m), 7.65 (1H, d, J=7.5 Hz), 7.70 (1H, d, J=8.0 Hz), 8.04 (1H, s), 8.27 (1H, d, J=8.7 Hz), 8.39 (1H, dd, J=4.9, 1.5 Hz); LRMS (ESI): m/z [M+H]⁺ 372.

(R)-6-(6-(3-fluoropiperidine-1-carbonyl)naphthalen-1-yl)-5,6,7,8-tetrahydro-2,6-naphthyridin-1 (2H)-one

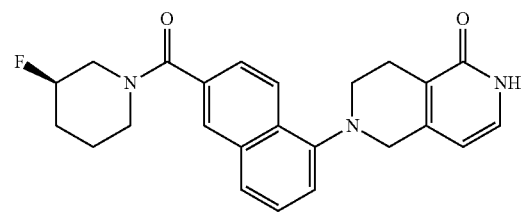

¹H NMR (400 MHz, CDCl₃) δ 1.51-2.13 (5H, m), 2.85 (2H, br s), 3.13-3.72 (3H, m), 3.84-3.95 (1H, m), 4.19 (2H, s), 4.26-4.52 (2H, m), 6.31 (1H, d, J=6.7 Hz), 7.30-7.35 (2H, m), 7.49-7.57 (2H, m), 7.69 (1H, d, J=7.6 Hz), 7.95 (1H, s), 8.29 (1H, d, J=8.7 Hz); LRMS (ESI): m/z [M+H]⁺ 406.

6-(6-(piperidine-1-carbonyl)naphthalen-1-yl)-5,6,7,8-tetrahydro-2,6-naphthyridin-1(2H)-one was prepared in accordance with the general procedure 12 (Scheme 12) using the method described below in detail.

Synthesis of 6-(6-(piperidine-1-carbonyl)naphthalen-1-yl)-5,6,7,8-tetrahydro-2,6-naphthyridin-1 (2H)-one

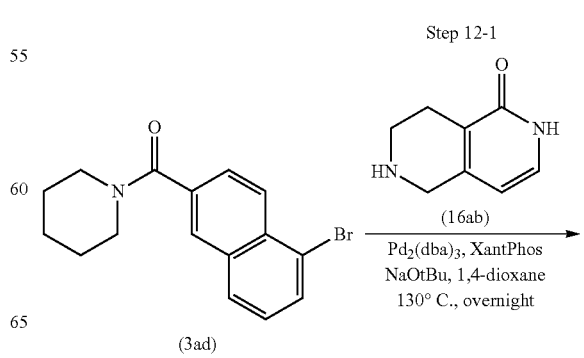

-continued

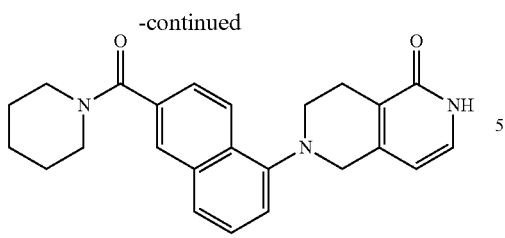

A reaction vessel containing a mixture of (5-bromo-2-naphthyl)-(1-piperidyl)methanone (3ad) (50.0 mg, 0.157 mmol), Pd$_2$(dba)$_3$ (14.4 mg, 0.016 mmol) and XantPhos (18.2 mg, 0.031 mmol) was degassed and charged with nitrogen three times. After the addition of 1,4-dioxane (1 mL), the reaction mixture was degassed, backfilled with nitrogen, and stirred at r.t. for 15 min. To this, 5,6,7,8-tetrahydro-2H-2,6-naphthyridin-1-one (16ab) (28.3 mg, 0.189 mmol) and NaOtBu (45.3 mg, 0.471 mmol) were added, and the mixture was heated at 130° C. overnight. After cooling to r.t., the mixture was filtered through celite, and the filtrate was concentrated. The residue was purified by prep HPLC (CH$_3$CN/0.1% TFA-H$_2$O/0.1% TFA) to give the expected product as a white solid (9.4 mg).

$^1$H NMR (400 MHz, CDCl$_3$) δ 1.45-1.78 (6H, m), 2.92 (2H, br s), 3.41 (4H, br s), 3.77 (2H, br s), 4.13 (2H, s), 6.06 (1H, d, J=6.7 Hz), 7.19 (1H, d, J=7.4 Hz), 7.27 (1H, d, J=6.7 Hz), 7.47 (1H, dd, J=8.3, 7.4 Hz), 7.49 (1H, dd, J=8.7, 1.5 Hz), 7.61 (1H, d, J=8.3 Hz), 7.89 (1H, d, J=1.5 Hz), 8.23 (1H, d, J=8.7 Hz), 12.01 (NH, br s); LRMS (ESI): m/z [M+H]$^+$ 388.

The following compounds were synthesized using conditions analogous to 6-(6-(piperidine-1-carbonyl)naphthalen-1-yl)-5,6,7,8-tetrahydro-2,6-naphthyridin-1(2H)-one in accordance with the general procedure 12 (Scheme 12).

6-(6-(4,4-difluoropiperidine-1-carbonyl)naphthalen-1-yl)-5,6,7,8-tetrahydro-2,6-naphthyridin-1 (2H)-one

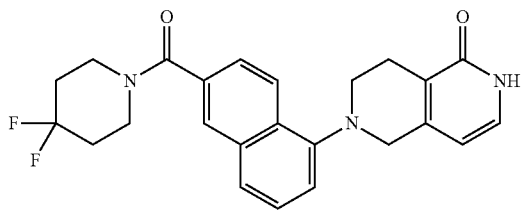 [SMILES: O=C(c1ccc2c(N3CCc4c(cc[nH]c4=O)C3)cccc2c1)N1CCC(F)(F)CC1]

$^1$H NMR (400 MHz, CDCl$_3$) δ 1.85-2.26 (4H, m), 2.94 (2H, br s), 3.29-4.04 (6H, m), 4.13 (2H, s), 6.08 (1H, d, J=6.8 Hz), 7.22 (1H, d, J=7.0 Hz), 7.25 (1H, d, J=6.8 Hz), 7.47-7.52 (2H, m), 7.65 (1H, d, J=8.2 Hz), 7.92 (1H, d, J=1.4 Hz), 8.26 (1H, d, J=8.7 Hz), 11.40 (NH, br s); LRMS (ESI): m/z [M+H]$^+$ 424.

2-methyl-6-(6-(piperidine-1-carbonyl)naphthalen-1-yl)-5,6,7,8-tetrahydro-2,6-naphthyridin-1 (2H)-one

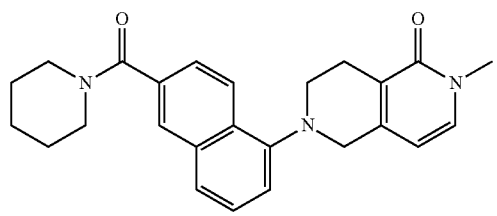 [SMILES: Cn1ccc2c(c1=O)CCN(c1cccc3cc(C(=O)N4CCCCC4)ccc13)C2]

$^1$H NMR (400 MHz, CDCl$_3$) δ 1.45-1.78 (6H, m), 2.91 (2H, br s), 3.40 (4H, br s), 3.58 (3H, s), 3.76 (2H, br s), 4.08 (2H, s), 5.98 (1H, d, J=6.9 Hz), 7.15-7.19 (2H, m), 7.42-7.50 (2H, m), 7.60 (1H, d, J=8.2 Hz), 7.88 (1H, d, J=1.5 Hz), 8.21 (1H, d, J=8.7 Hz); LRMS (ESI): m/z [M+H]$^+$ 402.

(5-(5-methoxy-3,4-dihydro-2,6-naphthyridin-2 (1H)-yl)naphthalen-2-yl) (piperidin-1-yl)methanone

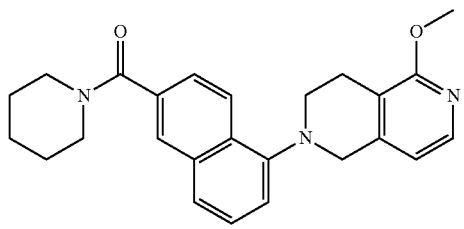 [SMILES: COc1nccc2c1CCN(c1cccc3cc(C(=O)N4CCCCC4)ccc13)C2]

$^1$H NMR (400 MHz, CDCl$_3$) δ 1.46-1.79 (6H, m), 2.94 (2H, br s), 3.28-3.55 (4H, m), 3.76 (2H, br s), 4.01 (3H, s), 4.23 (2H, s), 6.67 (1H, d, J=5.3 Hz), 7.18 (1H, d, J=6.8 Hz), 7.38-7.52 (2H, m), 7.60 (1H, d, J=8.2 Hz), 7.88 (1H, d, J=1.4 Hz), 7.98 (1H, d, J=5.3 Hz), 8.22 (1H, d, J=8.7 Hz); LRMS (ESI): m/z [M+H]$^+$ 402.

7-(6-(piperidine-1-carbonyl)naphthalen-1-yl)tetrahydroimidazo[1,5-a]pyrazine-1,3(2H,5H)-dione

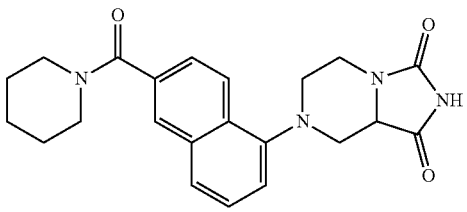 [SMILES: O=C1NC(=O)N2CCN(c3cccc4cc(C(=O)N5CCCCC5)ccc34)CC12]

$^1$H NMR (400 MHz, CD$_3$OD) δ 1.60 (2H, br s), 1.75 (4H, br s), 2.81-2.94 (2H, m), 3.42-3.53 (3H, m), 3.63 (1H, dd, J=11.7, 5.0 Hz), 3.79 (2H, br s), 4.18 (1H, dd, J=11.9, 3.9 Hz), 4.53 (1H, dd, J=11.0, 4.5 Hz), 7.29 (1H, dd, J=7.6, 1.0 Hz), 7.53 (1H, t, J=8.2 Hz), 7.56 (1H, dd, J=8.7, 1.8 Hz), 7.73 (1H, d, J=8.3 Hz), 7.94 (1H, d, J=1.5 Hz), 8.38 (1H, d, J=8.7 Hz); LRMS (ESI): m/z [M+H]$^+$ 393.

2-methyl-7-(6-(piperidine-1-carbonyl)naphthalen-1-yl)hexahydroimidazo[1,5-a]pyrazin-3(2H)-one

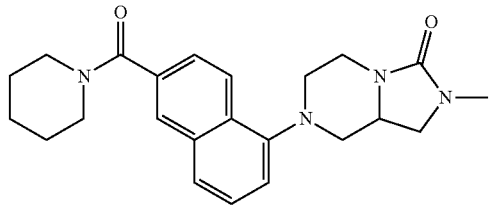 [SMILES: CN1CC2CN(c3cccc4cc(C(=O)N5CCCCC5)ccc34)CCN2C1=O]

¹H NMR (400 MHz, CD₃OD) δ 1.59 (2H, br s), 1.75 (4H, br s), 2.73-2.82 (2H, m), 2.84 (3H, s), 3.14 (1H, dd, J=9.3, 4.3 Hz), 3.22-3.29 (1H, m), 3.35-3.41 (2H, m), 3.45 (2H, br s), 3.57 (1H, t, J=9.2 Hz), 3.79 (2H, br s), 3.90-3.97 (1H, m), 4.08-4.16 (1H, m), 7.24 (1H, dd, J=7.5, 1.0 Hz), 7.49-7.54 (2H, m), 7.68 (1H, d, J=8.4 Hz), 7.91 (1H, d, J=1.6 Hz), 8.36 (1H, d, J=8.7 Hz); LRMS (ESI): m/z [M+H]⁺ 393.

(5-(1-methyl-1,4,6,7-tetrahydro-5H-imidazo[4,5-c]pyridin-5-yl)naphthalen-2-yl) (piperidin-1-yl)methanone was prepared in accordance with the general procedure 12 (Scheme 12) using the method described below in detail.

Synthesis of (5-(1-methyl-1,4,6,7-tetrahydro-5H-imidazo[4,5-c]pyridin-5-yl)naphthalen-2-yl) (piperidin-1-yl)methanone

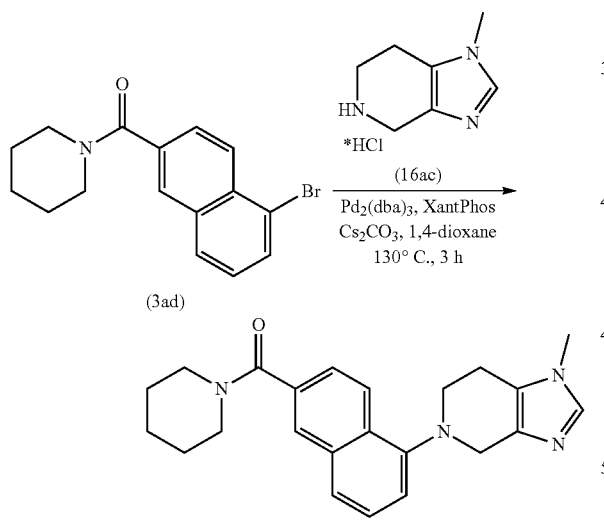

A reaction vessel containing a mixture of (5-bromo-2-naphthyl)-(1-piperidyl)methanone (3ad) (32.0 mg, 0.10 mmol), Pd₂(dba)₃ (18.4 mg, 0.02 mmol) and XantPhos (11.6 mg, 0.02 mmol) was degassed and charged with nitrogen three times. After the addition of 1,4-dioxane (1 mL), the reaction mixture was degassed, backfilled with nitrogen, and stirred at r.t. for 15 min. To this, 1-methyl-4,5,6,7-tetrahydroimidazo[4,5-c]pyridine HCl (16ac) (20.9 mg, 0.12 mmol) and Cs₂CO₃ (130.6 mg, 0.40 mmol) were added, and the mixture was then heated at 130° C. for 3 h. After cooling to r.t., the mixture was filtered through celite, and the filtrate was concentrated. The residue was purified by prep HPLC (CH₃CN/0.1% TFA-H₂O/0.1% TFA) to give the expected product as a white solid (7.3 mg).

¹H NMR (400 MHz, CD₃OD) δ 1.60 (2H, br s), 1.75 (4H, br s), 2.90 (2H, br s), 3.47-3.52 (4H, m) 3.69 (3H, s), 3.78 (2H, br s), 4.15 (2H, s), 7.32 (1H, dd, J=7.5, 0.9 Hz), 7.50 (1H, t, J=9.2 Hz), 7.50 (1H, d, J=8.4 Hz), 7.59 (1H, s), 7.67 (1H, d, J=8.3 Hz), 7.92 (1H, d, J=1.6 Hz), 8.31 (1H, d, J=8.7 Hz); LRMS (ESI): m/z [M+H]⁺ 375.

The following compounds were synthesized using conditions analogous to (5-(1-methyl-1,4,6,7-tetrahydro-5H-imidazo[4,5-c]pyridin-5-yl)naphthalen-2-yl) (piperidin-1-yl)methanone in accordance with the general procedure 12 (Scheme 12).

(5-(2-methyl-5,6-dihydro-[1,2,4]triazolo[1,5-a]pyrazin-7(8H)-yl)naphthalen-2-yl) (piperidin-1-yl)methanone

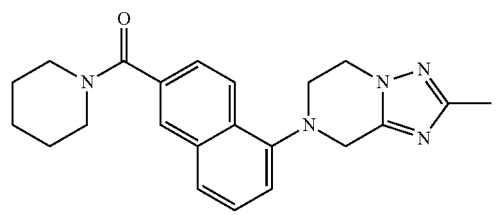 [SMILES: Cc1nc2n(n1)CCN(c1cccc3cc(C(=O)N4CCCCC4)ccc13)C2]

¹H NMR (400 MHz, CD₃OD) δ 1.59 (2H, br s), 1.75 (4H, br s), 2.40 (3H, s), 3.46 (2H, br s), 3.71 (2H, br s), 3.79 (2H, br s), 4.36 (2H, br s), 4.44 (2H, s), 7.36 (1H, dd, J=8.5, 0.9 Hz) 7.55 (1H, t, J=8.2 Hz), 7.55 (1H, dd, J=8.7, 1.7 Hz), 7.77 (1H, d, J=8.3 Hz), 7.96 (1H, d, J=1.7 Hz), 8.31 (1H, d, J=8.7 Hz); LRMS (ESI): m/z [M+H]⁺ 376.

(5-(2-methyl-6,7-dihydrooxazolo[4,5-c]pyridin-5(4H)-yl)naphthalen-2-yl) (piperidin-1-yl)methanone

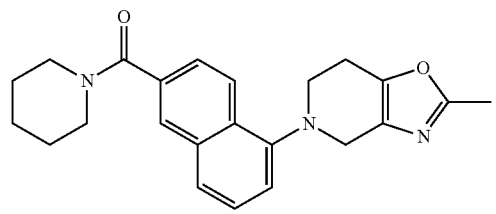 [SMILES: Cc1nc2c(o1)CCN(c1cccc3cc(C(=O)N4CCCCC4)ccc13)C2]

¹H NMR (400 MHz, CD₃OD) δ 1.59 (2H, br s), 1.75 (4H, br s), 2.50 (3H, s), 2.90 (2H, br s) 3.47 (2H, s), 3.50 (2H, br s), 3.79 (2H, br s) 4.10 (2H, s), 7.34 (1H, dd, J=7.6, 0.9 Hz) 7.50-7.54 (2H, m), 7.69 (1H, d, J=8.2 Hz), 7.92 (1H, d, J=1.7 Hz), 8.30 (1H, d, J=8.7 Hz); LRMS (ESI): m/z [M+H]⁺ 376.

(5-(2-methyl-7,8-dihydro-1,6-naphthyridin-6(5H)-yl)naphthalen-2-yl) (piperidin-1-yl)methanone

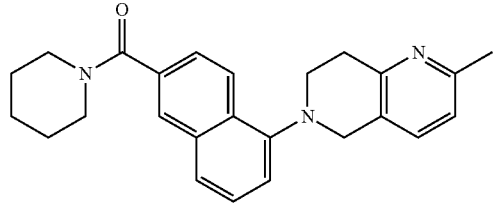 [SMILES: Cc1ccc2c(n1)CCN(c1cccc3cc(C(=O)N4CCCCC4)ccc13)C2]

¹H NMR (400 MHz, CD₃OD) δ 1.60 (2H, br s), 1.75 (4H, br s), 2.56 (3H, s), 3.24 (2H, br s), 3.47 (2H, br s), 3.54 (2H, br s), 3.79 (2H, br s), 4.32 (2H, s), 7.18 (1H, d, J=7.9 Hz) 7.35 (1H, dd, J=7.5, 0.9 Hz), 7.50-7.58 (3H, m), 7.70 (1H, d, J=8.3 Hz), 7.93 (1H, d, J=1.6 Hz), 8.30 (1H, d, J=8.7 Hz); LRMS (ESI): m/z [M+H]⁺ 386.

(5-(2-methyl-2,4,6,7-tetrahydro-5H-pyrazolo[4,3-c]pyridin-5-yl)naphthalen-2-yl) (piperidin-1-yl)methanone

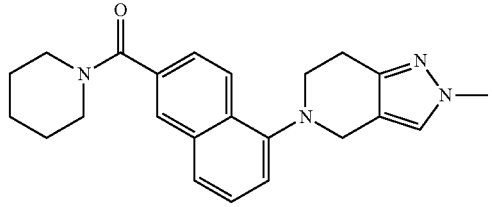 [SMILES: Cn1cc2c(n1)CCN(c1cccc3cc(C(=O)N4CCCCC4)ccc13)C2]

¹H NMR (400 MHz, CD₃OD) δ 1.61 (2H, br s), 1.75 (4H, br s), 2.98 (2H, br s), 3.42-3.53 (4H, br m) 3.79 (2H, br s), 3.89 (3H, s), 4.19 (2H, s), 7.32 (1H, dd, J=7.5, 0.9 Hz), 7.42 (1H, s), 7.50 (1H, dd, J=8.4, 1.7 Hz), 7.51 (1H, t, J=8.4 Hz), 7.66 (1H, d, J=8.3 Hz), 7.93 (1H, d, J=1.7 Hz), 8.31 (1H, d, J=8.7 Hz); LRMS (ESI): m/z [M+H]⁺ 375.

7-methyl-2-(6-(piperidine-1-carbonyl)naphthalen-1-yl)hexahydropyrrolo[1,2-a]pyrazin-6 (2H)-one

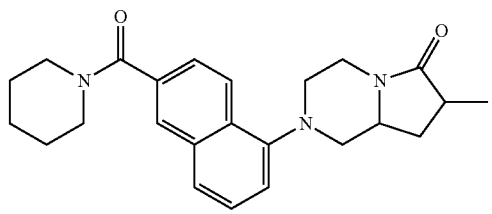 [SMILES: CC1CC2CN(c3cccc4cc(C(=O)N5CCCCC5)ccc34)CCN2C1=O]

¹H NMR (400 MHz, CD₃Cl₃) δ 1.09-1.15 (3H, m), 1.40-1.70 (6H, m), 1.75-1.95 (1H, m), 2.40-2.55 (1H, m), 2.6-2.75 (1H, m), 3.10-3.90 (9H, m), 3.92-4.01 (2H, m), 7.20 (1H, t, J=7.3 Hz), 7.47-7.53 (2H, m), 7.71 (1H, d, J=8.1 Hz), 7.93 (1H, s), 8.22 (1H, dd, J=8.6, 4.5 Hz); LRMS (ESI): m/z [M+H]⁺ 392.

2-(6-(piperidine-1-carbonyl)naphthalen-1-yl)hexahydropyrrolo[1,2-a]pyrazin-6 (2H)-one

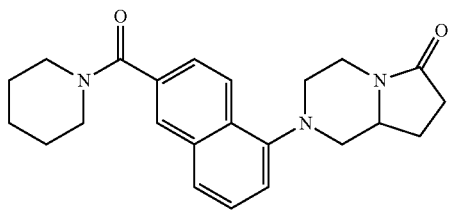 [SMILES: O=C(c1ccc2c(N3CCN4C(=O)CCC4C3)cccc2c1)N1CCCCC1]

¹H NMR (400 MHz, CD₃Cl₃) δ 1.40-1.70 (7H, m), 2.13-2.23 (1H, m), 2.23-2.40 (2H, m), 2.53 (1H, t, J=10.9 Hz), 2.65 (1H, td, J=11.9, 3.5 Hz), 3.15 (1H, td, J=11.9, 3.5 Hz), 3.25-3.45 (4H, m), 3.55-3.71 (2H, m), 3.90-4.01 (2H, m), 7.20 (1H, d, J=7.5 Hz), 7.50 (1H, t, J=7.7 Hz), 7.50 (1H, dd, J=8.6, 1.6 Hz), 7.71 (1H, d, J=8.1 Hz), 7.93 (1H, d, J=1.6 Hz). 8.22 (1H, d, J=8.7 Hz); LRMS (ESI): m/z [M+H]⁺ 378, [M+Na]⁺ 400.

2-methyl-8-(6-(piperidine-1-carbonyl)naphthalen-1-yl)-2,8-diazaspiro[4.5]decan-1-one

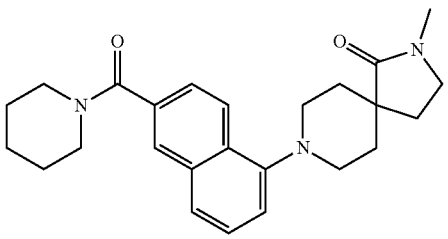 [SMILES: CN1CCC2(CCN(c3cccc4cc(C(=O)N5CCCCC5)ccc34)CC2)C1=O]

¹H NMR (400 MHz, CD₃Cl₃) δ 1.5-1.8 (8H, m), 2.09 (2H, t, J=7.0 Hz), 2.33 (2H, t, J=11.0 Hz), 2.88 (2H, t, J=11.0 Hz), 2.93 (3H, s), 3.35-3.50 (6H, m), 3.78 (2H, br s), 7.14 (1H, d, J=6.6 Hz), 7.44 (1H, t, J=8.1 Hz), 7.49 (1H, dd, J=8.7, 1.7 Hz), 7.57 (1H, t, J=8.3 Hz), 7.87 (1H, d, J=1.6 Hz), 8.27 (1H, d, J=8.7 Hz); LRMS (ESI): m/z [M+H]⁺ 406

7-(6-(4,4-difluoropiperidine-1-carbonyl)-4-fluoroisoquinolin-1-yl)-2-methyl-5,6,7,8-tetrahydro-[1,2,4]triazolo[4,3-a]pyrazin-3(2H)-one was prepared in accordance with the general procedure 13 (Scheme 13) using the method described below in detail.

Synthesis of 7-(6-(4,4-difluoropiperidine-1-carbonyl)-4-fluoroisoquinolin-1-yl)-2-methyl-5,6,7,8-tetrahydro-[1,2,4]triazolo[4,3-a]pyrazin-3(2H)-one

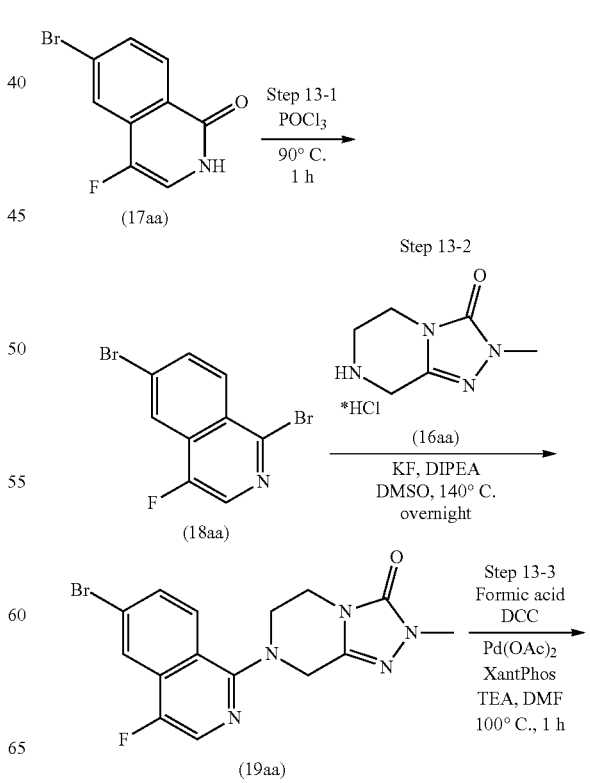

Step 13-4

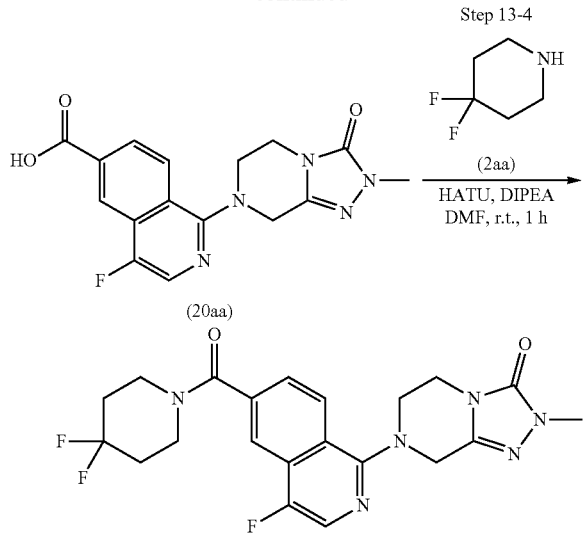

Step 13-1

A solution of 6-bromo-4-fluoro-2H-isoquinolin-1-one (17aa) (181 mg, 0.75 mmol) in phosphoryl chloride (3 mL, 32.19 mmol) was stirred and heated at 90° C. for 1 h. After cooling to r.t., the excess amount of phosphoryl chloride was evaporated in vacuo. To the residue, cold $H_2O$ was added, and the mixture was stirred at r.t. for 10 min to give a precipitate. The solid was filtered, washed with cold $H_2O$, and dried to give 6-bromo-1-chloro-4-fluoro-isoquinoline as a pale pink solid which was used in the next step without further purification (176 mg); LRMS (ESI): m/z [M+H]$^+$ 260, 262.

Step 13-2

A mixture of 6-bromo-1-chloro-4-fluoro-isoquinoline (18aa) (200 mg, 0.77 mmol), 2-methyl-5,6,7,8-tetrahydro-[1,2,4]triazolo[4,3-a]pyrazin-3-one HCl (16aa) (190 mg, 1.00 mmol), KF (400 mg, 6.91 mmol) and DIPEA (0.53 mL, 3.07 mmol) in DMSO (6 mL) was heated at 140° C. overnight. After cooling to r.t., the mixture was concentrated. The residue was purified by silica gel column chromatography (0-100% EtOAc/Hexane) to give 7-(6-bromo-4-fluoro-1-naphthyl)-2-methyl-6,8-dihydro-5H-[1,2,4]triazolo[4,3-a]pyrazin-3-one as a brown solid (33 mg); LRMS (ESI): m/z [M+H]$^+$ 378, 380.

Step 13-3

A reaction vessel containing Pd(OAc)$_2$ (1.2 mg, 0.005 mmol) and XantPhos (3.0 mg, 0.005 mmol) was degassed and charged with nitrogen three times. To this, a solution of 7-(6-bromo-8-fluoro-1-naphthyl)-2-methyl-6,8-dihydro-5H-[1,2,4]triazolo[4,3-a]pyrazin-3-one (19aa) (20.0 mg, 0.053 mmol) and formic acid (14 μL, 0.370 mmol) in DMF (1 mL) was added. Subsequently, DCC (6.5 mg, 0.032 mmol) and TEA (22 μL, 0.158 mmol) were added. The reaction vessel was immediately sealed, and the mixture was stirred and heated at 100° C. for 1 h. After cooling to r.t., the mixture was filtered through celite. The filtrate was concentrated, and the residue was purified by silica gel column chromatography (0-100% EtOAc/Hexane, then 0-10% MeOH in DCM) to give 4-fluoro-1-(2-methyl-3-oxo-6,8-dihydro-5H-[1,2,4]triazolo[4,3-a]pyrazin-7-yl)isoquinoline-6-carboxylic acid as a yellow solid (9.3 mg); LRMS (ESI): m/z [M+H]$^+$ 344.

Step 13-4

A mixture of 4-fluoro-1-(2-methyl-3-oxo-6,8-dihydro-5H-[1,2,4]triazolo[4,3-a]pyrazin-7-yl)isoquinoline-6-carboxylic acid (20aa) (4.6 mg, 0.013 mmol), 4,4-difluoropiperidine (2aa) (2 μL, 0.017 mmol), HATU (8.1 mg, 0.021 mmol) and DIPEA (7 μL, 0.040 mmol) in DMF (0.5 mL) was stirred at r.t. for 1 h. The mixture was purified by prep HPLC (CH$_3$CN/0.1% TFA-H$_2$O/0.1% TFA) to give the expected product (7-(6-(4,4-difluoropiperidine-1-carbonyl)-4-fluoroisoquinolin-1-yl)-2-methyl-5,6,7,8-tetrahydro-[1,2,4]triazolo[4,3-a]pyrazin-3(2H)-one) as a white solid (2.1 mg).

$^1$H NMR (400 MHz, CD$_3$OD) δ 1.95-2.24 (4H, m), 3.45 (3H, s), 3.56 (2H, br s), 3.82 (4H, s), 3.94 (2H, br s), 4.50 (2H, s), 7.78 (1H, dd, J=8.7, 1.6 Hz), 8.10 (1H, d, J=1.9 Hz), 8.17 (1H, dd, J=1.6, 0.5 Hz), 8.34 (1H, ddd, J=8.7, 2.1, 0.5 Hz); LRMS (ESI): m/z [M+H]$^+$ 447.

7-(6-(4,4-difluoropiperidine-1-carbonyl)-8-fluoroisoquinolin-1-yl)-2-methyl-5,6,7,8-tetrahydro-[1,2,4]triazolo[4,3-a]pyrazin-3(2H)-one was synthesized starting from 6-bromo-8-fluoro-2H-isoquinolin-1-one using conditions analogous to 7-(6-(4,4-difluoropiperidine-1-carbonyl)-4-fluoroisoquinolin-1-yl)-2-methyl-5,6,7,8-tetrahydro-[1,2,4]triazolo[4,3-a]pyrazin-3 (2H)-one in accordance with the general procedure 13 (Scheme 13).

7-(6-(4,4-difluoropiperidine-1-carbonyl)-8-fluoroisoquinolin-1-yl)-2-methyl-5,6,7,8-tetrahydro-[1,2,4]triazolo[4,3-a]pyrazin-3 (2H)-one $^1$H NMR (400 MHz, CDCl$_3$) δ 1.84-2.27 (4H, m), 3.47 (3H, s), 3.50-3.78 (4H, m), 3.91 (4H, t, J=5.4 Hz), 4.52 (2H, s), 7.23 (1H, d, J=1.3 Hz), 7.31 (1H, dd, J=5.8, 2.2 Hz), 7.62 (1H, d, J=1.3 Hz), 8.18 (1H, d, J=5.8 Hz); LRMS (ESI): m/z [M+H]$^+$ 447.

6-(6-(cyclohexyl(hydroxy)methyl)naphthalen-1-yl)isoquinolin-1(2H)-one was prepared in accordance with the general procedure 14 (Scheme 14) using the method described below in detail.

Synthesis of 6-(6-(cyclohexyl(hydroxy)methyl)naphthalen-1-yl) isoquinolin-1 (2H)-one

207
-continued

Step 14-2

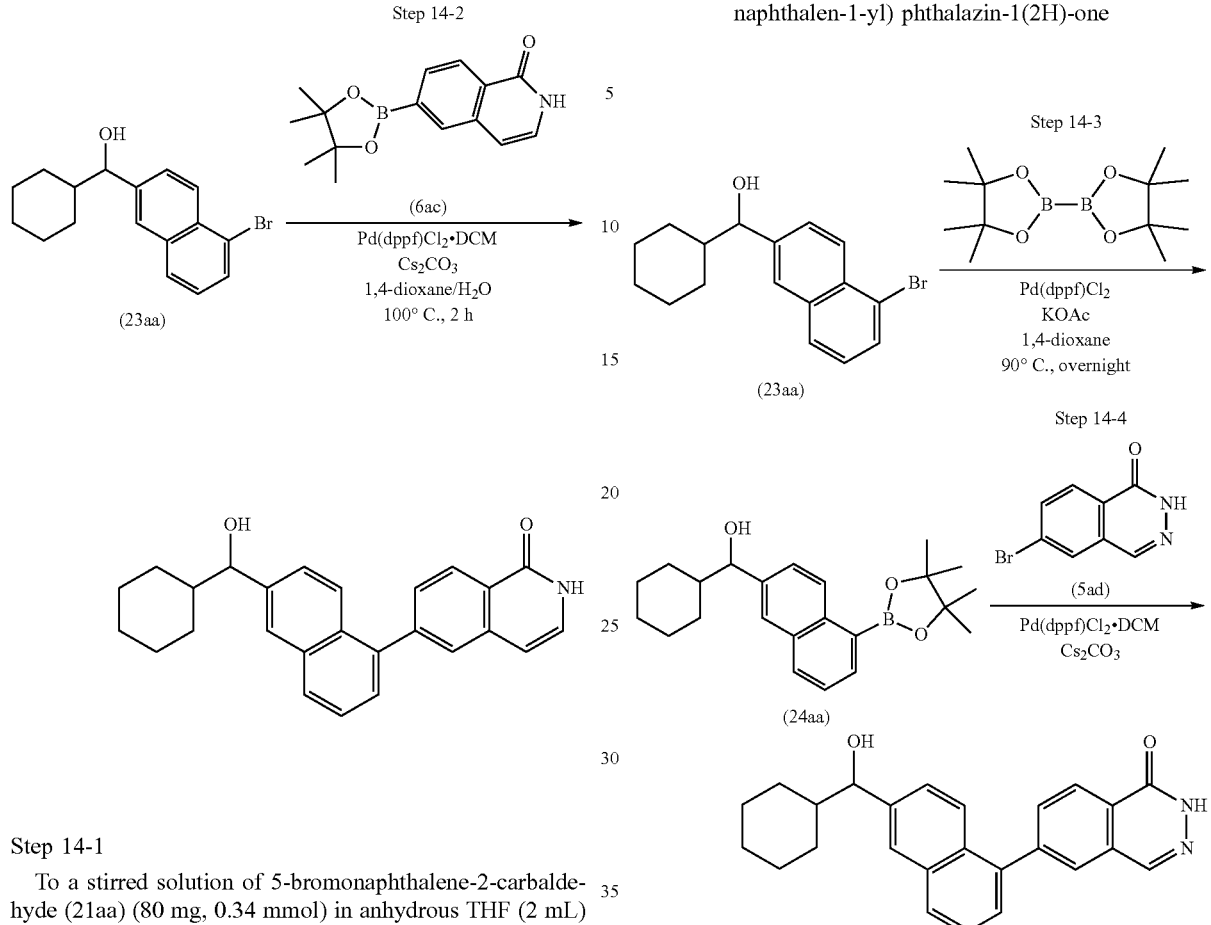

Step 14-1

To a stirred solution of 5-bromonaphthalene-2-carbaldehyde (21aa) (80 mg, 0.34 mmol) in anhydrous THF (2 mL) was added (cyclohexyl)magnesium bromide (22aa) (1M solution in THF) (0.68 mL, 0.68 mmol) at 0° C. The reaction mixture was stirred for 6 h while warmed to r.t., then left overnight. The mixture was quenched with saturated aqueous NH$_4$Cl solution and extracted with EtOAc (×2). The combined organics were concentrated and the residue was purified by silica gel column chromatography (0-40% EtOAc/Hexane) to give (5-bromonaphthalen-2-yl) (cyclohexyl)methanol as a colorless oil (62 mg); LRMS (ESI): m/z [M+H−18]$^+$ 301.

Step 14-2

A mixture of (5-bromonaphthalen-2-yl)(cyclohexyl)methanol (23aa) (62 mg, 0.19 mmol), 6-(4,4,5,5-tetramethyl-1,3,2-dioxaborolan-2-yl)-2H-isoquinolin-1-one (6ac) (64 mg, 0.23 mmol), Pd(dppf)Cl$_2$·DCM (15.8 mg, 0.02 mmol) and Cs$_2$CO$_3$ (190 mg, 0.58 mmol) in 1,4-dioxane (1.2 mL) and H$_2$O (0.3 mL) was degassed and charged with nitrogen, then heated at 100° C. for 2 h. The mixture was filtered through celite, and the filtrate was subjected to silica gel column chromatography (0-100% EtOAc/Hexane) to give 6-(6-(cyclohexyl(hydroxy)methyl)naphthalen-1-yl)isoquinolin-1(2H)-one (34 mg) as a white solid.

$^1$H NMR (400 MHz, d$_6$-DMSO) δ 0.94-1.18 (5H, m), 1.32-1.38 (1H, m), 1.50-1.75 (4H, m), 1.80-1.90 (1H, m), 4.43 (1H, d, J=6.1 Hz), 5.25 (1H, br s), 6.65 (1H, d, J=7.2 Hz), 7.23-7.26 (1H, m), 7.44-7.48 (2H, m), 7.57-7.62 (2H, m), 7.73-7.78 (2H, m), 7.86 (1H, s), 7.98 (1H, d, J=8.2 Hz), 8.31 (1H, d, J=8.1 Hz), 11.32 (1H, d, J=5.0 Hz); LRMS (ESI): m/z [M+H]$^+$ 384.

208
Synthesis of 6-(6-(cyclohexyl(hydroxy)methyl)naphthalen-1-yl) phthalazin-1(2H)-one

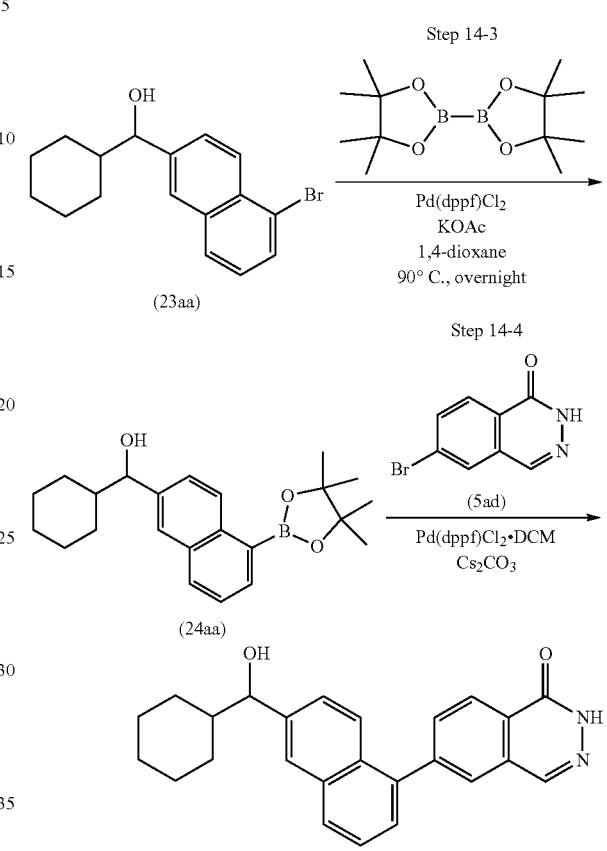

Step 14-3

A reaction mixture of (5-bromo-2-naphthyl)-cyclohexyl-methanol (23aa) (94 mg, 0.29 mmol), KOAc (63.6 mg, 0.65 mmol), Pd(dppf)Cl$_2$ (43.1 mg, 0.06 mmol) and bis(pinacolato)diboron (89.7 mg, 0.35 mmol) in 1,4-dioxane (4 mL) was degassed then charged with nitrogen. The reaction mixture was heated at 90° C. overnight, then cooled down to r. t., and filtered through a syringe filter. The filtrate was concentrated, and the residue was purified by silica gel column chromatography (0-70% EtOAc/Hexane). The combined fractions were concentrated to give the product as colorless gel (83.2 mg). LRMS (ESI): m/z [M+Na]$^+$389.

Step 14-4

A reaction mixture of cyclohexyl-[5-(4,4,5,5-tetramethyl-1,3,2-dioxaborolan-2-yl)-2-naphthyl]methanol (27aa) (20 mg, 0.055 mmol), 6-bromo-2H-phthalazin-1-one (5ad) (14.7 mg, 0.065 mmol), Pd(dppf)Cl$_2$·DCM (8.9 mg, 0.011 mmol) and Cs$_2$CO$_3$ (53.4 mg, 0.16 mmol) in a mixed solvent 1,4-dioxane (1.2 mL) and H$_2$O (0.3 mL) was heated at 100° C. for 2 h. The reaction mixture was filtered through a syringe filter, the filtrate was concentrated, and the residue was purified by silica gel column chromatography (0-100% EtOAc/Hexane), followed by prep HPLC (CH$_3$CN/0.1% TFA-H$_2$O/0.1% TFA). The combined fractions were lyophilized to give the product as a white solid (8.7 mg).

$^1$H NMR (400 MHz, DMSO-d$_6$) δ 0.94-1.18 (5H, m), 1.32-1.38 (1H, m), 1.50-1.75 (4H, m), 1.80-1.90 (1H, m), 4.42-4.46 (1H, m), 5.27 (1H, d, J=4.4 Hz), 7.47-7.52 (2H, m), 7.62 (1H, t, J=7.5 Hz), 7.73 (1H, d, J=8.8 Hz), 7.88 (1H, s), 7.96 (1H, dd, J=8.2, 1.6 Hz), 8.00-8.04 (1H, m), 8.08 (1H, d, J=1.2 Hz), 8.36 (1H, d, J=8.2 Hz), 8.46 (1H, s), 12.75 (1H, s); LRMS (ESI): m/z [M+H]$^+$ 385.

The following compounds were synthesized using conditions analogous to 6-[6-(cyclohexyl(hydroxy)methyl]-1-naphthyl]-2H-phthalazin-1-one in accordance with the general procedure 14 (Steps 14-3 and 14-4).

3-[6-cyclohexyl(hydroxy)methyl]-1-naphthyl]-6-methyl-5H-pyrrolo[3,4-b]pyridin-7-one

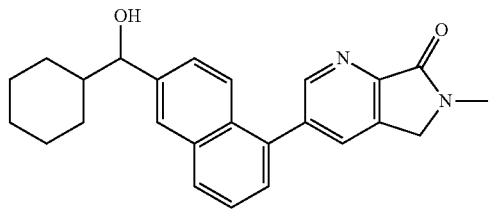 [SMILES: CN1Cc2cc(-c3cccc4cc(C(O)C5CCCCC5)ccc34)cnc2C1=O]

$^1$H NMR (400 MHz, DMSO-d$_6$) δ 0.94-1.18 (5H, m), 1.32-1.38 (1H, m), 1.50-1.75 (4H, m), 1.80-1.90 (1H, m), 3.18 (3H, s), 4.44 (1H, d, J=6.1 Hz), 4.59 (2H, s), 7.47-7.52 (2H, m), 7.62 (1H, t, J=7.5 Hz), 7.70 (1H, d, J=8.8 Hz), 7.89 (1H, s), 8.03 (1H, d, J=8.1 Hz), 8.20 (1H, d, J=1.4 Hz), 8.78 (1H, d, J=1.6 Hz); LRMS (ESI): m/z [M+H]$^+$ 387.

7-[6-cyclohexyl(hydroxy)methyl]-1-naphthyl]-3H-pyrido[3,2-d]pyrimidin-4-one

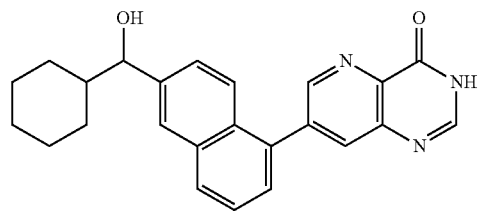 [SMILES: O=c1[nH]cnc2cc(-c3cccc4cc(C(O)C5CCCCC5)ccc34)cnc12]

$^1$H NMR (400 MHz, DMSO-d$_6$) δ 0.96-1.18 (5H, m), 1.33-1.40 (1H, m), 1.53-1.72 (4H, m), 1.80-1.90 (1H, m), 4.42-4.47 (1H, m), 5.29 (1H, d, J=4.2 Hz), 7.50-7.53 (1H, m), 7.55-7.58 (1H, m), 7.62-7.66 (1H, m), 7.73 (1H, d, J=9.0 Hz), 7.90 (1H, s), 8.05 (1H, d, J=8.1 Hz), 8.14-8.17 (1H, m), 8.25 (1H, d, J=1.8 Hz), 8.87-8.90 (1H, m), 12.66 (1H, s); LRMS (ESI): m/z [M+H]$^+$ 386.

Intermediate 6-(4,4-difluoropiperidine-1-carbonyl)-2-fluoronaphthalen-1-yl trifluoromethanesulfonate (3ae) was prepared in accordance with the general procedure 15 (Scheme 15) using the methods described below in detail.

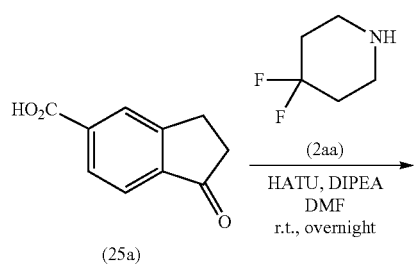

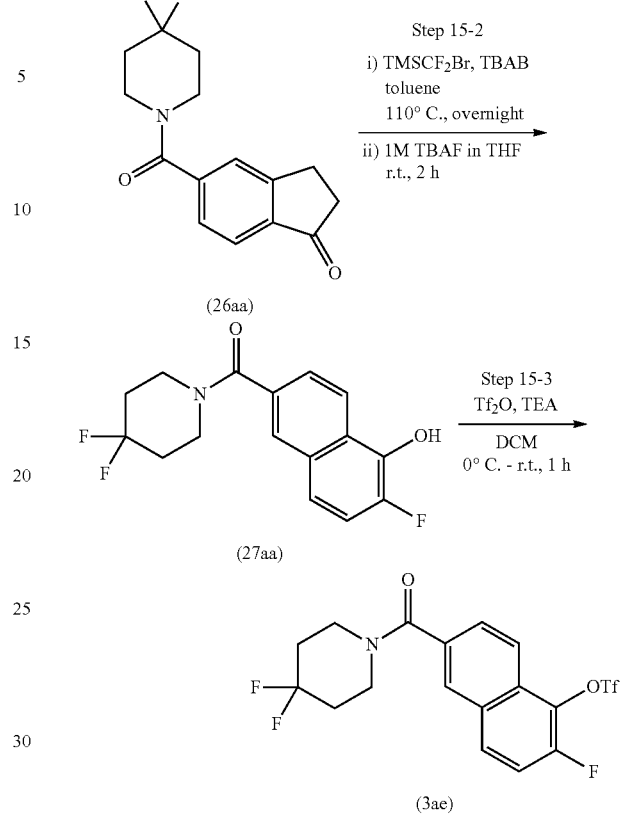

Step 15-1

A mixture of 2,3-dihydro-1-oxo-1H-indene-5-carboxylic acid (25a) (0.7 g, 3.97 mmol), 4,4-difluoropiperidine (2aa) (0.57 mL, 5.17 mmol), HATU (2.27 g, 5.96 mmol) and DIPEA (0.61 mL, 8.74 mmol) in DMF (8 mL) was stirred at r.t. overnight. The solvent was evaporated in vacuo, and the crude mixture was purified by silica gel column chromatography (0-100% EtOAc/Hexane) to give the expected product as a white solid (358 mg); LRMS (ESI): m/z [M+H]$^+$ 280.

Step 15-2 (i, ii)

To a 40 mL vial were added 5-(4,4-difluoropiperidine-1-carbonyl)indan-1-one (26aa) (358 mg, 1.28 mmol), TMSCF$_2$Br (388 mg, 1.93 mmol), tetrabutylammoniumbromide (TBAB) (41.2 mg, 0.13 mmol), followed by toluene (5 mL) at r.t. The vial was sealed, degassed and charged with nitrogen. The reaction mixture was stirred at 110° C. for 3 h, then additional TMSCF$_2$Br (388 mg, 1.93 mmol) was added. The reaction mixture was stirred at 110° C. overnight. The reaction mixture was cooled to r.t., then a 1M solution of TBAF in THF (0.25 mL) was added and the reaction was stirred at r.t. for 2 h. The resulting mixture was poured into 1M HCl (20 mL) and extracted with EtOAc (×2). The organic layers were combined and dried over Na$_2$SO$_4$. After removal of the solvents in vacuo, the residue was purified by silica gel column chromatography (0-60% EtOAc/Hexane) to give the expected compound as a white solid (367 mg, 93%); LRMS (ESI): m/z [M+H]$^+$ 310.

Step 15-3

To a stirred solution of (4,4-difluoro-1-piperidyl)-(6-fluoro-5-hydroxy-2-naphthyl)methanone (27aa) (367 mg, 1.19 mmol) and TEA (0.36 mL, 2.61 mmol) in DCM (6 mL) at 0° C. was added trifluoromethanesulfonic anhydride (0.26 mL, 1.54 mmol). The reaction mixture was stirred at 0° C.

for 30 min and warmed to r.t. for another 30 min. The reaction mixture was diluted with 1M HCl and the product was extracted with DCM (×2). The combined organics were dried over Na$_2$SO$_4$, filtered, and concentrated. The residue was purified by silica gel column chromatography (0-60% EtOAc/Hexane) to give the expected compound as a clear oil (476 mg); LRMS (ESI): m/z [M+H]$^+$ 442.

6-(6-(cyclohexanecarbonyl) naphthalen-1-yl) isoquinolin-1(2H)-one was prepared in accordance with the general procedure 16 (Scheme 16) using the method described below in detail.

Synthesis of 6-(6-(cyclohexanecarbonyl)naphthalen-1-yl) isoquinolin-1 (2H)-one

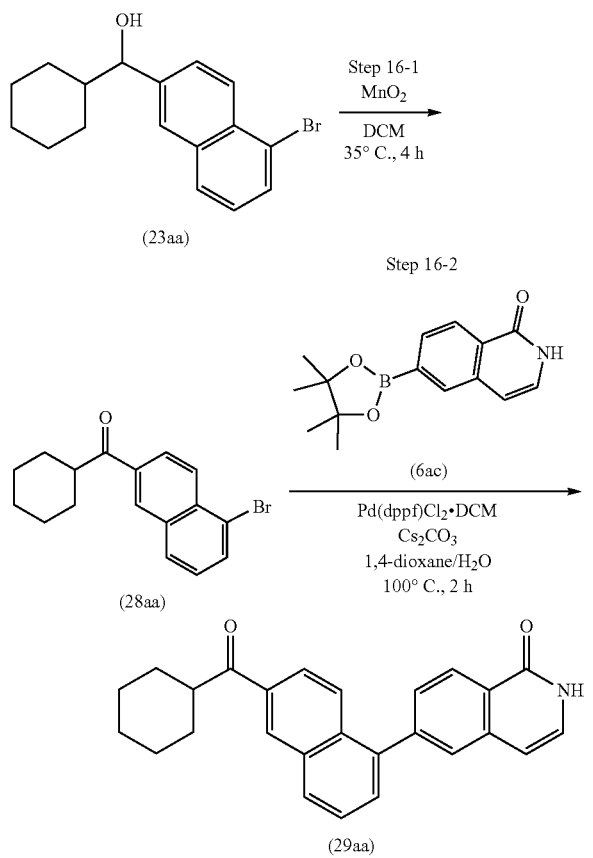

Step 16-1

To a solution of (5-bromo-2-naphthyl)-cyclohexyl-methanol (23aa) (70 mg, 0.22 mmol) in DCM (4 mL) was added MnO$_2$ (192 mg, 2.2 mmol) at r.t.; the reaction mixture was stirred at 35° C. for 4 h. The reaction mixture was filtered through celite, the filtrate was concentrated, and the residue was purified by silica gel column chromatography (0-40% EtOAc/Hexane) to give the product as a pale oil (61 mg, 87%). LRMS (ESI): m/z [M+H]$^+$ 317.

Step 16-2

A reaction mixture of (5-bromo-2-naphthyl)-cyclohexyl-methanone (28aa) (122 mg, 0.38 mmol), 6-(4,4,5,5-tetramethyl-1,3,2-dioxaborolan-2-yl)-2H-isoquinolin-1-one (6ac) (135.6 mg, 0.50 mmol), Cs$_2$CO$_3$ (375.9 mg, 1.15 mmol) and Pd(dppf)Cl$_2$·DCM (31.4 mg, 0.039 mmol) in the mixed solvent 1,4-dioxane (2.5 mL) and H$_2$O (0.5 mL) was degassed and charged with nitrogen, then heated at 100° C. for 2 h. The mixture was filtered through a syringe filter then concentrated, and the residue was purified by silica gel column chromatography (0-100% EtOAc/Hexane) to give the product as a white solid (94 mg).

$^1$H NMR (400 MHz, DMSO-d$_6$) δ 1.17-1.30 (1H, m), 1.35-1.53 (4H, m), 1.69-1.81 (3H, m), 1.84-1.90 (2H, m), 3.56-3.64 (1H, m), 6.64 (1H, d, J=7.1 Hz), 7.26 (1H, t, J=7.0 Hz), 7.60 (1H, dd, J=8.1, 1.6 Hz), 7.68 (1H, dd, J=7.0, 1.3 Hz), 7.73 (1H, dd, J=8.0, 7.5 Hz), 7.80 (1H, d, J=1.5 Hz), 7.89 (1H, d, J=8.8 Hz), 7.98 (1H, dd, J=8.9, 1.8 Hz), 8.26 (1H, d, J=8.0 Hz), 8.33 (1H, d, J=8.2 Hz), 8.80 (1H, d, J=1.3 Hz), 11.36 (1H, d, J=4.8 Hz); LRMS (ESI): m/z [M+H]$^+$ 382.

6-(6-(cyclohexyl(methylamino)methyl)naphthalen-1-yl) isoquinolin-1(2H)-one was prepared in accordance with the general procedure 17 (Scheme 17) using the method described below in detail.

Synthesis of 6-(6-(cyclohexyl(methylamino)methyl) naphthalen-1-yl) isoquinolin-1 (2H)-one

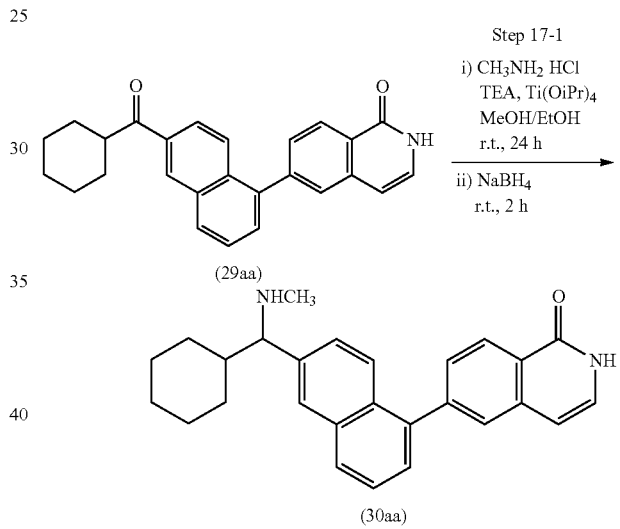

Step 17-1

To a stirred solution of 6-[6-(cyclohexanecarbonyl)-1-naphthyl]-2H-isoquinolin-1-one (29aa) (15 mg, 0.039 mmol) in MeOH/EtOH (2 mL/2 mL) were added methylamine hydrochloride (13.1 mg, 0.20 mmol), TEA (27 μL, 0.20 mmol) and Ti(OiPr)$_4$ (58 μL, 0.20 mmol). The reaction mixture was stirred at r. t. for 2 h. 10 more equivalents of methylamine hydrochloride and TEA as well as 5 equivalents of Ti(OiPr)$_4$ were added. The reaction mixture was stirred at r.t. for one day. The reaction was cooled down in ice-water bath, then NaBH$_4$ (3 mg, 0.79 mmol) was added slowly. The reaction mixture was stirred at r.t. for additional 2 h. The solvent was evaporated, and the residue was purified by HPLC (CH$_3$CN/0.1% TFA-H$_2$O/0.1% TFA). The combined fractions were lyophilized to give the product (30aa) as a white solid (7 mg).

$^1$H NMR (400 MHz, DMSO-d$_6$) δ 0.83-1.19 (6H, m), 1.32-1.39 (1H, m), 1.51-1.61 (3H, m), 1.66-1.73 (1H, m), 1.96-2.02 (1H, m), 2.09 (3H, s), 6.65 (1H, d, J=7.2 Hz), 7.23-7.26 (1H, m), 7.44-7.48 (2H, m), 7.57-7.62 (2H, m), 7.74 (1H, d, J=8.8 Hz), 7.79 (1H, d, J=1.6 Hz), 7.82 (1H, m), 7.96 (1H, d, J=8.2 Hz), 8.31 (1H, d, J=8.1 Hz), 11.32 (1H, d, J=5.2 Hz); LRMS (ESI+) m/z [M+H]+ 397.

6-(6-(amino(cyclohexyl)methyl)naphthalen-1-yl)isoquinolin-1(2H)-one was prepared in accordance with the general procedure 18 (Scheme 18) using the method described below in detail.

Synthesis of 6-(6-(amino(cyclohexyl)methyl)naphthalen-1-yl) isoquinolin-1 (2H)-one

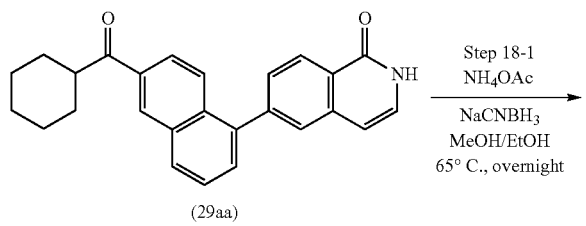

(29aa)

Step 18-1
NH₄OAc
NaCNBH₃
MeOH/EtOH
65° C., overnight

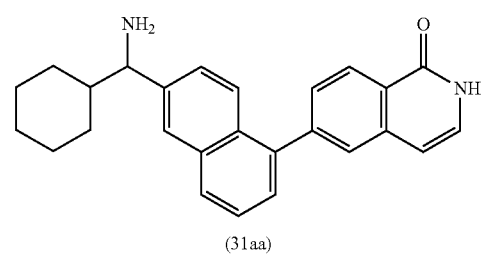

(31aa)

Step 18-1

To a solution of 6-[6-(cyclohexanecarbonyl)-1-naphthyl]-2H-isoquinolin-1-one (29aa) (30 mg, 0.078 mmol) in MeOH/EtOH (1.5 mL/2 mL) was added NH₄OAc (72.8 mg, 0.94 mmol), followed by NaCNBH₃ (19.8 mg, 0.31 mmol). The reaction mixture was degassed and charged with nitrogen, then heated at 65° C. overnight. The reaction mixture was cooled down and evaporated under reduced pressure. 0.5 M NaOH aqueous solution (8 mL) was added, and the product was extracted with EtOAc. The combined organics were concentrated to give the crude, which was purified by prep HPLC (CH₃CN/0.1% TFA-H₂O/0.1% TFA). The combined fractions were lyophilized to give the product (31aa) as a white solid (23.2 mg).

¹H NMR (400 MHz, DMSO-d₆) δ 0.83-1.19 (5H, m), 1.32-1.39 (1H, m), 1.46-1.62 (3H, m), 1.66-1.73 (1H, m), 1.88-1.94 (1H, m), 3.73 (1H, d, J=6.8 Hz), 6.65 (1H, d, J=7.2 Hz), 7.24 (1H, d, J=7.1 Hz), 7.44-7.52 (2H, m), 7.56-7.62 (2H, m), 7.73 (1H, d, J=8.8 Hz), 7.77 (1H, m), 7.86 (1H, s), 7.95 (1H, d, J=8.3 Hz), 8.31 (1H, d, J=8.2 Hz), 11.33 (1H, br s); LRMS (ESI*) m/z [M+H]+ 383.

6-(6-((4,4-difluoropiperidin-1-yl) sulfonyl)naphthalen-1-yl)isoquinolin-1(2H)-one was prepared in accordance with the general procedure 19 (Scheme 19) using the method described below in detail.

Synthesis of 6-(6-((4,4-difluoropiperidin-1-yl) sulfonyl)naphthalen-1-yl) isoquinolin-1 (2H)-one Step 16-2

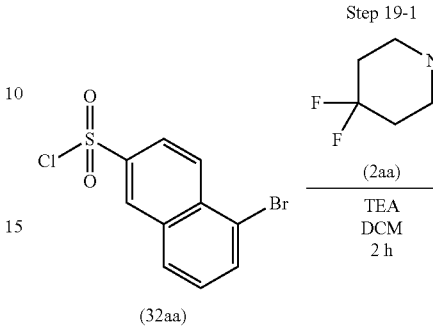

(32aa)

Step 19-1

(2aa)
TEA
DCM
2 h

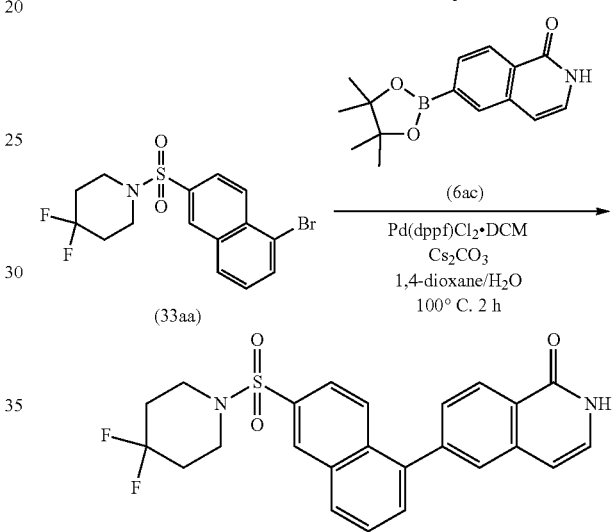

(33aa)

(6ac)
Pd(dppf)Cl₂·DCM
Cs₂CO₃
1,4-dioxane/H₂O
100° C. 2 h

Step 19-1

To a solution of 5-bromonaphthalene-2-sulfonyl chloride (32aa) (128 mg, 0.42 mmol) (prepared according to the methods described in ACS Med. Chem. Letts., 2016, 7, 1062-1067) in DCM (4 mL) was added TEA (175 μL, 1.26 mmol) followed by 4,4-difluoropiperidine (2aa) (56 μL, 0.50 mmol) at r. t. The reaction mixture was stirred at r. t. for 2 h, then concentrated. The crude was purified by silica gel column chromatography (0-100% EtOAc/Hexane) to give the product as an off-white solid (144 mg). LRMS (ESI): m/z [M+H]+ 390, 392.

Step 19-2

A reaction mixture of 1-[(5-bromo-2-naphthyl)sulfonyl]-4,4-difluoro-piperidine (33aa) (25 mg, 0.064 mmol), 6-(4,4,5,5-tetramethyl-1,3,2-dioxaborolan-2-yl)-2H-isoquinolin-1-one (6ac) (20.8 mg, 0.077 mmol), Pd(dppf)Cl₂.DCM (5.2 mg, 0.0064 mmol) and Cs₂CO₃ (62.6 mg, 0.19 mmol) in 1,4-dioxane (0.8 mL) and H₂O (0.2 mL) was heated at 100° C. for 2 hr. The reaction mixture was filtered through a celite plug, and the filtrate was subjected to silica gel column chromatography (0-100% EtOAc/Hexane), followed by prep HPLC (CH₃CN/0.1% TFA-H₂O/0.1% TFA). The combined fractions were lyophilized to give the product as a white solid (23.4 mg).

¹H NMR (400 MHz, DMSO-d₆) δ 2.03-2.14 (4H, m), 3.13-3.19 (4H, m), 6.64 (1H, d, J=7.1 Hz), 7.24-7.28 (1H, m), 7.60-7.63 (1H, dd, J=8.2, 1.7 Hz), 7.75-7.84 (4H, m), 8.02 (1H, d, J=9.0 Hz), 8.32 (1H, s), 8.34 (1H, s), 8.61 (1H, d, J=1.7 Hz), 11.37 (1H, d, J=5.1 Hz); LRMS (ESI*) m/z [M+H]$^+$ 455.

6-(6-(cyclohexylthio)naphthalen-1-yl) isoquinolin-1 (2H)-one was prepared in accordance with the general procedure 20 (Scheme 20) using the method described below in detail.

Synthesis of 6-(6-(cyclohexylthio)naphthalen-1-yl) isoquinolin-1 (2H)-one

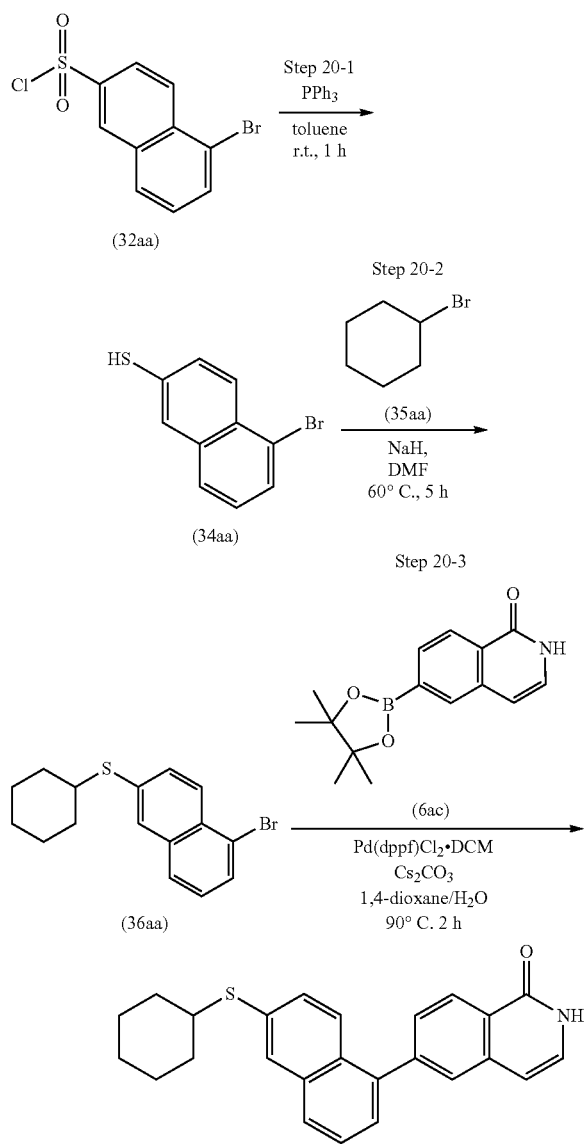

(32aa)

(34aa)

(36aa)

Step 20-1

To a solution of 5-bromonaphthalene-2-sulfonyl chloride (32aa) (150 mg, 0.49 mmol) in toluene (3 mL) was added triphenylphosphine (386.3 mg, 1.47 mmol) under nitrogen at r. t. The reaction mixture was stirred at r. t. for 1 h, then diluted with H$_2$O, and extracted with Et$_2$O. The combined organics were concentrated, and the residue was purified by silica gel column chromatography (0-10% EtOAc/Hexane) to give the product as a white solid (66 mg). $^1$H NMR (400 MHz, CDCl$_3$) δ 3.66 (1H, s), 7.28-7.33 (1H, m), 7.45 (1H, dd, J=8.9, 1.9 Hz), 7.67 (1H, d, J=8.2 Hz), 7.70-7.74 (2H, m), 8.12 (1H, d, J=8.8 Hz).

Step 20-2

To a vial containing NaH, 60% in mineral oil (10 mg, 0.25 mmol) was added 5-bromonaphthalene-2-thiol (34aa) (40 mg, 0.17 mmol) in DMF (2 mL) under nitrogen at r. t. The reaction mixture was heated at 50° C. for 15 min, then bromocyclohexane (35aa) (41 µL, 0.33 mmol) in DMF (0.3 mL) was added. The reaction mixture was stirred at 60° C. for 5 h, then cooled down, diluted with H$_2$O, and extracted with EtOAc. The combined organics were concentrated, and the residue was purified by silica gel column chromatography (0-10% EtOAc/Hexane) to give the product as a colorless oil (32 mg).

$^1$H NMR (400 MHz, CDCl$_3$) δ 1.25-1.52 (5H, m), 1.63-1.70 (1H, m), 1.78-1.87 (2H, m), 2.02-2.09 (2H, m), 3.27-3.33 (1H, m), 7.28-7.35 (1H, m), 7.59 (1H, dd, J=8.9, 1.9 Hz), 7.72-7.76 (2H, m), 7.82 (1H, d, J=1.8 Hz), 8.16 (1H, d, J=8.9 Hz).

Step 20-3

A reaction mixture of 1-bromo-6-cyclohexylsulfanyl-naphthalene (36aa) (32 mg, 0.10 mmol), 6-(4,4,5,5-tetramethyl-1,3,2-dioxaborolan-2-yl)-2H-isoquinolin-1-one (6ac) (32.4 mg, 0.12 mmol), Pd(dppf)Cl$_2$.DCM (16.3 mg, 0.02 mmol) and Cs$_2$CO$_3$ (97.4 mg, 0.30 mmol) in 1,4-dioxane (1.2 mL) and H$_2$O (0.3 mL) was heated at 90° C. for 2 h. The crude was filtered through a syringe filter, and the filtrate was subjected to silica gel column chromatography (0-100% EtOAc/Hexane) to give the product as a white solid (35 mg).

$^1$H NMR (400 MHz, DMSO-d$_6$) δ 1.21-1.43 (5H, m), 1.56-1.63 (1H, m), 1.66-1.75 (2H, m), 1.94-2.01 (2H, m), 3.35-3.48 (1H, m), 6.64 (1H, d, J=7.3 Hz), 7.23-7.27 (1H, m), 7.47-7.51 (2H, m), 7.55-7.64 (2H, m), 7.72 (1H, d, J=9.0 Hz), 7.78 (1H, m), 7.97 (1H, d, J=8.6 Hz), 8.02 (1H, m), 8.31 (1H, d, J=8.3 Hz), 11.35 (1H, br s); LRMS (ESI*) m/z [M+H]$^+$ 386.

6-(6-(cyclohexylsulfonyl)naphthalen-1-yl) isoquinolin-1 (2H)-one was prepared in accordance with the general procedure 21 (Scheme 21) using the method described below in detail.

Synthesis of 6-(6-(cyclohexylsulfonyl)naphthalen-1-yl) isoquinolin-1 (2H)-one

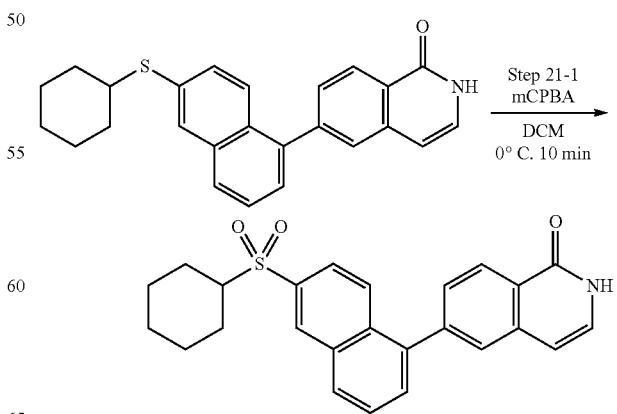

Step 21-1

To a stirred solution of 6-(6-cyclohexylsulfanyl-1-naphthyl)-2H-isoquinolin-1-one (14 mg, 0.036 mmol) in DCM (1.5 mL) in an ice-water bath was added mCPBA (16.3 mg, 0.073 mmol). The reaction mixture was stirred for 10 min at 0° C., then concentrated, and purified by HPLC (CH$_3$CN/0.1% TFA-H$_2$O/0.1% TFA). The combined fractions were lyophilized to give the product as a white solid (7.1 mg).

$^1$H NMR (400 MHz, DMSO-d$_6$) δ 1.03-1.37 (5H, m), 1.53-1.61 (1H, m), 1.72-1.78 (2H, m), 1.89-1.98 (2H, m), 3.25-3.35 (1H, m), 6.65 (1H, d, J=7.2 Hz), 7.25-7.29 (1H, m), 7.60 (1H, dd, J=8.3, 1.5 Hz), 7.75-7.87 (4H, m), 8.01 (1H, d, J=8.8 Hz), 8.32-8.36 (2H, m), 8.65 (1H, d, J=1.8 Hz), 11.38 (1H, d, J=4.5 Hz); LRMS (ESI$^+$) m/z [M+H]$^+$ 418.

6-(6-(cyclohexylsulfinyl)naphthalen-1-yl) isoquinolin-1 (2H)-one was prepared in accordance with the general procedure 22 (Scheme 22) using the method described below in detail.

Synthesis of 6-(6-(cyclohexylsulfinyl)naphthalen-1-yl) isoquinolin-1 (2H)-one

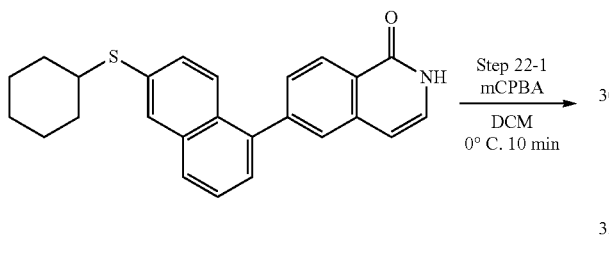

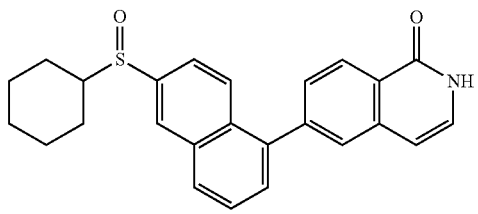

Step 22-1

To a stirred solution of 6-(6-cyclohexylsulfanyl-1-naphthyl)-2H-isoquinolin-1-one (14 mg, 0.036 mmol) in DCM (1.5 mL) in an ice-water bath was added mCPBA (8.2 mg, 0.036 mmol). The reaction mixture was stirred at 0° C. for 10 min, then concentrated. The crude was purified by HPLC (CH$_3$CN/0.1% TFA-H$_2$O/0.1% TFA). The combined fractions were lyophilized to give the product as a white solid (8.5 mg, 56.5%).

$^1$H NMR (400 MHz, DMSO-d$_6$) δ 1.09-1.62 (7H, m), 1.70-1.82 (2H, m), 1.89-1.94 (1H, m), 2.78-2.86 (1H, m), 6.65 (1H, d, J=7.1 Hz), 7.26 (1H, d, J=7.0 Hz), 7.59-7.77 (4H, m), 7.81 (1H, s), 7.94 (1H, d, J=8.8 Hz), 8.20 (1H, d, J=7.9 Hz), 8.31 (1H, s), 8.32 (1H, d, J=8.9 Hz), 11.38 (1H, br s); LRMS (ESI$^+$) m/z [M+H]$^+$ 402.

Synthesis of (3-bromo-1-methyl-1H-indazol-6-yl) (4,4-difluoropiperidin-1-yl)methanone (3eh-ai) and (3-bromo-2-methyl-2H-indazol-6-yl) (4,4-difluoropiperidin-1-yl)methanone (3ei-ai)

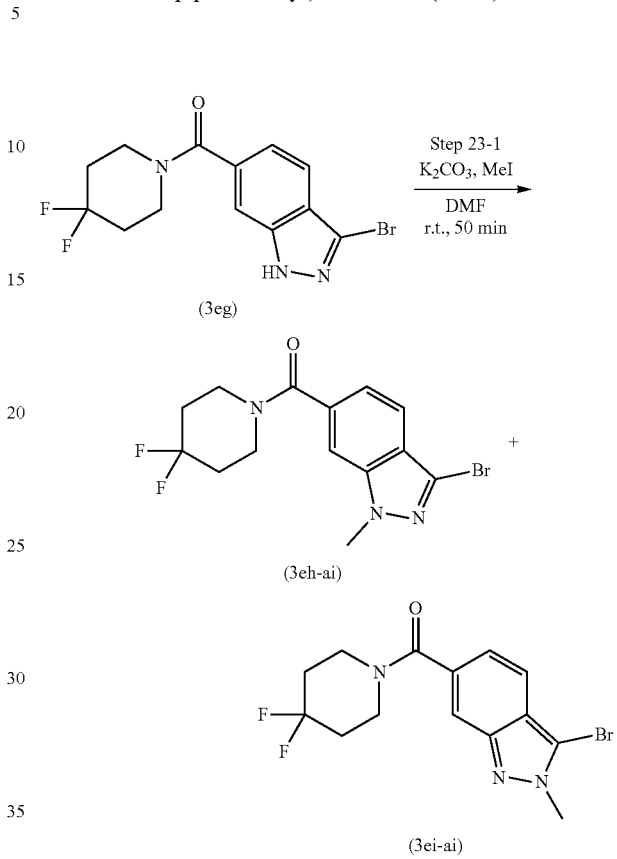

Step 23-1

To a solution of (3-bromo-1H-indazol-6-yl)-(4,4-difluoro-1-piperidyl)methanone (240.0 mg, 0.70 mmol) in DMF (3.5 mL) was added potassium carbonate (674.6 mg, 4.88 mmol) and MeI (0.13 mL, 2.09 mmol). The reaction was stirred at r.t. for 50 min. The mixture was quenched with water and partitioned between EtOAc and H$_2$O. The product was extracted with EtOAc from the aq. layer (×2). The combined organic layers were dried over Na$_2$SO$_4$ and concentrated. The residue was purified by silica gel chromatography (0-34% EtOAc/hexane) to obtain (3-bromo-1-methyl-1H-indazol-6-yl) (4,4-difluoropiperidin-1-yl)methanone as a white solid (167.8 mg).

$^1$H NMR (400 MHz, DMSO-d$_6$) δ 2.05 (4H, br s), 3.41-3.78 (4H, m), 4.08 (3H, s), 7.29 (1H, d, J=8.4 Hz), 7.65 (1H, d, J=8.3 Hz), 7.87 (1H, s); LRMS (ESI): m/z [M+H]$^+$ 358, 360.

(3-bromo-2-methyl-2H-indazol-6-yl) (4,4-difluoropiperidin-1-yl)methanone as a yellow solid (13.2 mg).

$^1$H NMR (400 MHz, DMSO-d$_6$) δ 2.05 (4H, br s), 3.45-3.74 (4H, m), 4.19 (3H, s), 7.17 (1H, d, J=8.6 Hz), 7.59 (1H, d, J=8.6 Hz), 7.74 (1H, s); LRMS (ESI): m/z [M+H]$^+$ 358, 360.

Next, results that evidence the effectiveness of the compounds of the present invention are given in the Experimental example.

Experimental Example 1

15-PGDH Enzyme Inhibition Test

Test compounds and 4 nM recombinant human 15-PGDH (R&D systems) in 50 mM Tris-HCl (pH 8.0) containing 0.01% TWEEN 20 (Sigma) and 0.01% bovine gamma globulin (Sigma) were put into 384 Flat Bottom Black plates (Corning, 3820) and allowed to stand for 12 minutes at room temperature. Then, 30 μM $PGE_2$ (Cayman chemical) and 1 mM $NAD^+$ (Sigma) were added to start reaction. Sixty minutes after the start of reaction, signals were measured at an excitation wavelength of 340 nm and a fluorescence emission wavelength of 440 nm using Synergy 2 (BioTeck). The intensity of the fluorescent signal obtained when an assay buffer was added in place of the test compounds and $NAD^+$ was defined as 100% and that obtained with the addition of $NAD^+$ was defined as 0%. Concentrations for 50% inhibition from concentration-response curves of the test compounds were represented as $IC_{50}$ values.

+++: $IC_{50}$ values<3 nM
++: 3 nM≤$IC_{50}$ values<10 nM
+: 10 nM≤$IC_{50}$ values

TABLE I

| Test compounds | $IC_{50}$ (nM) |
|---|---|
| 1 | +++ |
| 2 | +++ |
| 3 | +++ |
| 4 | +++ |
| 5 | +++ |
| 6 | +++ |
| 7 | + |
| 8 | +++ |
| 9 | +++ |
| 10 | +++ |
| 11 | ++ |
| 12 | ++ |
| 13 | ++ |
| 14 | +++ |
| 15 | +++ |
| 16 | ++ |
| 17 | +++ |
| 18 | +++ |
| 19 | +++ |
| 20 | ++ |
| 21 | +++ |
| 22 | ++ |
| 23 | +++ |
| 24 | +++ |
| 25 | +++ |
| 26 | +++ |
| 27 | +++ |
| 28 | ++ |
| 29 | +++ |
| 30 | +++ |
| 31 | +++ |
| 32 | +++ |
| 33 | +++ |
| 34 | +++ |
| 35 | +++ |
| 36 | + |
| 37 | +++ |
| 38 | +++ |
| 39 | +++ |
| 40 | ++ |
| 41 | +++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 51 | ++ |
| 52 | ++ |
| 53 | ++ |
| 54 | +++ |
| 55 | +++ |
| 56 | ++ |
| 57 | +++ |
| 58 | +++ |
| 59 | +++ |
| 60 | +++ |
| 61 | +++ |
| 62 | +++ |
| 63 | +++ |
| 64 | +++ |
| 65 | +++ |
| 66 | +++ |
| 67 | +++ |
| 68 | +++ |
| 69 | +++ |
| 70 | + |
| 71 | +++ |
| 72 | +++ |
| 73 | + |
| 74 | +++ |
| 75 | +++ |
| 76 | +++ |
| 77 | +++ |
| 78 | +++ |
| 79 | + |
| 80 | +++ |
| 81 | +++ |
| 82 | +++ |
| 83 | +++ |
| 84 | +++ |
| 85 | ++ |
| 86 | +++ |
| 87 | +++ |
| 88 | +++ |
| 89 | + |
| 90 | ++ |
| 91 | +++ |
| 92 | +++ |
| 93 | +++ |
| 94 | +++ |
| 95 | ++ |
| 96 | ++ |
| 97 | ++ |
| 98 | +++ |
| 99 | ++ |
| 100 | +++ |
| 101 | +++ |
| 102 | ++ |
| 103 | +++ |
| 104 | +++ |
| 105 | +++ |
| 106 | ++ |
| 107 | +++ |
| 108 | +++ |
| 109 | +++ |
| 110 | +++ |
| 111 | +++ |
| 112 | +++ |
| 113 | ++ |
| 114 | ++ |
| 115 | +++ |
| 116 | +++ |
| 117 | +++ |
| 118 | +++ |
| 119 | +++ |
| 120 | +++ |
| 121 | +++ |
| 122 | +++ |
| 123 | +++ |
| 124 | +++ |
| 125 | +++ |
| 126 | +++ |
| 127 | +++ |

TABLE I-continued

| Test compounds | IC$_{50}$ (nM) |
| --- | --- |
| 128 | +++ |
| 129 | +++ |
| 130 | +++ |
| 131 | +++ |
| 132 | +++ |
| 133 | ++ |
| 134 | +++ |
| 135 | +++ |
| 136 | +++ |
| 137 | ++ |
| 138 | +++ |
| 139 | +++ |
| 140 | +++ |
| 141 | +++ |
| 142 | +++ |
| 143 | +++ |
| 144 | + |
| 145 | ++ |
| 146 | ++ |
| 147 | +++ |
| 148 | ++ |
| 149 | + |
| 150 | +++ |
| 151 | +++ |
| 152 | +++ |
| 153 | +++ |
| 154 | +++ |
| 155 | +++ |
| 156 | ++ |
| 157 | ++ |
| 158 | +++ |
| 159 | +++ |
| 160 | +++ |
| 161 | +++ |
| 162 | +++ |
| 163 | +++ |
| 164 | +++ |
| 165 | +++ |
| 166 | ++ |

It is shown in Table I that the compound (I) of the present invention and pharmacologically acceptable salts thereof have a strong 15-PGDH inhibitory function.

It is shown in Tables I and II that the compound (1) of the present invention and pharmacologically acceptable salts thereof have a strong 15-PGDH inhibitory function.

15-hydroxyprostaglandin dehydrogenase (15-PGDH) is an important enzyme in the inactivation of active prostaglandins (e.g., PGD$_2$, PGE$_1$, PGE$_2$, PGF$_{2\alpha}$, and PGI$_2$), hydroxyeicosatetraenoic acids (HETEs), and pro-resolving lipid mediators (e.g., RvD1, RvD2, RvE1, MaR1, and LXA$_4$) (hereinafter, they are collectively referred to as "substrates for 15-PGDH"). For example, 15-PGDH converts PGE$_2$ into 15-keto PGE$_2$ by catalyzing the oxidation of the hydroxyl group at the C15 position. 15-oxo derivatives, which are substrates for 15-PGDH, oxidized by 15-PGDH, usually have lower biological activities than their 15-hydroxyl counterparts. Human 15-PGDH is encoded by the HPGD gene and is a homodimer of 29-kD subunits. The enzyme belongs to an evolutionarily conserved superfamily of short-chain dehydrogenase/reductase enzymes (SDRs) and is named SDR36C1. So far, two forms of 15-PGDH have been identified: NAD$^+$-dependent type-I 15-PGDH and the NADP$^+$-dependent type-II 15-PGDH which is also known as carbonyl reductase 1 (CBR1, SDR21C1). The preference of CBR1 for NADP$^+$ and the high K$_m$ values of CBR1 for most prostaglandins, however, suggest that the majority of the in-vivo activity can be attributed to the type-I 15-PGDH (see Tai HH. et al. (2002), Prostaglandins Other Lipid Mediat., 68-69, 483-493).

The prostaglandins (e.g., PGD$_2$, PGE$_1$, PGE$_2$, PGF$_{2\alpha}$, and PGI$_2$), HETEs, and pro-resolving lipid mediators (e.g., RvD1, RvD2, RvE1, MaR1, and LXA$_4$) act via specific receptors which are present on their target cells. Receptors for substrates for 15-PGDH are distributed widely, being expressed at different sites in a living body and exhibit diversity in their roles in vivo, depending on the variety in the kind of receptors, the diversity in signaling, and the wide distribution in expression.

For example, PGE$_1$ is known as drugs useful for the treatment of chronic arterial occlusions (thromboangiitis obliterans (TAO), arteriosclerosis obliterans(ASO)) and skin ulcers because it acts on blood vessels to widen them and thus increase blood flow as well as acts on platelets to inhibit platelet aggregation. PGF$_2$a stimulates uterine contractions and lowers intraocular pressure (see, for example, Shimizu T. et al. (2007). *Practica oto-rhino-laryngologica*, 100(3), 157-166), and its derivatives are used as therapeutic agents for glaucoma. PGD$_2$ is known to suppress inflammation by enhancing the vascular barrier function in the lung (see, for example, Murata, T. et al. (2013). *PNAS*, 110(13), 5205-5210). In addition, PGE$_2$ has a vasodilation function as well as various functions such as involvement in blood pressure, pain, bone formation, cell proliferation, and differentiation of stem cells and anti-fibrotic and anti-inflammatory functions (see, for example, Shimizu T. et al. (2007). *Practica oto-rhino-laryngologica*, 100(3), 157-166; North, T. E. et al. (2007). Nature, 447(7147), 1007-1011; and Bozyk, P. D. et al. (2011). *Am. J. Respir. Cell Mol. Biol.*, 45, 445-452). PGI$_2$ is known to inhibit platelet activation and mediate relaxation of vascular smooth muscle, and its derivatives are used as therapeutic agents for chronic arterial occlusion and primary pulmonary hypertension.

Furthermore, there are some antiulcer drugs whose mechanism of action lies in the increase of PGE$_2$ and PGI$_2$ production (see, for example, Kinoshita M. et al. (1995), *J. Pharmacol. Exp. Ther.*, 275(1), 494-501).

Pro-resolving lipid mediators (e.g., RvD1, RvD2, RvE1, MaR1, and LXA$_4$) suppress the migration and activation of neutrophils and promote the apoptosis of neutrophils. They have an important role in effectively removing debris remained at inflammatory sites and derived from neutrophils and tissue which have undergone apoptosis, by enhancing macrophage phagocytosis that is not accompanied by secretion of inflammatory cytokines. These responses actively resolve inflammation to restore homeostasis (see, for example, Arita M. et al. (2012), *Japanese Journal of Rhinology*, 51(1), 60-62).

The pro-resolving lipid mediators have been reported to exhibit efficacy in various disease models such as mouse models of lung injury (see Liao Z. et al. (2012), *Respiratory Research*, 13, 110-121), models of colitis (see Bento A. F. et al. (2011), *J. Immunol.*, 187, 1957-1969), and models of liver injury (see Chen X. et al. (2016), *Immunopharmacol. Immunotoxicol.*, 38(2), 61-67).

Since 15-PGDH is an important enzyme in the inactivation of substrates for 15-PGDH that have many functions in vivo, 15-PGDH inhibitors can be used for prevention and treatment of diseases associated with 15-PGDH level and/or its substrate level, and/or in cases that increasing the substrate level in a subject is desirable.

As described above, some substrates for 15-PGDH have one or more of functions of anti-fibrosis, anti-inflammation, improving blood flow, promoting cell proliferation, promoting proliferation of stem cells, contracting and relaxing smooth muscles, immunosuppression, and bone remodeling. Thus, 15-PGDH inhibitors can be effective for treating or preventing fibrosis (e.g., pulmonary fibrosis, idiopathic pulmonary fibrosis, liver fibrosis, sclerosis, and myelofibrosis), inflammatory diseases (e.g., aggravation of chronic obstructive pulmonary disease (COPD), acute lung injury, sepsis, asthma, and lung diseases, inflammatory bowel disease (ulcerative colitis, Crohn's disease, and the like), gastric ulcer (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, and prostatitis syndrome (chronic premature gland inflammation/chronic pelvic pain syndrome, and the like)), cardiovascular diseases (e.g., pulmonary hypertension, angina pectoris, myocardial infarction, chronic kidney disease, cerebral apoplexy, renal failure, and peripheral circulatory disturbance), wound (e.g., diabetic ulcers, burn, and bedsore), autoimmune diseases (e.g., multiple sclerosis and rheumatoid arthritis), graft-versus-host disease, hair growth, bone marrow transplantations, organ transplantations, osteoporosis, hearing loss, glaucoma, diabetes or underactive bladder.

At present, as prophylactic and therapeutic agents for the aforementioned various disease conditions, no compound that has a superior 15-PGDH inhibitory function and can be satisfactory pharmaceutical products has been found.

An object of the present invention is to provide compounds or pharmacologically acceptable salts thereof having a 15-PGDH inhibitory function, pharmaceutical compositions containing them, and their medical use.

INDUSTRIAL APPLICABILITY

The compounds of the present invention are useful as therapeutic and/or prophylactic agents for Fibrosis (pulmonary fibrosis, idiopathic pulmonary fibrosis, liver fibrosis, renal fibrosis, cardiac fibrosis, scleroderma, myelofibrosis, and the like), inflammatory diseases (chronic obstructive pulmonary disease (COPD), acute lung injury, sepsis, asthma and exacerbation of lung diseases, inflammatory bowel disease (ulcerative colitis, Crohn's disease, and the like), gastric ulcer (NSAIDs causative ulcer, and the like), autoinflammatory diseases (Behcet's disease, and the like), vascular inflammatory syndrome, acute liver injury, acute kidney injury, non-alcoholic steatohepatitis, atopic dermatitis, psoriasis, Interstitial cystitis, prostatitis syndrome (chronic premature gland inflammation/chronic pelvic pain syndrome, and the like), and the like), cardiovascular diseases (pulmonary hypertension, angina pectoris, myocardial infarction, ischemic heart damage, heart failure, chronic kidney disease, kidney failure, stroke, peripheral circulatory disorders, ischemic heart damage, and the like), wound healing (diabetic ulcer, burns, pressure ulcer, healing of acute mucosal damage in diseases of acute mucosal injury including Stevens-Johnson Syndrome, the mucosal damage (mucositis or stomatitis) associated with anti-cancer chemotherapeutics such as alkylating agents, DNA synthesis inhibitors, DNA gyrase inhibitors, antimetabolites amongst others, and cellular or humoral immunotherapies or radiation and graft-versus-host disease, and the like), autoimmune diseases (multiple sclerosis, rheumatoid arthritis, and the like), graft-versus-host disease, hair growth, osteoporosis, otologic diseases (hearing loss, tinnitus, dizziness, disorder of equilibrium, and the like), ophthalmic disorders (glaucoma, dry eye, and the like), diabetes, underactive bladder, enhancement of stem cell and bone marrow engraftment in organ or stem cell transplantation, neurogenesis and inhibition of nerve cell death (neuropsychiatric disorders, neural injury, neural toxicity disorders, neuropathic pain, neural degenerative disorders), muscle regeneration (muscular atrophy, dystrophy, and/or injury), cervical ripening because of their strong 15-PGDH inhibitory functions.

Obviously, numerous modifications and variations of the present invention are possible in light of the above teachings. It is therefore to be understood that within the scope of the appended claims, the invention may be practiced otherwise than as specifically described herein.

The invention claimed is:

1. A compound of formula (1) or a pharmacologically acceptable salt thereof, wherein the formula (1) is selected from the group consisting of

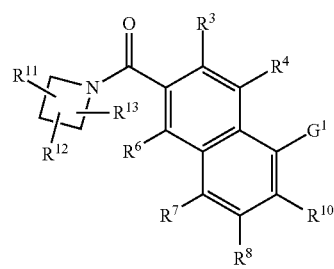

B1)

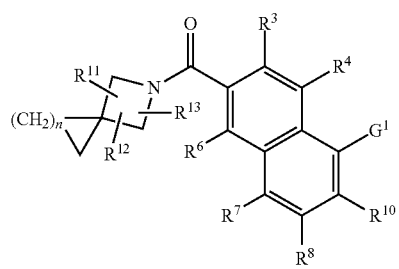

B2)

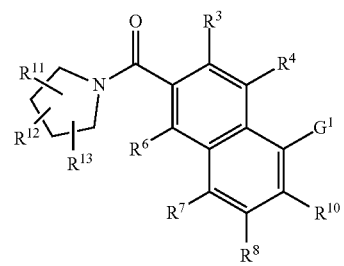

B3)

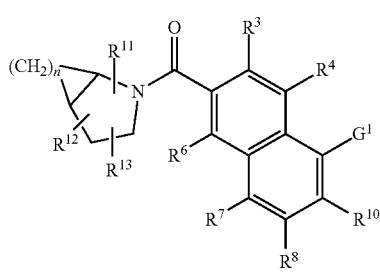

B4)

225
-continued

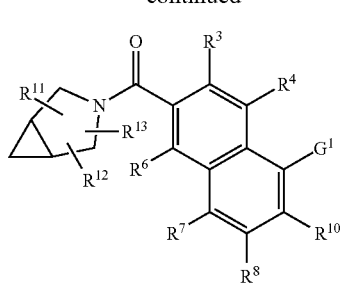

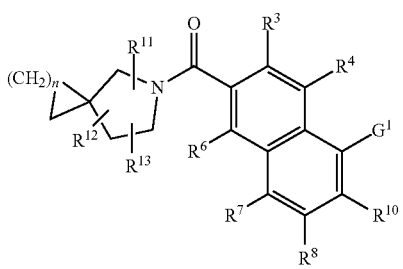

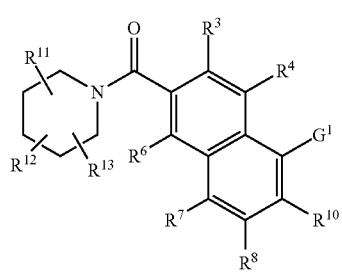

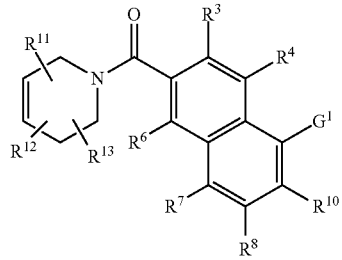

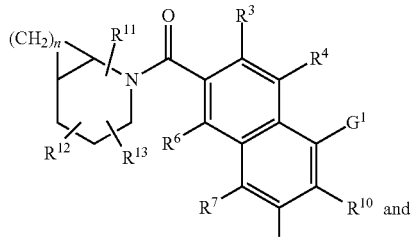

and

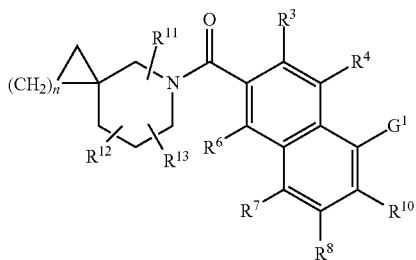

226 where $G^1$ is a phenyl group optionally having at least one substituent selected from group A, a 5-membered aromatic heterocyclic group optionally having at least one substituent selected from the group A, a 6-membered aromatic heterocyclic group optionally having at least one substituent selected from the group A, a bicyclic aromatic heterocyclic group having 8 to 10 atoms and optionally having at least one substituent selected from the group A, a fused heterocyclic group having 9 or 10 atoms and optionally having at least one substituent selected from the group A, $C_3$-$C_8$ cycloalkyl group optionally having at least one substituent selected from the group A or 3 to 8-membered heterocycloalkyl group optionally having at least one substituent selected from the group A;

$R^3$ and $R^4$ are each independently selected from hydrogen, halogen, —CN, —COOY, —NHC(O)Y, $C_1$-$C_6$ alkyl optionally having at least one substituent selected from group C, $C_1$-$C_6$ alkoxy optionally having at least one substituent selected from the group C or $C_3$-$C_8$ cycloalkyl optionally having at least one substituent selected from the group C;

$R^6$ is hydrogen, halogen, —CN, —COOY, —NHC(O)Y, C, $C_1$-$C_6$ alkyl optionally having at least one substituent selected from the group C, $C_1$-$C_6$ alkoxy optionally having at least one substituent selected from the group C or $C_3$-$C_8$ cycloalkyl optionally having at least one substituent selected from the group C;

$R^7$ and $R^8$ are each independently selected from hydrogen, halogen, —CN, —COOY, —NHC(O)Y, $C_1$-$C_6$ alkyl optionally having at least one substituent selected from the group C, $C_1$-$C_6$ alkoxy optionally having at least one substituent selected from the group C or $C_3$-$C_8$ cycloalkyl optionally having at least one substituent selected from the group C;

$R^{10}$ is hydrogen, halogen, —CN, —COOY, —NHC(O)Y, $C_1$-$C_6$ alkyl optionally having at least one substituent selected from the group C, $C_1$-$C_6$ alkoxy optionally having at least one substituent selected from the group C or $C_3$-$C_8$ cycloalkyl optionally having at least one substituent selected from the group C; Y is independently selected from hydrogen, $C_1$-$C_6$ alkyl optionally having at least one substituent selected from the group C, $C_1$-$C_6$ alkoxy optionally having at least one substituent selected from the group C or $C_3$-$C_8$ cycloalkyl optionally having at least one substituent selected from the group C;

the group A is halogen, hydroxyl, carbonyl, nitrile, carboxyl, formyl, $C_1$-$C_6$ alkyl optionally having at least one substituent selected from group A1, $C_1$-$C_6$ alkylcarbonyl optionally having at least one substituent selected from the group A1, $C_1$-$C_6$ alkoxy optionally having at least one substituent selected from the group A1, $C_1$-$C_6$ alkoxycarbonyl optionally having at least one substituent selected from the group A1, $C_1$-$C_6$ alkylsulfonyl optionally having at least one substituent selected from the group A1, $C_1$-$C_6$ alkylsulfonylamino optionally having at least one substituent selected from the group A1, $C_3$-$C_8$ cycloalkyl optionally having at least one substituent selected from the group A1, $C_3$-$C_8$ cycloalkylcarbonyl optionally having at least one substituent selected from the group A1, $C_3$-$C_8$ cycloalkoxy optionally having at least one substituent selected from the group A1, $C_3$-$C_8$ cycloalkylsulfonyl optionally having at least one substituent selected from the group A1, $C_3$-$C_8$ cycloalkylsulfonylamino optionally having at least one substituent selected from the group A1, $C_5$-$C_7$ heterocycloalkyl optionally having at least one substituent selected from the group A1, $C_5$-$C_7$ heterocycloalkylcarbonyl optionally having at least one substituent selected from the group A1, $C_5$-$C_7$ heterocycloalkylamino optionally having at least one substituent selected from the group A1, $C_5$-$C_7$ heterocycloalkylaminocarbonyl optionally having at least one substituent selected from the group A1, aminocarbonyl optionally substituted with one or two $C_1$-$C_6$ alkyl optionally at least one having substituent selected from the group A1, aminosulfonyl optionally substituted with one or two $C_1$-$C_6$ alkyl optionally having at least one substituent selected from the group A1, amino optionally substituted with one or two $C_1$-$C_6$ alkyl optionally having at least one substituent selected from the group A1, phenyl optionally having at least one substituent selected from the group B, 5-membered aromatic heterocyclic group optionally having at least one substituent selected from the group B, 6-membered aromatic heterocyclic group optionally having at least one substituent selected from the group B or heterocyclic group optionally having substituent(s) selected from the group B;

the group A1 is halogen, hydroxyl, amino, carbonyl, nitrile, carboxyl, formyl, $C_1$-$C_6$ alkyl optionally having at least one substituent selected from group A2, $C_1$-$C_6$ alkylcarbonyl optionally having at least one substituent selected from the group A2, $C_1$-$C_6$ alkoxy optionally having at least one substituent selected from the group A2, $C_1$-$C_6$ alkoxycarbonyl optionally having at least one substituent selected from the group A2, $C_1$-$C_6$ alkylsulfonyl optionally having at least one substituent selected from the group A2, $C_1$-$C_6$ alkylsulfonylamino optionally having at least one substituent selected from the group A2, $C_3$-$C_8$ cycloalkyl optionally having at least one substituent selected from the group A2, $C_5$-$C_7$ heterocycloalkyl optionally having at least one substituent selected from the group A2, $C_5$-$C_7$ heterocycloalkylcarbonyl optionally having at least one substituent selected from the group A2, $C_5$-$C_7$ heterocycloalkylamino optionally having at least one substituent selected from the group A2, $C_5$-$C_7$ heterocycloalkylaminocarbonyl optionally having at least one substituent selected from the group A2, aminocarbonyl optionally substituted with one or two $C_1$-$C_6$ alkyl optionally having at least one substituent selected from the group A2, amino optionally substituted with one or two $C_1$-$C_6$ alkyl optionally having at least one substituent selected from the group A2, 5-membered aromatic heterocyclic group optionally having at least one substituent selected from the group B, 6-membered aromatic heterocyclic group optionally having at least one substituent selected from the group B or heterocyclic group optionally having at least one substituent selected from the group B;

the group A2 is halogen, hydroxyl, nitrile, carboxyl, formyl, $C_1$-$C_6$ alkyl, $C_1$-$C_6$ alkylcarbonyl, $C_1$-$C_6$ alkoxy, $C_1$-$C_6$ alkoxycarbonyl, $C_1$-$C_6$ alkylsulfonylamino, 5-membered aromatic heterocyclic group, 6-membered aromatic heterocyclic group, heterocyclic group or 5 to 7-membered heterocycloalkyl group;

the group B is halogen, hydroxyl, carbonyl, carboxyl, $C_1$-$C_6$ alkyl, halo-$C_1$-$C_6$ alkyl, hydroxy-$C_1$-$C_6$ alkyl, $C_1$-$C_6$ alkylcarbonyl, $C_1$-$C_6$ alkoxy, halo-$C_1$-$C_6$ alkoxy, $C_1$-$C_6$ alkoxycarbonyl, $C_1$-$C_6$ alkyl substituted with $C_1$-$C_6$ alkoxy, $C_1$-$C_6$ alkoxy substituted with $C_1$-$C_6$ alkoxycarbonyl, $C_3$-$C_8$ cycloalkyl, $C_3$-$C_8$ cycloalkylcarbonyl, $C_3$-$C_8$ cycloalkoxy, aminocarbonyl optionally substituted with one or two $C_1$-$C_6$ alkyl, $C_1$-$C_6$ alkylsulfonyl, aminosulfonyl optionally substituted with one or two $C_1$-$C_6$ alkyl, $C_1$-$C_6$ alkylsulfonylamino, amino optionally substituted with one or two $C_1$-$C_6$ alkyl or 5 to 7-membered heterocycloalkyl group;

the group C is halogen, hydroxyl, carboxyl, $C_1$-$C_6$ alkylcarbonyl, $C_1$-$C_6$ alkoxy, $C_1$-$C_6$ alkoxycarbonyl, aminocarbonyl optionally substituted with one or two $C_1$-$C_6$ alkyl, amino optionally substituted with one or two $C_1$-$C_6$ alkyl or 5 to 7-membered heterocycloalkyl group; and $R^{11}$, $R^{12}$ and $R^{13}$ are the same or different and are hydrogen, halogen, $C_1$-$C_6$ alkyl, halo ($C_1$-$C_6$) alkyl, $C_1$-$C_6$ alkoxy or halo ($C_1$-$C_6$) alkoxy, and n is an integer of 1 to 3.

2. The compound or a pharmacologically acceptable salt thereof according to claim 1, wherein $G^1$ is selected from the group consisting of

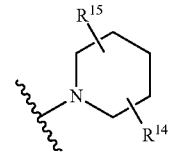

C1)

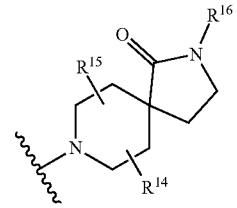

C2)

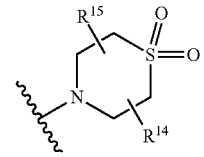

C3)

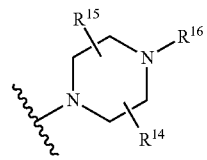

C4)

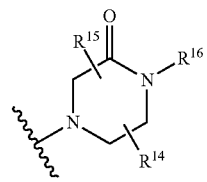

C5)

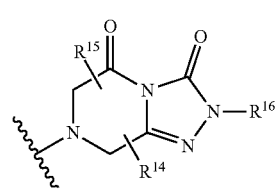

C6)

229
-continued
C7)
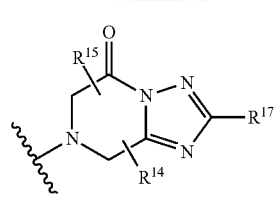
C8)
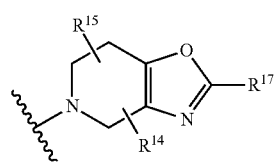
C9)
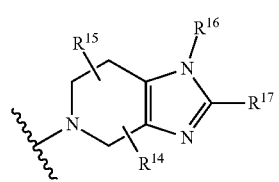
C10)
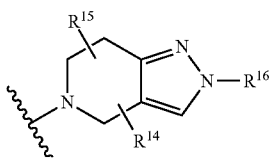
C11)
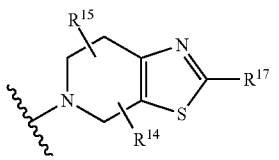
C12)
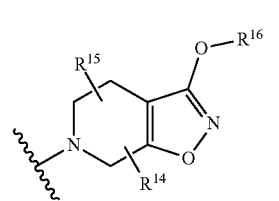
C13)
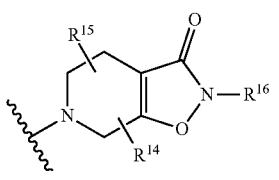
C14)
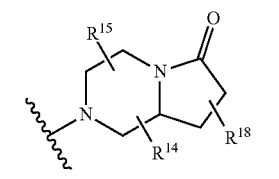
C15)
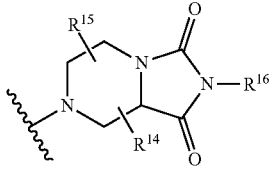
230
-continued
C16)
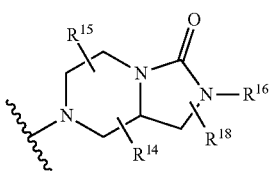
C17)
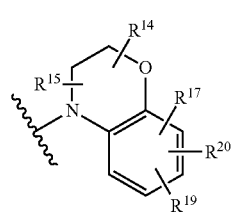
C18)
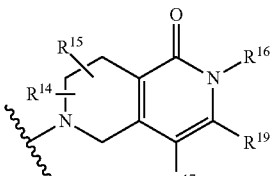
C19)
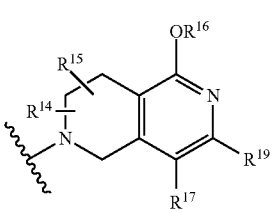
C20)
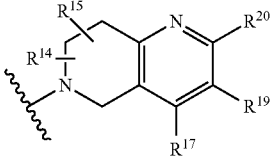
C21)
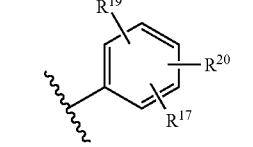
C22)
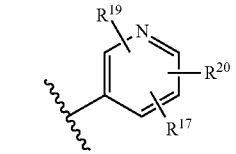
C23)
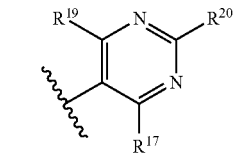

231
-continued
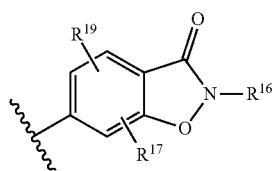
C24)
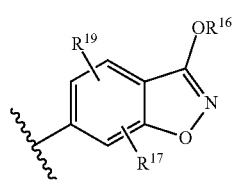
C25)
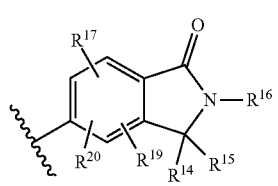
C26)
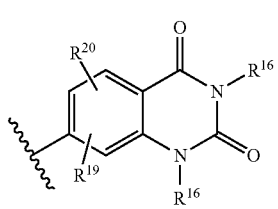
C27)
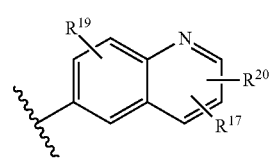
C28)
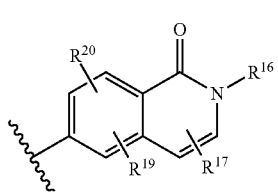
C29)
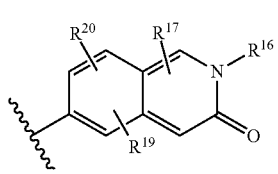
C30)
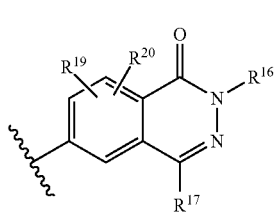
C31)
232
-continued
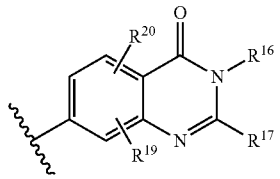
C32)
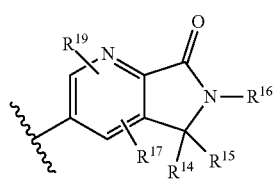
C33)
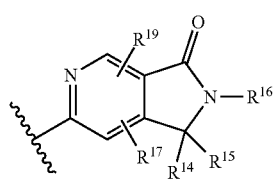
C34)
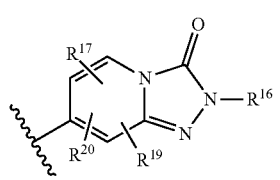
C35)
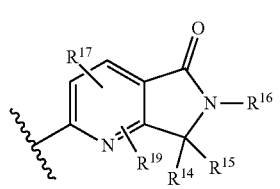
C36)
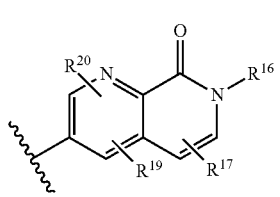
C37)
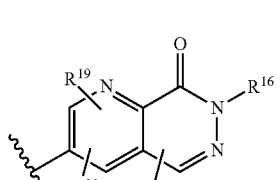
C38)
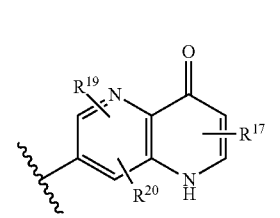
C39)

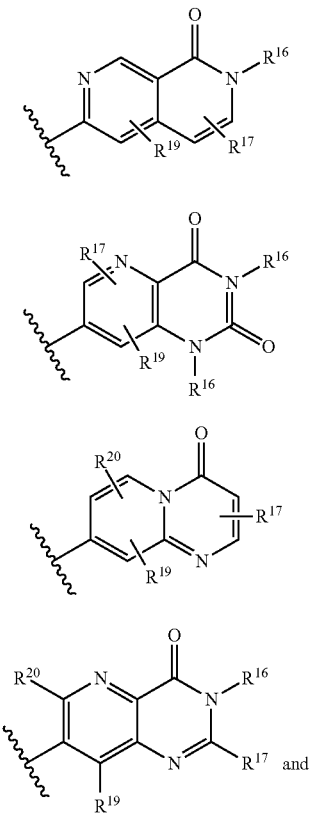
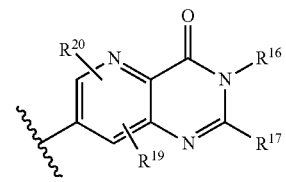

where the nitrogen atom or atoms in the aromatic ring is/are optionally N-oxide, $R^{14}$, $R^{15}$, $R^{17}$, $R^{18}$, $R^{19}$ and $R^{20}$ are the same or different and are hydrogen, halogen, hydroxy, nitrile, carboxyl, formyl, aminocarbonyl having an amino group which optionally contains one or more substituents selected from the group A1, and optionally containing 1 or 2 $C_1$-$C_6$ alkyl groups, or one selected from $C_1$-$C_6$ alkyl, amino, $C_1$-$C_6$ alkylcarbonyl, $C_1$-$C_6$ alkoxy, $C_1$-$C_6$ alkoxycarbonyl, $C_1$-$C_6$ alkylsulfonylamino, $C_1$-$C_6$ alkylsulfonyl, and $C_3$-$C_8$ cycloalkyl, which are optionally substituted with one or more substituents selected from the group A1; and $R^{16}$ is hydrogen, $C_1$-$C_6$ alkylaminosulfonyl, one selected from $C_1$-$C_6$ alkyl, $C_1$-$C_6$ alkylcarbonyl, $C_1$-$C_6$ alkoxycarbonyl, $C_1$-$C_6$ alkylsulfonyl, $C_3$-$C_8$ cycloalkyl, 5- to 7-membered heterocycloalkylcarbonyl, and 5- to 7-membered heterocycloalkylaminocarbonyl, which are optionally substituted with at least one substituent selected from the group A1, aminocarbonyl optionally containing 1 or 2 $C_1$-$C_6$ alkyl groups optionally substituted with at least one substituent selected from the group A1, or a 5- or 6-membered heteroaromatic ring optionally substituted with one or more substituents selected from the group B.

3. The compound or a pharmacologically acceptable salt thereof according to claim 1, wherein the formula (1) is

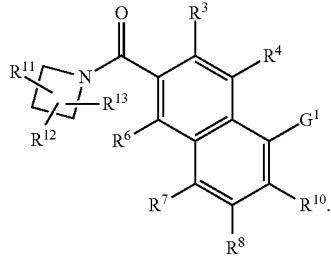

4. The compound or a pharmacologically acceptable salt thereof according to claim 1, wherein the formula (1) is

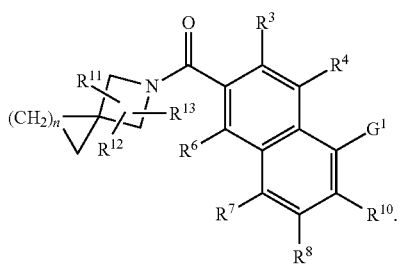

5. The compound or a pharmacologically acceptable salt thereof according to claim 1, wherein the formula (1) is

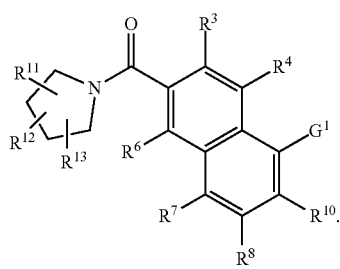

6. The compound or a pharmacologically acceptable salt thereof according to claim 1, wherein the formula (1) is

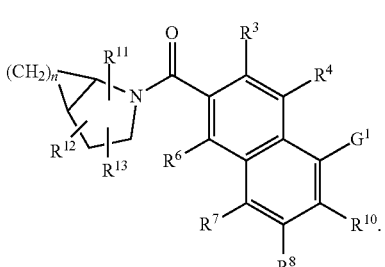

7. The compound or a pharmacologically acceptable salt thereof according to claim 1, wherein the formula (1) is

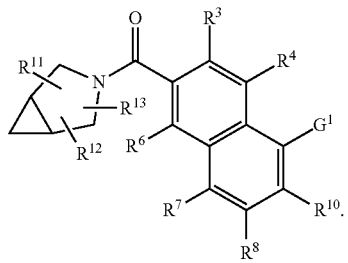

B5)

8. The compound or a pharmacologically acceptable salt thereof according to claim 1, wherein the formula (1) is

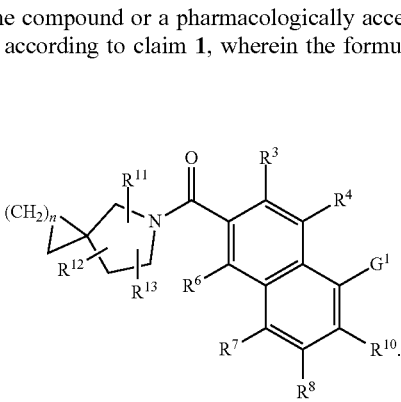

B6)

9. The compound or a pharmacologically acceptable salt thereof according to claim 1, wherein the formula (1) is

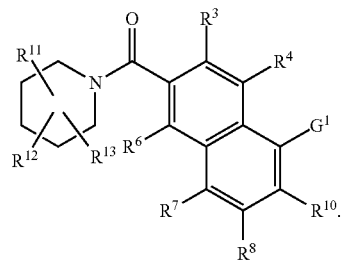

B7)

10. The compound or a pharmacologically acceptable salt thereof according to claim 1, wherein the formula (1) is

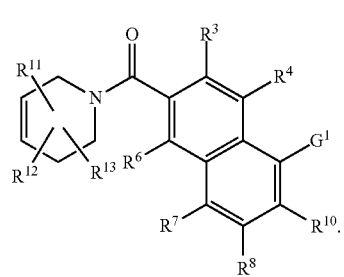

B8)

11. The compound or a pharmacologically acceptable salt thereof according to claim 1, wherein the formula (1) is

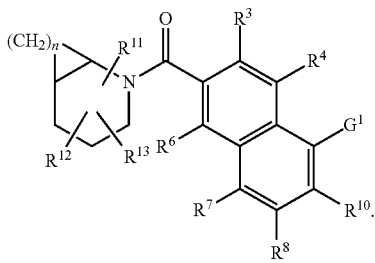

B9)

12. The compound or a pharmacologically acceptable salt thereof according to claim 1, wherein the formula (1) is

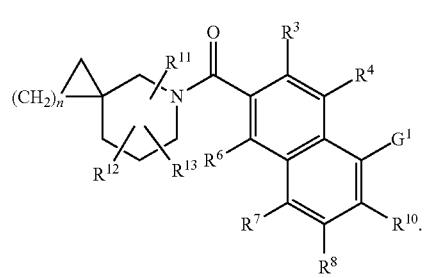

B10)

13. The compound or a pharmacologically acceptable salt thereof according to claim 2, wherein the formula (1) is

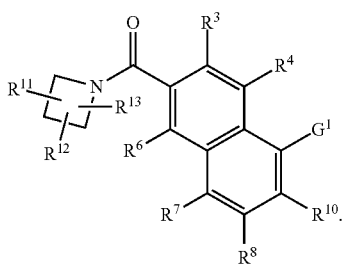

B1)

14. The compound or a pharmacologically acceptable salt thereof according to claim 2, wherein the formula (1) is

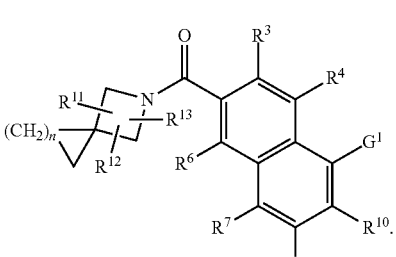

B2)

15. The compound or a pharmacologically acceptable salt thereof according to claim 2, wherein the formula (1) is

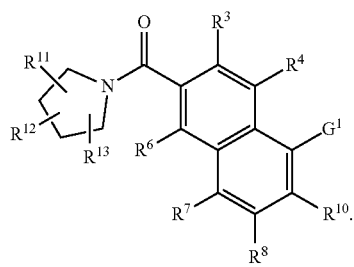
B3)

16. The compound or a pharmacologically acceptable salt thereof according to claim 2, wherein the formula (1) is

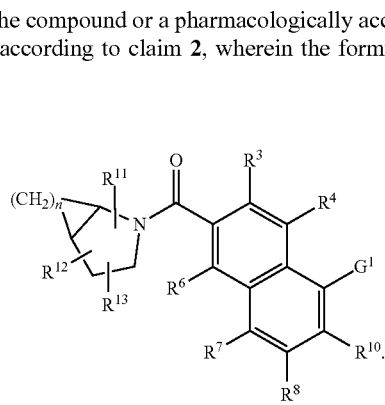
B4)

17. The compound or a pharmacologically acceptable salt thereof according to claim 2, wherein the formula (1) is

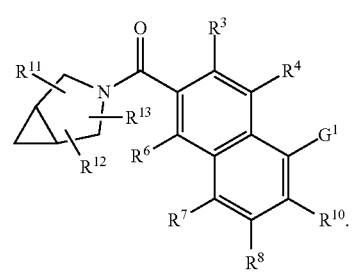
B5)

18. The compound or a pharmacologically acceptable salt thereof according to claim 2, wherein the formula (1) is

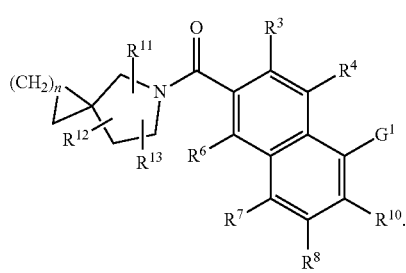
B6)

19. The compound or a pharmacologically acceptable salt thereof according to claim 2, wherein the formula (1) is

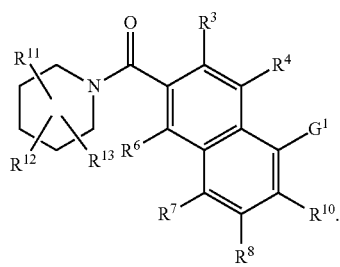
B7)

20. The compound or a pharmacologically acceptable salt thereof according to claim 2, wherein the formula (1) is

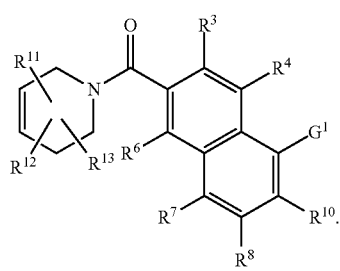
B8)

21. The compound or a pharmacologically acceptable salt thereof according to claim 2, wherein the formula (1) is

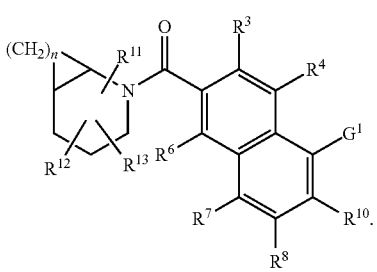
B9)

22. The compound or a pharmacologically acceptable salt thereof according to claim 2, wherein the formula (1) is

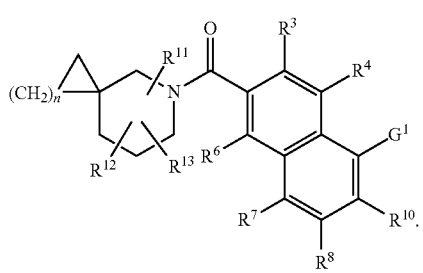
B10)

23. A compound or a pharmacologically acceptable salt thereof, wherein the compound has a structure selected from the group consisting of
1
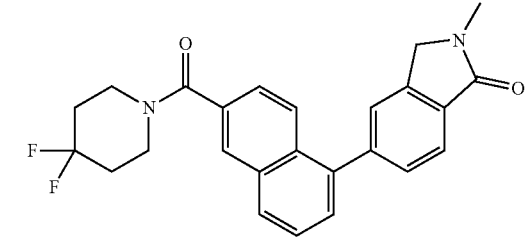
2
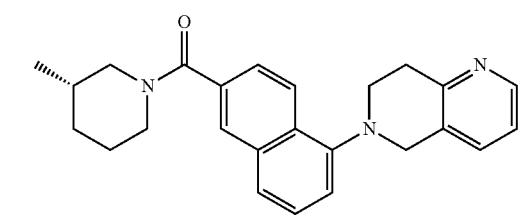
3
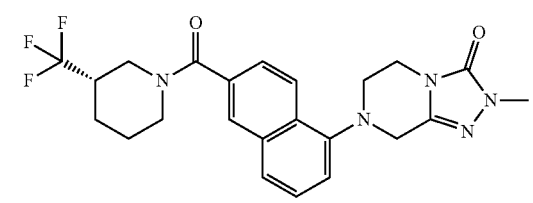
4
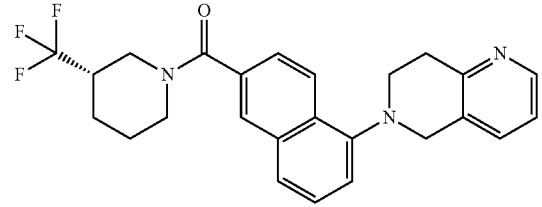
5
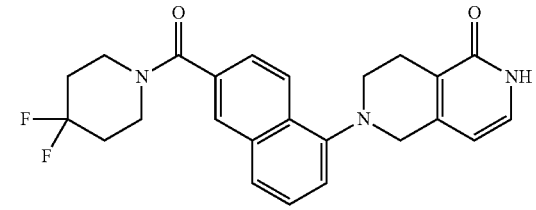
6
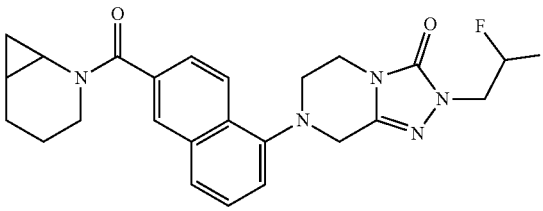
7
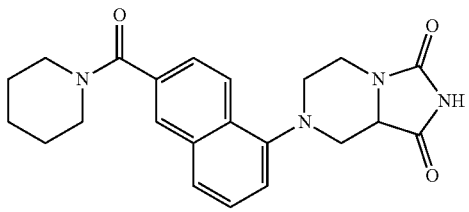
8
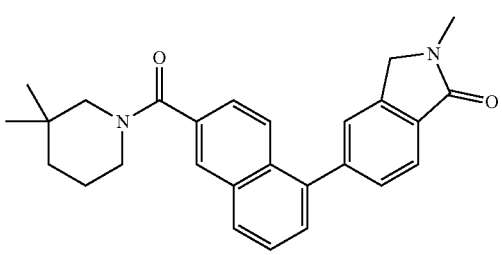
9
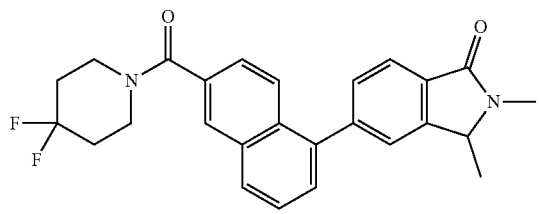
10
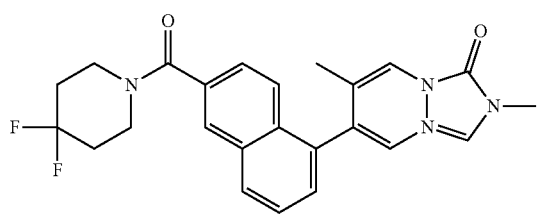
11
12
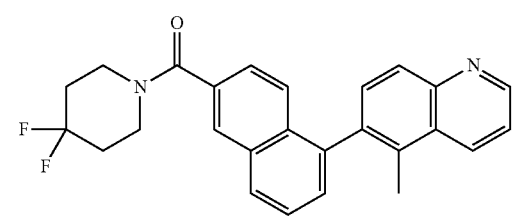
13
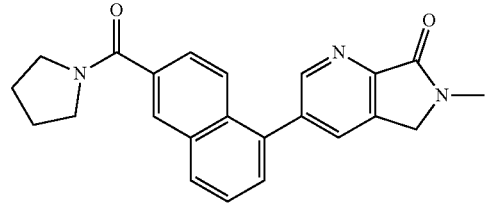

15
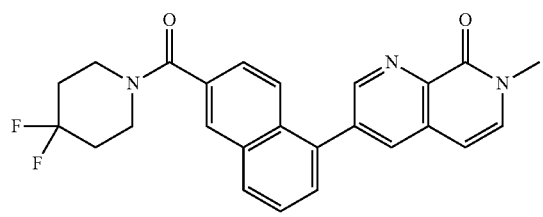
16
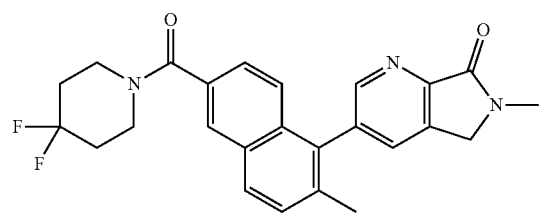
17
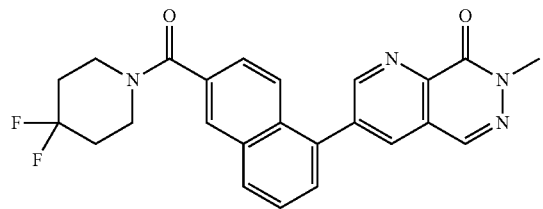
18
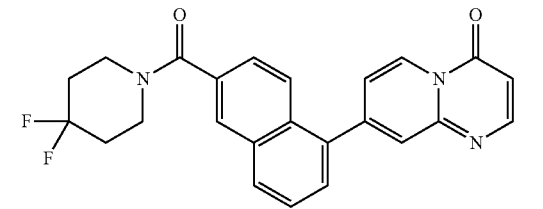
19
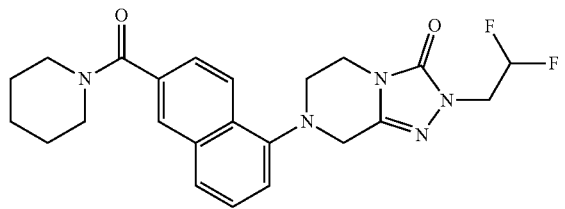
20
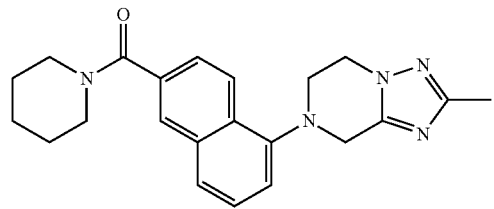
21
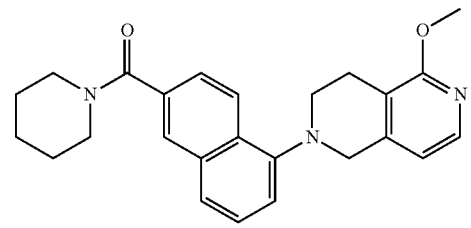
23
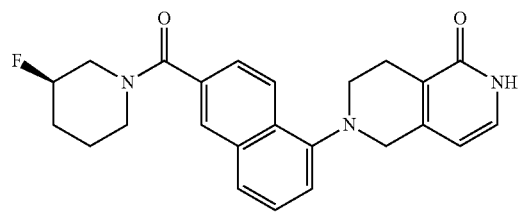
24
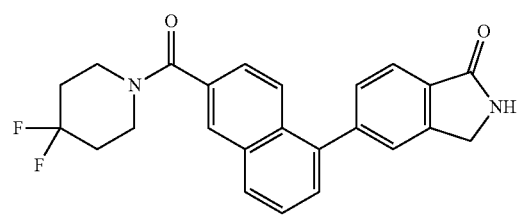
25
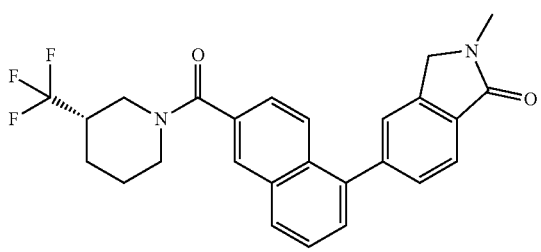
26
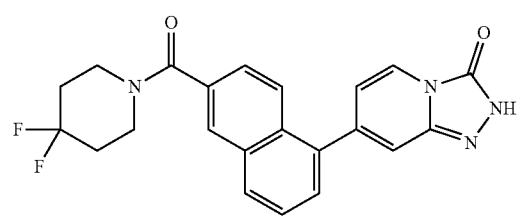
27
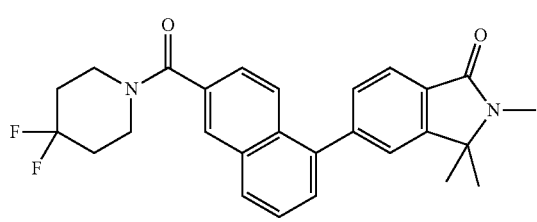
28
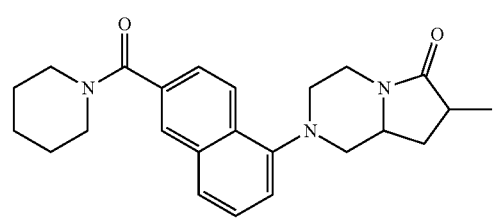
29
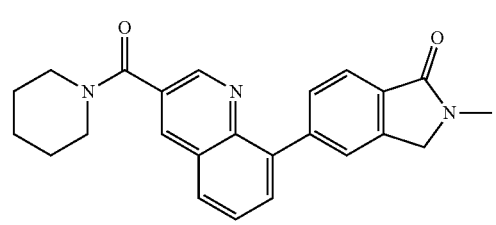

30 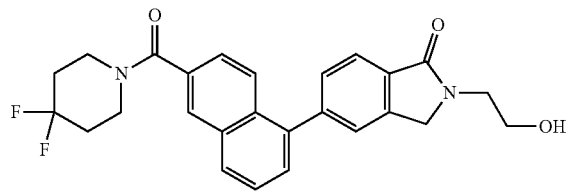
31 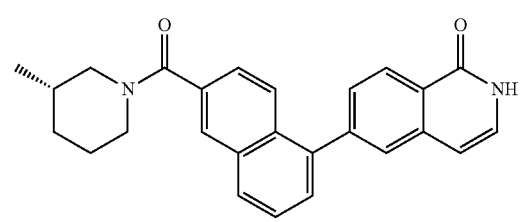
32 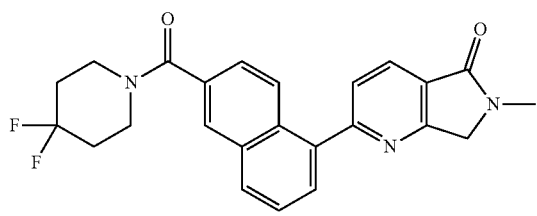
33 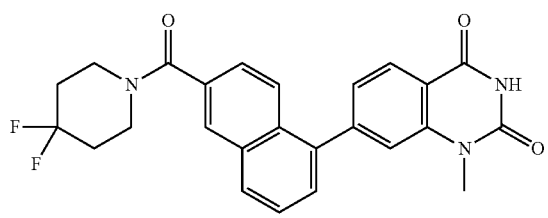
34 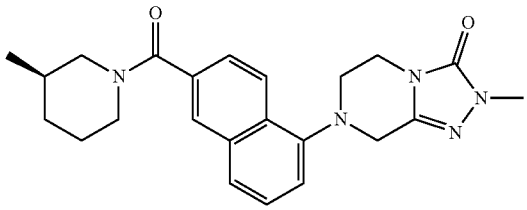
35 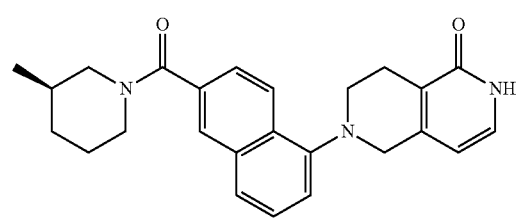
36 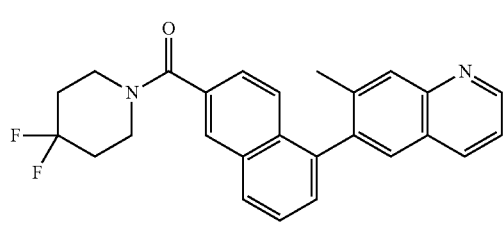
37 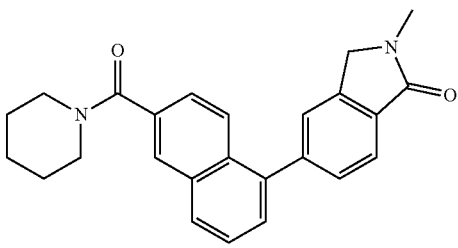
38 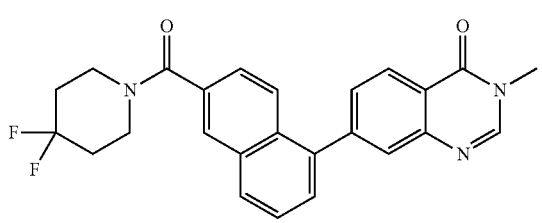
39 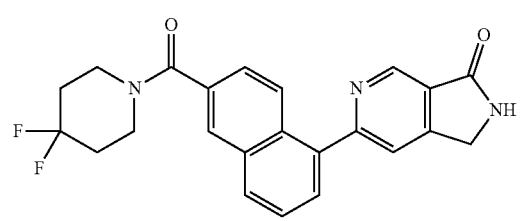
40 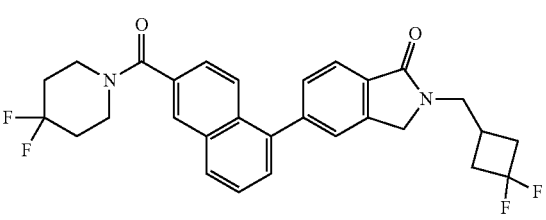
41 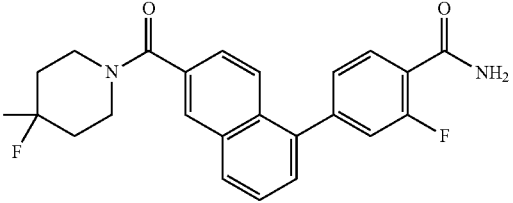
43 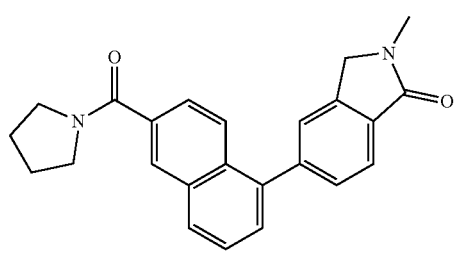
44 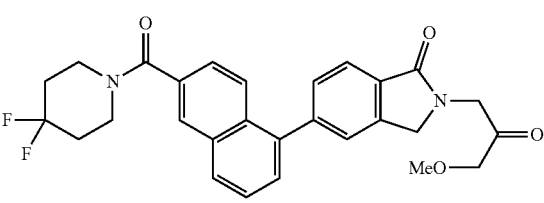

45
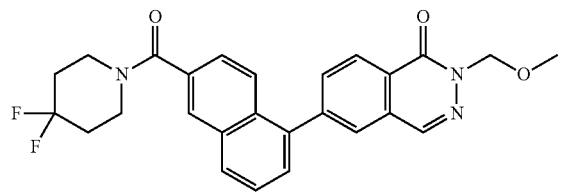
46
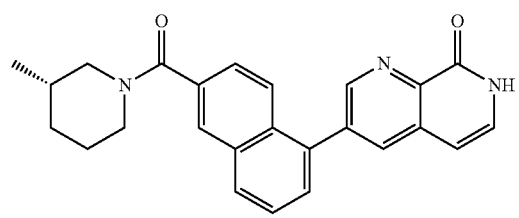
47
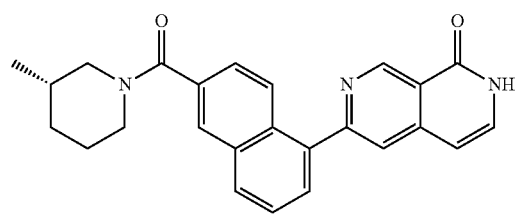
48
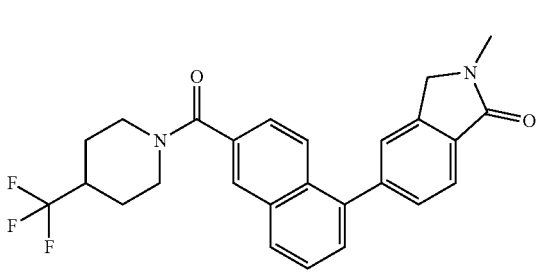
49
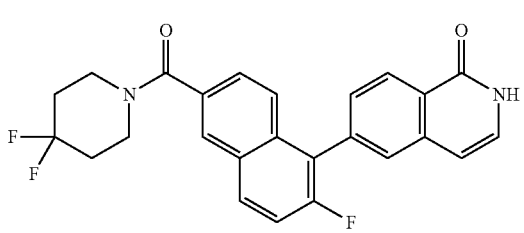
50
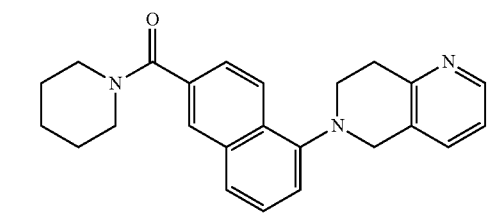
51
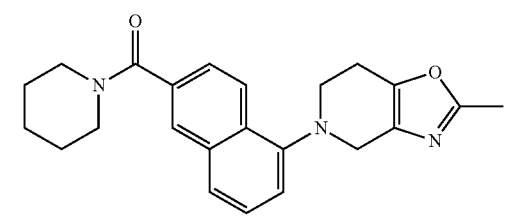
52
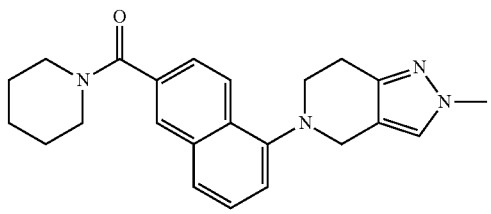
53
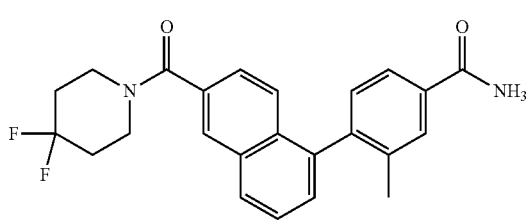
54
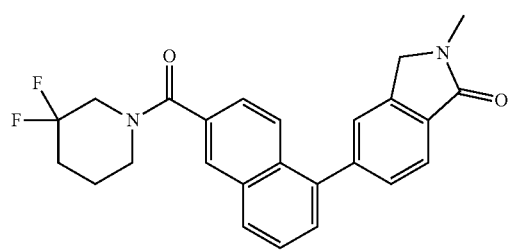
55
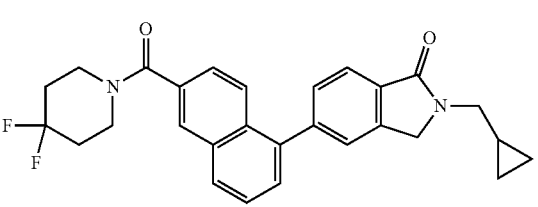
56
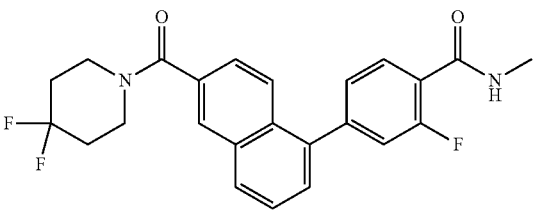
57
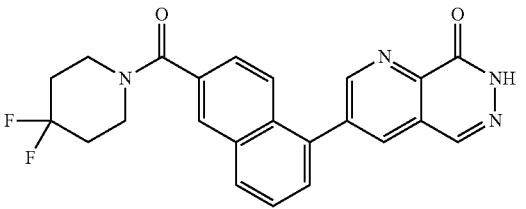
58
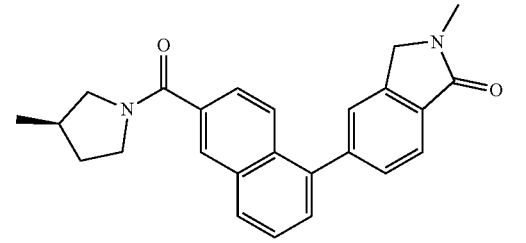

59
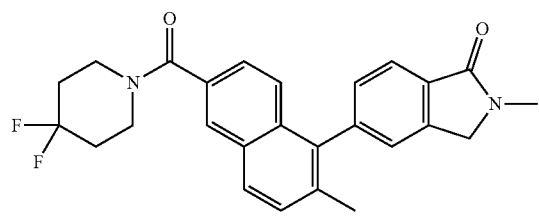
60
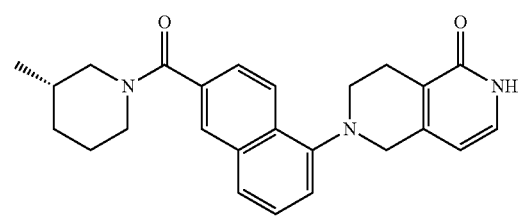
61
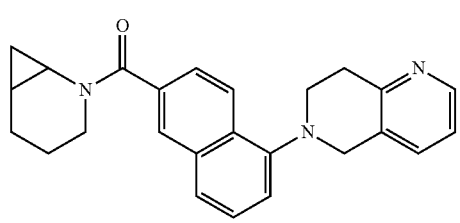
62
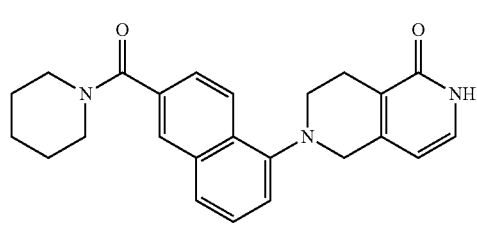
63
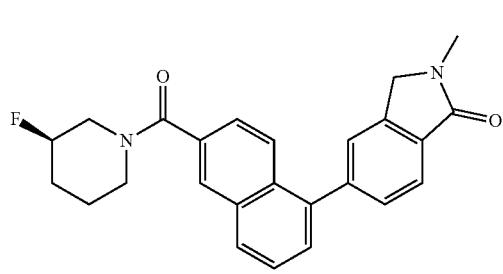
64
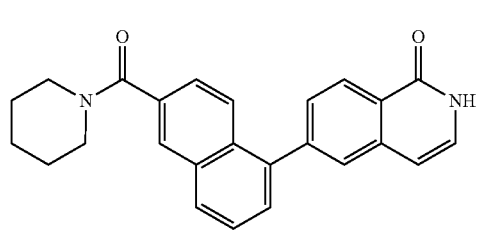
65
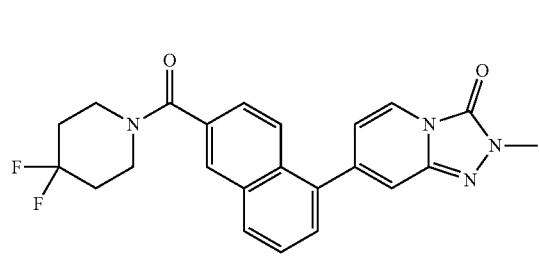
66
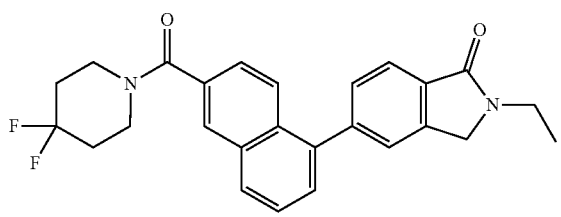
67
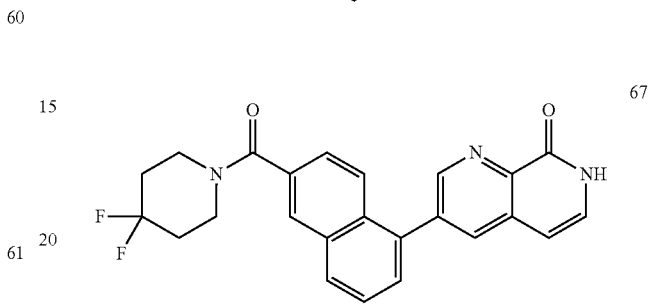
68
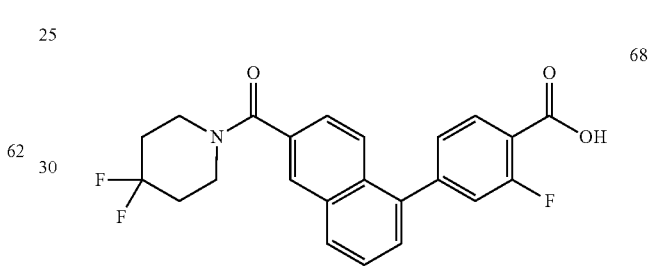
71
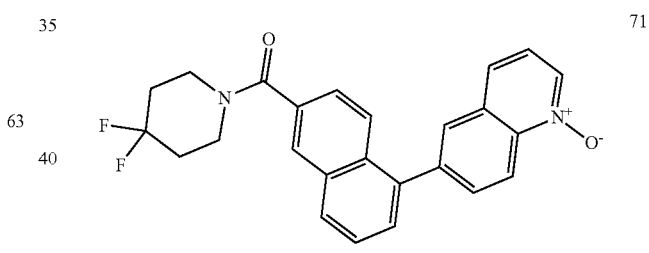
72
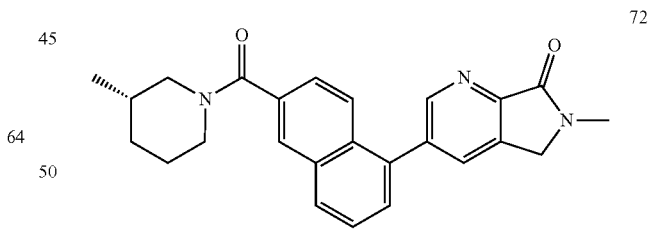
73
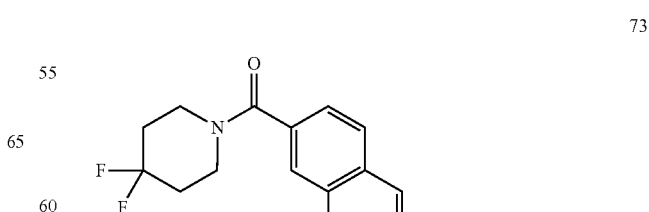
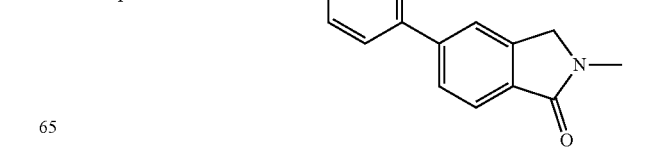

249
-continued
74
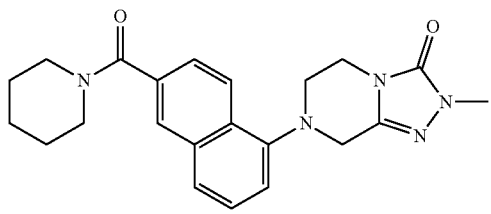
75
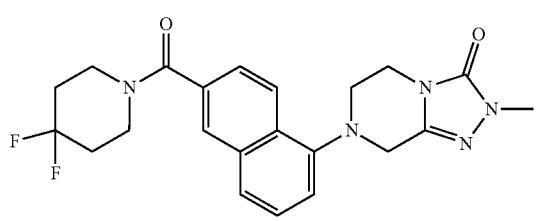
76
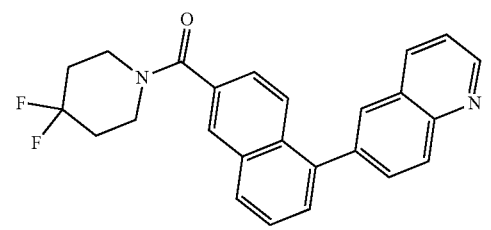
77
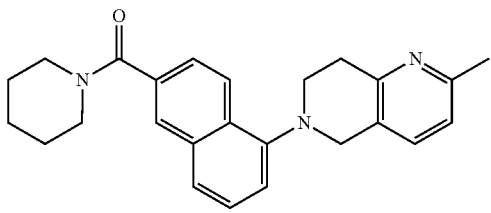
78
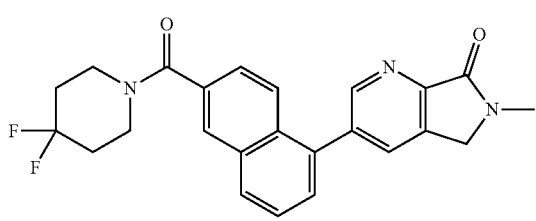
79
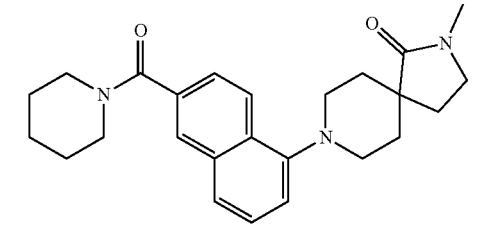
80
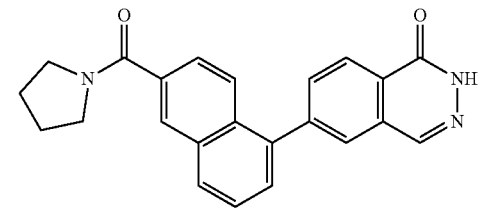
250
-continued
81
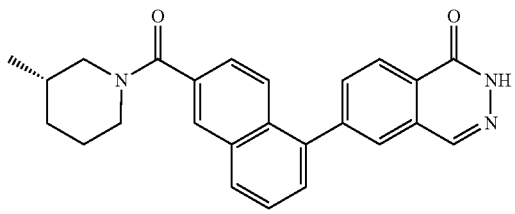
82
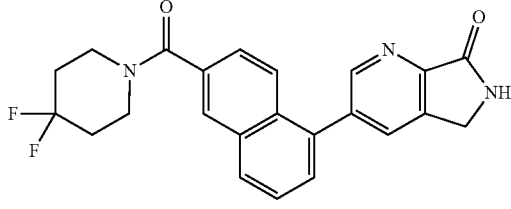
83
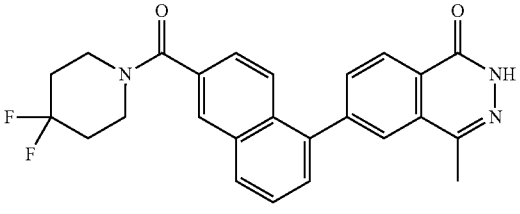
84
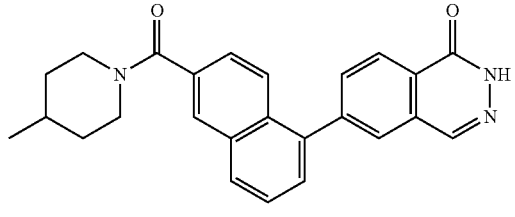
85
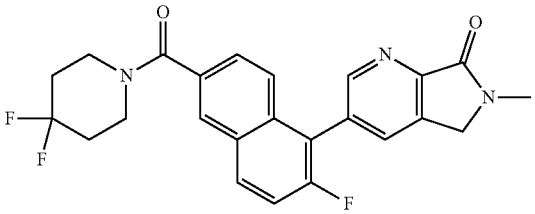
86
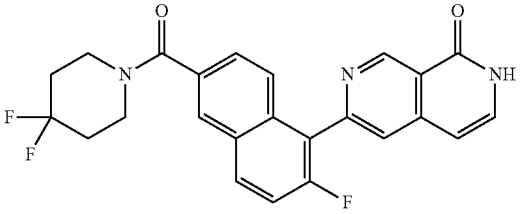
87
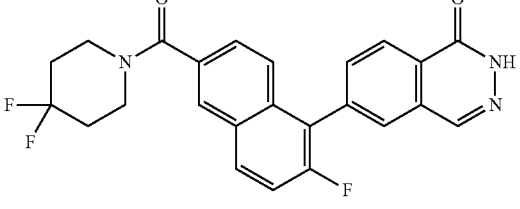

88
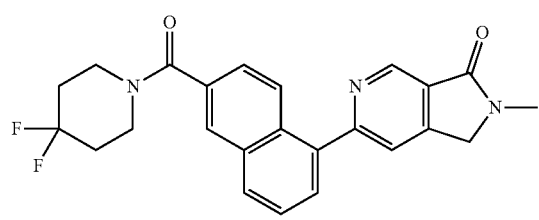
90
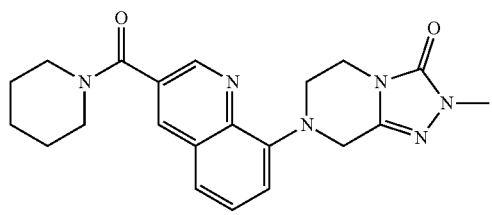
91
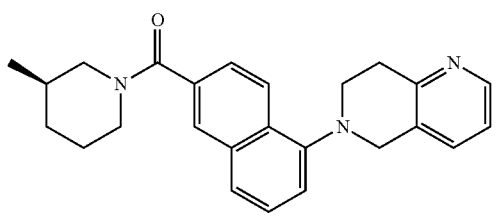
92
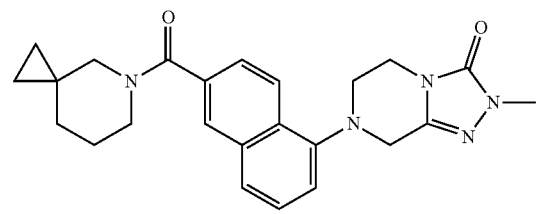
93
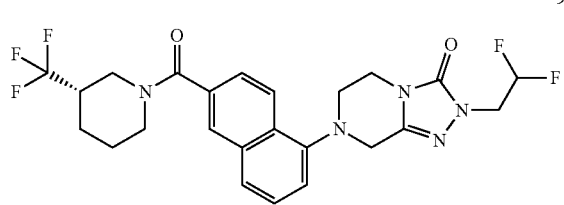
94
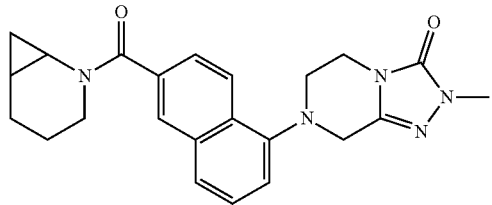
95
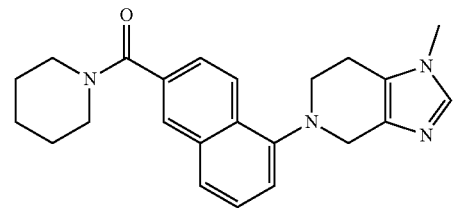
96
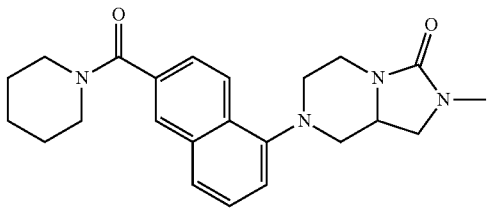
97
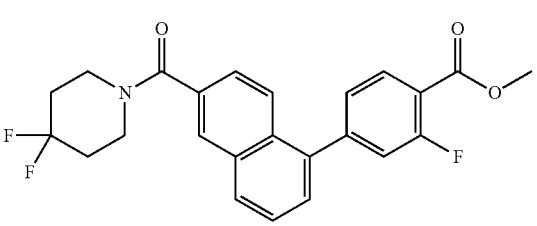
99
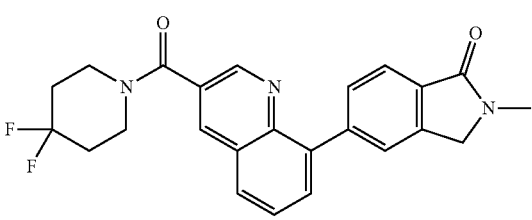
100
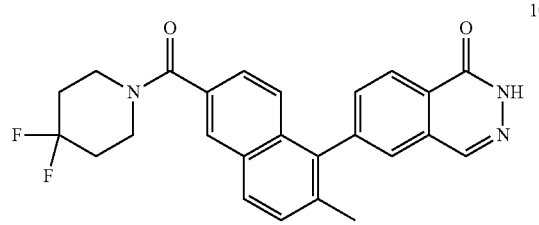
101
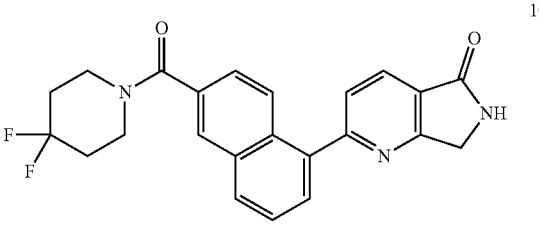
102
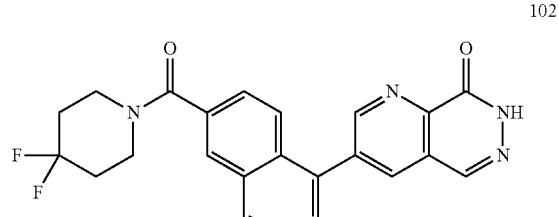
103
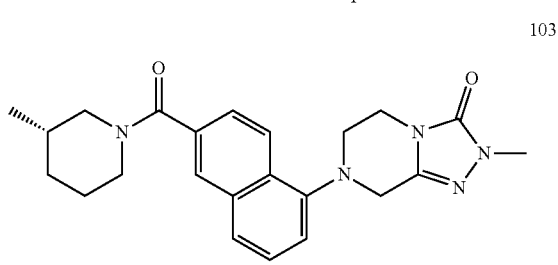

-continued
104
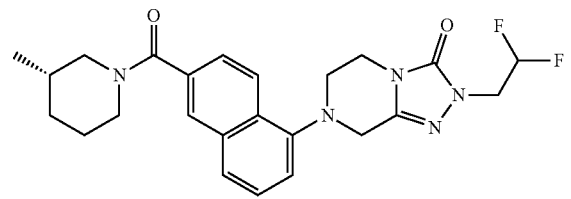
105
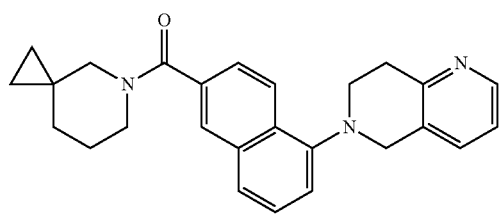
107
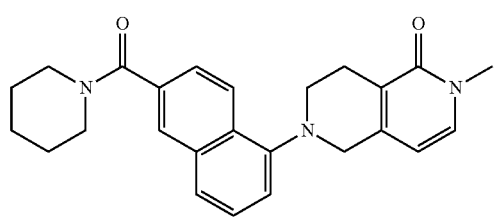
108
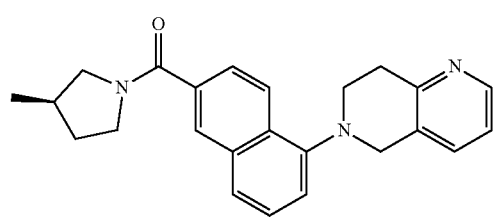
109
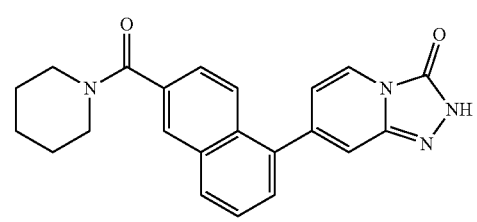
110
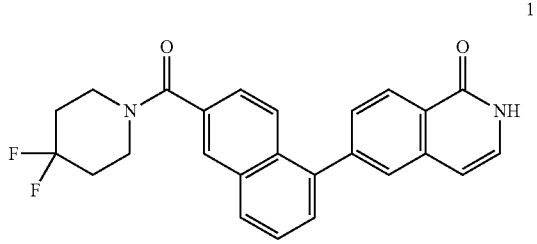
111
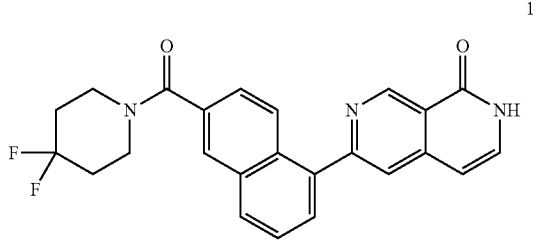
-continued
112
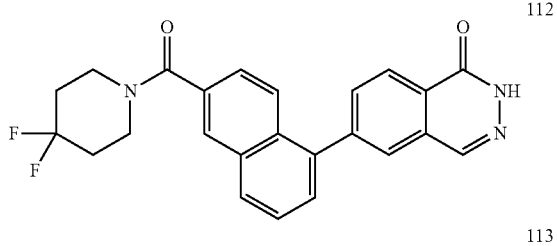
113
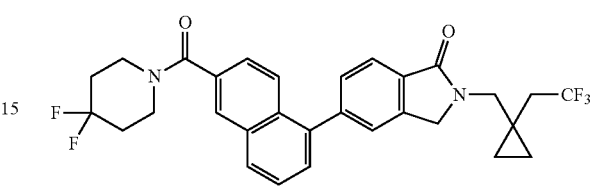
114
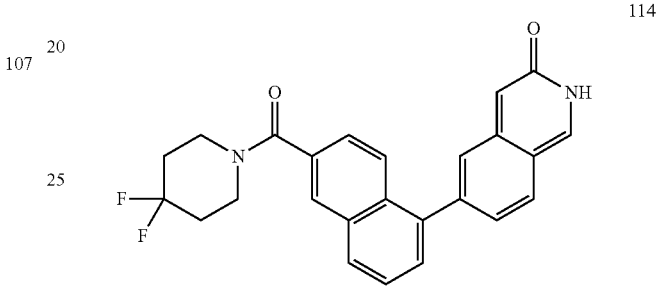
115
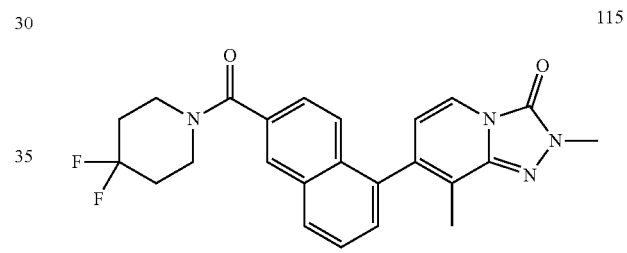
116
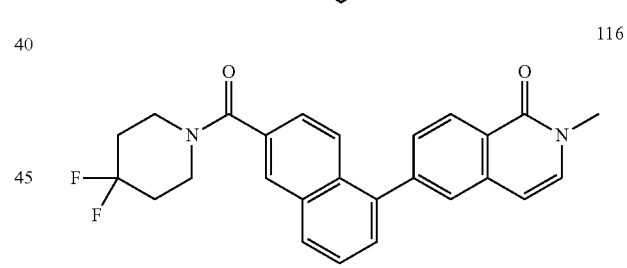
117
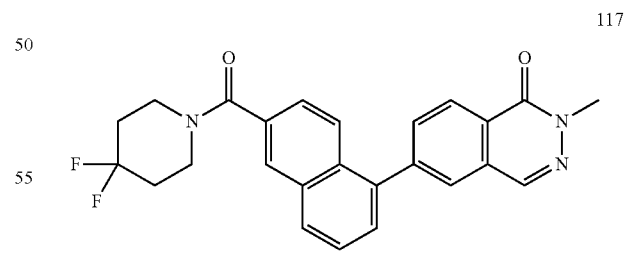
118
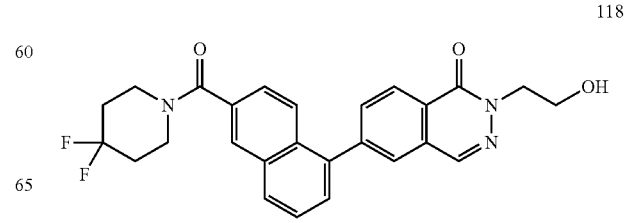

134
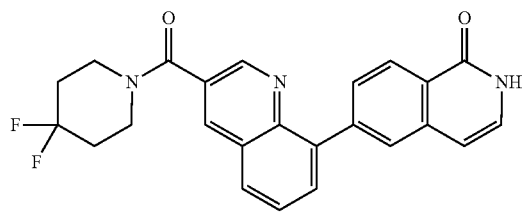
135
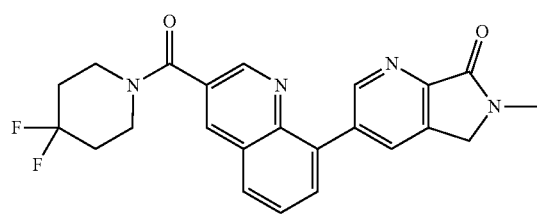
136
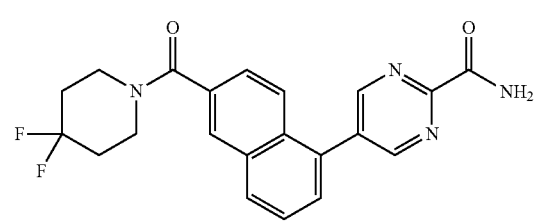
137
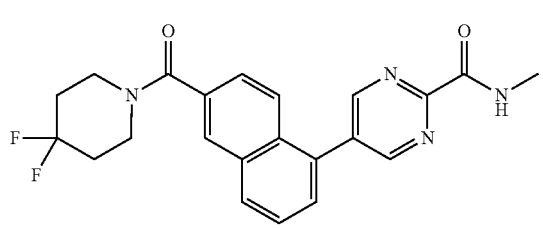
140
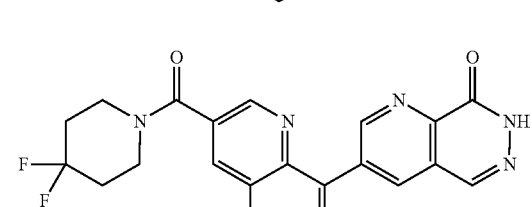
141
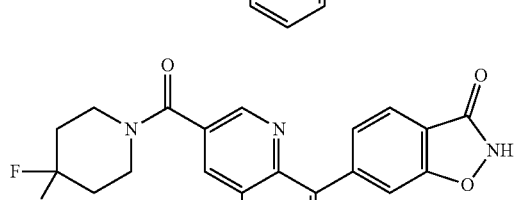
142
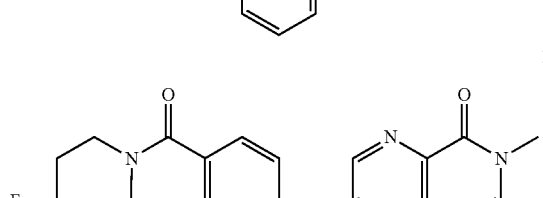
143
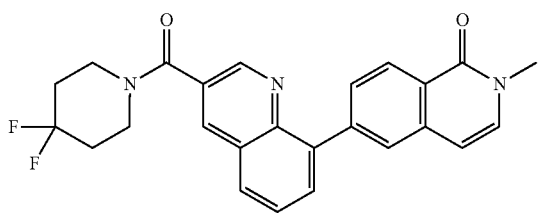
144
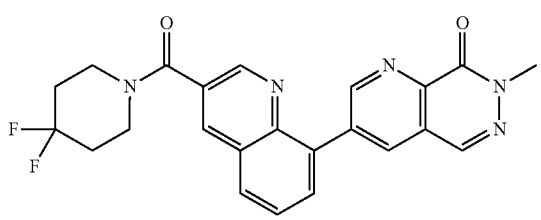
145
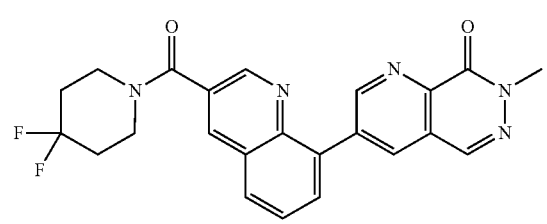
146
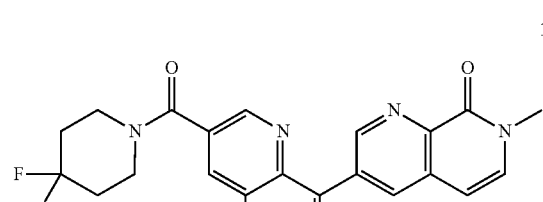
146
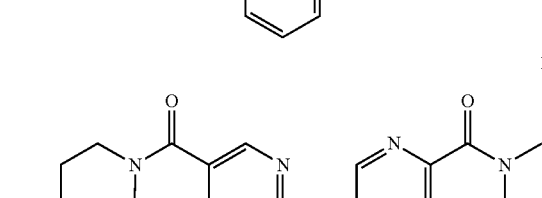
147
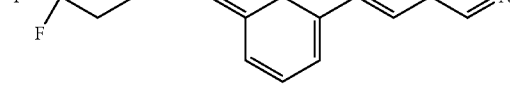

259          260
-continued    -continued
148 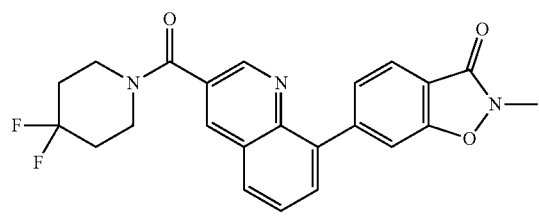
154 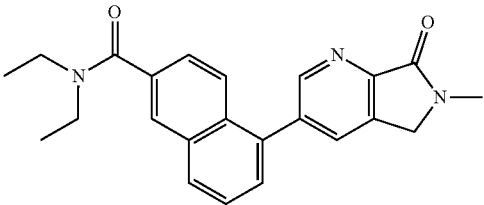
149 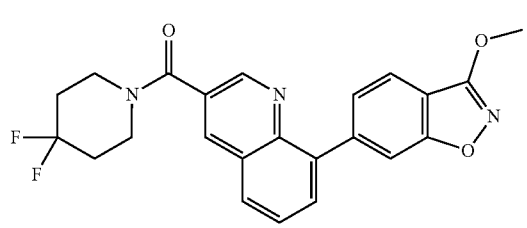
155 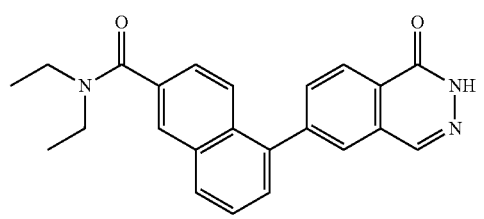
150 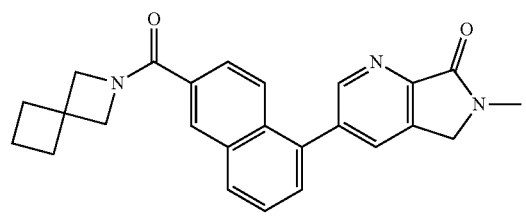
157 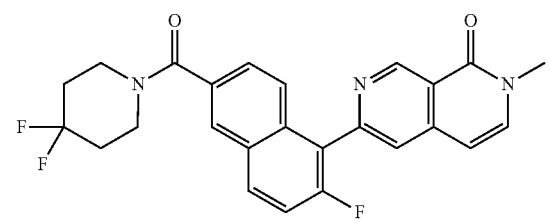
158 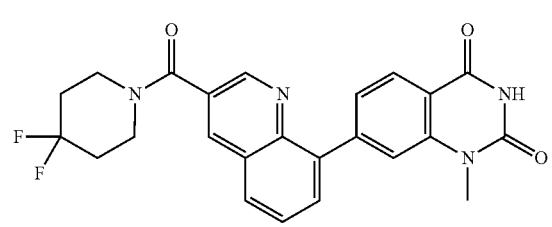
151 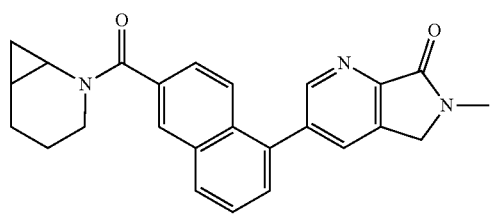
159 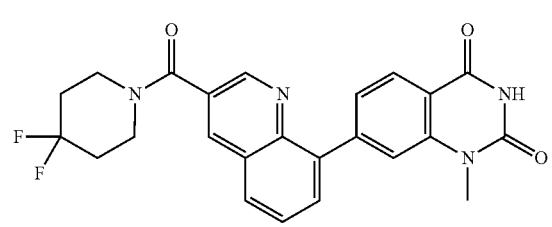
152 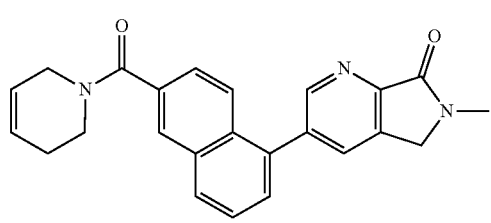
160 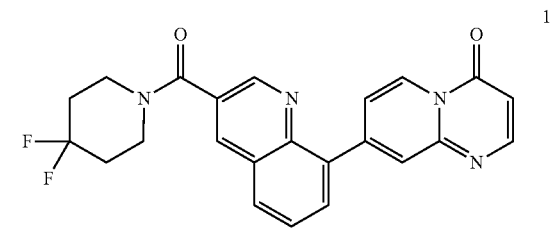
153 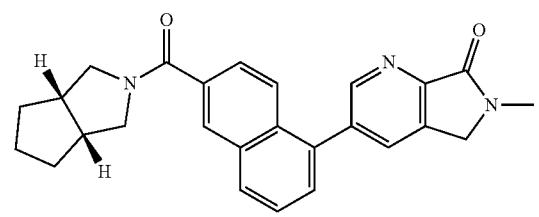
161 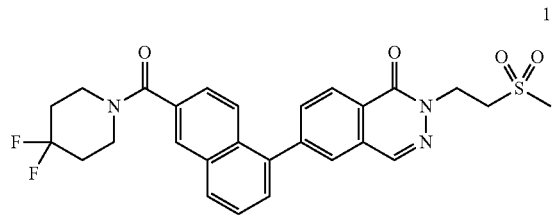

261
-continued
162
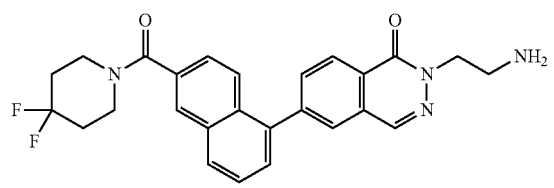
163
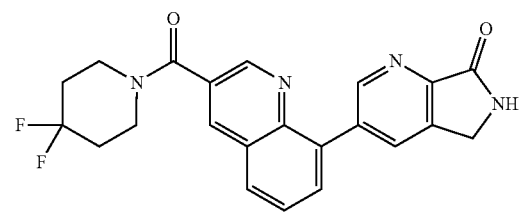
164
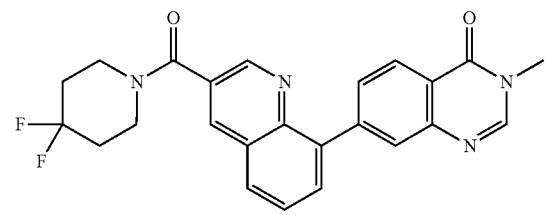
165
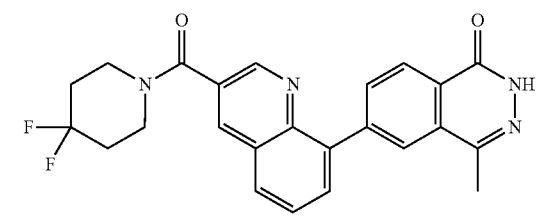
178
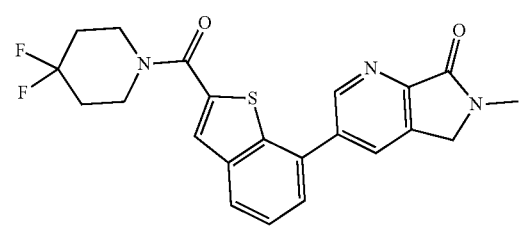
179
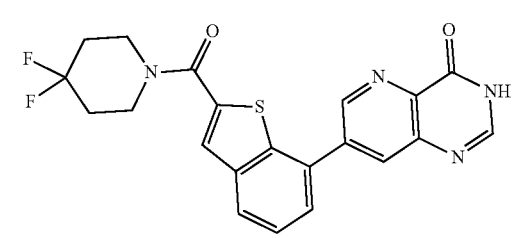
180
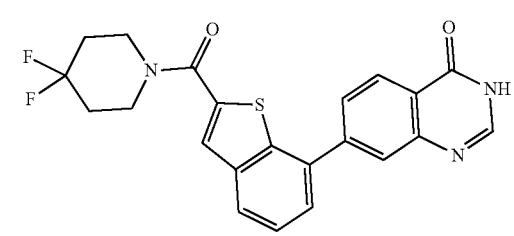
262
-continued
181
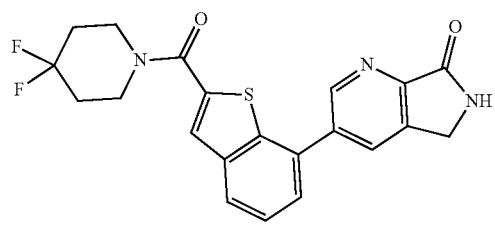
182
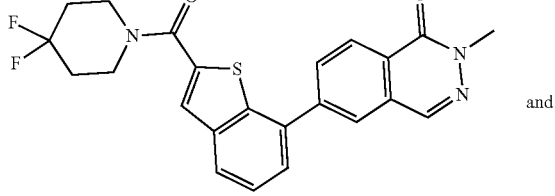
183
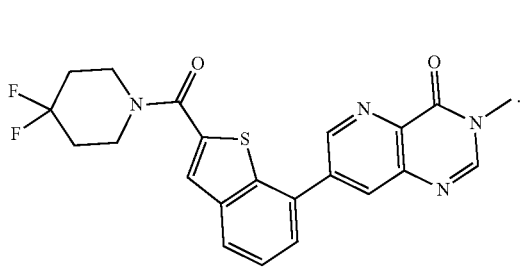
and
24. A compound or a pharmacologically acceptable salt thereof, wherein the compound has a structure selected from the group consisting of
1
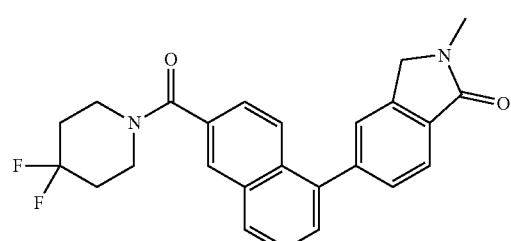
2
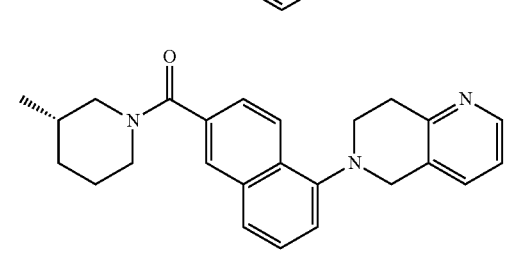
3
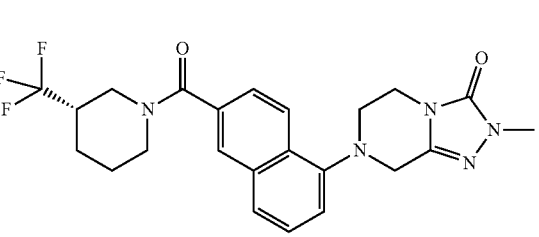

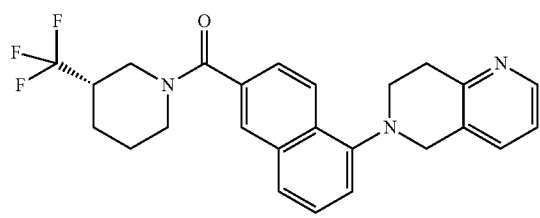
4
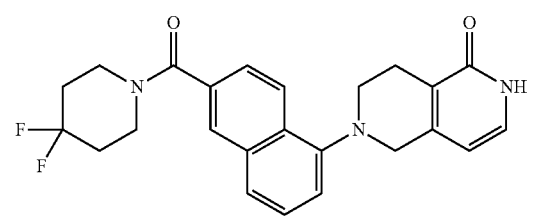
5
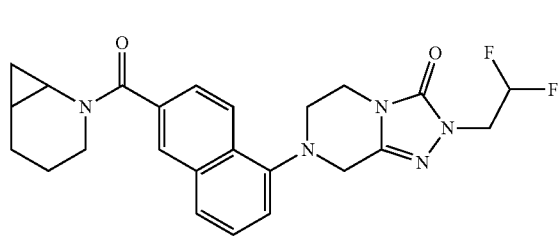
6
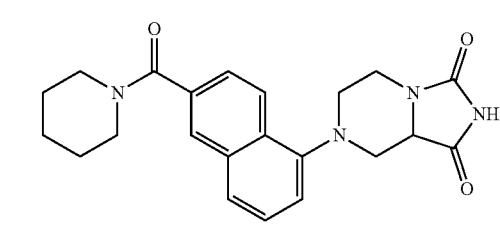
7
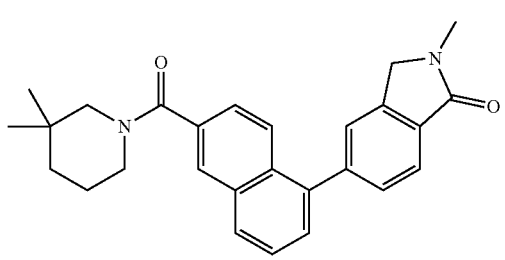
8
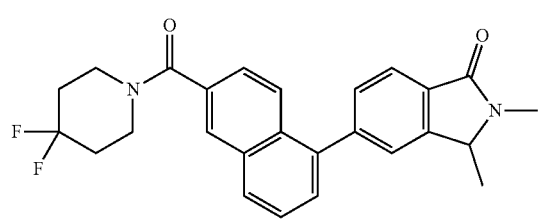
10
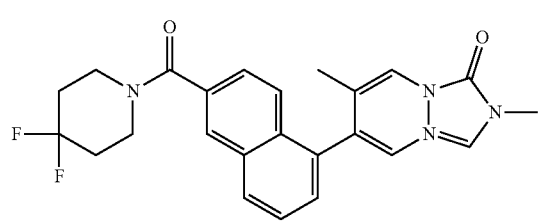
11
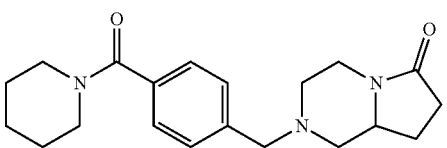
12
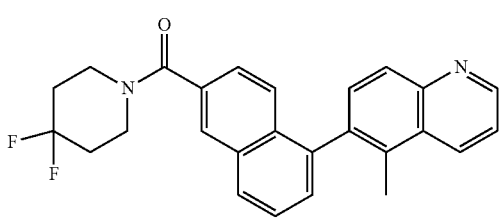
13
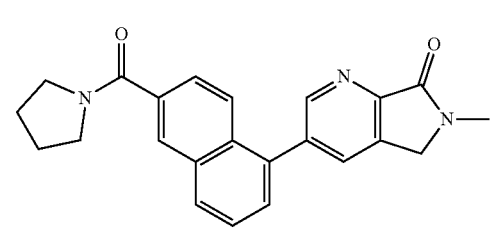
14
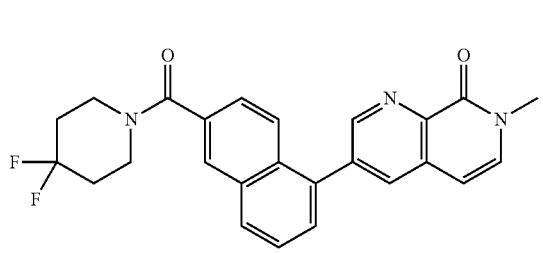
15
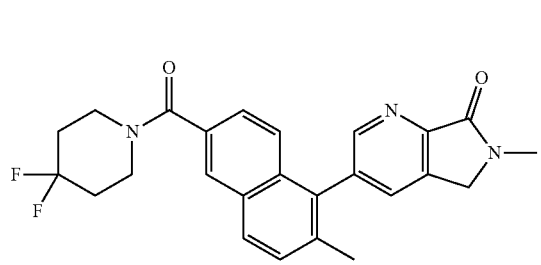
16
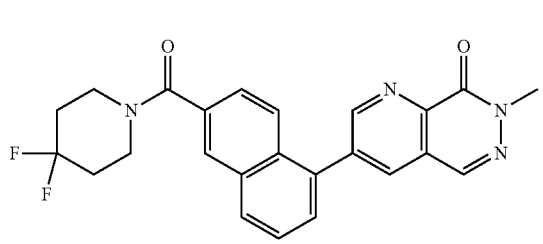
17
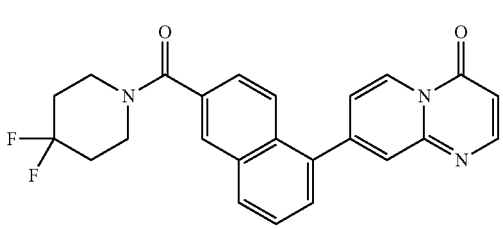
18

19
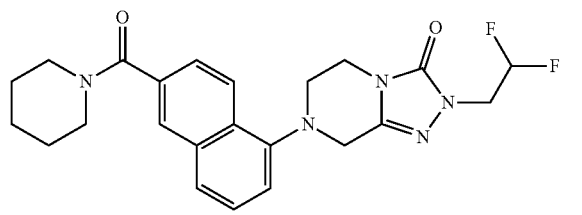
21
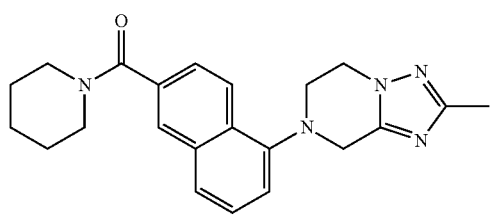
22
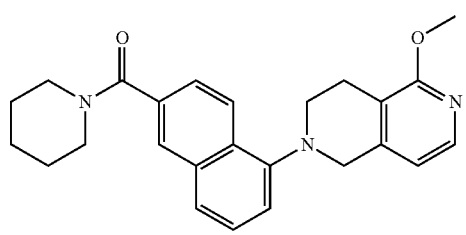
23
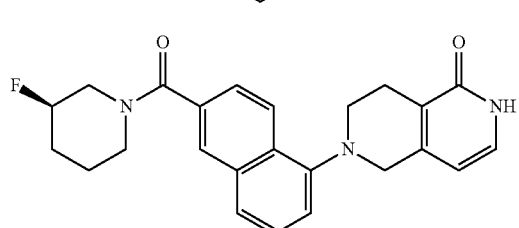
24
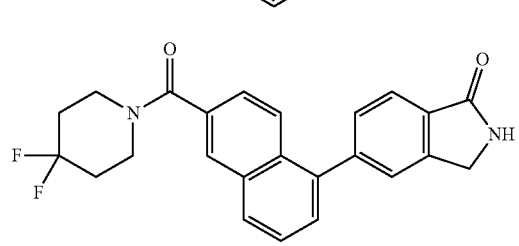
25
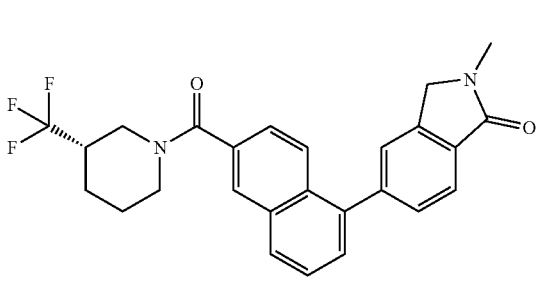
26
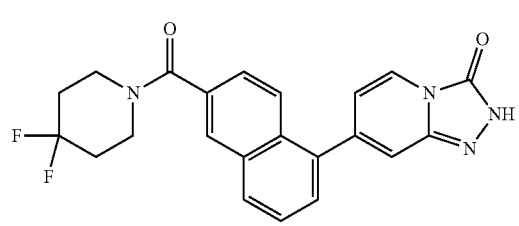
27
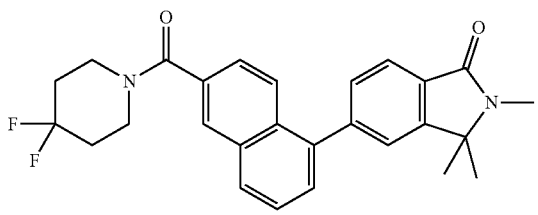
28
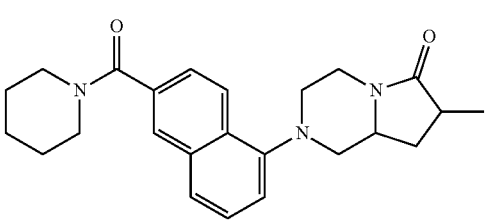
30
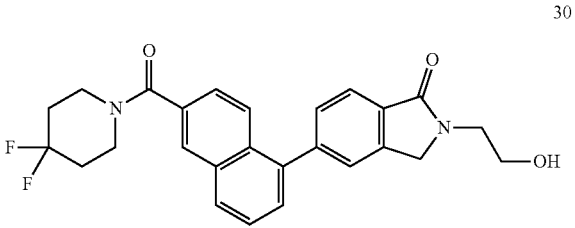
31
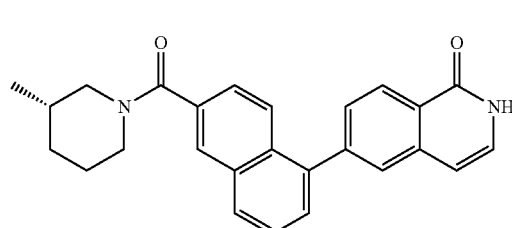
31
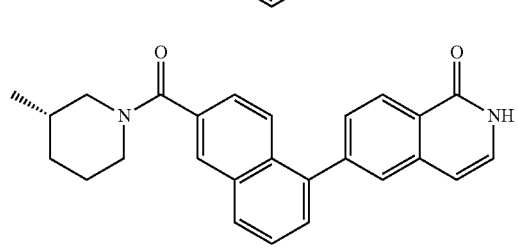
32
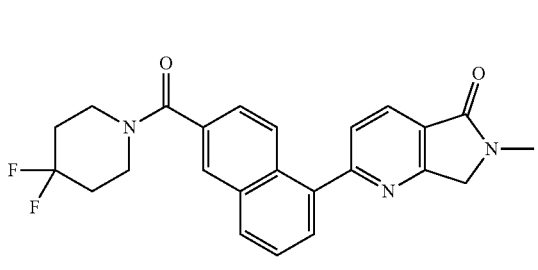
33
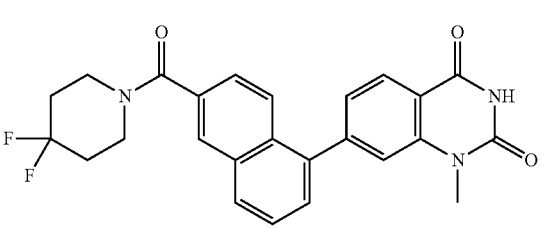

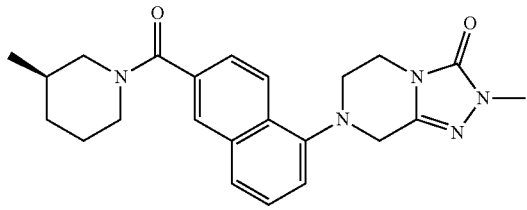
34
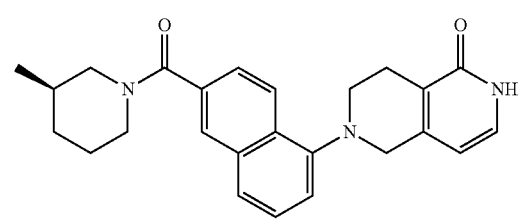
35
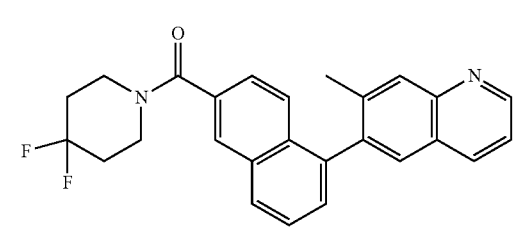
36
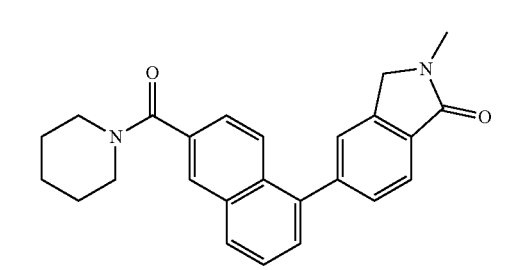
37
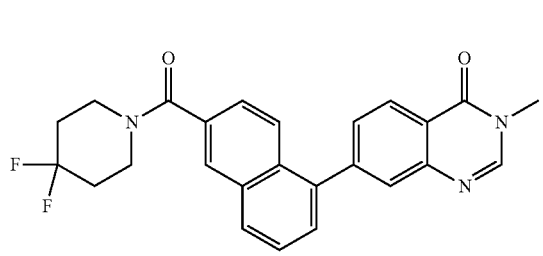
38
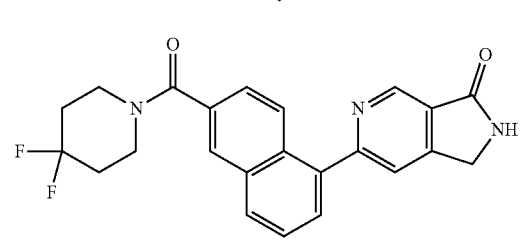
39
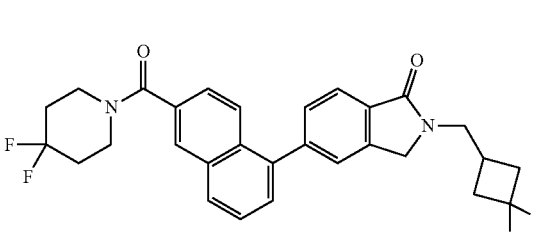
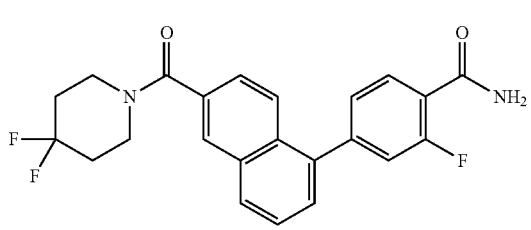
41
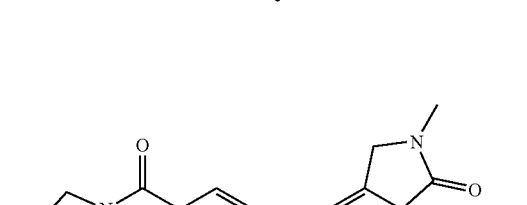
43
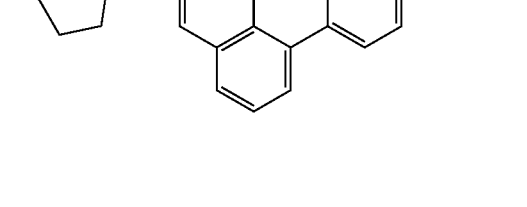
44
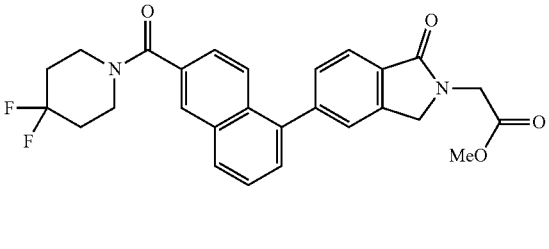
45
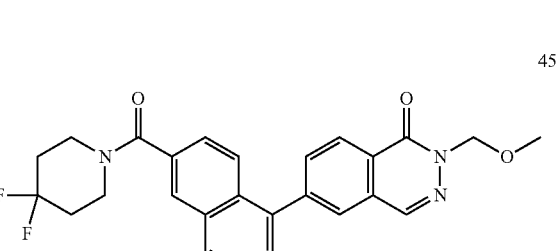
46
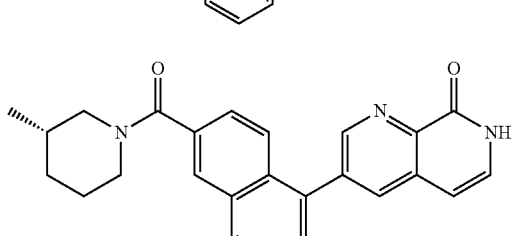
47
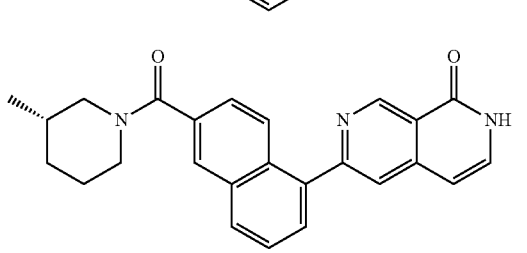

269
-continued
48
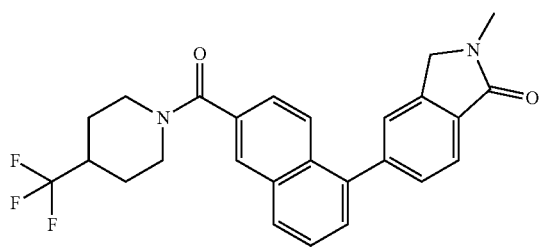
49
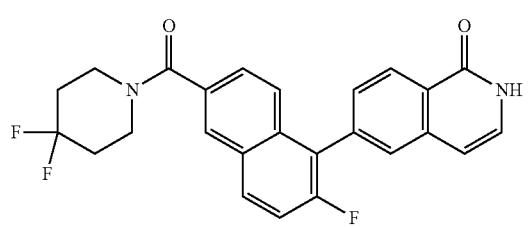
50
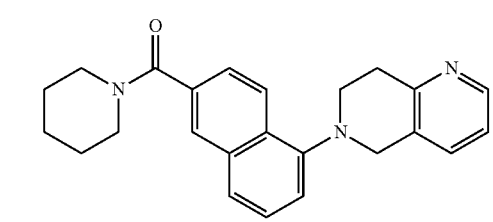
51
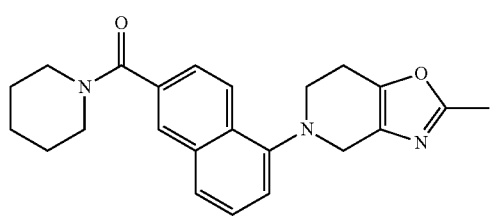
52
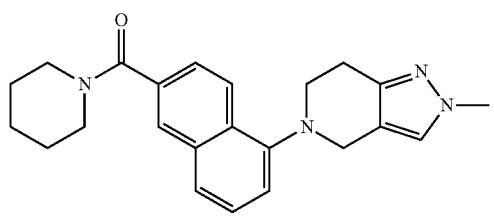
53
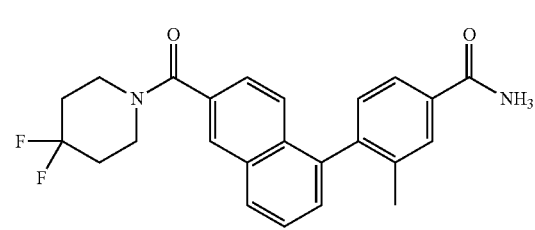
54
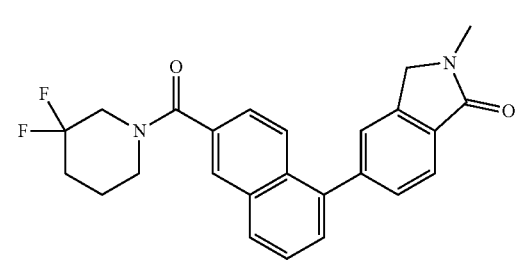
270
-continued
55
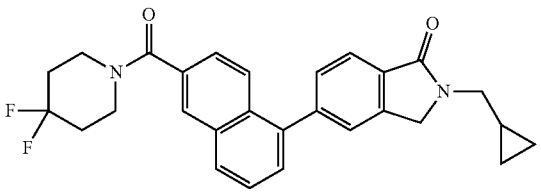
56
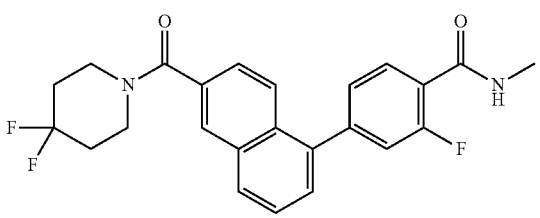
57
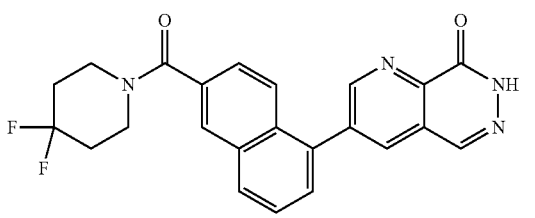
58
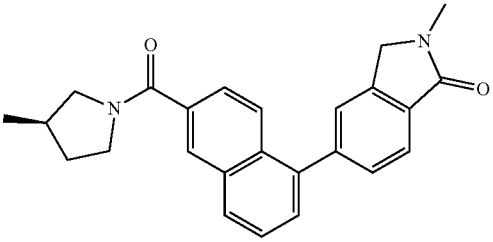
59
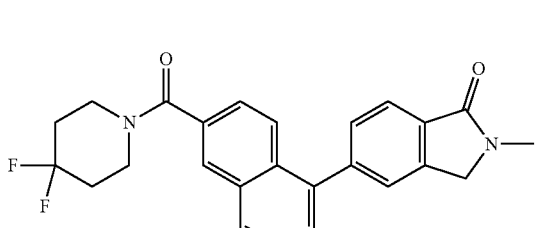
60
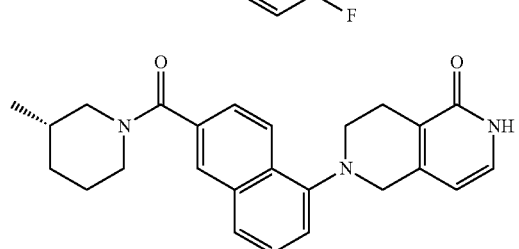
61
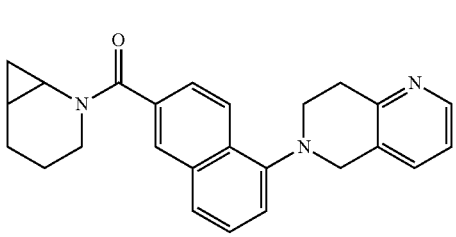

62
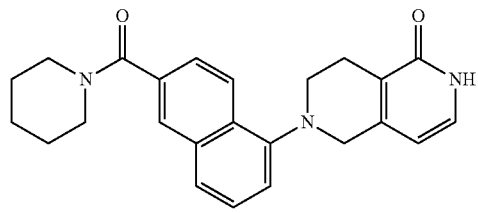
63
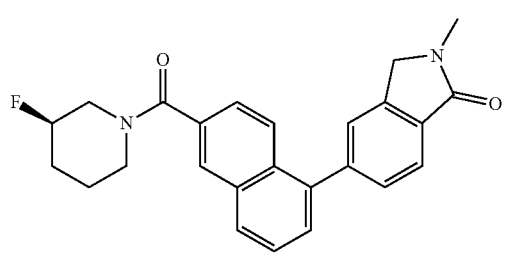
64
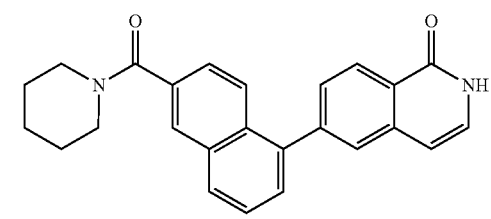
65
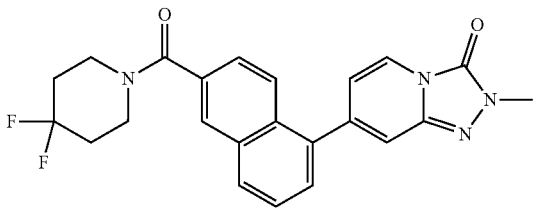
66
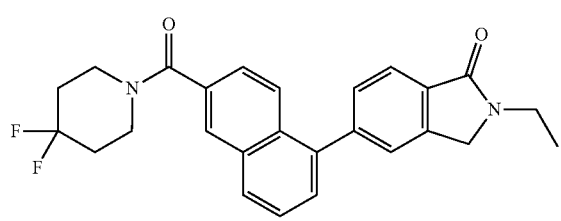
67
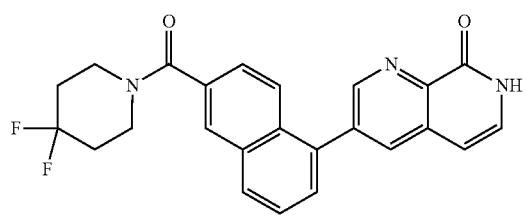
68
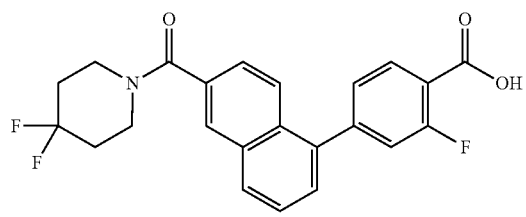
71
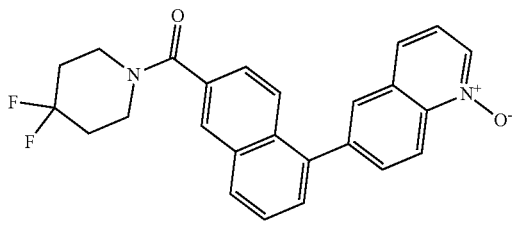
72
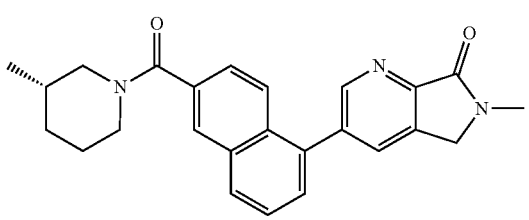
73
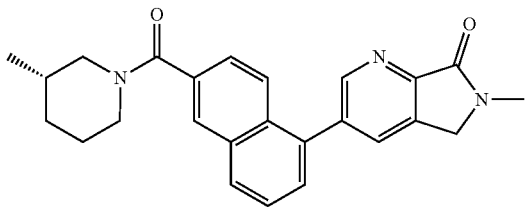
74
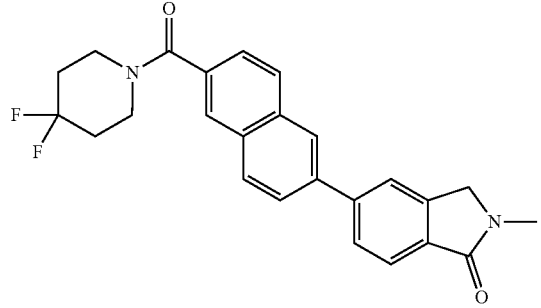
75
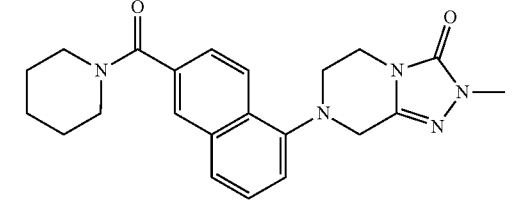
76
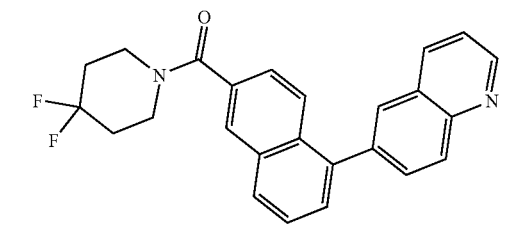

-continued
77
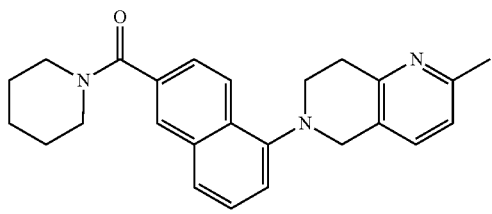
78
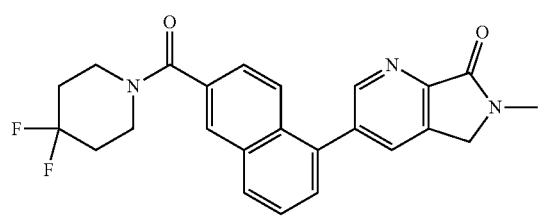
79
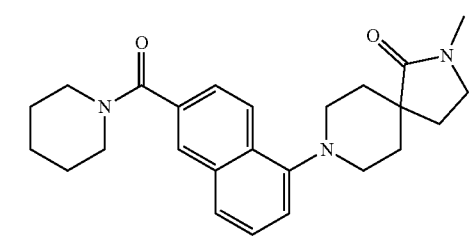
80
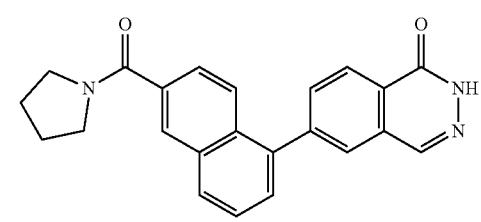
81
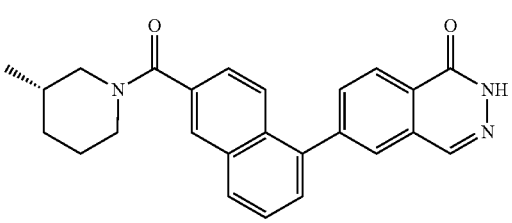
82
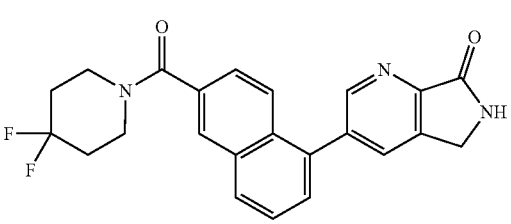
83
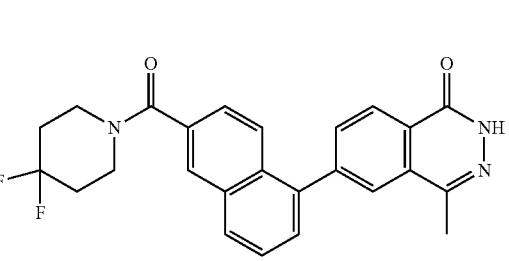
-continued
84
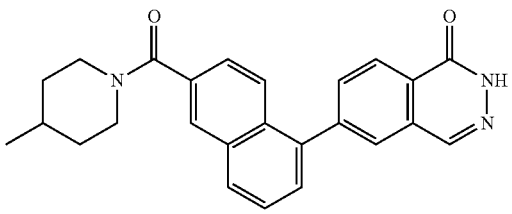
85
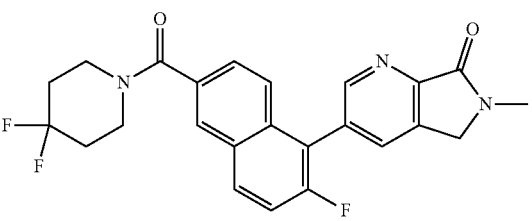
86
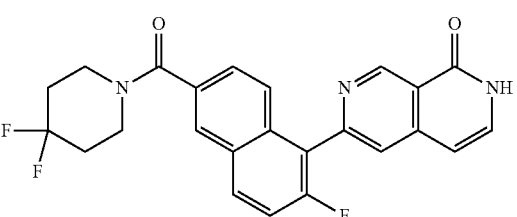
87
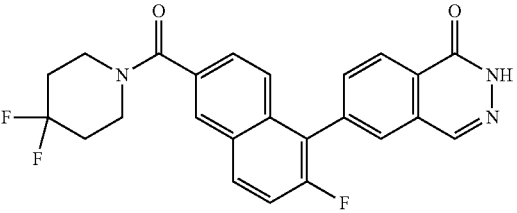
88
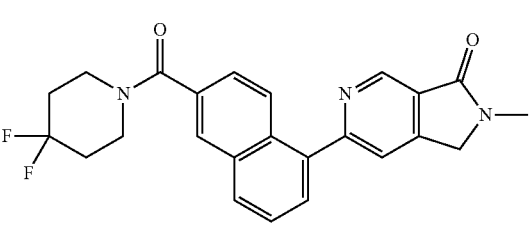
89
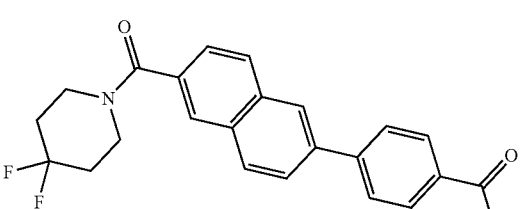
91
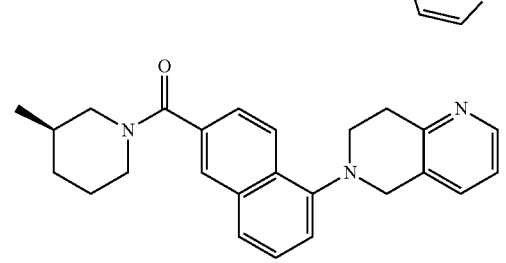

92
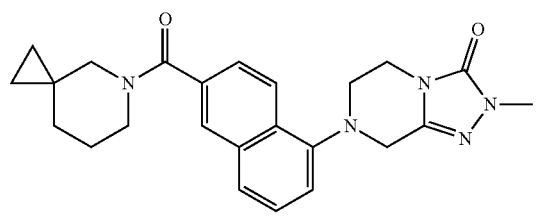
93
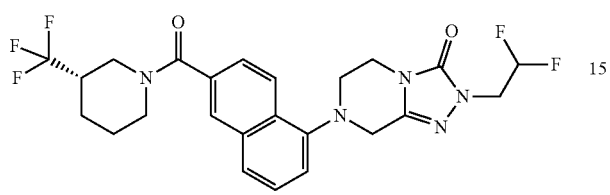
94
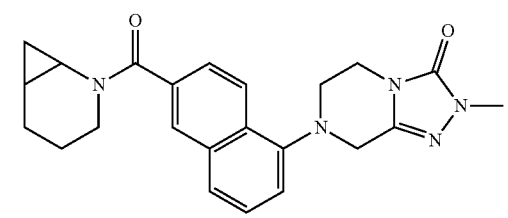
95
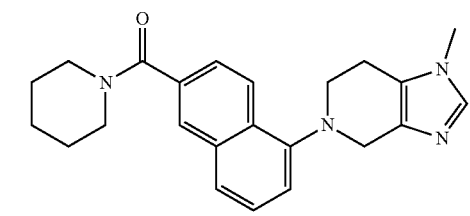
96
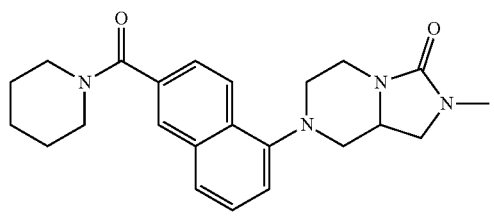
97
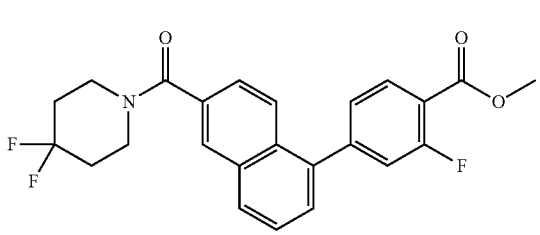
100
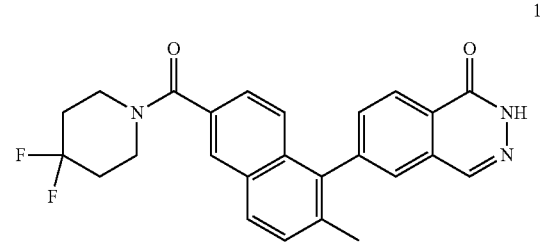
100
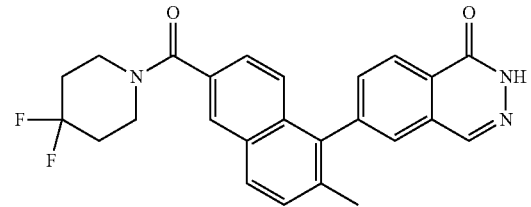
101
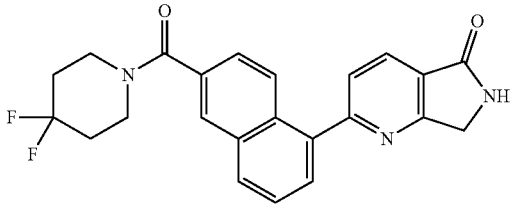
102
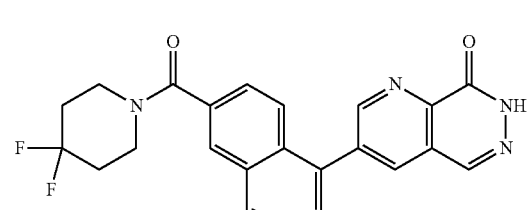
103
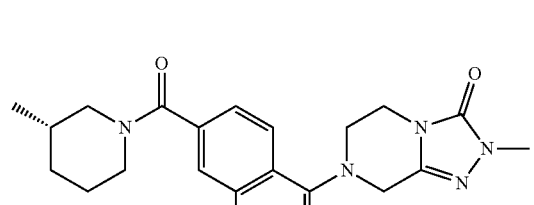
104
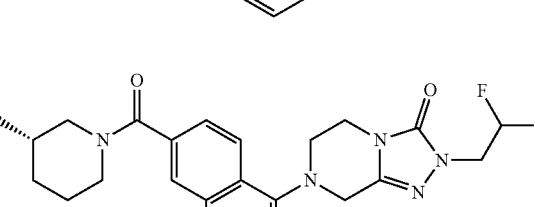
105
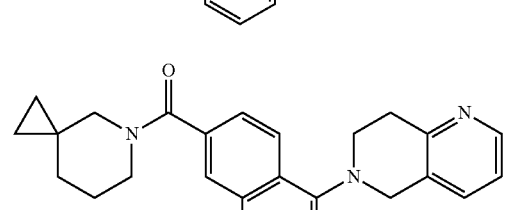
107
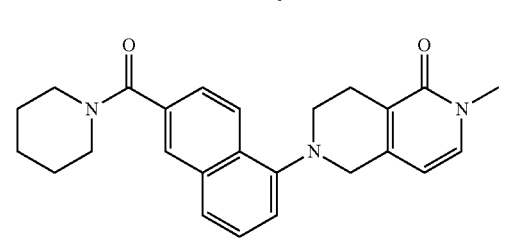

108
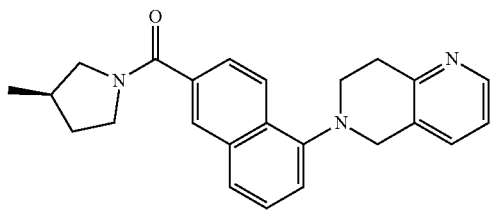
109
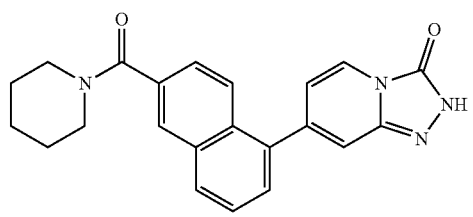
110
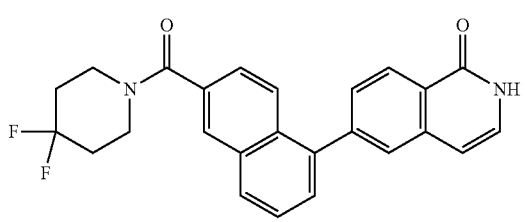
111
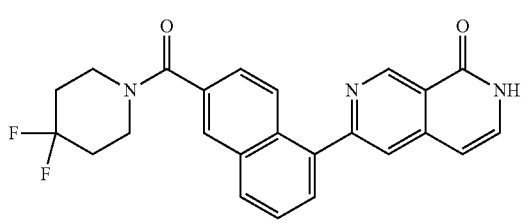
112
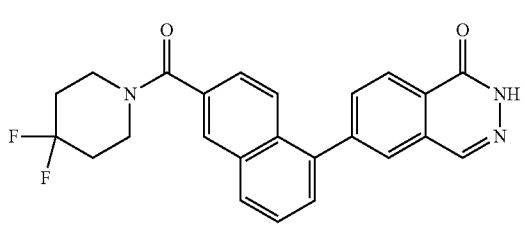
113
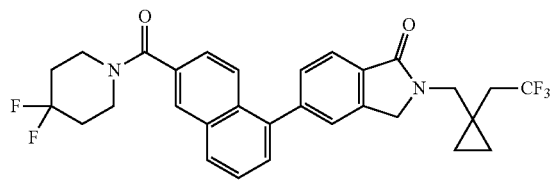
114
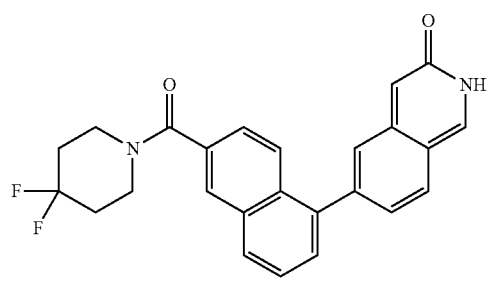
115
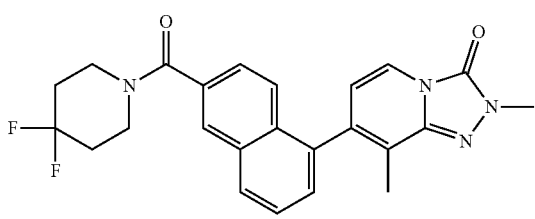
116
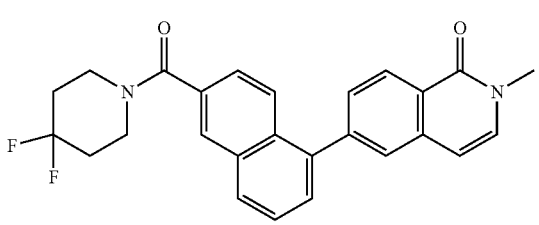
117
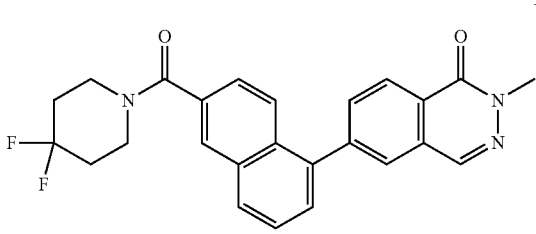
118
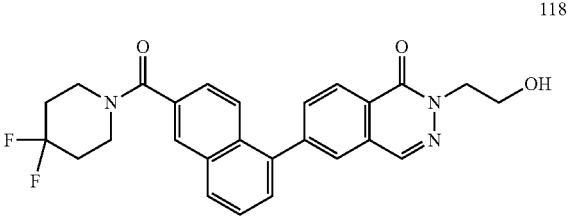
119
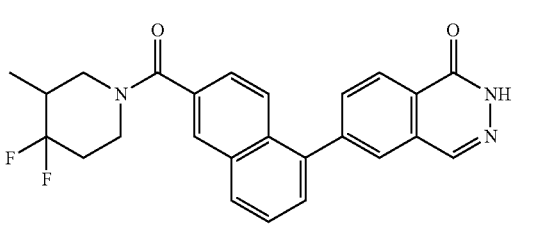
121
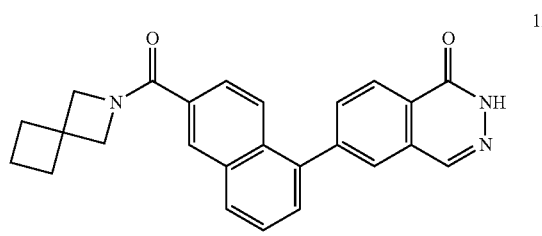
122
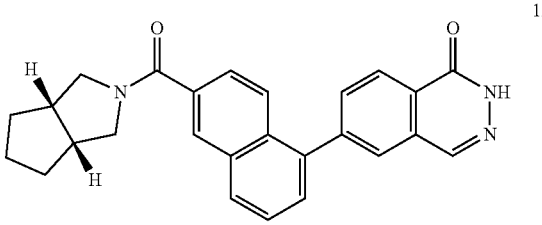

123 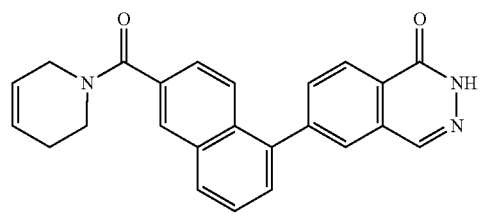
124 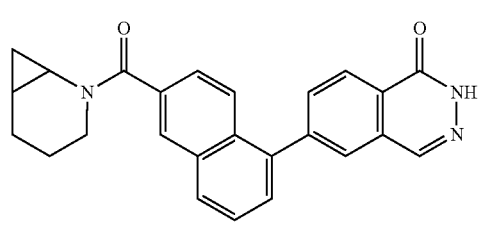
125 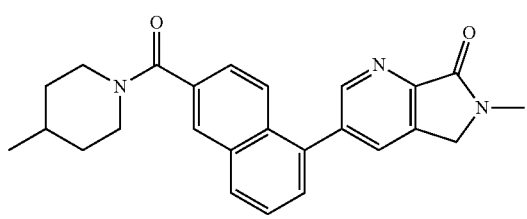
126 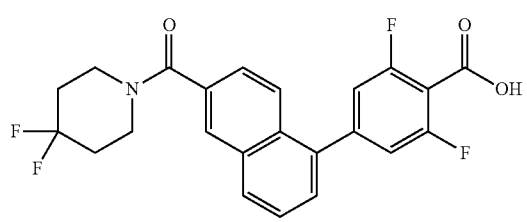
127 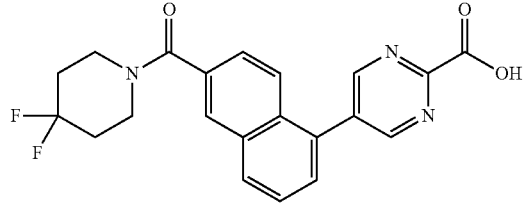
128 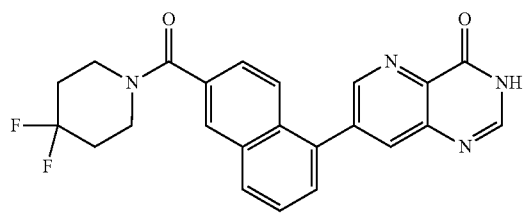
129 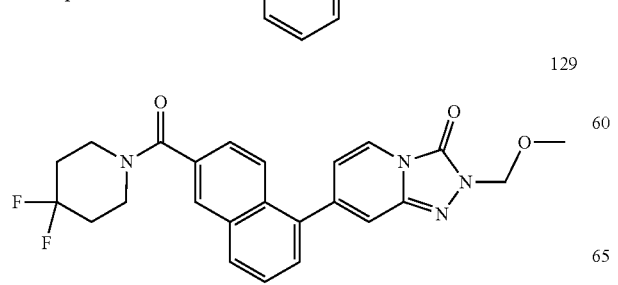
130 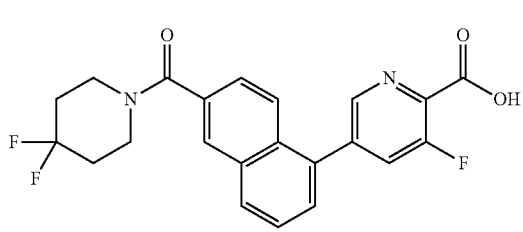
131 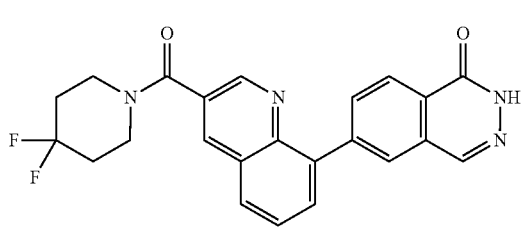
136 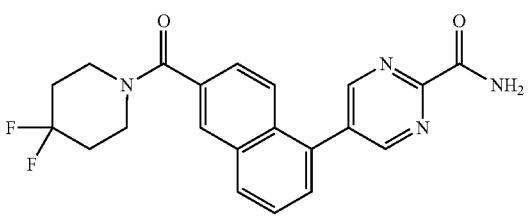
137 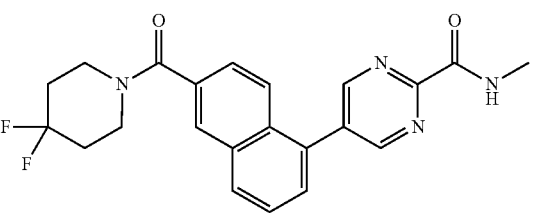
138 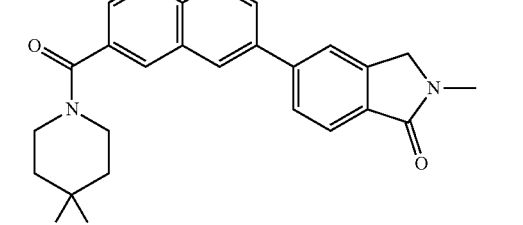
139 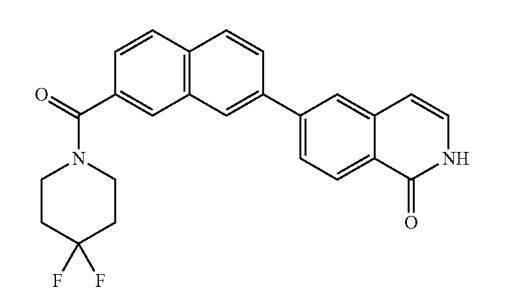

-continued

191 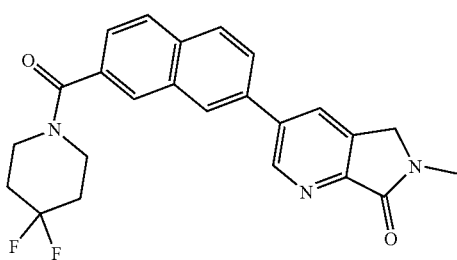
192 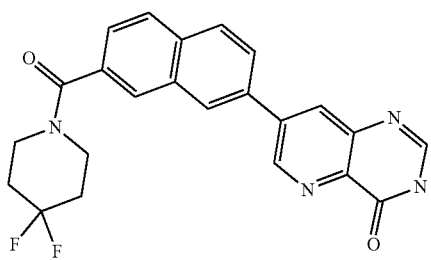
200 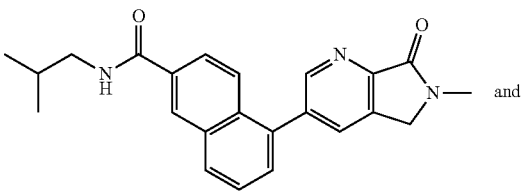
and
201 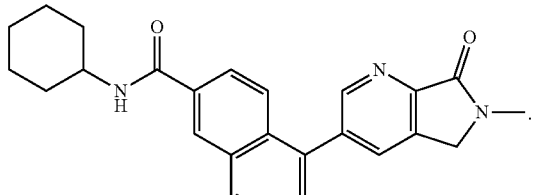
.
* * * * *